(12) United States Patent
Zhang et al.

(10) Patent No.: US 7,846,941 B2
(45) Date of Patent: Dec. 7, 2010

(54) COMPOUNDS MODULATING C-KIT AND C-FMS ACTIVITY AND USES THEREFOR

(75) Inventors: Chao Zhang, Moraga, CA (US); Jiazhong Zhang, Oakland, CA (US); Prabha N. Ibrahim, Mountain View, CA (US); Clarence R. Hurt, San Ramon, CA (US); Rebecca Zuckerman, Alameda, CA (US); Dean R. Artis, Kensington, CA (US); Ryan Bremer, Emeryville, CA (US); Wayne Spevak, Berkeley, CA (US); Guoxian Wu, Palo Alto, CA (US); Hongyao Zhu, Berkeley, CA (US)

(73) Assignee: Plexxikon, Inc., Berkeley, CA (US)

( * ) Notice: Subject to any disclaimer, the term of this patent is extended or adjusted under 35 U.S.C. 154(b) by 891 days.

(21) Appl. No.: 11/435,381

(22) Filed: May 16, 2006

(65) Prior Publication Data

US 2007/0032519 A1 Feb. 8, 2007

Related U.S. Application Data

(60) Provisional application No. 60/682,063, filed on May 17, 2005, provisional application No. 60/682,042, filed on May 17, 2005, provisional application No. 60/682,051, filed on May 17, 2005, provisional application No. 60/692,960, filed on Jun. 22, 2005, provisional application No. 60/692,750, filed on Jun. 22, 2005.

(51) Int. Cl.
*A61K 31/437* (2006.01)
*C07D 471/04* (2006.01)

(52) U.S. Cl. .................. 514/300; 546/113; 544/127; 514/234.5

(58) Field of Classification Search ............. 514/300, 514/234.5; 546/113; 544/127
See application file for complete search history.

(56) References Cited

U.S. PATENT DOCUMENTS

| | | | |
|---|---|---|---|
| 2,234,705 A | 4/1940 | Normington et al. |
| 2,413,258 A | 12/1946 | Soday |
| 4,150,949 A | 4/1979 | Smith |
| 4,568,649 A | 2/1986 | Bertoglio-Matte |
| 4,626,513 A | 12/1986 | Burton et al. |
| 4,727,395 A | 2/1988 | Oda et al. |
| 5,120,782 A | 6/1992 | Hubsch et al. |
| 5,143,854 A | 9/1992 | Pirrung et al. |
| 5,338,849 A | 8/1994 | Festal et al. |
| 5,426,039 A | 6/1995 | Wallace et al. |
| 5,432,177 A | 7/1995 | Baker et al. |
| 5,434,049 A | 7/1995 | Okano et al. |
| 5,449,614 A | 9/1995 | Danos et al. |
| 5,474,935 A | 12/1995 | Chatterjee et al. |
| 5,556,752 A | 9/1996 | Lockhart et al. |
| 5,576,319 A | 11/1996 | Baker et al. |
| 5,580,859 A | 12/1996 | Felgner et al. |
| 5,631,236 A | 5/1997 | Woo et al. |
| 5,632,957 A | 5/1997 | Heller et al. |
| 5,658,775 A | 8/1997 | Gilboa |
| 5,681,959 A | 10/1997 | Bishop et al. |
| 5,700,637 A | 12/1997 | Southern |
| 5,700,809 A | 12/1997 | Leeson et al. |
| 5,712,285 A | 1/1998 | Curtis et al. |
| 5,721,118 A | 2/1998 | Scheffler |
| 5,744,305 A | 4/1998 | Fodor et al. |
| 5,747,276 A | 5/1998 | Hoch et al. |
| 5,763,198 A | 6/1998 | Hirth et al. |
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,877,007 A | 3/1999 | Housey |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,025,155 A | 2/2000 | Hadlaczky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |

(Continued)

FOREIGN PATENT DOCUMENTS

DE 2413258 A1 10/1975

(Continued)

OTHER PUBLICATIONS

Minakata et al., "Functionalzation of 1*H*-Pyrrolo[2,3-*b*]pyridine." Bulletin of the Chemical Society of Japan (1992), 65(11): 2992-2997.

(Continued)

*Primary Examiner*—Charanjit S Aulakh
(74) *Attorney, Agent, or Firm*—Foley & Lardner LLP

(57) ABSTRACT

Compounds active on the receptor protein tyrosine kinases c-kit and c-fms are provided herewith. Also provided herewith are compositions useful for treatment of c-kit mediated diseases or condition and c-fms-mediated diseases or condition, and methods for the use thereof.

9 Claims, No Drawings

U.S. PATENT DOCUMENTS

| | | | |
|---|---|---|---|
| 6,096,718 A | 8/2000 | Weitzman et al. | |
| 6,107,478 A | 8/2000 | Pedersen et al. | |
| 6,110,456 A | 8/2000 | During | |
| 6,110,458 A | 8/2000 | Freeman et al. | |
| 6,113,913 A | 9/2000 | Brough et al. | |
| 6,117,681 A | 9/2000 | Salmons et al. | |
| 6,161,776 A | 12/2000 | Byles | |
| 6,178,384 B1 | 1/2001 | Kolossvary | |
| 6,235,769 B1 | 5/2001 | Clary | |
| 6,243,980 B1 | 6/2001 | Bronstein et al. | |
| 6,258,606 B1 | 7/2001 | Kovacs | |
| 6,261,776 B1 | 7/2001 | Pirrung et al. | |
| 6,277,489 B1 | 8/2001 | Abbott et al. | |
| 6,277,628 B1 | 8/2001 | Johann et al. | |
| 6,288,234 B1 | 9/2001 | Griffin | |
| 6,294,330 B1 | 9/2001 | Michnick et al. | |
| 6,310,074 B1 | 10/2001 | Depreux et al. | |
| 6,545,014 B2 | 4/2003 | Verner | |
| 6,858,860 B2 | 2/2005 | Hosono et al. | |
| 7,259,165 B2 | 8/2007 | Bernotas et al. | |
| 7,361,763 B2 | 4/2008 | Arnold et al. | |
| 7,361,764 B2 | 4/2008 | Arnold et al. | |
| 7,452,993 B2 | 11/2008 | Arnold et al. | |
| 7,498,342 B2 * | 3/2009 | Ibrahim et al. | 514/300 |
| 7,504,509 B2 * | 3/2009 | Ibrahim et al. | 546/113 |
| 7,582,637 B2 | 9/2009 | Arnold et al. | |
| 7,601,839 B2 | 10/2009 | Arnold et al. | |
| 7,626,021 B2 | 12/2009 | Arnold et al. | |
| 2001/0008765 A1 | 7/2001 | Shinoki et al. | |
| 2001/0012537 A1 | 8/2001 | Anderson et al. | |
| 2001/0014448 A1 | 8/2001 | Chappa et al. | |
| 2001/0014449 A1 | 8/2001 | Nerenberg et al. | |
| 2001/0016322 A1 | 8/2001 | Caren et al. | |
| 2001/0018642 A1 | 8/2001 | Balaban et al. | |
| 2001/0019827 A1 | 9/2001 | Dawson et al. | |
| 2004/0002534 A1 | 1/2004 | Lipson et al. | |
| 2004/0077595 A1 | 4/2004 | Cheng et al. | |
| 2004/0142864 A1 | 7/2004 | Bremer et al. | |
| 2004/0167030 A1 | 8/2004 | Bernotas et al. | |
| 2005/0085463 A1 | 4/2005 | Weiner et al. | |
| 2005/0154014 A1 | 7/2005 | Bloxham et al. | |
| 2005/0164300 A1 | 7/2005 | Artis et al. | |
| 2005/0170431 A1 | 8/2005 | Ibrahim et al. | |
| 2005/0256151 A1 | 11/2005 | Salom et al. | |
| 2006/0035898 A1 | 2/2006 | Arnold et al. | |
| 2006/0058339 A1 | 3/2006 | Ibrahim et al. | |
| 2006/0058340 A1 | 3/2006 | Ibrahim et al. | |
| 2007/0032519 A1 | 2/2007 | Zhang et al. | |
| 2007/0049615 A1 | 3/2007 | Ibrahim et al. | |
| 2007/0287711 A1 | 12/2007 | Arnold et al. | |
| 2008/0167338 A1 | 7/2008 | Spevak et al. | |
| 2008/0188514 A1 | 8/2008 | Wu et al. | |
| 2009/0005356 A1 | 1/2009 | Blaney et al. | |
| 2009/0143352 A1 | 6/2009 | Arnold et al. | |
| 2009/0306056 A1 | 12/2009 | Arnold et al. | |

FOREIGN PATENT DOCUMENTS

| | | |
|---|---|---|
| EP | 0154734 | 9/1985 |
| EP | 0 465 970 | 1/1992 |
| EP | 1 057 826 | 12/2000 |
| EP | 870768 | 5/2002 |
| EP | 1 267 111 | 12/2002 |
| EP | 1 749 829 | 2/2007 |
| GB | 2 292 143 | 2/1996 |
| GB | 2 292 145 | 2/1996 |
| GB | 2 298 198 | 8/1996 |
| GB | 2299581 | 10/1996 |
| JP | 6135946 | 5/1994 |
| JP | 10-130269 | 5/1998 |
| JP | 15-073357 | 3/2003 |
| WO | WO93/13099 | 7/1993 |
| WO | WO 94/14808 | 7/1994 |
| WO | WO94/20459 | 9/1994 |
| WO | WO-94/20497 | 9/1994 |
| WO | WO95/04742 | 2/1995 |
| WO | WO-95/07910 | 3/1995 |
| WO | WO-95/28387 | 10/1995 |
| WO | WO-96/00226 | 1/1996 |
| WO | WO96/11929 | 2/1996 |
| WO | WO96/05200 | 4/1996 |
| WO | WO 96/18738 | 6/1996 |
| WO | WO 96/17958 | 9/1996 |
| WO | WO 97/46313 | 12/1997 |
| WO | WO-97/46558 | 12/1997 |
| WO | WO97/49703 | 12/1997 |
| WO | WO-98/06433 | 2/1998 |
| WO | WO98/22457 | 5/1998 |
| WO | WO98/47899 | 10/1998 |
| WO | WO-99/00386 | 1/1999 |
| WO | WO 99/09217 | 2/1999 |
| WO | WO99/51231 | 10/1999 |
| WO | WO-99/51232 | 10/1999 |
| WO | WO-99/51233 | 10/1999 |
| WO | WO-99/51234 | 10/1999 |
| WO | WO-99/51595 | 10/1999 |
| WO | WO-99/51596 | 10/1999 |
| WO | WO 99/51773 | 10/1999 |
| WO | WO-00/09162 | 2/2000 |
| WO | WO00/12074 | 3/2000 |
| WO | WO00/12514 | 3/2000 |
| WO | WO-00/29411 | 5/2000 |
| WO | WO00/53582 | 9/2000 |
| WO | WO-00/64898 | 11/2000 |
| WO | WO00/71537 | 11/2000 |
| WO | WO00/75139 | 12/2000 |
| WO | WO01/09121 | 2/2001 |
| WO | WO-01/24236 | 4/2001 |
| WO | WO-01/29036 | 4/2001 |
| WO | WO 01/46196 | 6/2001 |
| WO | WO-01/60822 | 8/2001 |
| WO | WO01/62255 | 8/2001 |
| WO | WO01/98299 | 12/2001 |
| WO | WO02/00657 | 1/2002 |
| WO | WO02/18346 | 3/2002 |
| WO | WO02/083175 | 10/2002 |
| WO | WO02/085896 | 10/2002 |
| WO | WO02/102783 | 12/2002 |
| WO | WO03/000258 | 1/2003 |
| WO | WO 03/003004 | 1/2003 |
| WO | WO03/006459 | 1/2003 |
| WO | WO03/008422 | 1/2003 |
| WO | WO03/011868 | 2/2003 |
| WO | WO-03/020698 | 3/2003 |
| WO | WO03/028724 | 4/2003 |
| WO | WO03/037862 | 5/2003 |
| WO | WO03/051838 | 6/2003 |
| WO | WO-03/064413 | 8/2003 |
| WO | WO03/068221 | 8/2003 |
| WO | WO03/082289 | 10/2003 |
| WO | WO03/082868 | 10/2003 |
| WO | WO03/082869 | 10/2003 |
| WO | WO03/087087 | 10/2003 |
| WO | WO03/101990 | 12/2003 |
| WO | WO2004/009600 | 1/2004 |
| WO | WO-2004/009601 | 1/2004 |
| WO | WO 2004/016609 | 2/2004 |
| WO | WO 2004/016610 | 2/2004 |
| WO | WO-2004/024895 | 3/2004 |
| WO | WO2004/065393 | 8/2004 |
| WO | WO2004/065394 | 8/2004 |
| WO | WO2004/074286 | 9/2004 |
| WO | WO2004/078756 | 9/2004 |
| WO | WO-2004/078923 | 9/2004 |

| | | |
|---|---|---|
| WO | WO2004/101565 | 11/2004 |
| WO | WO2005/028475 | 3/2005 |
| WO | WO-2005/028624 | 3/2005 |
| WO | WO2005/044181 | 5/2005 |
| WO | WO2005/058891 | 6/2005 |
| WO | WO 2005/062795 | 7/2005 |
| WO | WO2005/062795 | 7/2005 |
| WO | WO2005/063746 | 7/2005 |
| WO | WO2005/063747 | 7/2005 |
| WO | WO2005/082367 | 9/2005 |
| WO | WO2005/085244 | 9/2005 |
| WO | WO2005/095400 | 10/2005 |
| WO | WO2005/103050 | 11/2005 |
| WO | WO2005/115363 | 12/2005 |
| WO | WO2006/004984 | 1/2006 |
| WO | WO 2006/009755 | 1/2006 |
| WO | WO 2006/009797 | 1/2006 |
| WO | WO2006/015123 | 2/2006 |
| WO | WO-2006/015124 | 2/2006 |
| WO | WO-2006/114180 | 11/2006 |
| WO | WO2006/127587 | 11/2006 |
| WO | WO-2007/002325 | 1/2007 |
| WO | WO-2007/002433 | 1/2007 |
| WO | WO 2007/013896 | 2/2007 |
| WO | WO 2007/106236 | 9/2007 |

OTHER PUBLICATIONS

Sawada et al., "4-(Benzoylindolizinyl)butyric acids; Novel nonsteroidal inhibitors of steroid 5α-reductase. III." Chemical and Pharmaceutical Bulletin (2001), 49(7): 799-813.

Song et al., "Isomerism of Bis(7-azaindolyl)methane." Organic Letters (2002), 4:23, 4049-4052, "Table of content" p. 1-16 and "Supporting information" p. 1-15.

Yakhontov et al., Derivatives of 7-azaindole. XV. Electrophilic substitution of 4-methyl-7-azaindole and its derivatives. Zhurnal Obshchei Khimii (1965), 1(11): 2032-2040. (English abstract only).

Yeung et al., "Friedel-Crafts acylation of indoles in acidic imidazolium chloroaluminate ionic liquid at room temperature." Tetrahedron Letters (2002), 43(33), 5793-5795.

Zhang et al., "An effective procedure for the acylation of azaindoles at C-3." Journal of Organic Chemistry (2002), 67(17): 6226-6227 and p. S1-S30.

International Search report for PCT Patent Application No. PCT/US2007/083910.

International Search report for PCT Patent Application No. PCT/US2007/085289.

International Search report for PCT Patent Application No. PCT/US2007/085299.

Examination Report for Pakistan Patent Application No. 0679/2006.

Examination Report for Guatemala Patent Application No. PI-2005-00164.

Alfthan, (1998) "Surface plasmon resonance biosensors as a tool in antibody engineering"; Biosensors & Bioelectornics 13 (1998) 653-663.

Baghestanian, et al., A Case of Malignant Mastocytosis With Circulating Mast Cell Precursors:Biological and Phenotypic Characterization of the Malignant Clone; 1996, Leuk.:116-122.

Bagshawe, "Antibody-Directed Enzyme Prodrug Therapy: A Review"; 1995, *Drug Dev. Res.*, 34:220-230.

Basta et al, "High-dose Intravenous Immunoglobulin Exerts Its Beneficial Effect in Patients with Dermatomyositis by Blocking Endomysial Deposition of Activated Complement Fragments"; J Clin Invest 1994, 94:1729-1735.

Bedi, et al., "BCR-ABL-Mediated Inhibition of Apoptosis With Delay of G2/M Transition After DNA Damage: A Mechanism of Resistance to Multiple Anticancer Agents"; Blood 1995, 86:1148-1158.

Bell, (1981) "Spectroscopy In Biochemistry", vol. I, pp. 155-194, CRC Press.

Bellone, et al., "Growth Stimulatin of Colorectal Carcinoma Cells Via and C-Kit Receptor Is Inhibited by TGF-β1"; 1997, J. Cell Physiol. 172: 1-11.

Berdel, et al., "Recombinant Human Stem Cell Factor Stimulates Growth of a Human Glioblastoma Cell Line Expressing C-kit Protooncogene"; 1992, Canc. Res. 52:3498-3502.

Bertolini et al., "A new Rational Hypothesis for the Pharmacophore of the Active Metabolite of Leflunomide, a Potent Immunosuppressive Drug"; 1997, *J. Med. Chem.*, 40:2011-2016.

Bjorntrop, "Neuroendocrine Pertuirbations as a Cause of Insulin Resistance"; Diabetes Metab. Res. Rev., 1999, 15: 427-441.

Robinson et al., "Stimulation of Bone Marrow Colony Growth In Vitro by Human Urine"; Blood. 1969, 33:396-9.

Bokenmeyer, et al., "Expression of Stem-Cell Factor and its Receptor C-Kit Protein in Normal Testicular Tissue and Malignant Germ-Cell Tumors"; 1996, J. Cancer Res. Clin. Oncol. 122:301-306.

Bowtell, "Options Available—From Start to Finish—For Obtaining Expression Data by Microarray"; (1999) Nature Genetics Supp. 21:25-32.

Buchschacher, "Hjman Immunodeficiency Virus Vectors for Inducible Expressin of Foreign Genes"; (1992) J. Virol. 66:2731-2739.

Capon et al., "Designing CD4 Immunoadhesins for AIDS Therapy", *Nature* 377:525-531 (1989).

Carpino, et al., "p62dok: A Constitutively Tyrosine-Phosphorylated, GAP-Associated Protein in Chronic Myelogenous Leukemia Progenitor Cells"; Cell 1997, 88:197-204.

Castells, et al., "The Presence of Membrane-bound Stem Cell Factor on Highly Immature Nonmetachromatic Mast Cells in the Peripheral Blood of a Patient with Aggressive Systemic Mastocytosis"; 1996, J. Aller. Clin. Immunol. 98:831-840.

Checovich, W. J., et al., "Fluorescence Polarization—a new tood for cell and molecular biology"; (1995) Nature 375:254-256.

Clohisy et al, "Review of Cellular Mechanisms of Tumor Osteolysis"; Clin. Orthop. 2000, 373: 104-14.

Cohen, et al., "Expression of Stem Cell Factor and C-Kit in Human Neuroblastoma"; 1994, Blood 84:3465-3472.

Colliuod et al., "Oriented andCovalent Immobilization of Target Molecules to Solid Supports: Synthesis and Application of a Light-Activatable and Thiol-Reactive Cross-Linking Reagent"; (1993) Bioconjugate Chem. 4:528-536.

Columbo, et al., "The Human Recombinant c-kit Receptor Ligand, rhSCF, Induces Mediator Release From Human Cutaneous Mast Cells and Enhances IgE-Dependent Mediator Release From Both Skin Mast Cells and Peripheral Blood Basophils"; 1992, J. Immunol 149:599-602.

Costa, et al., "The Cells of the Allergic Response"; 1997, JAMA 778:1815-1822.

Creighton, Thomas E., "An Empirical Approach to Protein Conformation Stability and Flexibility"; (1983) Biopolymers 22(1):49-58.

Dai et al., "Targeted disruption of the mouse colony-stimulating factor 1 receptor gene results in osteopetrosis, mononuclear phagocyte deficiency, increased primitive progenitor cell frequencies, and reproductive defects"; Blood, 2002, 99: 111-120.

Dandliker, W. B., et al., "Equilibrium and Kinetic Inhibition Assays Based Upon Fluorescence Polarization"; (1981) Methods in Enzymology 74:3-28.

Dastych, et al., "Stem Cell Factor Induces Mast Cell Adhesion to Fibronectin"; 1994, J. Immunol. 152:213-219.

Dewar et al., "Inhibition of c-fms by Imatinib Expanding the Spectrum of Treatment"; Cell Cycle 2005, 4(7):851-3.

Dobeli, H., et al., "Recombinant Fusion Proteins for the Industrial Production of Disulfide Bridge containing Peptides: Purification, Oxidation without Cancatamer Formation, and Selective Cleavage"; (1998) Protein Expr. Purif. 12:404-414.

Doyle and Bryker, Alkyl Nitrite-metal halide Deamination Reactions. 6. Direct Synthesis of Arenediazonium Tetrafluoroborate Salts from Aromatic Amines, tert-Butyl Nitrite, and Boron Trifluoride Etherate in Anhydrous Media; J. Org. Chem. 1979, 44:1572.

Dyson, et al., "The Human Papilloma Virus—16 E7 Oncoprotein is Able to Bind to the Retinoblastoma Gene Product"; 1989, Science 243:934-937.

Taylor et al. "The Rapid Generation of Oligonucleotide-directed Mutations at High Frequency Using Phosphorothloate-Modified DNA"; (1985) Nucl. Acids Res. 13:8764-8785.

Feng, M., et al., "Stable in vivo gene transduction via a novel adenoviral/retroviral chimeric vector"; (1997) Nature Biotechnology 15:866-870.

Feng et al, "Tyrosines 559 and 807 in the Cytoplasmic Tail of the Macrophage colony-Stimulating Factor Receptor Play Distinct Roles in Osteoclast Differentiation and Function"; Endocrinology 2002, 143: 4868-74.

Finotto, et al., "Glucocorticoids Decrease Tissue Mast Cell Number by Reducing the Production of the C-kit Ligand, Stem Cell Factor, by Resident Cells"; 1997, J. Clin. Invest. 99 1721-1728.

Fivash et al., "BIAcore for macromolecular interaction"; (1998) BIAcore for macromolecular interaction, Current Opinion in Biotechnology. 9:97-101.

Flanagan & Lader, "Macrophages and the various isoforms of macrophage colony-stimulating factor"; Curr Opin Hematol. 1998, 5:181-5.

Furitsu, et al., "Identificatin of Mutations in the Coding Sequence of the Proto-oncogene c-kit in a Human Mast Cell Leukemia Cell Line Causing Ligand-independent Activation of the c-kit Product"; 1993, J. Clin. Invest. 92:1736-1744.

Furuta, et al., "Stem Cell Factor Influences Mast Cell Mediator Release in Response to Eosinophil-Derived Granule Major Basic Protein"; 1998, Blood 92:1055-1061.

Girgis, N. et.al., "The Synthesis of 5-Azaindoles by Substitution-Rearrangement of 7-Azaindoles upon Treatment with Certain Primary Amines"; J. Heterocyclic. Chem. 1989, 26:317-325.

Golkar, et al., "Mastocytosis"; 1997, Lancet 349:1379-1385.

Sperling, C., et al.; "Expression of the Stem Cell Factor Receptor C-Kit (CD117) in Acute Leukemias" Haematologica 1997; 82:617-621.

Hafner et al., "Isothermal Amplificatino and Multimerization of DNA by Bst DNA Polymerase"; Biotechniques Apr. 2001;30(4):852-6, 858, 860 passim.

Hallek, et al., "Interation of the receptor tyrosine kinase P145$^{c-kit}$ with the P210$^{bcr/abl}$ kinase in myeloid cells"; Brit. J Haem. 1996, 94:5-16.

Hamel, et al., "The road less traveled: c-kit and stem cell factor"; 1997, J. Neuro-Onc. 35:327-333.

Hands et. al., "A convenient Method for the Preparation of 5-, 6- and 7-Azaindoles and Their Derivatives"; Synthesis 1996, 877-882.

Hanselman et al., "A cDNA-dependent scintillation proximity assay for quantifying apolipoprotein A-1"; (1997) J. Lipid Res. 38:2365-2373.

Hassan, et al., "Stem Cell Factor as a Survival and Growth Factor in Human Normal and Malignant Hematopoiesis"; 1996, Acta. Hem. 95:257-262.

Hassan, et al., "Expression of Protooncogene c-kit and Its Ligand Stem Cell Factor (SCF) in Gastric Carcinoma Cell Lines"; 1998, Digest. Dis. Science 43:8-14.

Heim et al., "Engineering green fluorescent protein for improved brightness, longer wavelengths and fluorescence resonance energy transfer"; (1996) Curr. Biol. 6:178-182.

Heinrich et al.; "PDGFRA Activating Mutations in Gastrointestinal Stromal Tumors"; (Science 2003, 299:708-10).

Herbst et al., "Differential Effects of W Mutations on p145$^{c-kit}$ Tyrosine Kinase Activity and Substrate Interaction"; (J. Biol. Chem., 1992, 267: 13210-13216.

Hibi, et al., "Coexpression of the stem cell factor and the c-kit genes in small-cell lung cancer"; 1991, Oncogene 6:2291-2296.

Hirota, et al., "Gain-of-function Mutations of c-kit in Human Gastrointestinal Stromal Tumors"; 1998, Science 279:577-580.

Hogaboam, et al., "Novel Role of Transmembrane SCF for Mast Cell Activation and Eotaxin Production in Mast Cell-Fibroblast Interactions"; 1998, J. Immunol. 160:6166-6171.

Iemura, et al., "The c-kit Ligand, Stem Cell Factor, Promotes Mast Cell survival by Suppressing Apoptosis"; 1994, Amer. J. Pathol 144:321-328.

Isbel et al., "Local macrophage proliferation correlates with increased renal M-CSF expression in human glomerulonephritis"; (Nephrol Dial Transplant 2001, 16: 1638-1647.

Isozaki, et al., "Deficiency of c-kit cells in patients with a myopathic form of chronic idiopathic intestinal pseudo-obstruction"; 1997, Amer. J. of Gast. 9 332-334.

Iwane, A.H., et al., "Myosin Subfragment-1 is Fully Equipped with Factors Essential for Motor Function"; (1997) Biophys. Biochem. Res. Comm. 230:76-80.

Izquierdo, et al., "Differential Expression of the c-kit Proto-Oncogene in Germ Cell tumors"; 1995, J. Pathol. 177:253-258.

Johann, S., et al., "GLVR1, a Receptor for gibbon Ape Leukemia Virus, Is Homologous to a Phosphate Permease of Neurospora crassa and is Expressed at High Levels in the Brain and Thymus"; (1992) J. Virol. 66:1635-1640.

Johnston, M., "Gene Chips: Array of hope for understanding gene regulation"; (1998) Curr. Biol. 8:R171-R174.

Jones, R.J., "Biology and treatment of chronic myeloid leukemia"; Curr. Opin. Onc. 1997, 9:3.

Jose et al., "Blockade or Macrophage colony-Stimulating Factor Reduces Macrophage Proliferation and Accumulation in Renal Allograft Rejection"; Am J Transplant 2003, 3(3):294-300.

Kahl et al., "A Multiple-Approach Scintillation Proximity Assay to Measure the Association between Ras and Raf"; (1996) Anal. Biochem. 243:282-283.

Kay, et al., "Eosinophils and Eosinophil-Associated Cytokines in Allergic Inflammation"; 1997, Int. Arch. Aller. Immunol. 113:196-199.

Kern "Direct Hybridization of Large-Inssert Genomic Clones on High-Density Gridded cDNA Filter Arrays"; (1997) Biotechniques 23:120-124.

Kinashi, et al., "Steel Factor and c-kit Regulate Cell-Matrix Adhesion"; 1994, Blood 83:1033-1038.

Kitamura, et al., Synthesis of Quinolines and 2H-Dihydropyrroles by Nucleophilic Substitution at the Nitrogen Atom of Oxime Derivatives; 1995, Int. Arch. Aller. Immunol. 107:54-56.

Kodama et al, "Congenital Osteoclast Deficiency in Osteopetrotic (op/op) Mice Is Cured by Injections of Macrophage colony-stimulating Factor"; J. Exp,. Med. 1991, 173: 269-72.

Kondoh, et al., "Very High Incidence of Germ Cell tumorigenesis (Seminomagenesis) in Human Papillomavirus Type 16 Transgenic Mice"; 1991, J. Virol. 65:3335-3339.

Kondoh, et al., "Establishment and Further Characterization of a Line of Transgenic Mice Showing Testicular Tumorigenesis at 100% Incidence"; 1994, J. Urol. 152:2151-2154.

Kondoh, et al., "An in vivo model for receptor tyrosine kinase autocrine/paracrine activation: auto-stimulated Kit receptor acts as a tumor promoting factor in papillomavirus-induced tumorigenesis"; 1995, Oncogene 10:341-347.

Kroll, David J., et al., "A Malfunctional Prokaryotic Protein Expression System: Overproduction, Affinity Purification, and Selective Detection"; (1993) DNA Cell. Biol. 12:441-53.

Kunisada, et al., "Murine Cutaneous Mastocytosis and Epidermal Melanocytosis Induced by Keratinocyte Expression of Transgenic Stem Cell Factor"; 1998, J. Exp. Med. 187:1565-1573.

Kunkel, "Rapid and efficient site-specific mutagenesis without phenotypic selection"; (1985) Proc. Natl. Acad. Sci. 82:488-492.

Lahm, et al., "Interleukin 4 down-regulates expression of c-kit and autocrine stem cell factor in human colorectal carcinoma cells"; 1995, Cell Growth &Differ 6:1111-1118.

Le Meur et.al., "Macrophage accumulation at a site of renal inflammation is dependent on the M-CSF/c-fms pathway"; J Leukocyte Biology, 2002, 72: 530-537.

Lee et al., "Mast cells: A cellular line between autoantibodies and inflammatory arthritis"; 2002, Science 297:1689-1692.

Lee, et al., "HLA-DR-triggered inhibition of hemopoiesis involves Fas/Fas ligand interactions and is prevented by c-kit ligand"; 1997, J. Immunol. 159:3211-3219.

Verfaillie, "Chronic myelogenous leukemia: too much or too little growth, or both?"; Leukemia, 1998, 12:136-138.

Levin, et al., "Neoplasms of the central nervous system"; 1997, Principles & Practice of Oncology:2022-2082.

Li, et al., "Abrogation of c-kit/Steel factor-dependent Tumorigenesis by Kinase Defective Mutants of the c-kit Receptor: c-kit kinase defective mutants as candidate tools for cancer gene therapy"; 1996, Canc. Res. 56:4343-4346.

Libby, "Inflammation in atherosclerosis"; Nature. 2002;420:868-874.

Liparoto et al., "Biosensor analysis of the interleukin-2 receptor complex, Journal of Molecular Recognition"; (1999)12:316-21.

Lipschultz et al., "Experimental design for analysis of complex kinetics using surface plasmon resonance, Methods"; (2000) 20(3):310-8.

London, et al., "Expression of Stem Cell Factor Receptor (c-kit) by the Malignant Mast Cells from Spontaneous Canine Mast Cell Tumors", 1996, J. Compar. Pathol. 115:399-414.

Longley, et al., "Altered Metabolism of Mast-cell Growth Factor (c-kit Ligand) in Cutaneous Mastocytosis", 1993, New Engl. J. Med. 328:1302-1307.

Longley, et al., "Somatic c-Kit activating mutation in urticaria pigmentosa and aggressive mastocytosis: establishment of clonality in a human mast cell neoplasm", 1996, Nat. Gen. 12:312-314.

Longley, et al., "Chymase cleavage of stem cell factor yields a bioactive, soluble product", 1997, Proc. Natl. Acad. Sci. 94:9017-9021.

Loveland, et al., "Stem cell factor and c-kit in the mammalian testis: lessons originating from Mother Nature's gene knockouts", 1997, J. Endocrinol 153:337-344.

Lu, B., et al., "Oriented Immobilization of Fab' Fragments on Silica Surfaces", (1995) Anal. Chem. 67:83-87.

Luckacs, et al., "Stem Cell Factor (c-kit Ligand) Influences Eosinophil Recruitment and Histamine Levels in Allergic Airway Inflammation", 1996, J. Immunol. 156:3945-3951.

Ma et al., "Indolinone Derivatives Inhibit Constitutively Activated KIT Mutants and Kill Neoplastic Mast Cells", 2000, J Invest Dermatol. 114:392-394.

Ma et al., "The c-kit mutation causing human mastocytosis is resistant to ST1571 and other KIT kinase inhibitors; kinase with enzymatic site mutations show different inhibitor sensitivity profiles than wild-type kinase and those with regulatory-type mutations", 2002, Blood 99:1741-1744.

Malmborg et al., "BIAcore as a tool in antibody engineering", (1995) Journal of Immunological Methods. 183:7-13.

Malmqvist et al, "Biomolecular interaction analysis: affinity biosensor technologies for functional analysis of proteins, Current Opinion in Chemical Biology" (1997) 1:378-83.

Malmqvist., "BIACORE: an affinity biosensor system for characterization of biomolecular interactions", (1999) Biochemical Society Transactions 27:335-40.

Mazeas et. al., "Synthesis of New Melatoninergic Ligands Including Azaindole Moiety", Heterocycles 1999, 50:1065-1080.

Mekori, et al., "Transforming Growth Factor-β Prevents Stem Cell Factor-Mediated Rescue of Mast Cells from Apoptosis After IL-3 Deprivation", 1994, J. Immunol 153:2194-2203.

Mekori, et al., "The Role of c-Kit and Its Ligand, Stem Cell Factor, in Mast Cell Apoptosis", 1995, Int. Arch. Allergy Immunol. 107:137-138.

Meltzer, "The pharmacological basis for the treatment of perennial allergic rhinitis and non-allergic rhinitis with topical corticosteroids", 1997, Aller. 52:33-40.

Merour and Joseph, "Synthesis and Reactivity of 7-Azaidoles (1H-Pyrrolo[2,3-b]pyridine)", Curr. Org. Chem. 2001, 5:471-506.

Metcalf, et al., "Lineage commitment in the progeny of murine hematopoietic preprogenitor cells: Influence of thrombopoietin and interleukin 5", 1998, Proc. Natl. Acad. Sci., USA 95:6408-6412.

Metcalfe, "Classification and Diagnosis of Mastocytosis: Current Status", 1991, J. Invest. Derm 93:2S-4S.

Metcalfe, et al., "Mast Cells", 1997, Physiol Rev 77:1033-1079.

Mitra et al., "Fluorescence resonance energy transfer between blue-emitting and re-shifted excitation derivatives of the gree fluorescent protein", (1996) Gene 173:13-17.

Motoyoshi, "Biological activities and clinical application of M-CSF", Int J Hematol. 1998, 67:109-22.

Murty, et al., "A Genetic Perspective of Male Germ Cell tumors", 1998, Sem. Oncol. 25:133-144.

Muyaura and Suzuki, "Palladium-Catalyzed Cross-Coupling Reactions of Organoboron Compounds", Chem. Rev. 1995, 95:2457.

Naclerio, et al., "Rhinitis and Inhalant Allergens", 1997, JAMA 278:1842-1848.

Nagata, et al., "elevated expression of the proto-oncogene c-kit in patients with mastocytosis", 1998, Leukemia 12:175-181.

Ng, K., et al., "Engineering Protein-Lipid Interactions: Targeting of Histidine-Tagged Proteins to Metal-Chelating Lipid Monolayers", (1995) Langmuir 11:4048-55.

Nichols et al., "Development of a Scintillation Proximity Assay for Peroxisome Proliferator-Activated Receptor γ Ligand Binding Domain", (1998) Anal. Biochem. 257:112-119.

O'Shannessy et al., "Interpretation of deviations from pseudo-first-order kinetic behavior in the characterization of ligand binding by biosensor technology", (1996) Analytical Biochemistry. 236:275-83.

O'Shannessy, "Determination of kinetic rate and equilibrium binding constants for macromolecular interactions: a critique of the surface plasmon resonance literature", (1994) Current Opinions in Biotechnology. 5:65-71.

Okada, H., et al., "gene therapy against an experimental glioma using adeno-associated virus vectors", (1996) Gene Ther. 3:957-964.

Okayama, et al., "Activation of Eosinophilis with Cytokines Produced by Lung Mast Cells", 1997, Int. Arch. Aller. Immunol. 114:75-77.

Okayama, et al., "Human lung mast cells are enriched in the capacity to produce granulocyte-macrophage colony-stimulating factor in response to IgE-dependent stimulation", 1998, Eur. J. Immunol. 28:708-715.

Owicki et al., "Application of Fluorescence Polarization Assays in High-Throughput Screening", (1997), Genetic Engineering News, 17:27.

Parker et al., "Development of high throughput screening assays using fluorescence polarization: nuclear receptor-ligand-binding and kinase/phosphatase assays", (2000) J Biomol Screen 5:77-88.

Price et al.; "Summary report on the ISOBM TD-4 Workshop: analysis of 56 monoclonal antibodies against the MUC1 mucin", (1998) Tumour Biology 19 Suppl 1:1-20.

Qiao, et. al., "Role of Macrophage Colony-Stimulating Factor in Atherosclerosis", Am. J. Path. 1997;150:1687-1699.

Rajavashisth, et. al., "Heterozygous Osteopetrotic (op) Mutation Reduces Atherosclerosis in LDL Receptor-deficient Mice", J. Clin. Invest. 1998;101:2702-2710.

Rajpert-de Meyts, et al., "Expression of the c-kit protein product in carcinoma-in-situ and invasive testicular germ cell tumors", 1994, Int. J. Androl. 17:85-92.

Ricotti, et al., "c-kit Is Expressed in soft tissue Sarcoma of Neuroectodermic Origin and Its Ligand Prevents Apoptosis of Neoplastic Cells", 1998, Blood 91:2397-2405.

Ridge et al, "FMS mutations in myelodysplastic, leukemic, and normal subjects", Proc. Nat. Acad. Sci., 1990, 87:1377-1380.

Roberts, S., et al., "Generation of an antibody with enhanced affinity and specificity for its antigen by protein engineering", (1987) Nature 328:731.

Robinson, "7-Azaindole. I. Synthesis and conversion to 7-Azatryptophan and Other Derivatives", J. Am. Chem. Soc., 1955, 77, p. 457.

Rodan, G., et al., "Therapeutic Approaches to Bone Diseases", Science. 2000;289:1508.

Rosenfeld, "Human artificial chromosomes get real", (1997) Nat. Genet. 15:333-335.

Ryan, et al., "Role for the Stem Cell Factor/Kit Complex in Schwann Cell Neoplasia and Mast Cell Proliferation Associated with Neurofibromatosis", 1994, J. Neuro. Res. 37:415-432.

Saiki, "Amplification of Genomic DNA" in PCR Protocols, Innis et al., Eds., Academic Press, San Diego, CA 1990, pp. 13-20.

Sambrook et al, "Molecular Cloning: A Laboratory Manua", 1989, Cold Spring Harbor Laboratory Press, Cold Spring Harbor N.Y, pp. 16.30-16.37.

Sandlow, et al., "Expression of c-KIT and its Ligand, Stem Cell Factor, in Normal and Subfertile Human Testicular Tissue", 1996, J. A,drol. 17:403-408.

Sawada, et al., "role of Cytokines in Leukemic type Growth of Myelodysplastic CD34+ Cells", 1996, Blood 88:319-327.

Sawai, et al., "Aberrant growth of granulocyte-macrophage progenitors in juvenile chronic myelogenous leukemia in serum-free culture", 1996, Exp. Hem. 2:116-122.

Scheffner, et al., "The E6 Oncoprotein Encoded by Human Papillomavirus Types 16 and 18 Promotes the Degradation of p53", 1990, Cell 63:1129-1136.

Schneider, et al., "Functional Purification of a Bacterial ATP-Binding Cassette Transporter Protein (MalK) from the Cytoplasmic Fraction of an Overproducing Strain", (1995) Protein Exp. Purif. 6435:10.

Schneller et. al., "Synthesis of 4-Amino-1 H-pyrrolo[2,3-b]pyridine {1,7-Dideazaadenine) and 1H-Pyrrolo[2,3-b]pyridine-4-ol (1,7-Dideazahypoxanthine)", J. Org. Chem. 1980, 45:4045.

Schuhmann et al., "Immobilization f Enzymes on Languir-Blodgett Films via a Membrane-Bound Receptor, Possible Applications for Amperometric Biosensors", (1991) Adv. Mater. 3:388-391.

Schummer "Inexpensive Handheld Device for the Construction of High-Density Nucleic Acid Arrays", (1997) Biotechniques 23:1087-1092.

Secor et al., "Mast Cells Are Essential for Early Onset and Severe Disease in a Murine Model of Multiple Sclerosis", 2000, J Exp Med 191:813-821.

Selvin et al., "Fluorescence Resonance Energy Transfer", (1995) Meth. Enzymel. 246:300-345.

Jarugule et al., Nonlinear pharmacokinetics of 5-fluorouracil in rats. 1997, *J Pharm Sci* 86(7):756-757.

Shibata et al, "Alveolar macrophage deficiency in osteopetrotic mice deficient in macrophage colony-stimulating factor is spontaneously corrected with age and associated with matrix metalloproteinase expression and emphysema", Blood 2001, 98: pp. 2845-2852.

Sigal, et al., "A Self-Assembled Monolayer for the Binding and Study of histidine-Tagged Proteins by Surface Plasmon Resonance", (1996) Anal. Chem. 68:490-497.

Solinas-Toldo, et al., "Matrix-Based comparative Genomic Hybridization: Biochips to Screen for Genomic Imbalances", (1997) Genes, Chromosomes & Cancer 20:399-407.

Stanulla, et al., "Coexpression of stem cell factor and its receptor c-Kit in human malignant glioma cell lines", 1995, Act Neuropath 89:158-165.

Steinman, "Multiple Sclerosis: A coordinated Immunological Attack against Myelin in the Central Nervous System", 1996, Cell 85:299-302.

Strohmeyer, et al., "Expression of the hst-1 and c-kit Protooncogenes in Human Testicular Germ Cell Tumors", 1991, Canc. Res. 51:1811-1816.

Strohmeyer, et al., "Expression of the C-kit Proto-Oncogene and its Ligand Stem Cell Factor (SCF) in Normal and Malignant Human Testicular Tissue", 1995, J. Urol. 153:511-515.

Su & Tsou, "Synthesis of bromo-substituted Idoxyl Esters for Cytochemical Demonstration of Enzyme Activity", *J. Am. Chem. Soc.*,82, 1960, 1187.

Teitelbaum, "Bone Resorption by Osteoclasts", Science. 2000;289:1504.

Thibault et. al., "Concise and Efficient Synthesis of 4-fluoro-1H-pyrrolo[2,3-b] pyridine", Org. Lett. 2003, 5:5023-5025.

Thomas, et al., "The Eosinophil and its Role in Asthma", 1996, Gen. Pharmacol 27:593-597.

Toyota, et al., "Expression of c-kit and kit Ligand in Human Colon Carcinoma Cells", 1993, Turn Biol 14:295-302.

Tsujimura, "Role of c-kit receptor tyrosine kinase in the development, survival and neoplastic transformation of mast cells", 1996, Pathol Int 46:933-938.

Tsujimura, et al., "Ligand-Independent Activation of c-kit Receptor Ryrosine Kinase in a Murine Mastocytoma Cell Line P-815 generated by a Point Mutation", 1994, Blood 9:2619-2626.

Tsujimura, et al., "Substitution of an Aspartic Acid Results in Constitutive Activation of c-kit Receptor Tyrosine Kinase in a Rat Tumor Mast Cell Line RBL-2H3", 1995, Int. Arch. Aller. Immunol 106:377-385.

Turner, et al., "Nonhematopoeietic Tumor Cell Lines Express Stem Cell Factor and Display c-kit Receptors", 1992, Blood 80:374-381.

Undenfriend et al., "Scintillation Proximity Assay: A Sensitive and Continuous Isotopic Method for Monitoring Ligand/Receptor and Antigen/Antibody Interactions", (1987) Anal. Biochem. 161:494-500.

Valent, "biology, classification and treatment of human mastocytosis", 1996, Wein/Klin Wochenschr 108:385-397.

Van Regenmortel, "Use of biosensors to characterize recombinant proteins", (1994)Developments in Biological Standardization. 83:143-51.

Vely F. et al., "BIAcore® analysis to test phosphopeptide-SH2 domain interactions", (2000) Methods in Molecular Biology. 121:313-21.

Viskochil, "It takes two to tango: mast cell and Schwann cell interactions in neurofibromas", 2003, J Clin Invest. 112:1791-1793.

Werness, et al., "Associationo f Human Papillomavirus types 16 and 18 E6 Proteins with p53", 1990, Science 248:76-79.

Wharam et al., "Specific detection of DNA and RNA targets using a novel isothermal nucleic acid amplification assay based on the formation of a three-way junction structure", Nucleic Acids Res. Jun. 1, 2001;29(11):E54-E54.

Williams et al., "Dissection of the Extracellular Human Interferon γ Receptor α-Chain into two Immunoglobulin-like domains. Production in an *Escherichia coli* Thioredoxin Gene Fusion Expression system and Recognition by Neutralizing Antibodies", (1995) Biochemistry 34:1787-1797.

Woon et al., "Construction and Characterization of a 10-fold Genome Equivalent Rat P1-Derived Artificial Chromosome Library", (1998) Genomics 50:306-316.

Xu et al, "Modulation of Endothelial Cell function by Normal Polyspecific Human Intraveneous immunoglobulins", Am. J. Path. 1998;153:1257-1266.

Yang et al., "Neurofibromin-deficient Schwann cells secrete a potent migratory stimulus for Nf1+/- mast cells", 2003, J Clin Invest. 112:1851-1861.

Yee, et al., "Role of kit-Ligand in Proliferation and Suppression of Apoptosis in Mast Cells: Basis for Radiosensitivity of White Spotting and Steel Mutant Mice", 1994, J. Exp. Med. 179:1777-1787.

Yuan, et al., "Human Peripheral Blood Eosinophilis Express a Functional c-klit Receptor for Stem Cell Factor that Stimulates Very Late Antigen 4 (VLA-4)-mediated Cell Adhesion to Fibronectin and Vascular Cell Adhesion Molecule 1 (VCAM-1)"; 1997, J. Exp. Med. 186:313-323.

Hafner et al., "Isothermal Amplification and Multimerization of DNA by Bst DNA Polymerase", Biotechniques Apr. 2001;30(4):852-6, 858, 860 passim.

Barton et al, The chemistry of pentavalent organobismuth reagants. Part X. Studies on the phenylation and oxidation of phenols: TETRAHEDRON, vol. 43, No. 2, 1987, pp. 323-332, XP002402100.

Curtin et al., "Discovery and Evaluation of a Series of 3-Acylindole Imidazopyridine Platelet-Activating Factor Antagonists" J. Med. Chem., vol. 41, 1998, pp. 74-95, XP002402103.

Heacock et al., "Orientation and Relative Reaction rate Factors in aromatic Substition by the Benzensulfonimido Radical" J. Am. Chem. Soc., vol. 82, 1960, pp. 3460-3463, XP002402102.

Langham et al., "Metalation of Halogen-Metal Interconversion Reactions of Some Halogenated Phenyl Ethers" J. Am. Chem. Soc., vol. 63, 1941, pp. 545-549, XP002402101.

Pierce et al., "Local anaestetics. I. beta-Monoaklylaminoethyl Esters of Alkoxybenzoic Acids" J. Am. Chem. Soc., vol.. 64, 1942, pp. 1691-1694, XP002402104.

Ashman et al., The biology of stem cell factor and its receptor C-kit. The International Journal of Biochemistry & Cell Biology, 31: 1037-1051, 1999.

Al-Obeidi, et al., Peptide and Peptidomimetic Libraries, Mol Biotechnol 9:205-223, 1998.

Amersdorfer and Marks, Phage Libraries for Generation of Anti-Botulinum scFv Antibodies, Methods in Molecular Biology 145:219-240, 2000.

Baghestanian, et al., A Case of Malignant Mastocytosis with Circulating Mast Cell Precursors: Biologic and Phenotypic Characterization of the Malignant Clone, Leuk. 10:159-166 (1996).

Bagshaw et al, Measurement of Ligand Binding to Proteins Spectrophotometry and Spectrofluorimetry, 4:91-113, 1987.

Balak, et. al., Novel D761Y and common secondary T790M mutations in epidermal growth factor receptor-mutant lung adenocarcinomas with acquired resistance to kinase inhibitors. Clin. Cancer Res. 12:6494-501 (2006).

Bancalari, et al., Blood Markers of Early and Late Airway Responses to Allergen in Asthmatic Subjects. Relationship with Functional Findings Allergy 52:32-40, 1997.

Bartlett, et al., CAVEAT: A Program to Facilitate the Structure-Derived Design of Biologically Active Molecules Royal Society of Chemistry 78:180-196, 1989.

Bloom, A. and Day. A.R., The Preparation of 2-Alkylaminobenzimidazoles, J. Org. Chem. 14, 17 (1939).

Blundell et al., Knowledge-Based Protein Modelling and Design Eur. J. Biochem. 172:513-520 1988.

Böhm, H., On the Use of LUDI to Search the Fine Chemicals Directory for Ligands of Proteins of Known Three-Dimensional Structure, J. Comp. Aided Molec. Design 8:623-632, 1994.

Bolger et al, Computer Modeling of Combining Site Structure of Anti-Hapten Monoclonal Antibodies, Methods Enz., 203:21-45, 1991.

Bothwell, M., Keeping Track of Neurotrophin Receptors, Cell, 65:915-918, 1991.

Bouzakri, K. and Zierath, J.R., MAP4K4 Gene silencing in Human Skeletal Muscle Prevents Tumor Necrosis Factor-α-induced Insulin Resistance, J. Biol. Chem. 282:7783-7789 (2007).

Brenner et al., Encoded Combinatorial Chemistry, Proc. Natl. Acad. Sci. USA 89:5381-5383, 1992.

Broudy, V., Stem Cell Factor and Hematopoiesis, Blood 90:1345-1364 (1997).

Brünger, A., Free R Value: a Novel Statistical Quantity for Assessing the Accuracy of Crystal Structures, Nature 355:472-475 (1992).

Carell et al., New Promise in Combinatorial Chemistry: Synthesis, Characterization, and Screening of Small-Molecule Libraries in Solution, Chem. Biol. 2:171-183 (1995).

Chabala, J., Solid-Phase Combinatorial Chemistry and Novel Tagging Methods for Identifying Leads, Curr Opin Biotechnol 6:632-639 (1995).

Chou et al., Computerized Quantitation of Synergism and Antagonism of Taxol, Topotecan, and Cisplatin Against Human Teratocarcinoma Cell Growth: a Rational Approach to Clinical Protocol Design, J. Natl. Cancer Inst. 86:1517-24 (1994).

Chou, T. and Talalay, P., Quantitative analysis of Dose-Effect Relationships: The Combined Effects of Multiple Drugs or Enzyme Inhibitors, Adv. Enzyme Regul. 22:27-55 (1984).

Chou, T. et al., Chemotherapeutic Synergism, Potentiation and Antagonism, Encyclopedia of Human Biology, Academic Press, 2:371-9 (1991).

Chou, T.C. and Rideout, D.C., editors: Synergism and Antagonism in Chemotherapy, San Diego, CA: Academic Press, Chapter 2, 61-102 (1991).

Clark, et al., PRO_LIGAND: An Approach to De Novo Molecular Design. 1. Application to the Design of Organic Molecules, J. Comp. Aided Molec. Design 9:13-32 (1995).

Coe, et al., Solution-Phase Combinatorial Chemistry, Mol Divers. 4:31-38 (1999).

Collins et al., A small interfering RNA screen for modulators of tumor cell motility identifies MAP4K4 as a prommigratory kinase, Proc. Natl. Acad. Sci. USA, 103:3775-3780 (2006).

Office Action dated Aug. 2, 2007 in related U.S. Appl. No. 11/016,350.

Office Action dated May 15, 2008 in related U.S. Appl. No. 11/487,134.

Coulie et al, Recombinant Human Neurotropic Factors Accelerate Colonic Transit and Relieve Constipation in Humans, Gastroenterology 119:41-50 (2000).

Crouch et al., The use of ATP bioluminescence as a measure of cell proliferation and cytotoxicity. Journal of Immunological Methods, 160:81-8 (1993).

Crump, M., Inhibition of Raf Kinase in the Treatment of Acute Myeloid Leukemia, Curr. Pharm. Design 8(25):2243-8 (2002).

Cwirla et al., Peptides on Phage: A Vast Library of Peptides for Identifying Ligands, Biochemistry 87:6378-6382 (1990).

Demetri, Targeting c-kit mutations in solid tumors: Scientific rationale and novel therapeutic options, Seminars in Oncology, 28(5), Supp. 17, 19-26, 2001.

Dolle et al., Comprehensive Survey of Combinatorial Library Synthesis: 1998, J Comb Chem 1:235-282 (1999).

Douma, S. et al, Suppression of anoikis and induction of metastasis by the neurotropic receptor TrkB, Nature 430:1034-9 (2004).

Eklund and Joensuu, Treatment of rheumatoid arthritis with imatinib mesylate: clinical improvements in three refractory cases, Annals of Medicine, 35:362-367, 2003.

Eliseev et al, Dynamic Combinatorial Chemistry: Evolutionary Formation and Screening of Molecular Libraries, Current Topics in Microbiology & Immunology, 243:159-172 (1999).

Enjalbal, et al., Mass Spectrometry in Combinatorial Chemistry, Mass Spectrometry Reviews. 19:139-161 (2000).

Gallop et al., Applications of Combinatorial Technologies to Drug Discovery. 1. Background and Peptide Combinatorial Libraries, J. Med. Chem., 37:1233-1251 (1994).

Gassman et al., Journal of the American Chemical Society, 95(13), pp. 4453-5 (1973).

Goodford, P.J., A Computational Procedure for Determining Energetically Favorable Binding Sites on Biologically Important Macromolecules, J. Med. Chem. 28:849-857 (1985).

Goodsell et al, Automated Docking of Substrates to Proteins by Simulated Annealing, Proteins: Structure, Function, and Genetics 8:195-202 (1990).

Gordon et al., Applications of Combinatorial Technologies to Drug Discovery. 2. Combinatorial Organic Synthesis, Library Screening Strategies, and Future Directions, J. Med. Chem. 37:1384-1401 (1994).

Gram H., Phage Display in Proteolysis and Signal Transduction, Combinatorial Chemistry & High Throughput Screening 2:19-28 (1999).

Gravert et al, Synthesis on Soluble Polymers: New Reactions and the Construction of Small Molecules, Curr Opin Chem Biol 1:107-113 (1997).

Greer, J., Model Structure for the Inflammatory Protein C5a, Science 228:1055-1060 (1985).

Halvorson, K.G. et al., A Blocking Antibody to Nerve Growth Factor Attenuates Skeletal Pain Induced by Prostate Tumor Cells Growing in Bone, Cancer Res. 65:9426-35 (2005).

Hood, J.D. et al., Tumor Regression by Targeted Gene Delivery to the Neovasculature, Science 296, 2404 (2002).

Houghten, et al., Generation and Use of Synthetic Peptide Combinatorial Libraries for Basic Research and Drug Discovery, Nature 354:84-86 (1991).

Houghten, R., Parallel Array and Mixture-Based Synthetic Combinatorial Chemistry: Tools for the Next Millennium, Annu Rev Pharmacol Toxicol 40:273-282 (2000).

Houghten, R., Peptide Libraries: Criteria and Trends, Trends Genet. 9:235-239 (1993).

Hudson, P. B. et al., A Simple Method for the Determination of Serum Acid Phosphatase, Journal of Urology 58:89-92 (1947).

Hughes-Jones, et al., Synthesis of Rh Fv Phage-Antibodies Using VH and VL Germline Genes, British Journal of Haematology 105:811-816 (1999).

Inoue, et al., Coexpression of the c-kit Receptor and the Stem Cell Factor in Gynecological Tumors, Cancer Res. 54:3049-3053 (1994).

International Search Report and Written Opinion of the ISA dated Oct. 24, 2006 for PCT Application No. PCT/US2006/024524.

International Search Report and Written Opinion of the ISA dated Apr. 4, 2007 for PCT Application No. PCT/US2006/018726.

International Search Report and Written Opinion of the ISA dated Apr. 20, 2006 for PCT Application No. PCT/US2005/021231.

International Search Report and Written Opinion of the ISA dated Jun. 4, 2008 for PCT Application No. PCT/US2007/088231.

International Search Report and Written Opinion of the ISA dated Jun. 4, 2008 for PCT Application No. PCT/U52007/088237.

International Search Report and Written Opinion of the ISA dated Jun. 5, 2008 for PCT Application No. PCT/US2007/088243.

International Search Report and Written Opinion of the ISA dated Oct. 24, 2006 for PCT Application No. PCT/US2006/024361.

International Search Report and Written Opinion of the ISA dated Nov. 17, 2008 for PCT Application No. PCT/US07/088412.

International Search Report and Written Opinion of the ISA dated Nov. 25, 2005 for PCT Application No. PCT/U504/42470.

IntInternational Search Report and Written Opinion of the ISA dated Jul. 25, 2008 for PCT Application No. PCT/US2007/088443.

Jones, T., Interactive Computer Graphics: FRODO, Methods in Enzymology 115:157-171 (1985).

Joseph-McCarthy, D., Computational Approaches to Structure-Based Ligand Design, Pharmacology & Therapeutics 84:179-191 (1999).

Kassel, O, et al., Local increase in the number of mast cells and expression of nerve growth factor in the bronchus of asthmatic patients after repeated inhalation of allergen at low-dose, Clin. Exp. Allergy 31:1432-40 (2001).

Kim et al, A Merger of Rational Drug Design and Combinatorial Chemistry: Development and Application of Peptide Secondary Structure Mimetics, Combinatorial Chemistry & High Throughput Screening 3:167-183 (2000).

Kim et al, Database CAS on STN (Columbus, OH, USA) No. 138:55974, Preparation of 2-anilino-4-e indolylpyrimidines as tyrosine kinase inhibitors, abstract, 2002) see whole article.

Kirkpatrick, et al., Structure-Based Drug Design: Combinatorial Chemistry and Molecular Modeling, Combinatorial Chemistry & High Throughput Screening 2:211-221 (1999).

Kline et al., Studies by 1H Nuclear Magnetic Resonance and Distance Geometry of the Solution Conformation of the x-Amylase Inhibitor Tendamistat, J. Mol. Biol. 189:377-382 (1986).

Knighton, et al., Structural Basis of the Intrasteric Regulation of Myosin Light Chain Kinases, Science 258:130-135 (1992).

Kolaskar et al, A Semi-Empirical Method for Prediction of Antigenic Determinants on Protein Antigens, FEBS Lett. 276:172-174 (1990).

Komoyira, S. et. al., Design, synthesis and biological activity of amidinobicyclic compounds (derivatives of DX-9065a) as a factor Xa inhibitors: SAR study of S1 and aryl binding sites, Bioorg. Med. Chem. 12, 2099 (2004).

Kundu, et al., Combinatorial Chemistry: Polymer Supported Synthesis of Peptide and Non-Peptide Libraries, Progress in Drug Research 53:89-156 (1999).

Kunnimalaiyaan, M. and Chen, H. et al., The Raf-1 pathway: a molecular target for treatment of select neuroendocrine tumors? Anticancer Drugs 17(2):139-42 (2006).

Kuntz, et al., A Geometric Approach to Macromolecule-Ligand Interactions, J. Mol. Biot. 161:269-288 (1982).

Kuntz, et al., Structure-Based Molecular Design, Acc. Chem. Res. 27:117-123 (1994).

Lam et al., A new type of synthetic peptide library for identifying ligand-binding activity, Nature, 354: 82-84, 1991.

Lawicki et al., The pretreatment plasma level and diagnostic utility of M-CSF in benign breast tumor and breast cancer patients, Clinica Chimica Acta, 371: 112-116, 2006.

Lebl, et al., One-Bead-One-Structure Combinatorial Libraries, Biopolymers 37:177-198 (1995).

Lipinski, et al., Experimental and Computational Approaches to Estimate Solubility and Permeability in Drug Discovery and Development Settings, Advanced Drug Delivery Reviews 23:3-25 (1997).

Lyman, et al., c-kit Ligand and Flt3 Ligand: Stem/Progenitor Cell Factors With Overlapping Yet Distinct Activities, Blood 91:1101-1134 (1998).

Machida, N. et al., Mitogen-activated Protein Kinase Kinase Kinase Kinase 4 as a Putative Effector of Rap2 to Activate the c-Jun N-terminal Kinase, J. Biol. Chem. 279: 15711-15714 (2004).

Mack, K.D. et al., Functional identification of kinases essential for T-cell activation through a genetic suppression screen, Immunol. Lett. 96, 129-145 (2005).

Madden, et al., Synthetic Combinatorial Libraries: Views on Techniques and Their Application Perspectives in Drug Discovery and Design 2:269-285 (1994).

Markiewicz, et al., Synthetic Oligonucleotide Combinatorial Libraries and Their Applications, II Farmaco 55:174-177 (2000).

Martin, Y., Computer-Assisted Rational Drug Design, Methods Enz. 203:587-613 (1991).

Matayoshi, S. et al, Actions of brain-derived neurotrophic factor on spinal nociceptive transmission during inflammation in the rat, J Physiol. 569:685-95 (2005).

McCall, et al., Characterization of Anti-Mouse FcγRII Single-Chain Fv Fragments Derived from Human Phage Display Libraries, Immunotechnology 4:71-87 (1998).

McPherson, A., Current Approaches to Macromolecule Crystallization, Eur. J. Biochem. 189:1-23 (1990).

Meng, et al., Automated Docking with Grid-Based Energy Evaluation, J. Compt. Chem. 13:505-524 (1992).

Merritt, A., Solution Phase Combinatorial Chemistry, Comb Chem High Throughput Screen 1:57-72 (1998).

Miller, et al., FLOG: A System to Select Quasi-Flexible Ligands Complementary to a Receptor of Known Three-Dimensional Structure, J. Comp. Aided Molec. Design 8:153-174 (1994).

Miranker et al, Functionality Maps of Binding Sites: A Multiple Copy Simultaneous Search Method, Proteins: Structure, Function, and Genetics 11:29-34 (1991).

Mol, et al. Structural Basis for the Autoinhibition and STI-571 Inhibition of c-Kit Tyrosine Kinase, J. Biol. Chem. 279:31655-31663 (2004).

Mol, et al., Structure of a c-Kit Product Complex Reveals the Basis for Kinase Transactivation, J. Biol. Chem. 278:31461-31464 (2003).

Morgan, C., Pollard, J.W., and Stanley, E.R., Isolation and Characterization of a Cloned Growth Factor Dependent Macrophage Cell Line, BAC1.2F5, Journal of Cellular Physiology, 130:420-427 (1987).

Nakagawara, A. et al., Expression and Function of TRK-B an BDNF in Human Neuroblastomas, Mol. Cell Biol. 14:759-767 (1994).

Nassentein, C. et al, The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthma, J. Exp. Med. 198:455-467 2003.

Navaza, J., AMoRe: an Automated Package for Molecular Replacement, Acta Cryst. A50:157-163 (1994).

Neidle, et al., Molecular Modeling to Study DNA Intercalation by Anti-Tumor Drugs, Methods Enz. 203:433-458 (1991).

Nicholls, et al., Protein Folding and Association: Insights From the Interfacial and Thermodynamic Properties of Hydrocarbons, Proteins 11:281-296 (1991).

Niihori, T. et al., Germline KRAS and BRAF mutations in cardio-facio-cutaneous syndrome, Nature Genet. 38(3):294-6 (2006).

Notice of Allowance dated Dec. 26, 2007 for U.S. Appl. No. 11/016,350.

Ochs, G. et al, A phase I/II trial of recombinant methionyl human brain derived neurotrophic factor administered by intrathecal infusion to patients with amyotrophic lateral sclerosis, Amyotroph Lateral Scler Other Motor Neuron Disord. 1:201-6 (2000).

Otwinowski, Z., Maximum Likelihood Refinement of Heavy Atom Parameters, Dept. of Molecular Biophysics and Biochemistry pp. 80-86 (1991).

Perrin, D., Nucleic Acids for Recognition and Catalysis: Landmarks, Limitations, and Looking to the Future, Combinatorial Chemistry & High Throughput Screening 3:243-269 (2000).

Petty et al, The effect of systemically administered recombinant human nerve growth factor in healthy human subjects. Ann Neurol. 36:244-6 (1994).

Pflugrath, et al., Crystal Structure Determination, Refinement and the Molecular Model of the x-Amylase Inhibitor Hoe-467A, J. Mol. Biol. 189:383-386 (1986).

Pignon, J.M., C-kit mutations and mast cell disorders A model of activating mutations of growth factor receptors, Hermatol Cell Ther 39:114-116 (1997).

Plunkett et al, A Silicon-Based Linker for Traceless Solid-Phase Synthesis, J. Org. Chem. 60:6006-6007 (1995).

Poul, et al., Selection of Tumor-Specific Internalizing Human Antibodies from Phage Libraries, J. Mol. Biol. 301:1149-1161 (2000).

Saify et al, Database CAS on STN (Columbus, OH, USA) No. 124:170379, Synthesis of some 2-azaindole derivatives: their cyctotoxicity and antibacterial activity, abstract, (1996), See RN 271-63-6.

Saify et al., Synthesis of some 7-azaindole derivatives: Their cytotoxicity and antibacterial activity, Pakistan Journal of Scientific and Industrial Research, 37(10): 439-441, 1994.

Schweizer, et al., Combinatorial Synthesis of Carbohydrates, Curr Opin. Chem. Biol., 3:291-298 (1999).

Sclabas, G.M. et al, Overexpression of Tropomysin-Related Kinase B in Metastatic Human Pancreatic Cancer Cells, Clin. Cancer. Res. V11:440-449 (2005).

Sheets, et al., Efficient Construction of a Large Nonimmune Phage Antibody Library: The Production of High-Affinity Human Single-Chain Antibodies to Protein Antigens, Proc Natl Acad Sci USA 95:6157-6162 (1998).
Siegel, et al., Mass Spectral Analysis of a Protein Complex Using Single-Chain Antibodies Selected on a Peptide Target: Applications to Functional Genomics, Journal of Molecular Biology 302:285-293 (2000).
Smalley et al., c-Kit signaling as the driving oncogenic event in sub-groups of melanomas. Histol Histopathol, 24:643-650, 2009.
Steinman, Multiple sclerosis: A coordinated immunological attack against myelin in the central nervous system, Cell 85:299-302 (1996).
Sun, et al., Design, Synthesis, and Evaluations of Substituted 3-[(3- or 4-Carboxyethylpyrrol-2-yl) Methylidenyl]indolin-2-Ones as Inhibitors of VEGF, PGF, and PDGF Receptor Tyrosine Kinases, J. Med. Chem. 42:5120-5130 (1999).
Supplementary Search Report dated Aug. 4, 2009 for European Application No. 04814626.0.
Tada, et al., Analysis of Cytokine Receptor Messenger RNA Expression in Human Glioblastoma Cells and Normal Astrocytes by Reverse-Transcription Polymerase Chain Reaction, J. Neuro 80:1063-1073 (1994).
Takahashi et al, ret Transforming Gene Encodes a Fusion Protein Homologous to Tyrosine Kinases, Mol Cell Biol. 7:1378-1385 (1987).
Tang, X. et al., An RNA interference-based screen identifies MAP4K4/NIK as a negative regulator of PPAR?, adipogenesis, and insulin-responsive hexose transport, Proc. Natl. Acad. Sci. U. S. A. 103:2087-2092 (2006).
Uritskaya et al., STN Accession No. 1974-27133; Document No. 08:27133; Abstract of Khimiya Geterotsiklicheskikh Soedinenii (1973, (10), 1370-3).
US Notice of Allowance dated Jun. 6, 2008 for U.S. Appl. No. 11/154,988.
US Office Action Dec. 18, 2009 for U.S. Appl. No. 11/473,347.
US Office Action dated Jan. 4, 2008 for U.S. Appl. No. 11/154,988.
US Office Action dated Feb. 26, 2010 for U.S. Appl. No. 11/986,667.
US Office Action dated Jun. 6, 2007 for U.S. Appl. No. 11/016,350.
US Office Action dated Aug. 22, 2007 for U.S. Appl. No. 11/487,134.
US Office Action dated Sep. 22, 2009 for U.S. Appl. No. 11/986,667.
US Office Action dated Sep. 23, 2009 for U.S. Appl. No. 11/962,044.
US Office Action dated Oct. 19, 2007 for U.S. Appl. No. 11/154,988.
US Office Action dated Oct. 26, 2007 for U.S. Appl. No. 11/016,350.
US Office Action dated Feb. 17, 2010 for U.S. Appl. No. 11/962,044.
US Supplemental Notice of Allowance dated Jul. 23, 2008 for U.S. Appl. No. 11/154,988.
US Supplemental Notice of Allowance dated Sep. 8, 2008 for U.S. Appl. No. 11/154,988.
Vliagoftis, et al., The protooncogene c-kit and c-kit ligand in human disease, Journ. Clin. Immunol. 100:435-440 (1997).
Weber, P., Physical Principles of Protein Crystallization, Adv. Protein Chem., 41:1-36 (1991).
Wendt, et al, Identification of novel binding interactions in the development of potent, selective 2-naphthamidine inhibitors of urokinase, synthesis, structural analysis, and SAR of ?-Phenyl amide 6-substitution. J. Med. Chem., 47(2):303 (2004).
Wessjohann, L., Synthesis of Natural-Product-Based Compound Libraries, Curr Opin Chem Biol., 4:303-309 (2000).
Wild, K.D. et al, Antibodies to Nerve Growth Factor Reverse Established Tactile Allodynia in Rodent Models of Neuropathic Pain without Tolerance, J. Pharmacol. Exp. Ther. 322:282-287 (2007).
Wright, J.H. et al., The STE20 Kinase KGK Is Broadly Expressed in Human tumor Cells and Can Modulate Cellular Transformation, Invasion, and Adhesion, Mol. Cell. Biol. 23:2068-2082 (2003).
Wuthrich, K., Chapter 10: Three-Dimensional Protein Structures by NMR, NMR of Proteins and Nucleic Acids, 10:176-199 (1986).
Wyckoff et al., Direct visualization of macrophage-assisted tumor cell intravasation in mammary tumors. Cancer Research, 67(6): 2649-2656, 2007.
Yang et al., Nf1-Dependent tumors require a microenvironment containing Nf1+/_-and c-kit-Dependent bone marrow, Cell, 135:437-448, 2008.

Yang et. al., Synthesis of some 5-substituted indoles, Heterocycles, 34:1169 (1992).
Yang, Z.F. et al, Identification of Brain-Derived Neurotrophic Factor as a Novel Functional Protein in Hepatocellular Carcinoma, Cancer Res. 65:219-225 (2005).
Yao, Z. et al., A Novel Human STE20-related Protein Kinase, HGK, That Specifically Activates the c-Jun N-terminal Kinase Signaling Pathway, J. Biol. Chem. 274:2118-2125 (1999).
Allegretti, et al., Palladium-Catalysed Functionalisation at 4- and 6-Position of the 7-Azaindole System, Synlett 5:609-612 (2001).
Alvarez, et al., Synthesis of 3-Aryl- and 3-Heteroaryl-7-Azaindoles, Synthesis 4:615-620 (1999).
Anderson, et al., Cooperative Catalyst Effects in Palladium-Mediated Cyanation Reactions of Aryl Halides and Triflates, J. Org. Chem. 63:8224-8228 (1998).
Antonini, et al., Synthesis of 4-Amino-1-β-D-Ribofuranosyl-1H-pyrrolo[2,3-b]pyridine (1-Deazatubercidin) as a Potential Antitumor Agent, J. Med. Chem. 25:1258-1261 (1982).
Bongarzone, et al., High Frequency of Activation of Tyrosine Kinase Oncogenes in Human Papillary Thyroid Carcinoma, Oncogene 4(12):1457-1462 (1989).
Chayer, et al., Synthesis of Carboranylpyrroles, Tetrahedron Lett. 42(44):7759-7761 (2001).
Colman, P.M., Structure-Based Drug Design, Current Opinion in Struc. Biol. 4: 868-874 (1994).
Coste, et al., Coupling N-Methylated Amino Acids Using PyBroP1 and PyCloP Halogenophosphonium Salts: Mechanism and Fields of Application, Journal of Organic Chemistry 59:2437-2446 (1994).
Donis-Keller, et al., Mutations in the RET Proto-Oncogene are Associated with MEN 2A and FMTC, Hum Mol Genet. 2(7):851-856 (1993).
Dube and Scholte, Reductive N-Alkylation of Amides, Carbamates and Ureas, Tetrahedron Lett. 40:2295-2298 (1999).
Durbec, et al., GDNF Signalling Through the Ret Receptor Tyrosine Kinase, Nature 381:789-793 (1996).
Franz and Martin, Sulfuranes. X. A Reagent for the Facile Cleavage of Secondary Amides, JACS, 95(6):2017-2019 (1973).
Gordon, and Ford, Detection of Peroxides and Their Removal, The Chemist's Companion: A Handbook Of Practical Data, Techniques, And References p. 437 (1972).
Grieco, et al., PTC is a Novel Rearranged Form of the ret Proto-Oncogene and is Frequently Detected in Vivo in Human Thyroid Papillary Carcinomas, Cell 60(4):557-563 (1990).
Guida, W., Software for Structure-Based Drug Design, Current Opinion in Struc. Biol. 4:777-781 (1994).
Hayashi, et al., Dichloro[1,1 -bis(diphenylophosphino)ferrocene]palladium-(II): An Effective Catalyst for Cross-Coupling of Secondary and Primary Alkyl Grignard and Alkylzinc Reagents with Organic Halides, J. Am. Chem. Soc. 106:158-163 (1984).
Ishizaka, et al., Human ret Proto-Oncogene Mapped to Chromsome 10q11.2, Oncogene 4(12):1519-1521 (1989).
Jing, et al., GDNF-Induced Activation of the Ret Protein Tyrosine Kinase is Mediated by GDNFR-α, a Novel Receptor for GDNF, Cell 85:1113-1124 (1996).
Katritzky, et al., Regiospecific C-Acylation of Pyrroles and Indoles Using N-Acylbenzotriazoles, J. Org. Chem. 68:5720-5723 (2003).
Luo, et al., Close Linkage with the RET Proto-Oncogene and Boundaries of Deletion Mutations in Autosomal Dominant Hirschsprung Disease, Hum Mol Genet. 2(11):1803-1808 (1993).
Minakata, Regioselective Funtionalization of 1H-Pyrrold[2,3-b]pyridine Via its N-Oxide, Synthesis pp. 661-663 (1992).
Nagafuji and Cushman, A General Synthesis of Pyrroles and Fused Pyrrole Systems from Ketones and Amino Acids, J. Org. Chem. 61:4999-5003 (1996).
Nahm and Weinreb, N-Methoxy-N-Methylamides as Effective Acylating Agents, Tetrahedron Lett. 22(39):3815-3818 (1981).
Office Action dated Jan. 4, 2008 for U.S. Appl. No. 11/154,988.
Olah, et al., Synthetic Methods and Reactions: Part 209. Improved Preparation of Aldehydes and Ketones from N,N-Dimethylamides and Grignard Reagents, Synthesis pp. 228-230 (1984).
Ottoni, et al., Efficient and Simple Methods for the Introduction of the Sulfonyl, Acyl and Alkyl Protecting Groups on the Nitrogen of Indole and its Derivatives, Tetrahedron 54:13915-13928 (1998).

Saiki, R., "Amplification of Genomic DNA" PCR Protocols: A Guide to Meth. and Applic. 2:13-20 (1990).

Santoro, et al., The ret Proto-Oncogene is Consistently Expressed in Human Pheochromocytomas and Thyroid Medullary Carcinomas, Oncogene, 5(10):1595-1598 (1990).

Sun, C., Recent Advances in Liquid-Phase Combinatorial Chemistry, Comb. Chem. & High Throughput Screening 2:299-318 (1999).

Takahashi, et al., Activation of a Novel Human Transforming Gene, ret, by DNA Rearrangement, Cell 42(2):581-588 (1985).

Takahashi, et al., Cloning and Expression of the ret Proto-Oncogene Encoding a Tyrosine Kinase with Two Potential Transmembrane Domains, Oncogene 3(5):571-578 (1988).

Thomas, et. al., Light-Emitting Carbazole Derivatives: Potential Electroluminescent Materials, J. Am. Chem. Soc. 123:9404-9411 (2001).

Toste, et. al., A Versatile Procedure for the Preparation of Aryl Thiocyanates Using N-Thiocyanatosuccinimide (NTS), Synth. Comm. 25(8):1277-1286 (1995).

Trupp, et al., Functional Receptor for GDNF Encoded by the c-ret Proto-Oncogene, Nature 381:785-789 (1996).

Van Heyningen, V., One Gene - Four Syndromes, Nature 367:319-320 (1994).

Zanon, et. al., Copper-Catalyzed Domino Halide Exchange-Cyanation of Aryl Bromides, J. Am. Chem. Soc. 125:2890-2891 (2003).

* cited by examiner

SEQUENCE LISTING

<160> NUMBER OF SEQ ID NOS: 66

<210> SEQ ID NO 1
<211> LENGTH: 976
<212> TYPE: PRT
<213> ORGANISM: Homo sapiens

<400> SEQUENCE: 1

Met Arg Gly Ala Arg Gly Ala Trp Asp Phe Leu Cys Val Leu Leu Leu
 1               5                  10                  15

Leu Leu Arg Val Gln Thr Gly Ser Ser Gln Pro Ser Val Ser Pro Gly
            20                  25                  30

Glu Pro Ser Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
    370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

```
Phe Pro Glu Pro Thr Ile Asp Trp Tyr Phe Cys Pro Gly Thr Glu Gln
            435                 440                 445

Arg Cys Ser Ala Ser Val Leu Pro Val Asp Val Gln Thr Leu Asn Ser
        450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
            515                 520                 525

Phe Val Ile Val Ala Gly Met Met Cys Ile Ile Val Met Ile Leu Thr
            530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
            595                 600                 605

Tyr Gly Leu Ile Lys Ser Asp Ala Ala Met Thr Val Ala Val Lys Met
            610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Ala Leu Tyr Lys
            690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
            755                 760                 765

Leu Leu Ser Phe Ser Tyr Gln Val Ala Lys Gly Met Ala Phe Leu Ala
            770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
```

|  |  |  |  |  |  |  |  |  |  |  |  |
|--|--|--|--|--|--|--|--|--|--|--|--|
|  | 850 |  |  |  | 855 |  |  |  | 860 |  |  |
| Leu | Gly | Ser | Ser | Pro | Tyr | Pro | Gly | Met | Pro | Val | Asp | Ser | Lys | Phe | Tyr |
| 865 |  |  |  |  | 870 |  |  |  | 875 |  |  |  |  | 880 |  |
| Lys | Met | Ile | Lys | Glu | Gly | Phe | Arg | Met | Leu | Ser | Pro | Glu | His | Ala | Pro |
|  |  |  |  | 885 |  |  |  |  | 890 |  |  |  |  | 895 |  |
| Ala | Glu | Met | Tyr | Asp | Ile | Met | Lys | Thr | Cys | Trp | Asp | Ala | Asp | Pro | Leu |
|  |  |  | 900 |  |  |  |  | 905 |  |  |  |  | 910 |  |  |
| Lys | Arg | Pro | Thr | Phe | Lys | Gln | Ile | Val | Gln | Leu | Ile | Glu | Lys | Gln | Ile |
|  |  | 915 |  |  |  |  | 920 |  |  |  |  | 925 |  |  |  |
| Ser | Glu | Ser | Thr | Asn | His | Ile | Tyr | Ser | Asn | Leu | Ala | Asn | Cys | Ser | Pro |
|  | 930 |  |  |  |  | 935 |  |  |  |  | 940 |  |  |  |  |
| Asn | Arg | Gln | Lys | Pro | Val | Val | Asp | His | Ser | Val | Arg | Ile | Asn | Ser | Val |
| 945 |  |  |  |  | 950 |  |  |  |  | 955 |  |  |  |  | 960 |
| Gly | Ser | Thr | Ala | Ser | Ser | Ser | Gln | Pro | Leu | Leu | Val | His | Asp | Asp | Val |
|  |  |  |  | 965 |  |  |  |  | 970 |  |  |  |  | 975 |  |

<210> SEQ ID NO 2
<211> LENGTH: 5084
<212> TYPE: DNA
<213> ORGANISM: Homo sapiens

<400> SEQUENCE: 2

```
gatcccatcg cagctaccgc gatgagaggc gctcgcggcg cctgggattt tctctgcgtt      60
ctgctcctac tgcttcgcgt ccagacaggc tcttctcaac catctgtgag tccaggggaa     120
ccgtctccac catccatcca tccaggaaaa tcagacttaa tagtccgcgt gggcgacgag     180
attaggctgt tatgcactga tccgggcttt gtcaaatgga cttttgagat cctggatgaa     240
acgaatgaga ataagcagaa tgaatggatc acggaaaagg cagaagccac caacaccggc     300
aaatacacgt gcaccaacaa acacggctta agcaattcca tttatgtgtt tgttagagat     360
cctgccaagc ttttccttgt tgaccgctcc ttgtatggga agaagacaa cgacacgctg     420
gtccgctgtc ctctcacaga cccagaagtg accaattatt ccctcaaggg gtgccagggg     480
aagcctcttc ccaaggactt gaggtttatt cctgacccca ggcgggcat catgatcaaa     540
agtgtgaaac gcgcctacca tcggctctgt ctgcattgtt ctgtggacca ggagggcaag     600
tcagtgctgt cggaaaaatt catcctgaaa gtgaggccag ccttcaaagc tgtgcctgtt     660
gtgtctgtgt ccaaagcaag ctatcttctt agggaagggg aagaattcac agtgacgtgc     720
acaataaaag atgtgtctag ttctgtgtac tcaacgtgga aaagagaaaa cagtcagact     780
aaactacagg agaaatataa tagctggcat cacggtgact tcaattatga acgtcaggca     840
acgttgacta tcagttcagc gagagttaat gattctggag tgttcatgtg ttatgccaat     900
aatacttttg atcagcaaaa tgtcacaaca accttggaag tagtagataa aggattcatt     960
aatatcttcc ccatgataaa cactacagta tttgtaaacg atggagaaaa tgtagatttg    1020
attgttgaat atgaagcatt ccccaaacct gaacaccagc agtggatcta tatgaacaga    1080
accttcactg ataaatggga agattatccc aagtctgaga tgaaagtaa tatcagatac    1140
gtaagtgaac ttcatctaac gagattaaaa ggcaccgaag gaggcactta cacattccta    1200
gtgtccaatt ctgacgtcaa tgctgccata gcatttaatg tttatgtgaa tacaaaacca    1260
gaaatcctga cttacgacag gctcgtgaat ggcatgctcc aatgtgtggc agcaggattc    1320
ccagagccca caatagattg tatttttgt ccaggaactg agcagagatg ctctgcttct    1380
gtactgccag tggatgtgca gacactaaac tcatctgggc caccgtttgg aaagctagtg    1440
```

```
gttcagagtt ctatagattc tagtgcattc aagcacaatg gcacggttga atgtaaggct    1500
tacaacgatg tgggcaagac ttctgcctat tttaactttg catttaaagg taacaacaaa    1560
gagcaaatcc atccccacac cctgttcact cctttgctga ttggtttcgt aatcgtagct    1620
ggcatgatgt gcattattgt gatgattctg acctacaaat atttacagaa acccatgtat    1680
gaagtacagt ggaaggttgt tgaggagata aatggaaaca attatgttta catagaccca    1740
acacaacttc cttatgatca caaatgggag tttcccagaa acaggctgag ttttgggaaa    1800
accctgggtg ctggagcttt cgggaaggtt gttgaggcaa ctgcttatgg cttaattaag    1860
tcagatgcgg ccatgactgt cgctgtaaag atgctcaagc cgagtgccca tttgacagaa    1920
cgggaagccc tcatgtctga actcaaagtc ctgagttacc ttggtaatca catgaatatt    1980
gtgaatctac ttggagcctg caccattgga gggcccaccc tggtcattac agaatatttgt   2040 tgctatggtg atcttttgaa ttttttgaga agaaaacgtg attcatttat ttgttcaaag    2100
caggaagatc atgcagaagc tgcactttat aagaatcttc tgcattcaaa ggagtcttcc    2160
tgcagcgata gtactaatga gtacatggac atgaaacctg gagtttctta tgttgtccca    2220
accaaggccg acaaaaggag atctgtgaga ataggctcat acatagaaag agatgtgact    2280
cccgccatca tggaggatga cgagttggcc ctagacttag aagacttgct gagcttttct    2340
taccaggtgg caaagggcat ggcttttcctc gcctccaaga attgtattca cagagacttg    2400
gcagccagaa atatcctcct tactcatggt cggatcacaa agatttgtga ttttggtcta    2460
gccagagaca tcaagaatga ttctaattat gtggttaaag gaaacgctcg actacctgtg    2520
aagtggatgg cacctgaaag cattttcaac tgtgtataca cgtttgaaag tgacgtctgg    2580
tcctatggga ttttttcttg ggagctgttc tctttaggaa gcagcccta tcctggaatg    2640 ccggtcgatt ctaagttcta caagatgatc aaggaaggct tccggatgct cagccctgaa    2700
cacgcacctg ctgaaatgta tgacataatg aagacttgct gggatgcaga tccctaaaa    2760 agaccaacat tcaagcaaat tgttcagcta attgagaagc agatttcaga gagcaccaat    2820
catatttact ccaacttagc aaactgcagc cccaaccgac agaagcccgt ggtagaccat    2880
tctgtgcgga tcaattctgt cggcagcacc gcttcctcct cccagcctct gcttgtgcac    2940
gacgatgtct gagcagaatc agtgtttggg tcacccctcc aggaatgatc tcttcttttg    3000
gcttccatga tggttatttt cttttctttc aacttgcatc caactccagg atagtgggca    3060
ccccactgca atcctgtctt tctgagcaca ctttagtggc cgatgatttt tgtcatcagc    3120
caccatccta ttgcaaaggt tccaactgta tatattccca atagcaacgt agcttctacc    3180
atgaacagaa acattctga tttggaaaaa gagagggagg tatggactgg gggccagagt    3240
cctttccaag gcttctccaa ttctgcccaa aaatatggtt gatagtttac ctgaataaat    3300
ggtagtaatc acagttggcc ttcagaacca tccatagtag tatgatgata caagattaga    3360
agctgaaaac ctaagtcctt tatgtggaaa acagaacatc attagaacaa aggacagagt    3420
atgaacacct gggcttaaga aatctagtat ttcatgctgg gaatgagaca taggccatga    3480
aaaaaatgat ccccaagtgt gaacaaaaga tgctcttctg tggaccactg catgagcttt    3540
tatactaccg acctggtttt taaatagagt ttgctattag agcattgaat tggagagaag    3600
gcctccctag ccagcacttg tatatacgca tctataaatt gtccgtgttc atacatttga    3660
ggggaaaaca ccataaggtt tcgtttctgt atacaaccct ggcattatgt ccactgtgta    3720
tagaagtaga ttaagagcca tataagtttg aaggaaacag ttaataccat tttttaagga    3780
aacaatataa ccacaaagca cagtttgaac aaaatctcct cttttagctg atgaacttat    3840
```

```
tctgtagatt ctgtggaaca agcctatcag cttcagaatg gcattgtact caatggattt    3900
gatgctgttt gacaaagtta ctgattcact gcatggctcc cacaggagtg ggaaaacact    3960
gccatcttag tttggattct tatgtagcag gaaataaagt ataggtttag cctccttcgc    4020
aggcatgtcc tggacaccgg gccagtatct atatatgtgt atgtacgttt gtatgtgtgt    4080
agacaaatat ttggaggggt attttttgccc tgagtccaag agggtccttt agtacctgaa    4140
aagtaacttg gctttcatta ttagtactgc tcttgtttct tttcacatag ctgtctagag    4200
tagcttacca gaagcttcca tagtggtgca gaggaagtgg aaggcatcag tccctatgta    4260
tttgcagttc acctgcactt aaggcactct gttatttaga ctcatcttac tgtacctgtt    4320
ccttagacct tccataatgc tactgtctca ctgaaacatt taaattttac cctttagact    4380
gtagcctgga tattattctt gtagtttacc tctttaaaaa caaaacaaaa caaaacaaaa    4440 aactccccctt cctcactgcc aatataaaa ggcaaatgtg tacatggcag agtttgtgtg    4500
ttgtcttgaa agattcaggt atgttgcctt tatggtttcc cccttctaca tttcttagac    4560
tacatttaga gaactgtggc cgttatctgg aagtaaccat ttgcactgga gttctatgct    4620
ctcgcacctt tccaaagtta acagattttg gggttgtgtt gtcacccaag agattgttgt    4680
ttgccatact ttgtctgaaa aattccctttg tgtttctatt gacttcaatg atagtaagaa    4740
aagtggttgt tagttataga tgtctaggta cttcaggggc acttcattga gagtttttgtc    4800 ttgccatact ttgtctgaaa aattccctttg tgtttctatt gacttcaatg atagtaagaa    4860
aagtggttgt tagttataga tgtctaggta cttcaggggc acttcattga gagtttttgtc    4920 aatgtctttt gaatattccc aagcccatga gtccttgaaa atatttttta tatatacagt    4980
aactttatgt gtaaatacat aagcggcgta agtttaaagg atgttggtgt tccacgtgtt    5040
ttattcctgt atgttgtcca attgttgaca gttctgaaga attc                    5084
```

<210> SEQ ID NO 3
<211> LENGTH: 972
<212> TYPE: PRT
<213> ORGANISM: Homo sapiens

<400> SEQUENCE: 3

```
Met Gly Pro Gly Val Leu Leu Leu Leu Val Ala Thr Ala Trp His
 1               5                  10                  15

Gly Gln Gly Ile Pro Val Ile Glu Pro Ser Val Pro Glu Leu Val
                20                  25                  30

Lys Pro Gly Ala Thr Val Thr Leu Arg Cys Val Gly Asn Gly Ser Val
                35                  40                  45

Glu Trp Asp Gly Pro Pro Ser Pro His Trp Thr Leu Tyr Ser Asp Gly
     50                  55                  60

Ser Ser Ser Ile Leu Ser Thr Asn Asn Ala Thr Phe Gln Asn Thr Gly
 65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
        130                 135                 140

Gly Arg Pro Leu Met Arg His Thr Asn Tyr Ser Phe Ser Pro Trp His
```

-continued

```
            145                 150                 155                 160
        Gly Phe Thr Ile His Arg Ala Lys Phe Ile Gln Ser Gln Asp Tyr Gln
                        165                 170                 175

Cys Ser Ala Leu Met Gly Gly Arg Lys Val Met Ser Ile Ser Ile Arg
                        180                 185                 190

Leu Lys Val Gln Lys Val Ile Pro Gly Pro Ala Leu Thr Leu Val
                        195                 200                 205

Pro Ala Glu Leu Val Arg Ile Arg Gly Glu Ala Ala Gln Ile Val Cys
                210                 215                 220

Ser Ala Ser Ser Val Asp Val Asn Phe Asp Val Phe Leu Gln His Asn
        225                 230                 235                 240

Asn Thr Lys Leu Ala Ile Pro Gln Gln Ser Asp Phe His Asn Asn Arg
                        245                 250                 255

Tyr Gln Lys Val Leu Thr Leu Asn Leu Asp Gln Val Asp Phe Gln His
                        260                 265                 270

Ala Gly Asn Tyr Ser Cys Val Ala Ser Asn Val Gln Gly Lys His Ser
                        275                 280                 285

Thr Ser Met Phe Phe Arg Val Val Glu Ser Ala Tyr Leu Asn Leu Ser
                        290                 295                 300

Ser Glu Gln Asn Leu Ile Gln Glu Val Thr Val Gly Glu Gly Leu Asn
        305                 310                 315                 320

Leu Lys Val Met Val Glu Ala Tyr Pro Gly Leu Gln Gly Phe Asn Trp
                        325                 330                 335

Thr Tyr Leu Gly Pro Phe Ser Asp His Gln Pro Glu Pro Lys Leu Ala
                        340                 345                 350

Asn Ala Thr Thr Lys Asp Thr Tyr Arg His Thr Phe Thr Leu Ser Leu
                        355                 360                 365

Pro Arg Leu Lys Pro Ser Glu Ala Gly Arg Tyr Ser Phe Leu Ala Arg
                        370                 375                 380

Asn Pro Gly Gly Trp Arg Ala Leu Thr Phe Glu Leu Thr Leu Arg Tyr
        385                 390                 395                 400

Pro Pro Glu Val Ser Val Ile Trp Thr Phe Ile Asn Gly Ser Gly Thr
                        405                 410                 415

Leu Leu Cys Ala Ala Ser Gly Tyr Pro Gln Pro Asn Val Thr Trp Leu
                        420                 425                 430

Gln Cys Ser Gly His Thr Asp Arg Cys Asp Glu Ala Gln Val Leu Gln
                        435                 440                 445

Val Trp Asp Asp Pro Tyr Pro Glu Val Leu Ser Gln Glu Pro Phe His
                        450                 455                 460

Lys Val Thr Val Gln Ser Leu Leu Thr Val Glu Thr Leu Glu His Asn
        465                 470                 475                 480

Gln Thr Tyr Glu Cys Arg Ala His Asn Ser Val Gly Ser Gly Ser Trp
                        485                 490                 495

Ala Phe Ile Pro Ile Ser Ala Gly Ala His Thr His Pro Pro Asp Glu
                        500                 505                 510

Phe Leu Phe Thr Pro Val Val Ala Cys Met Ser Ile Met Ala Leu
                        515                 520                 525

Leu Leu Leu Leu Leu Leu Leu Leu Tyr Lys Tyr Lys Gln Lys Pro
                        530                 535                 540

Lys Tyr Gln Val Arg Trp Lys Ile Ile Glu Ser Tyr Glu Gly Asn Ser
        545                 550                 555                 560

Tyr Thr Phe Ile Asp Pro Thr Gln Leu Pro Tyr Asn Glu Lys Trp Glu
                        565                 570                 575
```

```
Phe Pro Arg Asn Asn Leu Gln Phe Gly Lys Thr Leu Gly Ala Gly Ala
            580                 585                 590
Phe Gly Lys Val Val Glu Ala Thr Ala Phe Gly Leu Gly Lys Glu Asp
        595                 600                 605
Ala Val Leu Lys Val Ala Val Lys Met Leu Lys Ser Thr Ala His Ala
    610                 615                 620
Asp Glu Lys Glu Ala Leu Met Ser Glu Leu Lys Ile Met Ser His Leu
625                 630                 635                 640
Gly Gln His Glu Asn Ile Val Asn Leu Leu Gly Ala Cys Thr His Gly
                645                 650                 655
Gly Pro Val Leu Val Ile Thr Glu Tyr Cys Cys Tyr Gly Asp Leu Leu
            660                 665                 670
Asn Phe Leu Arg Arg Lys Ala Glu Ala Met Leu Gly Pro Ser Leu Ser
        675                 680                 685
Pro Gly Gln Asp Pro Glu Gly Gly Val Asp Tyr Lys Asn Ile His Leu
    690                 695                 700
Glu Lys Lys Tyr Val Arg Arg Asp Ser Gly Phe Ser Ser Gln Gly Val
705                 710                 715                 720
Asp Thr Tyr Val Glu Met Arg Pro Val Ser Thr Ser Ser Asn Asp Ser
                725                 730                 735
Phe Ser Glu Gln Asp Leu Asp Lys Glu Asp Gly Arg Pro Leu Glu Leu
            740                 745                 750
Arg Asp Leu Leu His Phe Ser Ser Gln Val Ala Gln Gly Met Ala Phe
        755                 760                 765
Leu Ala Ser Lys Asn Cys Ile His Arg Asp Val Ala Ala Arg Asn Val
    770                 775                 780
Leu Leu Thr Asn Gly His Val Ala Lys Ile Gly Asp Phe Gly Leu Ala
785                 790                 795                 800
Arg Asp Ile Met Asn Asp Ser Asn Tyr Ile Val Lys Gly Asn Ala Arg
                805                 810                 815
Leu Pro Val Lys Trp Met Ala Pro Glu Ser Ile Phe Asp Cys Val Tyr
            820                 825                 830
Thr Val Gln Ser Asp Val Trp Ser Tyr Gly Ile Leu Leu Trp Glu Ile
        835                 840                 845
Phe Ser Leu Gly Leu Asn Pro Tyr Pro Gly Ile Leu Val Asn Ser Lys
    850                 855                 860
Phe Tyr Lys Leu Val Lys Asp Gly Tyr Gln Met Ala Gln Pro Ala Phe
865                 870                 875                 880
Ala Pro Lys Asn Ile Tyr Ser Ile Met Gln Ala Cys Trp Ala Leu Glu
                885                 890                 895
Pro Thr His Arg Pro Thr Phe Gln Gln Ile Cys Ser Phe Leu Gln Glu
            900                 905                 910
Gln Ala Gln Glu Asp Arg Arg Glu Arg Asp Tyr Thr Asn Leu Pro Ser
        915                 920                 925
Ser Ser Arg Ser Gly Gly Ser Gly Ser Ser Ser Glu Leu Glu Glu
    930                 935                 940
Glu Ser Ser Ser Glu His Leu Thr Cys Cys Glu Gln Gly Asp Ile Ala
945                 950                 955                 960
Gln Pro Leu Leu Gln Pro Asn Asn Tyr Gln Phe Cys
            965                 970

<210> SEQ ID NO 4
<211> LENGTH: 3985
```

```
<212> TYPE: DNA
<213> ORGANISM: Homo sapiens

<400> SEQUENCE: 4
gaagggcaga cagagtgtcc aaaagcgtga gagcacgaag tgaggagaag gtggagaaga      60
gagaagagga agaggaagag gaagagagga agcggaggga actgcggcca ggctaaaagg     120
ggaagaagag gatcagccca aggaggagga agaggaaaac aagacaaaca gccagtgcag     180
aggagaggaa cgtgtgtcca gtgtcccgat ccctgcggag ctagtagctg agagctctgt     240
gccctgggca ccttgcagcc ctgcacctgc ctgccacttc cccaccgagg ccatgggccc     300
aggagttctg ctgctcctgc tggtggccac agcttggcat ggtcagggaa tcccagtgat     360
agagcccagt gtccctgagc tggtcgtgaa gccaggagca acggtgacct tgcgatgtgt     420
gggcaatggc agcgtggaat gggatggccc cccatcacct cactggaccc tgtactctga     480
tggctccagc agcatcctca gcaccaacaa cgctaccttc caaaacacgg ggacctatcg     540
ctgcactgag cctggagacc ccctgggagg cagcgccgcc atccacctct atgtcaaaga     600
ccctgcccgg ccctggaacg tgctagcaca ggaggtggtc gtgttcgagg accaggacgc     660
actactgccc tgtctgctca cagacccggt gctggaagca ggcgtctcgc tggtgcgtgt     720
gcgtggccgg cccctcatgc gccacaccaa ctactccttc tcgccctggc atggcttcac     780
catccacagg gccaagttca ttcagagcca ggactatcaa tgcagtgccc tgatgggtgg     840
caggaaggtg atgtccatca gcatccggct gaaagtgcag aaagtcatcc cagggccccc     900
agccttgaca ctggtgcctg cagagctggt gcggattcga ggggaggctg cccagatcgt     960
gtgctcagcc agcagcgttg atgttaactt tgatgtcttc ctccaacaca acaacaccaa    1020
gctcgcaatc cctcaacaat ctgactttca taataccgt taccaaaaag tcctgaccct    1080
caacctcgat caagtagatt tccaacatgc cggcaactac tcctgcgtgg ccagcaacgt    1140
gcagggcaag cactccacct ccatgttctt ccgggtggta gagagtgcct acttgaactt    1200
gagctctgag cagaacctca tccaggaggt gaccgtgggg gagggctca acctcaaagt    1260
catggtggag gcctacccag gcctgcaagg ttttaactgg acctacctgg ccccttttc    1320
tgaccaccag cctgagccca gcttgctaa tgctaccacc aaggacacat acaggcacac    1380
cttcacccct ctctgccccg cctgaagcc ctctgaggct ggccgctact ccttcctggc    1440
cagaaaccca ggaggctgga gagctctgac gtttgagctc acccttcgat accccccaga    1500
ggtaagcgtc atatggacat tcatcaacgg ctctggcacc cttttgtgtg ctgcctctgg    1560
gtaccccag cccaacgtga catggctgca gtgcagtggc cacactgata ggtgtgatga    1620
ggcccaagtg ctgcaggtct gggatgaccc atacctgag gtcctgagcc aggagccctt    1680
ccacaaggtg acggtgcaga gcctgctgac tgttgagacc ttagagcaca accaaaccta    1740
cgagtgcagg gccacaacaa cgtgggggag tggctcctgg ccttcatac ccatctctgc    1800
aggagcccac acgcatcccc cggatgagtt cctcttcaca ccagtggtgg tcgcctgcat    1860
gtccatcatg gccttgctgc tgctgctgct cctgctgcta ttgtacaagt ataagcagaa    1920
gcccaagtac caggtccgct ggaagatcat cgagagctat gagggcaaca gttatacttt    1980
catcgaccccc acgcagctgc cttacaacga gaagtgggag ttccccgga caacctgca    2040
gtttggtaag accctcggag ctggagcctt tgggaaggtg gtgaggcca cggcctttgg    2100
tctgggcaag gaggatgctg tcctgaaggt ggctgtgaag atgctgaagt ccacggccca    2160
tgctgatgag aaggaggccc tcatgtccga gctgaagatc atgagccacc tgggccagca    2220
```

-continued

```
cgagaacatc gtcaaccttc tgggagcctg tacccatgga ggccctgtac tggtcatcac    2280
ggagtactgt tgctatggcg acctgctcaa ctttctgcga aggaaggctg aggccatgct    2340
gggacccagc ctgagcccg gccaggaccc cgagggaggc gtcgactata gaacatcca      2400 cctcgagaag aaatatgtcc gcagggacag tggcttctcc agccagggtg tggacaccta    2460
tgtggagatg aggcctgtct ccacttcttc aaatgactcc ttctctgagc aagacctgga    2520
caaggaggat ggacggcccc tggagctccg ggacctgctt cacttctcca gccaagtagc    2580
ccagggcatg gccttcctcg cttccaagaa ttgcatccac cgggacgtgg cagcgcgtaa    2640
cgtgctgttg accaatggtc atgtggccaa gattgggggac ttcgggctgg ctagggacat   2700
catgaatgac tccaactaca ttgtcaaggg caatgcccgc ctgcctgtga agtggatggc    2760
cccagagagc atctttgact gtgtctacac ggttcagagc gacgtctggt cctatggcat    2820
cctcctctgg gagatcttct cacttgggct gaatccctac cctggcatcc tggtgaacag    2880
caagttctat aaactggtga aggatggata ccaaatggcc cagcctgcat ttgccccaaa    2940
gaatatatac agcatcatgc aggcctgctg ggccttggag cccacccaca gacccacctt    3000
ccagcagatc tgctccttcc ttcaggagca ggcccaagag gacaggagag agcgggacta    3060
taccaatctg ccgagcagca gcagaagcgg tggcagcggc agcagcagca gtgagctgga    3120
ggaggagagc tctagtgagc acctgacctg ctgcgagcaa ggggatatcg cccagccctt    3180
gctgcagccc aacaactatc agttctgctg aggagttgac gacagggagt accactctcc    3240
cctcctccaa acttcaactc ctccatggat ggggcgacac ggggagaaca tacaaactct    3300
gccttcggtc atttcactca acagctcggc ccagctctga aacttgggaa ggtgagggat    3360
tcaggggagg tcagaggatc ccacttcctg agcatgggcc atcactgcca gtcaggggct    3420
gggggctgag ccctcacccc cccctcccct actgttctca tggtgttggc ctcgtgtttg    3480
ctatgccaac tagtagaacc ttctttccta atcccttat cttcatgaa atggactgac       3540 tttatgccta tgaagtcccc aggagctaca ctgatactga gaaaaccagg ctctttgggg    3600
ctagacagac tggcagagag tgagatctcc ctctctgaga ggagcagcag atgctcacag    3660
accacactca gctcaggccc cttggagcag gatggctcct ctaagaatct cacaggacct    3720
cttagtctct gccctatacg ccgccttcac tccacagcct caccctccc accccccatac    3780 tggtactgct gtaatgagcc aagtggcagc taaaagttgg gggtgttctg cccagtcccg    3840
tcattctggg ctagaaggca ggggaccttg gcatgtggct ggccacacca agcaggaagc    3900
acaaactccc ccaagctgac tcatcctaac taacagtcac gccgtgggat gtctctgtcc    3960
acattaaact aacagcatta atgca                                         3985
```

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
atgtacgaag ttcagtggaa agttgttgaa gaaatcaacg g                41

<210> SEQ ID NO 6
<211> LENGTH: 46
<212> TYPE: DNA
<213> ORGANISM: Artificial Sequence
<220> FEATURE:

```
<223> OTHER INFORMATION: Description of Artificial Sequence: Synthetic
      Primer

<400> SEQUENCE: 6
ggtcgatgta aacgtagttg ttaccgttga tttcttcaac aactttt                    46

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
aacaactacg tttacatcga cccgacccag ctgccgtacg ac                         42

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gttacgcggg aactcccatt tgtggtcgta cggcagctgg gtc                        43

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
aaatgggagt tcccgcgtaa ccgtctgtct ttcggtaaaa ccc                        43

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
accgaacgca cccgcaccca gggttttacc gaaagacaga c                          41

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
ggtgcgggtg cgttcggtaa agttgttgaa gcgaccgcgt acg                        43

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Synthetic
```

Primer

<400> SEQUENCE: 12
gccgcgtcag atttgatcag accgtacgcg gtcgcttcaa c        41

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
ctgatcaaat ctgacgcggc gatgaccgtt gcggttaaaa tgc        43

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
gtcaggtgcg cagacggttt cagcatttta accgcaacgg tca        43

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
aaaccgtctg cgcacctgac cgaacgtgaa gcgctgatgt ctg        43

<210> SEQ ID NO 16
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
ccaggtaaga cagaactttc agttcagaca tcagcgcttc acgt        44

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
ctgaaagttc tgtcttacct gggtaaccac atgaacatcg ttaa        44

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer -continued

```
<400> SEQUENCE: 18
ggtgcacgca cccagcaggt taacgatgtt catgtggtta c                          41

<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
ctgctgggtg cgtgcaccat cggtggtccg accctggtta tca                        43

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
gtcaccgtag cagcagtatt cggtgataac cagggtcgga cca                        43

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
gaatactgct gctacggtga cctgctgaac ttcctgcgtc gta                        43

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
agagcagatg aaagagtcac gtttacgacg caggaagttc agc                        43

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
cgtgactctt tcatctgctc taaacaggaa gaccacgcgg aag                        43

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer
```

-continued

```
<400> SEQUENCE: 24
cagcaggttt ttgtacagcg ccgcttccgc gtggtcttcc tgt                43

<210> SEQ ID NO 25
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
gcgctgtaca aaacctgctg cactctaaa gaatcttctt gctc               44

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
ccatgtattc gttggtagag tcagagcaag aagattcttt agagt             45

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
gactctacca acgaatacat ggacatgaaa ccgggtgttt ctta              44

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
tccgctttgg tcggaacaac gtaagaaaca cccggtttca tgt               43

<210> SEQ ID NO 29
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
gttgttccga ccaaagcgga caaacgtcgt tctgttcgta tcg               43

<210> SEQ ID NO 30
<211> LENGTH: 46
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
```

-continued taacgtcacg ttcgatgtaa gaaccgatac gaacagaacg acgttt        46

<210> SEQ ID NO 31
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
tcttacatcg aacgtgacgt taccccggcg atcatggaag acg        43

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
ccaggtccag cgccagttcg tcgtcttcca tgatcgccgg        40

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
gaactggcgc tggacctgga agacctgctg tctttctctt acc        43

<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
gaacgccata cctttcgcaa cctggtaaga gaaagacagc aggt        44

<210> SEQ ID NO 35
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
gttgcgaaag gtatggcgtt cctggcgtct aaaaactgca tcca        44

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
cgcgccgcca ggtcacggtg gatgcagttt ttagacgcc                                    39

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
cgtgacctgg cggcgcgtaa catcctgctg acccacggtc g                                 41

<210> SEQ ID NO 38
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
accgaagtcg cagattttgg tgatacgacc gtgggtcagc agg                               43

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
accaaaatct gcgacttcgg tctggcgcgt gacatcaaaa acg                               43

<210> SEQ ID NO 40
<211> LENGTH: 46
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40 gttacccttta acaacgtagt tagagtcgtt tttgatgtca cgcgcc                           46

<210> SEQ ID NO 41
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
tctaactacg ttgttaaagg taacgcgcgt ctgccggtta aatg                              44

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
gaagatagat tccggcgcca tccatttaac cggcagacgc gc                                42

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
atggcgccgg aatctatctt caactgcgtt tacaccttcg aatc                          44

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
gataccgtaa gaccaaacgt cagattcgaa ggtgtaaacg cag                           43

<210> SEQ ID NO 45
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 45
gacgtttggt cttacggtat cttcctgtgg gaactgttct ctc                           43

<210> SEQ ID NO 46
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 46
cctgtgggaa ctgttctctc tgggttcttc tccgtacccg g                             41

<210> SEQ ID NO 47
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 47
ggttcttctc cgtacccggg tatgccggtt gactctaaat tctat                         45

<210> SEQ ID NO 48
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 48
cggaaacctt ctttgatcat tttgtagaat ttagagtcaa ccggc                         45

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 49
aaaatgatca aagaaggttt ccgtatgctg tctccggaac acg                43

<210> SEQ ID NO 50
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 50
atgtcgtaca tttccgccgg cgcgtgttcc ggagacagca ta                 42

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 51
ccggcggaaa tgtacgacat catgaaaacc tgctgggacg cg                 42

<210> SEQ ID NO 52
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 52
aaggtcggac gtttcagcgg gtccgcgtcc cagcaggttt tc                 42

<210> SEQ ID NO 53
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 53
ccgctgaaac gtccgacctt caaacagatc gttcagctga tcg                43

<210> SEQ ID NO 54
<211> LENGTH: 46
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 54
ttggtagatt cagagatctg tttttcgatc agctgaacga tctgtt             46

```
<210> SEQ ID NO 55
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 55
aaacagatct ctgaatctac caaccacatc tactctaacc tggc            44

<210> SEQ ID NO 56
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 56
tgacggttcg gagagcagtt cgccaggtta gagtagatgt gg              42

<210> SEQ ID NO 57
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 57
aactgctctc cgaaccgtca gaaaccggtt gttgaccact ctg             43

<210> SEQ ID NO 58
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 58
gtagaaccaa cagagttgat acgaacagag tggtcaacaa ccggt           45

<210> SEQ ID NO 59
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 59
cgtatcaact ctgttggttc taccgcgtct tcttctcagc cg              42

<210> SEQ ID NO 60
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 60
aacgtcgtcg tgaaccagca gcggctgaga agaagacgcg                 40

<210> SEQ ID NO 61
```

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: Synthetic Primer

<400> SEQUENCE: 61
gttgtttcat atgtacgaag ttcagtggaa ag                                   32

<210> SEQ ID NO 62
<211> LENGTH: 36
<212> TYPE: DNA
<213> ORGANISM: Artificial Sequence
<220> FEATURE:
<223> OTHER INFORMATION: Description of Artificial Sequence: Synthetic Primer

<400> SEQUENCE: 62
gttgtttgtc gactaaacgt cgtcgtgaac cagcag                               36

<210> SEQ ID NO 63
<211> LENGTH: 34
<212> TYPE: DNA
<213> ORGANISM: Artificial Sequence
<220> FEATURE:
<223> OTHER INFORMATION: Description of Artificial Sequence: Synthetic Primer

<400> SEQUENCE: 63
gttcttgtcg actatttctg acggttcgga gagc                                 34

<210> SEQ ID NO 64
<211> LENGTH: 1325
<212> TYPE: DNA
<213> ORGANISM: Artificial Sequence
<220> FEATURE:
<221> NAME/KEY: CDS
<222> LOCATION: (88)..(1302)
<220> FEATURE:
<223> OTHER INFORMATION: Description of Artificial Sequence: Synthetic DNA Construct

<400> SEQUENCE: 64
taatacgact cactataggg gaattgtgag cggataacaa ttcccctcta gaaataattt     60
tgtttaactt taagaaggag atatacc atg ggt cac cac cat cac cat cat atg    114
                               Met Gly His His His His His His Met
                                 1               5 tac gaa gtt cag tgg aaa gtt gtt gaa gaa atc aac ggt aac aac tac      162
Tyr Glu Val Gln Trp Lys Val Val Glu Glu Ile Asn Gly Asn Asn Tyr
 10                  15                  20                  25 gtt tac atc gac ccg acc cag ctg ccg tac gac cac aaa tgg gag ttc      210
Val Tyr Ile Asp Pro Thr Gln Leu Pro Tyr Asp His Lys Trp Glu Phe
                 30                  35                  40 ccg cgt aac cgt ctg tct ttc ggt aaa acc ctg ggt gcg ggt gcg ttc      258
Pro Arg Asn Arg Leu Ser Phe Gly Lys Thr Leu Gly Ala Gly Ala Phe
             45                  50                  55 ggt aaa gtt gtt gaa gcg acc gcg tac ggt ctg atc aaa tct gac gcg      306
Gly Lys Val Val Glu Ala Thr Ala Tyr Gly Leu Ile Lys Ser Asp Ala
         60                  65                  70 gcg atg acc gtt gcg gtt aaa atg ctg aaa ccg tct gcg cac ctg acc      354
Ala Met Thr Val Ala Val Lys Met Leu Lys Pro Ser Ala His Leu Thr
     75                  80                  85 gaa cgt gaa gcg ctg atg tct gaa ctg aaa gtt ctg tct tac ctg ggt      402
Glu Arg Glu Ala Leu Met Ser Glu Leu Lys Val Leu Ser Tyr Leu Gly

```
                                                                 -continued
         90                 95                100                105
aac cac atg aac atc gtt aac ctg ctg ggt gcg tgc acc atc ggt ggt        450
Asn His Met Asn Ile Val Asn Leu Leu Gly Ala Cys Thr Ile Gly Gly
                            110                 115                120 ccg acc ctg gtt atc acc gaa tac tgc tgc tac ggt gac ctg ctg aac        498
Pro Thr Leu Val Ile Thr Glu Tyr Cys Cys Tyr Gly Asp Leu Leu Asn
                125                 130                 135 ttc ctg cgt cgt aaa cgt gac tct ttc atc tgc tct aaa cag gaa gac        546
Phe Leu Arg Arg Lys Arg Asp Ser Phe Ile Cys Ser Lys Gln Glu Asp
                140                 145                 150 cac gcg gaa gcg gcg ctg tac aaa aac ctg ctg cac tct aaa gaa tct        594
His Ala Glu Ala Ala Leu Tyr Lys Asn Leu Leu His Ser Lys Glu Ser
            155                 160                 165 tct tgc tct gac tct acc aac gaa tac atg gac atg aaa ccg ggt gtt        642
Ser Cys Ser Asp Ser Thr Asn Glu Tyr Met Asp Met Lys Pro Gly Val
170                 175                 180                 185 tct tac gtt gtt ccg acc aaa gcg gac aaa cgt cgt tct gtt cgt atc        690
Ser Tyr Val Val Pro Thr Lys Ala Asp Lys Arg Arg Ser Val Arg Ile
                190                 195                 200 ggt tct tac atc gaa cgt gac gtt acc ccg gcg atc atg gaa gac gac        738
Gly Ser Tyr Ile Glu Arg Asp Val Thr Pro Ala Ile Met Glu Asp Asp
                205                 210                 215 gaa ctg gcg ctg gac ctg gaa gac ctg ctg tct ttc tct tac cag gtt        786
Glu Leu Ala Leu Asp Leu Glu Asp Leu Leu Ser Phe Ser Tyr Gln Val
            220                 225                 230 gcg aaa ggt atg gcg ttc ctg gcg tct aaa aac tgc atc cac cgt gac        834
Ala Lys Gly Met Ala Phe Leu Ala Ser Lys Asn Cys Ile His Arg Asp
235                 240                 245 ctg gcg gcg cgt aac atc ctg ctg acc cac ggt cgt atc acc aaa atc        882
Leu Ala Ala Arg Asn Ile Leu Leu Thr His Gly Arg Ile Thr Lys Ile
250                 255                 260                 265 tgc gac ttc ggt ctg gcg cgt gac atc aaa aac gac tct aac tac gtt        930
Cys Asp Phe Gly Leu Ala Arg Asp Ile Lys Asn Asp Ser Asn Tyr Val
                270                 275                 280 gtt aaa ggt aac gcg cgt ctg ccg gtt aaa tgg atg gcg ccg gaa tct        978
Val Lys Gly Asn Ala Arg Leu Pro Val Lys Trp Met Ala Pro Glu Ser
                285                 290                 295 atc ttc aac tgc gtt tac acc ttc gaa tct gac gtt tgg tct tac ggt       1026
Ile Phe Asn Cys Val Tyr Thr Phe Glu Ser Asp Val Trp Ser Tyr Gly
            300                 305                 310 atc ttc ctg tgg gaa ctg ttc tct ctg ggt tct tct ccg tac ccg ggt       1074
Ile Phe Leu Trp Glu Leu Phe Ser Leu Gly Ser Ser Pro Tyr Pro Gly
        315                 320                 325 atg ccg gtt gac tct aaa ttc tac aaa atg atc aaa gaa ggt ttc cgt       1122
Met Pro Val Asp Ser Lys Phe Tyr Lys Met Ile Lys Glu Gly Phe Arg
330                 335                 340                 345 atg ctg tct ccg gaa cac gcg ccg gcg gaa atg tac gac atc atg aaa       1170
Met Leu Ser Pro Glu His Ala Pro Ala Glu Met Tyr Asp Ile Met Lys
            350                 355                 360 acc tgc tgg gac gcg gac ccg ctg aaa cgt ccg acc ttc aaa cag atc       1218
Thr Cys Trp Asp Ala Asp Pro Leu Lys Arg Pro Thr Phe Lys Gln Ile
            365                 370                 375 gtt cag ctg atc gaa aaa cag atc tct gaa tct acc aac cac atc tac       1266
Val Gln Leu Ile Glu Lys Gln Ile Ser Glu Ser Thr Asn His Ile Tyr
        380                 385                 390 tct aac ctg gcg aac tgc tct ccg aac cgt cag aaa tagtcgactg            1312
Ser Asn Leu Ala Asn Cys Ser Pro Asn Arg Gln Lys
        395                 400                 405 aaaaaggaag agt                                                         1325
```

<210> SEQ ID NO 65
<211> LENGTH: 405
<212> TYPE: PRT
<213> ORGANISM: Artificial Sequence
<220> FEATURE:
<223> OTHER INFORMATION: Description of Artificial Sequence: Synthetic
      Protein Construct

<400> SEQUENCE: 65

Met Gly His His His His His His Met Tyr Glu Val Gln Trp Lys Val
1               5                   10                  15

Val Glu Glu Ile Asn Gly Asn Asn Tyr Val Tyr Ile Asp Pro Thr Gln
            20                  25                  30

Leu Pro Tyr Asp His Lys Trp Glu Phe Pro Arg Asn Arg Leu Ser Phe
        35                  40                  45

Gly Lys Thr Leu Gly Ala Gly Ala Phe Gly Lys Val Val Glu Ala Thr
    50                  55                  60

Ala Tyr Gly Leu Ile Lys Ser Asp Ala Ala Met Thr Val Ala Val Lys
65                  70                  75                  80

Met Leu Lys Pro Ser Ala His Leu Thr Glu Arg Glu Ala Leu Met Ser
                85                  90                  95

Glu Leu Lys Val Leu Ser Tyr Leu Gly Asn His Met Asn Ile Val Asn
            100                 105                 110

Leu Leu Gly Ala Cys Thr Ile Gly Gly Pro Thr Leu Val Ile Thr Glu
        115                 120                 125

Tyr Cys Cys Tyr Gly Asp Leu Leu Asn Phe Leu Arg Arg Lys Arg Asp
    130                 135                 140

Ser Phe Ile Cys Ser Lys Gln Glu Asp His Ala Glu Ala Ala Leu Tyr
145                 150                 155                 160

Lys Asn Leu Leu His Ser Lys Glu Ser Ser Cys Ser Asp Ser Thr Asn
                165                 170                 175

Glu Tyr Met Asp Met Lys Pro Gly Val Ser Tyr Val Val Pro Thr Lys
            180                 185                 190

Ala Asp Lys Arg Arg Ser Val Arg Ile Gly Ser Tyr Ile Glu Arg Asp
        195                 200                 205

Val Thr Pro Ala Ile Met Glu Asp Asp Glu Leu Ala Leu Asp Leu Glu
    210                 215                 220

Asp Leu Leu Ser Phe Ser Tyr Gln Val Ala Lys Gly Met Ala Phe Leu
225                 230                 235                 240

Ala Ser Lys Asn Cys Ile His Arg Asp Leu Ala Ala Arg Asn Ile Leu
                245                 250                 255

Leu Thr His Gly Arg Ile Thr Lys Ile Cys Asp Phe Gly Leu Ala Arg
            260                 265                 270

Asp Ile Lys Asn Asp Ser Asn Tyr Val Val Lys Gly Asn Ala Arg Leu
        275                 280                 285

Pro Val Lys Trp Met Ala Pro Glu Ser Ile Phe Asn Cys Val Tyr Thr
    290                 295                 300

Phe Glu Ser Asp Val Trp Ser Tyr Gly Ile Phe Leu Trp Glu Leu Phe
305                 310                 315                 320

Ser Leu Gly Ser Ser Pro Tyr Pro Gly Met Pro Val Asp Ser Lys Phe
                325                 330                 335

Tyr Lys Met Ile Lys Glu Gly Phe Arg Met Leu Ser Pro Glu His Ala
            340                 345                 350

Pro Ala Glu Met Tyr Asp Ile Met Lys Thr Cys Trp Asp Ala Asp Pro

```
                355                 360                 365
Leu Lys Arg Pro Thr Phe Lys Gln Ile Val Gln Leu Ile Glu Lys Gln
    370                 375                 380
Ile Ser Glu Ser Thr Asn His Ile Tyr Ser Asn Leu Ala Asn Cys Ser
385                 390                 395                 400
Pro Asn Arg Gln Lys
                405

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 66

Lys Lys Lys Ser Pro Gly Glu Tyr Val Asn Ile Glu Phe Gly
  1               5                  10
```

COMPOUNDS MODULATING C-KIT AND C-FMS ACTIVITY AND USES THEREFOR

RELATED PATENT APPLICATIONS

This application claims the benefit of U.S. Provisional App. No. 60/682,063, entitled "Compounds Modulating c-Kit Activity and Uses Therefor", filed May 17, 2005, U.S. Provisional App. No. 60/682,051, entitled "Compounds Modulating c-Fms Activity and Uses Therefor", filed May 17, 2005, U.S. Provisional App. No. 60/682,042, entitled "Compounds Modulating c-Kit and c-Fms Activity and Uses Therefor", filed May 17, 2005, U.S. Provisional App. No. 60/692,750, entitled "Compounds Modulating c-Kit and c-Fms Activity and Uses Therefor", filed Jun. 22, 2005, and U.S. Provisional App. No. 60/692,960, entitled "Compounds and Methods for Kinase Modulation, and Indications Therefor", filed Jun. 22, 2005, all of which are incorporated herein by reference in their entireties and for all purposes.

FIELD OF THE INVENTION

This invention relates to ligands for c-kit and c-fms, and to methods for use thereof. The information provided is intended solely to assist the understanding of the reader. None of the information provided nor references cited is admitted to be prior art to the present invention. Each of the references cited is incorporated herein in its entirety and for any purpose.

BACKGROUND OF THE INVENTION

C-kit and c-fms are both type III transmembrane receptor protein tyrosine kinases (RPTKs) that regulate key signal transduction cascades that control cellular growth and proliferation. Both receptors have similar structural features comprising five extracellular immunoglobulin (IG) domains, a single transmembrane domain, and a split cytoplasmic kinase domain separated by a kinase insert segment.

c-Kit

The Stem Cell Factor (SCF) receptor c-kit plays an important role in the development of melanocytes and mast, germ and hematopoietic cells. Stem Cell Factor (SCF) is a protein encoded by the S1 locus, and has also been called "kit ligand" (KL) and mast cell growth factor (MGF), based on the biological properties used to identify it (reviewed in Tsujimura, Pathol Int 1996, 46:933-938; Loveland, et al., J. Endocrinol 1997, 153:337-344; Vliagoftis, et al., Clin Immunol 1997, 100:435-440; Broudy, Blood 1997, 90:1345-1364; Pignon, Hermatol Cell Ther 1997, 39:114-116; and Lyman, et al., Blood 1998, 91:1101-1134.). Herein the abbreviation SCF refers to the physiological ligand for c-kit.

SCF is synthesized as a transmembrane protein with a molecular weight of 220 or 248 Dalton, depending on alternative splicing of the mRNA to encode exon 6. The larger protein can be proteolytically cleaved to form a soluble, glycosylated protein which noncovalently dimerizes. Both the soluble and membrane-bound forms of SCF can bind to and activate c-kit. For example, in the skin, SCF is predominantly expressed by fibroblasts, keratinocytes, and endothelial cells, which modulate the activity of melanocytes and mast cells expressing c-kit. In bone, marrow stromal cells express SCF and regulate hematopoiesis of c-kit expressing stem cells. In the gastrointestinal tract, intestinal epithelial cells express SCF and affect the interstitial cells of Cajal and intraepithelial lymphocytes. In the testis, sertoli cells and granulosa cells express SCF which regulates spermatogenesis by interaction with c-kit on germ cells.

c-Fms

C-fms is a member of the family of genes originally isolated from the Susan McDonough strain of feline sarcoma viruses. The cellular proto-oncogene FMS (c-fms, cellular feline McDonough sarcoma) codes for the receptor for the macrophage colony-stimulating factor (M-CSF). C-fms is crucial for the growth and differentiation of the monocyte-macrophage lineage, and upon binding of M-CSF to the extracellular domain of c-fms, the receptor dimerizes and trans-autophosphorylates cytoplasmic tyrosine residues.

M-CSF, first described by Robinson and co-workers (Blood. 1969, 33:396-9), is a cytokine that controls the production, differentiation, and function of macrophages. M-CSF stimulates differentiation of progenitor cells to mature monocytes, and prolongs the survival of monocytes. Furthermore, M-CSF enhances cytotoxicity, superoxide production, phagocytosis, chemotaxis, and secondary cytokine production of additional factors in monocytes and macrophages. Examples of such additional factors include granulocyte colony stimulating factor (G-CSF), interleukin-6 (IL-6), and interleukin-8 (IL-8). M-CSF stimulates hematopoiesis, promotes differentiation and proliferation of osteoclast progenitor cells, and has profound effects on lipid metabolism. Furthermore, M-CSF is important in pregnancy. Physiologically, large amounts of M-CSF are produced in the placenta, and M-CSF is believed to play an essential role in trophoblast differentiation (Motoyoshi, Int J Hematol. 1998, 67:109-22). The elevated serum levels of M-CSF in early pregnancy may participate in the immunologic mechanisms responsible for the maintenance of the pregnancy (Flanagan & Lader, Curr Opin Hematol. 1998, 5:181-5).

Related to c-fms and c-kit are two platelet-derived growth factor receptors, alpha (i.e., pdgfra) and beta (pdgfrb) (PDGF). The gene coding for pdgfra is located on chromosome 4q11-q12 in the same region of chromosome 4 as the oncogene coding for c-kit. The genes coding for pdgfra and c-fms appear to have evolved from a common ancestral gene by gene duplication, inasmuch as these two genes are tandemly linked on chromosome 5. They are oriented head-to-tail with the 5-prime exon of the c-fms gene located only 500 bp from the last 3-prime exon of the gene coding for pdgfra. Most gastrointestinal stromal tumors (GIST) have activating mutations in c-kit, and most patients with GISTs respond well to Gleevec, which inhibits c-kit. Heinrich et al. (Science 2003, 299:708-10) have shown that approximately 35% of GISTs lacking c-kit mutations have intragenic activation mutations in the gene encoding pdgfra, and that tumors expressing c-kit or pdgfra are indistinguishable with respect to activation of downstream signaling intermediates and cytogenetic changes associated with tumor progression. Thus, c-kit and pdgfra mutations appear to be alternative and mutually exclusive oncogenic mechanisms in GISTs.

Similarly, the observation that production of M-CSF, the major macrophage growth factor, is increased in tissues during inflammation points out a role for c-fms in diseases, such as for example inflammatory diseases. More particularly, because elevated levels of M-CSF are found in the disease state, modulation of the activity of c-fms can ameliorate disease associated with increased levels of M-CSF.

Accordingly, there is need in the art for potent and specific inhibitors and modulators of c-kit and/or c-fms and methods for designing them.

SUMMARY OF THE INVENTION

The present invention relates to compounds active on c-kit, c-fms, or both c-kit and c-fms. In accordance with one aspect of the present invention, it has been discovered that in the treatment of diseases amenable to treatment by an effective amount of a modulator of either c-kit alone or c-fms alone, the efficacy of treatment can be enhanced if said compounds are dual inhibitors of both c-kit and c-fms. In particular, the invention provides methods of using compounds of Formula I as described below. Thus, the invention provides methods of using compounds that can be used therapeutically and/or prophylactically involving modulation of c-kit, c-fms, or both c-kit and c-fms.

The compounds of Formula I have the following structure:

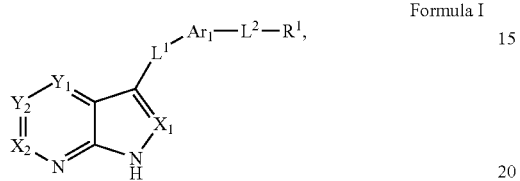

Formula I all salts, prodrugs, tautomers, and isomers thereof, wherein:
$X_1$ is N or $CR^2$, $X_2$ is N or $CR^6$, $Y_1$ is N or $CR^4$, and $Y_2$ is N or $CR^5$, provided, however, that not more than one of $X_2$, $Y_1$ and $Y_2$ is N;

$L^1$ is selected from the group consisting of optionally substituted lower alkylene, —S—, —O—, —C(O)—, —C(S)—, —S(O)—, —S(O)$_2$—, and —NR$^7$—;

$L^2$ is selected from the group consisting of a bond, optionally substituted lower alkylene, -(alk)$_a$-S-(alk)$_b$-, -(alk)$_a$-O-(alk)$_b$-, -(alk)$_a$-OC(O)-(alk)$_b$-, -(alk)$_a$-C(O)O-(alk)$_b$-, -(alk)$_a$-OC(S)-(alk)$_b$-, -(alk)$_a$-C(S)O-(alk)$_b$-, -(alk)$_a$-C(O)-(alk)$_b$-, -(alk)$_a$-C(S)-(alk)$_b$-, -(alk)$_a$-C(O)NR$^9$-(alk)$_b$-, -(alk)$_a$-OC(O)NR$^9$-(alk)$_b$-, -(alk)$_a$-OC(S)NR$^9$-(alk)$_b$-, -(alk)$_a$-C(S)NR$^9$-(alk)$_b$-, -(alk)$_a$-S(O)-(alk)$_b$-, -(alk)$_a$-S(O)-2-(alk)$_b$-, -(alk)$_a$-S(O)$_2$NR$^9$-(alk)$_b$-, -(alk)$_a$-NR$^9$-(alk)$_b$-, -(alk)$_a$-NR$^9$C(O)-(alk)$_b$-, -(alk)$_a$-NR$^9$C(S)-(alk)$_b$-, -(alk)$_a$-NR$^9$C(O)NR$^9$-(alk)$_b$-, -(alk)$_a$-NR$^9$C(S)NR$^9$-(alk)$_b$-, -(alk)$_a$-NR$^9$C(O)O-(alk)$_b$-, -(alk)$_a$-NR$^9$C(S)O-(alk)$_b$-, -(alk)$_a$-NR$^9$S(O)$_2$-(alk)$_b$-, and -(alk)$_a$-NR$^9$S(O)$_2$NR$^9$-(alk)$_b$-, wherein alk is optionally substituted $C_{1-3}$ alkylene and a and b are independently 0 or 1;

$R^1$ is selected from the group consisting of optionally substituted lower alkyl, optionally substituted cycloalkyl, optionally substituted heterocycloalkyl, optionally substituted aryl, and optionally substituted heteroaryl;

$R^2$, $R^4$, $R^5$ and $R^6$ are independently selected from the group consisting of hydrogen, halogen, optionally substituted lower alkyl, optionally substituted lower alkenyl, optionally substituted lower alkynyl, optionally substituted cycloalkyl, optionally substituted heterocloalkyl, optionally substituted aryl, optionally substituted heteroaryl, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —NR$^{10}$R$^{11}$, —NHR$^3$, —OR$^3$, —SR$^3$, —C(O)R$^3$, —C(S)R$^3$, —S(O)R$^3$, —S(O)$_2$R$^3$, —C(O)OR$^3$, —C(S)OR$^3$, —C(O)NHR$^3$, —C(O)NR$^3$R$^3$, —C(S)NHR$^3$, —C(S)NR$^3$R$^3$, —S(O)$_2$NHR$^3$, —S(O)$_2$NR$^3$R$^3$, —NHC(O)R$^3$, —NR$^3$C(O)R$^3$, —NHC(S)R$^3$, —NR$^3$C(S)R$^3$, —NHS(O)$_2$R$^3$, —NR$^3$S(O)$_2$R$^3$, —NHC(O)OR$^3$, —NR$^3$C(O)OH, —NR$^3$C(O)OR$^3$, —NHC(S)OR$^3$, —NR$^3$C(S)OH, —NR$^3$C(S)OR$^3$, —NHC(O)NHR$^3$, —NHC(O)NR$^3$R$^3$, —NR$^3$C(O)NH$_2$, —NR$^3$C(O)NHR$^3$, —NR$^3$C(O)NR$^3$R$^3$, —NHC(S)NHR$^3$, —NHC(S)NR$^3$R$^3$, —NR$^3$C(S)NH$_2$, —NR$^3$C(S)NHR$^3$, —NR$^3$C(S)NR$^3$R$^3$, —NHS(O)$_2$NHR$^3$, —NHS(O)$_2$NR$^3$R$^3$, —NR$^3$S(O)$_2$NH$_2$, —NR$^3$S(O)$_2$NHR$^3$, and —NR$^3$S(O)$_2$NR$^3$R$^3$;

$Ar_1$ is a 5 or 6 membered optionally substituted heteroarylene having the structure

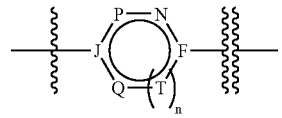

wherein

indicates the point of attachment of $L^1$ and

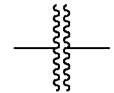

indicates the point of attachment of $L^2$, and wherein the indicated N is either =N— or —N=;

n is 0 or 1;

F and J are both C or one of F and J is C and the other of F and J is N;

P and Q are independently selected from CR, N, NR, O or S;

T is selected from CR or N;

wherein
when n is 1, F and J are C, and P, T and Q are CR, or any one of P, T and Q is N and the other two of P, T and Q are CR,
when n is 0 and F and J are both C, then one of P and Q are CR, N or NR and the other of P and Q is C, N, NR, O or S, provided both P and Q are not CR,
when n is 0, one of F and J is N and the other of F and J is C, then one of P and Q is N and the other of P and Q is CR or both P and Q are CR, and
R is hydrogen or an optional substituent as defined herein for optionally substituted heteroarylene that provides a stable compound;

$R^3$ at each occurrence is independently selected from the group consisting of optionally substituted lower alkyl, optionally substituted lower alkenyl, provided, however, that no alkene carbon thereof is bound to any —C(O)—, —C(S)—, —S(O)—, —S(O)$_2$—, —O—, —S—, or —N— of any of —OR$^3$, —SR$^3$, —C(O)R$^3$, —C(S)R$^3$, —S(O)R$^3$, —S(O)$_2$R$^3$, —C(O)OR$^3$, —C(S)OR$^3$, —C(O)NHR$^3$, —C(O)NR$^3$R$^3$, —C(S)NHR$^3$, —C(S)NR$^3$R$^3$, —S(O)$_2$NHR$^3$, —S(O)$_2$NR$^3$R$^3$, —NHR$^3$, —NHC(O)R$^3$, —NR$^3$C(O)R$^3$, —NHC(S)R$^3$, —NR$^3$C(S)R$^3$, —NHS(O)$_2$R$^3$, —NR$^3$S(O)$_2$R$^3$, —NHC(O)OR$^3$, —NR$^3$C(O)OH, —NR$^3$C(O)OR$^3$, —NHC(S)OR$^3$, —NR$^3$C(S)OH, —NR$^3$C(S)OR$^3$, —NHC(O)

NHR³, —NHC(O)NR³R³, —NR³C(O)NH₂, —NR³C(O)NHR³, —NR³C(O)NR³R³, —NHC(S)NHR³, —NHC(S)NR³R³, —NR³C(S)NH₂, —NR³C(S)NHR³, —NR³C(S)NR³R³, —NHS(O)₂NHR³, —NHS(O)₂NR³R³, —NR³S(O)₂NH₂, —NR³S(O)₂NHR³, or —NR³S(O)₂NR³R³, optionally substituted lower alkynyl, provided, however, that no alkyne carbon thereof is bound to any —C(O)—, —C(S)—, —S(O)—, —S(O)₂—, —O—, —S—, or —N— of any of —OR³, —SR³, —C(O)R³, —C(S)R³, —S(O)R³, —S(O)₂R³, —C(O)OR³, —C(S)OR³, —C(O)NHR³, —C(O)NR³R³, —C(S)NHR³, —C(S)NR³R³, —S(O)₂NHR³, —S(O)₂NR³R³, —NHR³, —NHC(O)R³, —NR³C(O)R³, —NHC(S)R³, —NR³C(S)R³, —NHS(O)₂R³, —NR³S(O)₂R³, —NHC(O)OR³, —NR³C(O)OH, —NR³C(O)OR³, —NHC(S)OR³, —NR³C(S)OH, —NR³C(S)OR³, —NHC(O)NHR³, —NHC(O)NR³R³, —NR³C(O)NH₂, —NR³C(O)NHR³, —NR³C(O)NR³R³, —NHC(S)NHR³, —NHC(S)NR³R³, —NR³C(S)NH₂, —NR³C(S)NHR³, —NR³C(S)NR³R³, —NHS(O)₂NHR³, —NHS(O)₂NR³R³, —NR³S(O)₂NH₂, —NR³S(O)₂NHR³, or —NR³S(O)₂NR³R³, optionally substituted cycloalkyl, optionally substituted heterocycloalkyl, optionally substituted aryl, and optionally substituted heteroaryl;

R⁷ is selected from the group consisting of hydrogen, optionally substituted lower alkyl, optionally substituted cycloalkyl, optionally substituted heterocycloalkyl, optionally substituted aryl, optionally substituted heteroaryl, —C(O)R⁸, and —S(O)₂R⁸;

R⁸ is selected from the group consisting of optionally substituted lower alkyl, optionally substituted cycloalkyl, optionally substituted heterocycloalkyl, optionally substituted aryl and optionally substituted heteroaryl;

R⁹ at each occurrence is independently selected from the group consisting of hydrogen, lower alkyl, and lower alkyl substituted with one or more substituents selected from the group consisting of fluoro, —OH, —NH₂, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and —NR¹²R¹³, provided, however, that when R⁹ is substituted lower alkyl, any substitution on the alkyl carbon bound to the —N— of —NR⁹— is fluoro;

R¹⁰ and R¹¹ at each occurrence are independently selected from the group consisting of optionally substituted lower alkyl, optionally substituted lower alkenyl, provided, however, that no alkene carbon thereof is bound to the nitrogen of —NR¹⁰R¹¹, optionally substituted lower alkynyl, provided, however, that no alkyne carbon thereof is bound to the nitrogen of —NR¹⁰R¹¹, optionally substituted cycloalkyl, optionally substituted heterocycloalkyl, optionally substituted aryl, and optionally substituted heteroaryl; or R¹⁰ and R¹¹ together with the nitrogen to which they are attached form a monocyclic 5-7 membered optionally substituted heterocycloalkyl or a monocyclic 5 or 7 membered optionally substituted nitrogen containing heteroaryl; and R¹² and R¹³ combine with the nitrogen to which they are attached to form a 5-7 membered heterocycloalkyl or 5-7 membered heterocycloalkyl substituted with one or more substituents selected from the group consisting of fluoro, —OH, —NH₂, lower alkyl, fluoro substituted lower alkyl, lower alkoxy, fluoro substituted lower alkoxy, lower alkylthio, and fluoro substituted lower alkylthio;

provided, however that when compounds have the structure

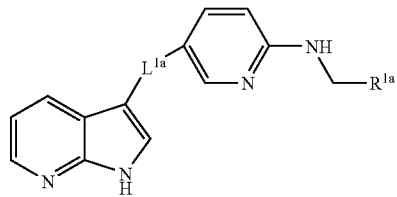

and L¹ᵃ is —CH₂—, —CH(OH)—, or —C(O)—, then R¹ᵃ is not phenyl, 4-trifluoromethyl-phenyl, 4-methoxyphenyl, 4-chloro-phenyl, 4-fluoro-phenyl, 4-methylphenyl, 3-fluoro-phenyl or thiophen-2-yl and compounds do not have the structure

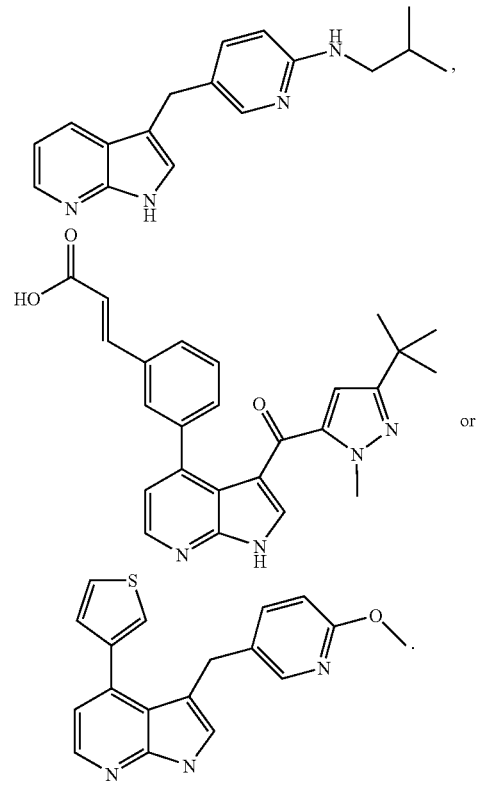

In reference to Formula I, the core structure shown above with X₁, X₂, Y₁ and Y₂ as CH and with L¹-Ar₁-L²-R¹ replaced with H is referred to as the "azaindole core." For that azaindole core, reference to ring atoms or ring positions is as shown in the following structure:

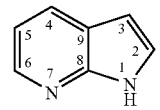

In one embodiment of compounds of Formula I, compounds have a structure selected from the following:

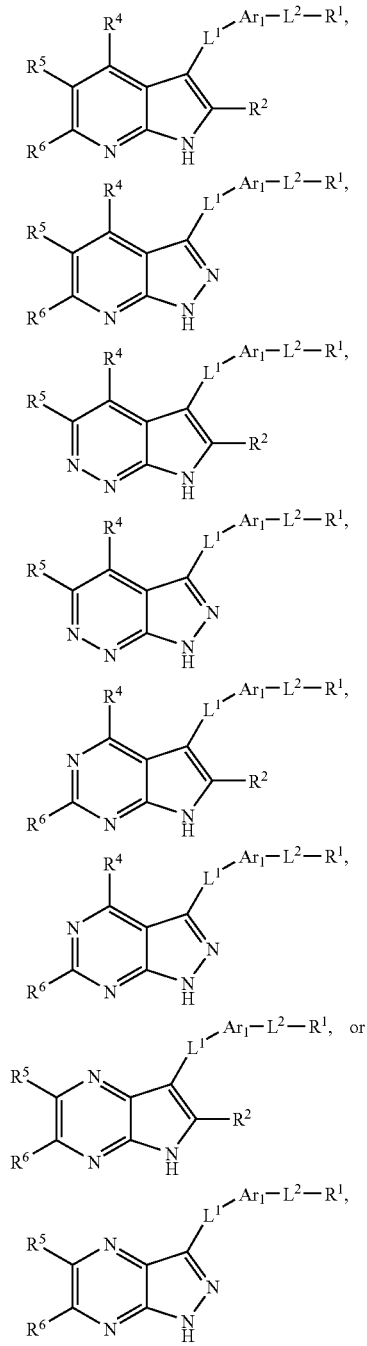

wherein $L^1$, $Ar_1$, $L^2$, $R^1$, $R^2$, $R^4$, $R^5$ and $R^6$ are as defined for Formula I.

In one embodiment of compounds of Formula I, $X_1$ and $X_2$ are N or CH. In another embodiment, $X_1$, $X_2$ and $Y_1$ are N or CH, where in a further embodiment, $Y_2$ is $CR^5$ and $R^5$ is other than hydrogen. In another embodiment, $X_1$, $X_2$ and $Y_2$ are N or CH, where in a further embodiment $Y_1$ is $CR^4$ and $R^4$ is other than hydrogen. In another embodiment, $X_1$, $X_2$ and $Y_1$ are CH, where in a further embodiment, $Y_2$ is $CR^5$ and $R^5$ is other than hydrogen. In another embodiment, $X_1$, $X_2$ and $Y_2$ are CH, where in a further embodiment $Y_1$ is $CR^4$ and $R^4$ is other than hydrogen.

In one embodiment of compounds of Formula I, wherein $X_1$, $X_2$, $Y_1$ and $Y_2$ are independently $CR^2$, $CR^6$, $CR^4$ and $CR^5$ respectively, one of $R^4$ or $R^5$ is other than hydrogen, preferably where $R^2$ and $R^6$ are hydrogen. In one embodiment, wherein $X_1$, $X_2$, $Y_1$ and $Y_2$ are independently $CR^2$, $CR^6$, $CR^4$ and $CR^5$ respectively, $R^2$, $R^5$ and $R^6$ are hydrogen and $R^4$ is other than hydrogen. In one embodiment, wherein $X_1$, $X_2$, $Y_1$ and $Y_2$ are independently $CR^2$, $CR^6$, $CR^4$ and $CR^5$ respectively, $R^2$, $R^4$ and $R^6$ are hydrogen and $R^5$ is other than hydrogen.

In one embodiment of compounds of Formula I, $X_1$ and $X_2$ are N or CH, preferably wherein both $X_1$ and $X_2$ are CH.

In one embodiment of compounds of Formula I, $L^1$ is selected from the group consisting of —S—, —O—, lower alkylene, —C(O)—, —C(S)—, —S(O)—, —S(O)$_2$—, and —NR$^7$—, wherein lower alkylene is optionally substituted with fluoro, and wherein when $L^2$ is optionally substituted lower alkylene or comprises optionally substituted $C_{1-3}$ alkylene, the alkylene is optionally substituted with fluoro or lower alkyl. In one embodiment, $L^1$ is selected from the group consisting of —S—, —O—, —CH$_2$—, —CF$_2$—, —C(O)—, —C(S)—, —S(O)—, —S(O)$_2$—, and —NH—.

In one embodiment of compounds of Formula I, $L^2$ is selected from the group consisting of a bond, optionally substituted lower alkylene, —O-(alk)$_b$-, —OC(O)-(alk)$_b$-, —C(O)O-(alk)$_b$-, —OC(S)-(alk)$_b$-, —C(S)O-(alk)$_b$-, —C(O)-(alk)$_b$-, —C(S)-(alk)$_b$-, —C(O)NR$^9$-(alk)$_b$-, —OC(O)NR$^9$-(alk)$_b$-, —OC(S)NR$^9$-(alk)$_b$-, —C(S)NR$^9$-(alk)$_b$-, —S(O)-(alk)$_b$-, —S(O)$_2$-(alk)$_b$-, S(O)$_2$NR$^9$-(alk)$_b$-, —NR$^9$-(alk)$_b$-, —NR$^9$C(O)-(alk)$_b$-, —NR$^9$C(O)O-(alk)$_b$-, —NR$^9$C(S)-(alk)$_b$-, —NR$^9$C(S)O-(alk)$_b$-, —NR$^9$C(O)NR$^9$-(alk)$_b$-, —NR$^9$C(S)NR$^9$-(alk)$_b$-, —NR$^9$S(O)$_2$-(alk)$_b$-, and —NR$^9$S(O)$_2$NR$^9$-(alk)$_b$-.

Further to any of the above embodiments of Formula I, when $L^1$ is substituted lower alkylene or when $L^2$ is substituted lower alkylene or comprises substituted $C_{1-3}$ alkylene, the alkylene is substituted with one or more, preferably 1, 2, or 3 substituents selected from the group consisting of fluoro, —OH, —NH$_2$, lower alkoxy, lower alkylthio, mono-alkylamino, di-alkylamino, and —NR$^{12}$R$^{13}$, wherein the alkyl chain(s) of lower alkoxy, lower alkylthio, mono-alkylamino or di-alkylamino are optionally substituted with one or more, preferably 1, 2, or 3 substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, or cycloalkylamino.

In one embodiment of the compounds of Formula I, the variables P, J, Q, T, F, and n are selected to provide structures of $Ar_1$ selected from the group consisting of

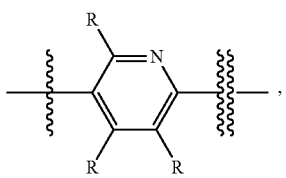

-continued

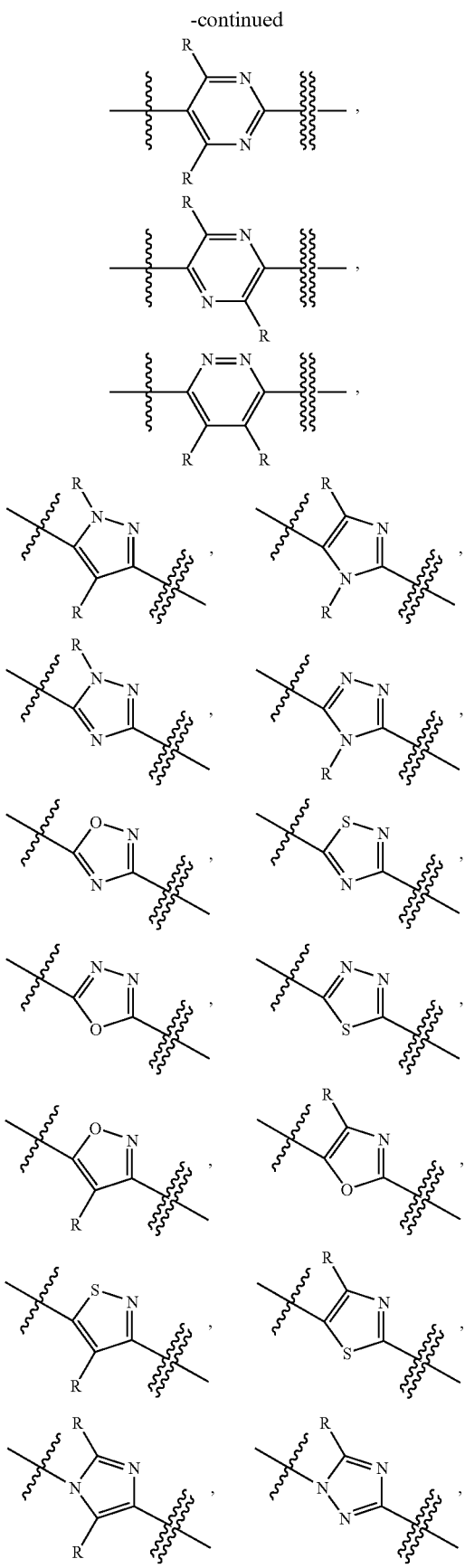

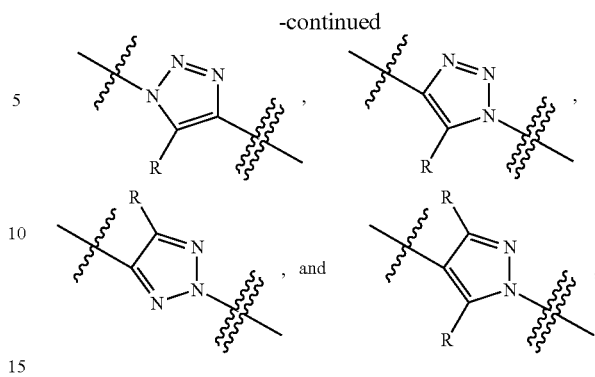

where each R is independently hydrogen or an optional substituent as defined herein for optionally substituted heteroaryl.

The compounds of Formula I, and all sub-embodiments detailed herein, may be used to treat a subject suffering from or at risk of a Kit and/or Fms protein kinase mediated disease or condition, such as those disclosed in this application.

In one embodiment, a compound of Formula I has a structure according to the following sub-generic structure, Formula Ia,

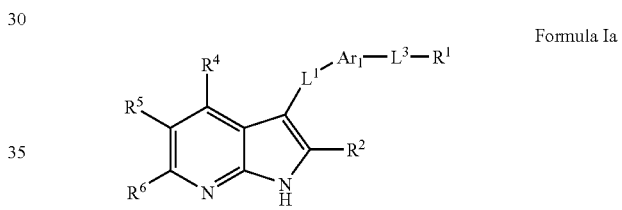

Formula Ia all salts, prodrugs, tautomers, and isomers thereof, wherein $L^1$, $Ar_1$, $R^1$, $R^2$, $R^4$, $R^5$ and $R^6$ are as defined for Formula I;

$L^3$ is selected from the group consisting of a bond, optionally substituted lower alkylene, —O-(alk)$_b$-, —S-(alk)$_b$-, —NR$^{14}$-(alk)$_b$-, —C(O)-(alk)$_b$-, —C(S)-(alk)$_b$-, —S(O)-(alk)$_b$-, —S(O)$_2$-(alk)$_b$-, —NR$^{14}$C(O)-(alk)$_b$-, —C(O)NR$^{14}$-(alk)$_b$-, —S(O)$_2$NR$^{14}$-(alk)$_b$-, —NR$^{14}$S(O)$_2$-(alk)$_b$-, —NR$^{14}$C(O)NR$^{14}$-(alk)$_b$-, —NR$^{14}$C(S)NR$^{14}$-(alk)$_b$-, and —NR$^{14}$S(O)$_2$NR$^{14}$-(alk)$_b$-;

alk is optionally substituted lower alkylene;

b is 0 or 1; and $R^{14}$ is hydrogen or lower alkyl.

In another embodiment of compounds of Formula Ia, $R^2$, $R^5$ and $R^6$ are hydrogen, further wherein $R^4$ is other than hydrogen. In another embodiment, $R^2$, $R^4$ and $R^6$ are hydrogen, further wherein $R^5$ is other than hydrogen.

The compounds of Formula Ia, and all sub-embodiments detailed herein, may be used to treat a subject suffering from or at risk of a Kit and/or Fms protein kinase mediated disease or condition, such as those disclosed in this application.

In particular embodiments the compound of Formula I has a structure according to the following sub-generic structure, Formula Ib, Formula Ib

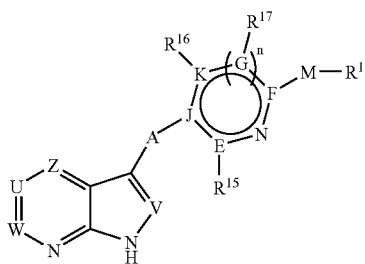

all salts, prodrugs, tautomers, and isomers thereof, wherein:
V and W are independently selected from the group consisting of N and CH;
U and Z are independently selected from the group consisting of N and $CR^{18}$, provided, however, that not more than one of W, U and Z is N;
A is selected from the group consisting of $-CR^{19}R^{20}-$, $-C(O)-$, $-C(S)-$, $-S-$, $-S(O)-$, $-S(O)_2-$, $-NR^{21}-$, and $-O-$;
n is 0 or 1;
F and J are both C or one of F and J is C and the other of F and J is N;
E and K are selected from C, N, O or S;
G is selected from C or N;
wherein
when n is 1, F and J are C, and E, G and K are C, or any one of E, G and K is N and the other two of E, G and K are C, provided that when E, G or K is N, $R^{15}$, $R^{17}$ and $R^{16}$, respectively, are absent,
when n is 0 and F and J are both C, then one of E and K is C or N and the other of E and K is C, N, O or S, provided both E and K are not C, and provided that when both E and K are N, one of $R^{15}$ and $R^{16}$ is absent, and provided that when one of E and K are N and the other is O or S, $R^{15}$ and $R^{16}$ are absent,
when n is 0, one of F and J is N and the other of F and J is C, then one of E and K is N and the other of E and K is C, or both E and K are C, provided that when E is N, $R^{15}$ is absent and when K is N, $R^{16}$ is absent;
$R^1$ is selected from the group consisting of optionally substituted lower alkyl, optionally substituted cycloalkyl, optionally substituted heterocycloalkyl, optionally substituted aryl and optionally substituted heteroaryl;
$R^{15}$ is selected from the group consisting of hydrogen, optionally substituted lower alkyl, $-OR^{22}$, $-SR^{22}$ and halogen when E is C, is absent when E is O or S or when n=1 and E is N, and is absent or selected from the group consisting of hydrogen and optionally substituted lower alkyl when n=0 and E is N;
$R^{16}$ is selected from the group consisting of hydrogen, optionally substituted lower alkyl, $-OR^{22}$, $-SR^{22}$ and halogen when K is C, is absent when K is O or S or when n=1 and K is N, and is absent or selected from the group consisting of hydrogen and optionally substituted lower alkyl when n=0 and K is N;
$R^{17}$ is selected from the group consisting of hydrogen, optionally substituted lower alkyl, $-OR^{22}$, $-SR^{22}$ and halogen when G is C, or is absent when G is N;
$R^{18}$ is selected from the group consisting of hydrogen, halogen, optionally substituted lower alkyl, optionally substituted aryl, optionally substituted heteroaryl, $-OH$, $-NH_2$, $-NO_2$, $-CN$, $-NHC(O)NH_2$, $-NHC(S)NH_2$, $-NHS(O)_2NH_2$, $-NR^{24}R^{25}$, $-NHR^{23}$, $-OR^{23}$, $-SR^{23}$, $-NHC(O)R^{23}$, $-NR^{23}C(O)R^{23}$, $-NHC(S)R^{23}$, $-NR^{23}C(S)R^{23}$, $-NHS(O)_2R^{23}$, $-NR^{23}S(O)_2R^{23}$, $-NHC(O)NHR^{23}$, $-NR^{23}C(O)NH_2$, $-NR^{23}C(O)NHR^{23}$, $-NHC(O)NR^{23}R^{23}$, $-NR^{23}C(O)NR^{23}R^{23}NHC(S)NHR^{23}$, $-NR^{23}C(S)NH_2$, $-NR^{23}C(S)NHR^{23}$, $-NHC(S)NR^{23}R^{23}$, $-NR^{23}C(S)NR^{23}R^{23}$, $-NHS(O)_2NHR^{23}$, $-NR^{23}S(O)_2NH_2$, $-NR^{23}S(O)_2NHR^{23}$, $-NHS(O)_2NR^{23}R^{23}$ and $-NR^{23}S(O)_2NR^{23}R^{23}$;

M is selected from the group consisting of a bond, $-(CR^{19}R^{20})_u-$, $-(CR^{19}R^{20})_t-C(O)-(CR^{19}R^{20})_s-$, $-(CR^{19}R^{20})_t-C(S)-(CR^{19}R^{20})_s-$, $-(CR^{19}R^{20})_t-C(O)O-(CR^{19}R^{20})_s-$, $-(CR^{19}R^{20})_t-C(S)O-(CR^{19}R^{20})_s-$, $-(CR^{19}R^{20})_t-C(O)NR^{26}-(CR^{19}R^{20})_s-$, $-(CR^{19}R^{20})_t-C(S)NR^{26}-(CR^{19}R^{20})_s-$, $-(CR^{19}R^{20})_t-S(O)-(CR^{19}R^{20})_s-$, $-(CR^{19}R^{20})_t-S(O)_2-(CR^{19}R^{20})_s-$, $-(CR^{19}R^{20})_t-S(O)_2NR^{26}-(CR^{19}R^{20})_s-$, $-(CR^{19}R^{20})_t-O-(CR^{19}R^{20})_s-$, $-(CR^{19}R^{20})_t-OC(O)-(CR^{19}R^{20})_s-$, $-(CR^{19}R^{20})_t-OC(S)-(CR^{19}R^{20})_s-$, $-(CR^{19}R^{20})_t-OC(O)NR^{26}-(CR^{19}R^{20})_s-$, $-(CR^{19}R^{20})_t-OC(S)NR^{26}-(CR^{19}R^{20})_s-$, $-(CR^{19}R^{20})_t-S-(CR^{19}R^{20})_s-$, $-(CR^{19}R^{20})_t-NR^{26}-(CR^{19}R^{20})_s-$, $-(CR^{19}R^{20})_t-NR^{26}C(O)-(CR^{19}R^{20})_s-$, $-(CR^{19}R^{20})_t-NR^{26}C(S)-(CR^{19}R^{20})_s-$, $-(CR^{19}R^{20})_t-NR^{26}C(O)O-(CR^{19}R^{20})_s-$, $-(CR^{19}R^{20})_t-NR^{26}C(S)O-(CR^{19}R^{20})_s-$, $-(CR^{19}R^{20})_t-NR^{26}C(O)NR^{26}-(CR^{19}R^{20})_s-$, $-(CR^{19}R^{20})_t-NR^{26}C(S)NR^{26}-(CR^{19}R^{20})_s-$, $-(CR^{19}R^{20})_t-NR^{26}S(O)_2-(CR^{19}R^{20})_s-$, and $-(CR^{19}R^{20})_t-NR^{26}S(O)_2NR^{26}-(CR^{19}R^{20})_s-$;

wherein $R^{19}$ and $R^{20}$ at each occurrence are independently selected from the group consisting of hydrogen, fluoro, $-OH$, $-NH_2$, lower alkyl, lower alkoxy, lower alkylthio, mono-alkylamino, di-alkylamino, and $-NR^{27}R^{28}$, wherein the alkyl chain(s) of lower alkyl, lower alkoxy, lower alkylthio, mono-alkylamino, or di-alkylamino are optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino, and cycloalkylamino; or any two of $R^{19}$ and $R^{20}$ on the same or different carbons combine to form a 3-7 membered monocyclic cycloalkyl or 5-7 membered monocyclic heterocycloalkyl and any others of $R^{19}$ and $R^{20}$ are independently selected from the group consisting of hydrogen, fluoro, $-OH$, $-NH_2$, lower alkyl, lower alkoxy, lower alklylthio, mono-alkylamino, di-alkylamino, and $-NR^{27}R^{28}$, wherein the alkyl chain(s) of lower alkyl, lower alkoxy, lower alkylthio, mono-alkylamino, or di-alkylamino are optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino, and cycloalkylamino, and wherein the monocyclic cycloalkyl or monocyclic heterocycloalkyl are optionally substituted with one or more substituents selected from the group consisting of halogen, $-OH$, $-NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^{21}$ and $R^{22}$ at each occurrence are independently hydrogen or optionally substituted lower alkyl;

$R^{23}$ at each occurrence is independently selected from the group consisting of optionally substituted lower alkyl, optionally substituted lower alkenyl, provided, however, that no alkene carbon thereof is bound to any —C(O)—, —C(S)—, —S(O)$_2$—, —O—, —S—, or —N— of any of —NHR$^{23}$, —OR$^{23}$, —SR$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$, —NR$^{23}$S(O)$_2$R$^{23}$, —NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, or —NR$^{23}$S(O)$_2$NR$^{23}$R$^{23}$, optionally substituted lower alkynyl, provided, however, that no alkyne carbon thereof is bound to any —C(O)—, —C(S)—, —S(O)—, —S(O)$_2$—, —O—, —S—, or —N— of any of —NHR$^{23}$, —OR$^{23}$, —SR$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$, —NR$^{23}$S(O)$_2$R$^{23}$, —NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$—NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, or —NR$^{23}$S(O)$_2$NR$^{23}$R$^{23}$, optionally substituted cycloalkyl, optionally substituted heterocycloalkyl, optionally substituted aryl, and optionally substituted heteroaryl;

$R^{24}$ and $R^{25}$ at each occurrence are independently selected from the group consisting of optionally substituted lower alkyl, optionally substituted lower alkenyl, provided, however, that no alkene carbon thereof is bound to the nitrogen of —NR$^{24}$R$^{25}$, optionally substituted lower alkynyl, provided, however, that no alkyne carbon thereof is bound to the nitrogen of —NR$^{24}$R$^{25}$, optionally substituted cycloalkyl, optionally substituted heterocycloalkyl, optionally substituted aryl, and optionally substituted heteroaryl; or $R^{24}$ and $R^{25}$ together with the nitrogen to which they are attached form a monocyclic 5-7 membered optionally substituted heterocycloalkyl or a monocyclic 5 or 7 membered optionally substituted nitrogen containing heteroaryl;

$R^{26}$ at each occurrence is independently selected from the group consisting of hydrogen, lower alkyl, and lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and —NR$^{27}$R$^{28}$, provided, however, that when R$^{26}$ is substituted lower alkyl, any substitution on the lower alkyl carbon bound to the —N— of —NR$^{26}$— is fluoro;

$R^{27}$ and $R^{28}$ combine with the nitrogen to which they are attached to form a 5-7 membered heterocycloalkyl or 5-7 membered heterocycloalkyl substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio;

u is 1-6;

t is 0-3; and s is 0-3;

provided that when V, W, U and Z are CH, n=1, E, F, G, J, and K are C, $R^{15}$, $R^{16}$ and $R^{17}$ are H, A is —CH$_2$—, —CH(OH)—, or —C(O)—, and M is —NHCH$_2$—, then R$^1$ is not phenyl, 4-trifluoromethyl-phenyl, 4-methoxy-phenyl, 4-chloro-phenyl, 4-fluoro-phenyl, 4-methyl-phenyl, 3-fluoro-phenyl or thiophen-2-yl, when V, W, U and Z are CH, n=1, E, F, G, J, and K are C, $R^{15}$, $R^{16}$ and $R^{17}$ are H, and A is —CH$_2$—, then M—R$^1$ is not —NHCH$_2$CH(CH$_3$)$_2$, when V, W, and U are CH, n=1, E, F, G, J, and K are C, $R^{15}$, $R^{16}$ and $R^{17}$ are H, A is —CH$_2$—, M—R$^1$ is —OCH$_3$, and Z is CR$^{18}$, then R$^{18}$ is not thiophen-3-yl, and when V, W, and U are CH, n=0, F, J, and K are C, E is N, $R^{15}$ is CH$_3$, $R^{16}$ is H, A is —C(O)—, M—R$^1$ is —CH(CH$_3$)$_3$, and Z is CR$^{18}$, then R$^{18}$ is not 3-((E)-2-carboxy-vinyl)phenyl.

In one embodiment of the compounds of Formula Ib, E, J, K, G, F, n, $R^{15}$, $R^{16}$ and $R^{17}$ are selected to provide structures selected from the group consisting of

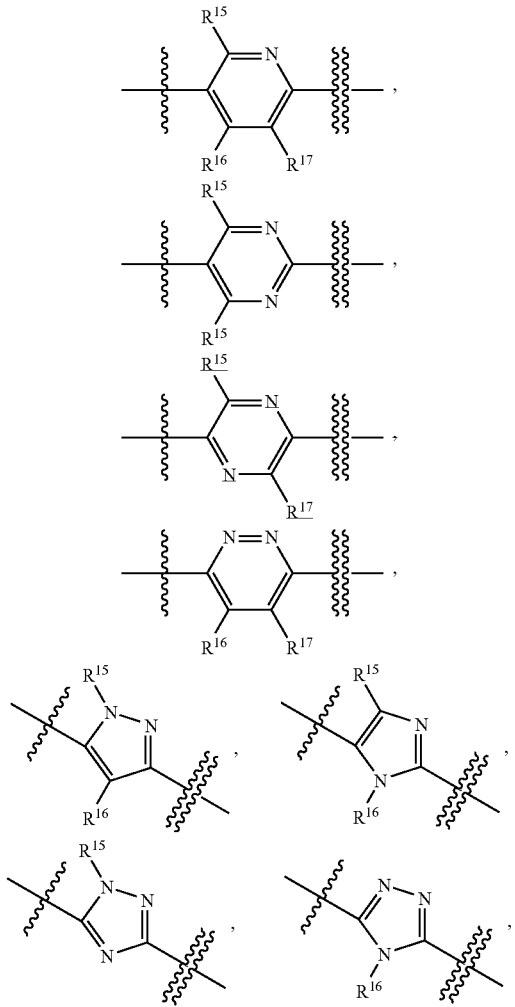

-continued

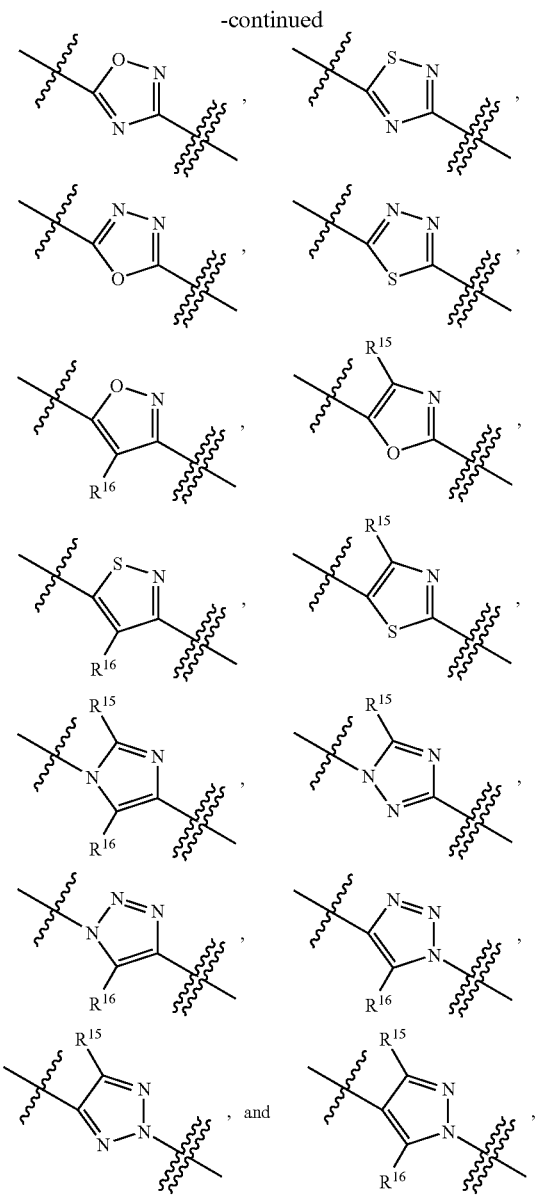

wherein $R^{15}$, $R^{16}$ and $R^{17}$ are as defined for compounds of Formula Ib and wherein

indicates the point of attachment of A and

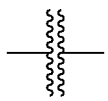

indicates the point of attachment of M.

In one embodiment of compounds of Formula Ib, M is selected from the group consisting of —O—$(CR^{19}R^{20})_s$—, —S—$(CR^{19}R^{20})_s$—, —OC(O)—$(CR^{19}R^{20})_s$—, —OC(S)—$(CR^{19}R^{20})_s$—, —OC(O)$NR^{26}$—$(CR^{19}R^{20})_s$—, —OC(S)$NR^{26}$—$(CR^{19}R^{20})_s$—, —C(O)$NR^{26}$—$(CR^{19}R^{20})_s$—, —C(S)$NR^{26}$—$(CR^{19}R^{20})_s$—, —S(O)$_2$$NR^{26}$—$(CR^{19}R^{20})_s$—, —$NR^{26}$—$(CR^{19}R^{20})_s$—, —$NR^{26}$C(O)—$(CR^{19}R^{20})_s$—, —$NR^{26}$C(S)—$(CR^{19}R^{20})_s$—, —$NR^{26}$C(O)O—$(CR^{19}R^{20})_s$—, —$NR^{26}$C(S)O—$(CR^{19}R^{20})_s$—, —$NR^{26}$C(O)$NR^{26}$—$(CR^{19}R^{20})_s$—, —$NR^{26}$C(S)$NR^{26}$—$(CR^{19}R^{20})_s$—, —$NR^{26}$S(O)$_2$—$(CR^{19}R^{20})_s$—, and —$NR^{26}$S(O)$_2$$NR^{26}$—$(CR^{19}R^{20})_s$—.

In one embodiment of compounds of Formula Ib, $R^{26}$ at each occurrence is independently selected from the group consisting of hydrogen, lower alkyl, or lower alkyl substituted with 1, 2, or 3 substituents selected from the group consisting of fluoro, —OH, —$NH_2$, alkoxy, lower alkylthio, mono-alkylamino, di-alkylamino and cycloalkylamino, provided that any substitution on the carbon that is bound to the nitrogen of —$NR^{26}$ is fluoro.

In one embodiment of compounds of Formula Ib, $R^1$ is selected from the group consisting of optionally substituted aryl and optionally substituted heteroaryl.

In one embodiment of the compounds of Formula Ib, Z is N or CH, n is 1, E-$R^{15}$ is N or CH, K—$R^{16}$ is N or CH, and G-$R^{17}$ is N or CH, provided no more than one of E-$R^{15}$, K—$R^{16}$ and G-$R^{17}$ is N. In one embodiment, Z is N or CH, n is 1, and E-$R^{15}$, K—$R^{16}$ and G-$R^{17}$ are CH.

In one embodiment of the compounds of Formula Ib, V, W and Z are CH, U is $CR^{18}$, n is 1, E-$R^{15}$ is N or CH, K—$R^{16}$ is N or CH, and G-$R^{17}$ is N or CH, provided no more than one of E-$R^{15}$, K—$R^{16}$ and G-$R^{17}$ is N. In another embodiment, V, W and Z are CH, U is $CR^{18}$, n is 1, and E-$R^{15}$, K—$R^{16}$ and G-$R^{17}$ are CH.

In one embodiment of the compounds of Formula Ib, Z is N or CH, n is 1, E-$R^{15}$, K—$R^{16}$ and G-$R^{17}$ are CH, A is —$CH_2$—, M is —$NHCH_2$—, further wherein $R^1$ is optionally substituted phenyl. In another embodiment, V, Z, U and W are CH, n is 1, E-$R^{15}$ is N or CH, K—$R^{16}$ is N or CH, and G-$R^{17}$ is N or CH, provided no more than one of E-$R^{15}$, K—$R^{16}$ and G-$R^{17}$ is N.

In one embodiment of the compounds of Formula Ib, Z is N or CH, n is 1, E-$R^{15}$ is N or CH, K—$R^{16}$ is N or CH, and G-$R^{17}$ is N or CH, provided no more than one of E-$R^{15}$, K—$R^{16}$ and G-$R^{17}$ is N, and $R^1$ is phenyl optionally substituted with one or more substituents selected from the group consisting of halogen, —OH, —$NH_2$, —$NO_2$, —CN, optionally substituted lower alkyl and —$OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl.

In one embodiment of the compounds of Formula Ib, V, Z, U and W are CH, n is 1, E-$R^{15}$, K—$R^{16}$ and Q-$R^{17}$ are CH, A is —$CH_2$—, M is —$NHCH_2$—, and $R^1$ is optionally substituted phenyl, further wherein $R^1$ is phenyl optionally substituted with one or more substituents selected from the group consisting of halogen, —OH, —$NH_2$, —$NO_2$, —CN, optionally substituted lower alkyl and —$OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl.

In one embodiment of the compounds of Formula Ib, V, W and Z are CH, U is $CR^{18}$, n is 1, E-$R^{15}$, K—$R^{16}$ and G-$R^{17}$ are CH, A is —$CH_2$—, M is —$NHCH_2$—, and $R^1$ is optionally substituted phenyl, further wherein $R^1$ is phenyl optionally substituted with one or more substituents selected from the group consisting of halogen, —OH, —NH$_2$, —NO$_2$, —CN, optionally substituted lower alkyl and —OR$^{29}$, where R$^{29}$ is selected from the group consisting of optionally substituted lower alkyl, optionally substituted cycloalkyl, optionally substituted heterocycloalkyl, optionally substituted aryl and optionally substituted heteroaryl.

In one embodiment of the compounds of Formula Ib, when n is 1, and E, K and G are C, at least one of R$^{15}$, R$^{16}$ and R$^{17}$ is other than hydrogen. In another embodiment, n is 1, one of E, K, and G are N and the other two of E, K, and G are C and at least one of R$^{15}$, R$^{16}$ and R$^{17}$ is other than hydrogen. In another embodiment, n is 1, E, K and G are C, and at least one of R$^{15}$, R$^{16}$ and R$^{17}$ is other than hydrogen.

In one embodiment of the compounds of Formula Ib, n is 1, V and W are CH, U and Z are independently CR$^{18}$, one of E, K, and G are N and the other two of E, K, and G are C and at least one of R$^{15}$, R$^{16}$ and R$^{17}$ is other than hydrogen. In another embodiment, n is 1, V and W are CH, U and Z are independently CR$^{18}$, E, K and G are C, and at least one of R$^{15}$, R$^{16}$ and R$^{17}$ is other than hydrogen.

In one embodiment of the compounds of Formula Ib, n is 1, one of E, K, and G are N and the other two of E, K, and G are C, at least one of R$^{15}$, R$^{16}$ and R$^{17}$ is other than hydrogen, A is —CH$_2$—, M is —NHCH$_2$—, further wherein R$^1$ is optionally substituted phenyl. In another embodiment, n is 1, E, K, and G are C, at least one of R$^{15}$, R$^{16}$ and R$^{17}$ is other than hydrogen, A is —CH$_2$—, M is —NHCH$_2$—, further wherein R$^1$ is optionally substituted phenyl.

In one embodiment of the compounds of Formula Ib, n is 1, V, Z, U and W are CH, one of E, K, and G are N and the other two of E, K, and G are C and at least one of R$^{15}$, R$^{16}$ and R$^{17}$ is other than hydrogen. In another embodiment, V, Z, U and W are CH, E, K and G are C, and at least one of R$^{15}$, R$^{16}$ and R$^{17}$ is other than hydrogen.

In one embodiment of the compounds of Formula Ib, Z is CR$^{18}$, wherein R$^{18}$ is other than hydrogen, n is 1, E-R$^{15}$ is N or CH, K—R$^{16}$ is N or CH and G-R$^{17}$ is N or CH. In another embodiment, Z is CR$^{18}$, wherein R$^{18}$ is other than hydrogen, n is 1, and E-R$^{15}$, K—R$^{16}$ and G-R$^{17}$ are CH. In another embodiment, Z is CR$^{18}$, wherein R$^{18}$ is other than hydrogen, U is CR$^{18}$, V and W are CH, n is 1, and E-R$^{15}$, K—R$^{16}$ and G-R$^{17}$ are CH, further wherein U is CH.

In one embodiment of the compounds of Formula Ib, Z is CR$^{18}$, wherein R$^{18}$ is other than hydrogen, n is 1, E-R$^{15}$, K—R$^{16}$ and G-R$^{17}$ are CH, A is —CH$_2$—, M is —NHCH$_2$—, further wherein R$^1$ is optionally substituted phenyl. In a further embodiment, Z is CR$^{18}$, wherein R$^{18}$ is other than hydrogen, U is CR$^{18}$, V and W are CH, n is 1, E-R$^{15}$, K—R$^{16}$ and G-R$^{17}$ are CH, A is —CH$_2$—, M is —NHCH$_2$—, further wherein R$^1$ is optionally substituted phenyl. In a further embodiment, Z is CR$^{18}$, wherein R$^{18}$ is other than hydrogen, V, U and W are CH, n is 1, E-R$^{15}$, K—R$^{16}$ and G-R$^{17}$ are CH, A is —CH$_2$—, M is —NHCH$_2$—, further wherein R$^1$ is optionally substituted phenyl.

In one embodiment of the compounds of Formula Ib, U is CR$^{18}$, wherein R$^{18}$ is other than hydrogen, n is 1, E-R$^{15}$ is N or CH, K—R$^{16}$ is N or CH and G-R$^{17}$ is N or CH. In another embodiment, U is CR$^{18}$, wherein R$^{18}$ is other than hydrogen, n is 1, and E-R$^{15}$, K—R$^{16}$ and G-R$^{17}$ are CH. In another embodiment, U is CR$^{18}$, wherein R$^{18}$ is other than hydrogen, Z is CR$^{18}$, V and W are CH, n is 1, and E-R$^{15}$, K—R$^{16}$ and G-R$^{17}$ are CH, further wherein Z is CH.

In one embodiment of the compounds of Formula Ib, U is CR$^{18}$, wherein R$^{18}$ is other than hydrogen, n is 1, E-R$^{15}$, K—R$^{16}$ and G-R$^{17}$ are CH, A is —CH$_2$—, M is —NHCH$_2$—, further wherein R$^1$ is optionally substituted phenyl. In a further embodiment, U is CR$^{18}$, wherein R$^{18}$ is other than hydrogen, Z is CR$^{18}$, V and W are CH, n is 1, E-R$^{15}$, K—R$^{16}$ and G-R$^{17}$ are CH, A is —CH$_2$—, M is —NHCH$_2$—, further wherein R$^1$ is optionally substituted phenyl. In a further embodiment, U is CR$^{18}$, wherein R$^{18}$ is other than hydrogen, V, Z and W are CH, n is 1, E-R$^{15}$, K—R$^{16}$ and G-R$^{17}$ are CH, A is —CH$_2$—, M is —NHCH$_2$—, further wherein R$^1$ is optionally substituted phenyl.

In one embodiment of the compounds of Formula Ib, further to any of the above embodiments, R$^{15}$, R$^{16}$ and R$^{17}$ are independently selected from the group consisting of halogen, —OH, lower alkyl, fluoro substituted lower alkyl, lower alkoxy, and fluoro substituted lower alkoxy. Further to any of these embodiments R$^1$ is phenyl optionally substituted with one or more substituents selected from the group consisting of halogen, —OH, —NH$_2$, —NO$_2$, —CN, optionally substituted lower alkyl and —OR$^{29}$, where R$^{29}$ is selected from the group consisting of optionally substituted lower alkyl, optionally substituted cycloalkyl, optionally substituted heterocycloalkyl, optionally substituted aryl and optionally substituted heteroaryl.

In one embodiment of the compounds of Formula Ib, further to any of the above embodiments, R$^{18}$ is selected from the group consisting of halogen, —OH, optionally substituted lower alkyl and —OR$^{29}$, where R$^{29}$ is selected from the group consisting of optionally substituted lower alkyl, optionally substituted cycloalkyl, optionally substituted heterocycloalkyl, optionally substituted aryl and optionally substituted heteroaryl. Further to any of these embodiments, R$^1$ is phenyl optionally substituted with one or more substituents selected from the group consisting of halogen, —OH, —NH$_2$, —NO$_2$, —CN, optionally substituted lower alkyl and —OR$^{29}$, where R$^{29}$ is selected from the group consisting of optionally substituted lower alkyl, optionally substituted cycloalkyl, optionally substituted heterocycloalkyl, optionally substituted aryl and optionally substituted heteroaryl.

In another embodiment of compounds of Formula Ib, M is a bond and R$^1$ is other than thiophenyl.

In another embodiment of the compounds of Formula Ib, Z is N or CR$^{18}$ wherein R$^{18}$ is not hydrogen. Further to this embodiment, as allowed in the description of Formula Ib, E is NR$^{15}$ or CR$^{15}$, K is NR$^{16}$ or CR$^{16}$ and G is CR$^{17}$, or combinations thereof, wherein at least one of R$^{15}$, R$^{16}$ and R$^{17}$ is not hydrogen.

The compounds of Formula Ib, and all sub-embodiments detailed herein, may be used to treat a subject suffering from or at risk of a Kit and/or Fms protein kinase mediated disease or condition, such as those disclosed in this application.

In one embodiment, a compound of Formula I has a structure according to the following sub-generic structure, Formula Ig,

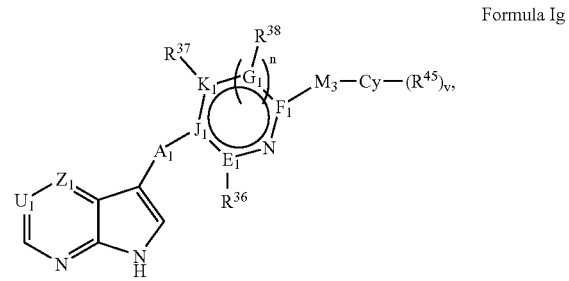

Formula Ig all salts, prodrugs, tautomers, and isomers thereof, wherein:
   $Z_1$ is selected from the group consisting of N and $CR^{34}$;
   $U_1$ is selected from the group consisting of N and $CR^{35}$;
   $A_1$ is selected from the group consisting of —$CH_2$— and —C(O)—;
   $M_3$ is selected from the group consisting of a bond, —$NR^{39}$—, —S—, —O—, —$NR^{39}CH_2$—, —$NR^{39}CH(R^{40})$—, —$SCH_2$—, —$OCH_2$—, —$C(O)NR^{39}$—, —$S(O)_2NR^{39}$—, —$CH_2NR^{39}$—, —$CH(R^{40})NR^{39}$—, —$NR^{39}C(O)$—, and —$NR^{39}S(O)_2$—;
   n is 0 or 1;
   v is 0, 1, 2 or 3;
   $F_1$ and $J_1$ are both C or one of $F_1$ and $J_1$ is C and the other of $F_1$ and $J_1$ is N;
   $E_1$ and $K_1$ are selected from C, N, O or S;
   $G_1$ is selected from C or N;
      wherein
         when n is 1, $F_1$ and $J_1$ are C, and $E_1$, $G_1$ and $K_1$ are C, or any one of $E_1$, $G_1$ and $K_1$ is N and the other two of $E_1$, $G_1$ and $K_1$ are C, provided that when $E_1$, $G_1$ or $K_1$ is N, $R^{36}$, $R^{37}$ and $R^{38}$, respectively, are absent.
         when n is 0 and $F_1$ and $J_1$ are both C, then one of $E_1$ and $K_1$ is C or N and the other of $E_1$ and $K_1$ is C, N, O or S, provided both $E_1$ and $K_1$ are not C, and provided that when both $E_1$ and $K_1$ are N, one of $R^{36}$ and $R^{37}$ is absent, and provided that when one of $E_1$ and $K_1$ are N and the other is O or S, $R^{36}$ and $R^{37}$ are absent,
         when n is 0, one of $F_1$ and $J_1$ is N and the other of $F_1$ and $J_1$ is C, then one of $E_1$ and $K_1$ is N and the other of $E_1$ and $K_1$ is C, or both $E_1$ and $K_1$ are C, provided that when $E_1$ is N, $R^{36}$ is absent and when $K_1$ is N, $R^{37}$ is absent;
   Cy is selected from the group consisting of cycloalkyl, heterocycloalkyl, aryl and heteroaryl;
   $R^{34}$ and $R^{35}$ are independently selected from the group consisting of hydrogen, —$OR^{41}$, —$SR^{41}$, —$NHR^{41}$, —$NR^{41}R^{41}$, —$NR^{39}C(O)R^{41}$, —$NR^{39}S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{34}$ or $R^{35}$, or as substituents of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino;
   $R^{45}$ at each occurrence is independently selected from the group consisting of —$OR^{41}$, —$SR^{41}$, —$NHR^{41}$, —$NR^{41}R^{41}$, —$NR^{39}C(O)R^{41}$, —$NR^{39}S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{45}$, or as substituents of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino;
   $R^{36}$ is selected from the group consisting of hydrogen, halogen, lower alkyl, fluoro substituted lower alkyl, lower alkoxy, and fluoro substituted lower alkoxy when $E_1$ is C, is absent when $E_1$ is O or S or when n=1 and $E_1$ is N, and is absent or selected from the group consisting of hydrogen, lower alkyl, and fluoro substituted lower alkyl when n=0 and $E_1$ is N;
   $R^{37}$ is selected from the group consisting of hydrogen, halogen, lower alkyl, fluoro substituted lower alkyl, lower alkoxy, and fluoro substituted lower alkoxy when $K_1$ is C, is absent when $K_1$ is O or S or when n=1 and $K_1$ is N, and is absent or selected from the group consisting of hydrogen, lower alkyl, and fluoro substituted lower alkyl when n=0 and $K_1$ is N;
   $R^{38}$ is selected from the group consisting of hydrogen, halogen, lower alkyl, fluoro substituted lower alkyl, lower alkoxy, and fluoro substituted lower alkoxy when $G_1$ is C, or is absent when $G_1$ is N;
   $R^{39}$ at each occurrence is independently selected from the group consisting of hydrogen and lower alkyl;
   $R^{40}$ is selected from the group consisting of lower alkyl, and fluoro substituted lower alkyl;
   $R^{41}$ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{41}$ or as substituents of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino; and
   $R^{42}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino.

In one embodiment of compounds of Formula Ig, n is 1, $G_1$ and $K_1$ are C, and E is N or C, preferably wherein E is C.

In one embodiment of compounds of Formula Ig, $M_3$ is selected from the group consisting of —$NR^{39}$—, —O—, —$NR^{39}CH_2$—, —$NR^{39}CH(R^{40})$—, —$SCH_2$—, —$OCH_2$—, —$CH_2NR^{39}$—, —$NR^{39}C(O)$—, and —$NR^{39}S(O)_2$—, preferably wherein $M_3$ is —$NR^{39}CH_2$—, —$NR^{39}CH(R^{40})$—, —$SCH_2$—, —$OCH_2$—, or —$CH_2NR^{39}$—.

In one embodiment of compounds of Formula Ig, n is 1, $G_1$ and $K_1$ are C, and E is N or C, preferably wherein E is C, and $M_3$ is selected from the group consisting of —$NR^{39}$—, —O—, —$NR^{39}CH_2$—, —$NR^{39}CH(R^{40})$—, —$SCH_2$—, —$OCH_2$—, —$CH_2NR^{39}$—, —$NR^{39}C(O)$—, and —$NR^{39}S(O)_2$—, preferably wherein $M_3$ is —$NR^{39}CH_2$—, —$NR^{39}CH(R^{40})$—, —$SCH_2$—, —$OCH_2$—, or —$CH_2NR^{39}$—.

In one embodiment of compounds of Formula Ig, each $R^{45}$ is selected from the group consisting of —OH, —$NH_2$, —CN, —NO$_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1.

In one embodiment of compounds of Formula Ig, n is 1, $G_1$ and $K_1$ are C, and E is N or C, preferably wherein E is C, $M_3$ is selected from the group consisting of —NR$^{39}$—, —O—, —NR$^{39}$CH$_2$—, —NR$^{39}$CH(R$^{40}$)—, —SCH$_2$—, —OCH$_2$—, —CH$_2$NR$^{39}$—, —NR$^{39}$C(O)—, and —NR$^{39}$S(O)$_2$—, preferably wherein $M_3$ is —NR$^{39}$CH$_2$—, —NR$^{39}$CH(R$^{40}$)—, —SCH$_2$—, —OCH$_2$—, or —CH$_2$NR$^{39}$—, and each R$^{45}$ is selected from the group consisting of —OH, —NH$_2$, —CN, —NO$_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1.

In one embodiment of compounds of Formula Ig, $Z_1$ is CR$^{34}$, $U_1$ is CR$^{35}$, and R$^{34}$ and R$^{35}$ are both hydrogen. In one embodiment, $Z_1$ is CR$^{34}$, $U_1$ is CR$^{35}$, and R$^{34}$ and R$^{35}$ are independently selected from the group consisting of hydrogen, —OR$^{41}$, halogen, lower alkyl, cycloalkyl, heterocycloalkyl, aryl and heteroaryl, wherein cycloalkyl, heterocycloalkyl, aryl and heteroaryl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino, and wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino. In a further embodiment, one of R$^{34}$ and R$^{35}$ is hydrogen, and the other of R$^{34}$ and R$^{35}$ is selected from the group consisting of hydrogen, halogen, lower alkyl, lower alkoxy, aryl and heteroaryl, wherein aryl and heteroaryl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino, and wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, further wherein the other of R$^{34}$ and R$^{35}$ is selected from the group consisting of halogen, lower alkyl, and lower alkoxy, wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino.

In one embodiment of compounds of Formula Ig, each R$^{45}$ is independently selected from the group consisting of —OH, —NH$_2$, —CN, —NO$_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1, $Z_1$ is CR$^{34}$, $U_1$ is CR$^{35}$, and R$^{34}$ and R$^{35}$ are independently selected from the group consisting of hydrogen, —OR$^{41}$, halogen, lower alkyl, cycloalkyl, heterocycloalkyl, aryl and heteroaryl, wherein cycloalkyl, heterocycloalkyl, aryl and heteroaryl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino, and wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino. In a further embodiment, both of R$^{34}$ and R$^{35}$ are hydrogen.

In one embodiment of compounds of Formula Ig, each R$^{45}$ is selected from the group consisting of —OH, —NH$_2$, —CN, —NO$_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1, $Z_1$ is CR$^{34}$, $U_1$ is CR$^{35}$, one of R$^{34}$ and R$^{35}$ is hydrogen, and the other of R$^{34}$ and R$^{35}$ is selected from the group consisting of hydrogen, halogen, lower alkyl, lower alkoxy, aryl and heteroaryl, wherein aryl and heteroaryl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino, and wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, further wherein the other of R$^{34}$ and R$^{35}$ is selected from the group consisting of halogen, lower alkyl, and lower alkoxy, wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino.

In one embodiment of compounds of Formula Ig, n is 1, $G_1$ and $K_1$ are C, and E is N or C, preferably wherein E is C, $M_3$ is selected from the group consisting of —NR$^{39}$—, —O—, —NR$^{39}$CH$_2$—, —NR$^{39}$CH(R$^{40}$)—, —SCH$_2$—, —OCH$_2$—, —CH$_2$NR$^{39}$—, —NR$^{39}$C(O)—, and —NR$^{39}$S(O)$_2$—, preferably wherein $M_3$ is —NR$^{39}$CH$_2$—, —NR$^{39}$CH(R$^{40}$)—, —SCH$_2$—, —OCH$_2$—, or —CH$_2$NR$^{39}$—, each R$^{45}$ is selected from the group consisting of —OH, —NH$_2$, —CN, —NO$_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1, $Z_1$ is CR$^{34}$, $U_1$ is CR$^{35}$, and R$^{34}$ and R$^{35}$ are both hydrogen.

In one embodiment of compounds of Formula Ig, n is 1, $G_1$ and $K_1$ are C, and E is N or C, preferably wherein E is C, $M_3$ is selected from the group consisting of —NR$^{39}$—, —O—, —NR$^{39}$CH$_2$—, —NR$^{39}$CH(R$^{40}$)—, —SCH$_2$—, —OCH$_2$—, —CH$_2$NR$^{39}$—, —NR$^{39}$C(O)—, and —NR$^{39}$S(O)$_2$—, preferably wherein $M_3$ is —NR$^{39}$CH$_2$—, —NR$^{39}$CH(R$^{40}$)—, —SCH$_2$—, —OCH$_2$—, or —CH$_2$NR$^{39}$—, each R$^{45}$ is selected from the group consisting of —OH, —NH$_2$, —CN, —NO$_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1, $Z_1$ is CR$^{34}$ and $U_1$ is CR$^{35}$, and R$^{34}$ and R$^{35}$ are independently selected from the group consisting of hydrogen, —OR$^{41}$, halogen, lower alkyl, cycloalkyl, heterocycloalkyl, aryl and heteroaryl, wherein cycloalkyl, heterocycloalkyl, aryl and heteroaryl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino, and wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino. In a further embodiment, one of R$^{34}$ and R$^{35}$ is hydrogen, and the other of R$^{34}$ and R$^{35}$ is selected from the group consisting of halogen, lower alkyl, lower alkoxy, aryl and heteroaryl, wherein aryl and heteroaryl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino, and wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, further wherein the other of R$^{34}$ and R$^{35}$ is selected from the group consisting of halogen, lower alkyl, and lower alkoxy, wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, further wherein R$^{34}$ is hydrogen.

The compounds of Formula Ig, and all sub-embodiments detailed herein, may be used to treat a subject suffering from or at risk of a Kit and/or Fms protein kinase mediated disease or condition, such as those disclosed in this application.

In certain embodiments of the above compounds, compounds are excluded where N (except where N is a heteroaryl ring atom), O, or S is bound to a carbon that is also bound to N (except where N is a heteroaryl ring atom), O, or S; or where N (except where N is a heteroaryl ring atom), O, C(S), C(O), or S(O)$_n$ (n is 0-2) is bound to an alkene carbon of an alkenyl group or bound to an alkyne carbon of an alkynyl group; accordingly, in certain embodiments compounds which include linkages such as the following are excluded from the present invention: —NR—CH$_2$—NR—, —O—CH$_2$—NR—, —S—CH$_2$—NR—, —NR—CH$_2$—O—, —O—CH$_2$—O—, —S—CH$_2$—O—, —NR—CH$_2$—S—, —O—CH$_2$—S—, —S—CH$_2$—S—, —NR—CH=CH—, —CH=CH—NR—, —NR—C≡C—, —C≡C—NR—, —O—CH=CH—, —CH=CH—O—, —O—C≡C—, —C≡C—O—, —S(O)$_{0-2}$—CH=CH—, —CH=CH—S(O)$_{0-2}$—, —S(O)$_{0-2}$—C≡C—, —C≡C—S(O)$_{0-2}$—, —C(O)—CH=CH—, —CH=CH—C(O)—, —C≡C—C(O)—, or —C(O)—C≡C—, —C(S)—CH=CH—, —CH=CH—C(S)—, —C≡C—C(S)—, or —C(S)—C≡C—.

In another aspect, the invention provides methods for treating a c-kit-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal c-kit activity (e.g. kinase activity). Invention methods involve administering to the subject suffering from or at risk of a c-kit-mediated disease or condition an effective amount of a compound of Formula I, Formula Ia, Formula Ib, or Formula Ig, and all sub-embodiments thereof. In one embodiment, the c-kit mediated disease is selected from the group consisting of malignancies, including mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including asthma, rheumatoid arthritis, allergic rhinitis, multiple sclerosis, inflammatory bowel syndrome, transplant rejection, and hypereosinophilia.

In a related aspect, compounds of Formula I, Formula Ia, Formula Ib, or Formula Ig, and all sub-embodiments thereof, can be used in the preparation of a medicament for the treatment of a c-kit-mediated disease or condition selected from the group consisting of malignancies, including mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including asthma, rheumatoid arthritis, allergic rhinitis, multiple sclerosis, inflammatory bowel syndrome, transplant rejection, and hypereosinophilia.

In a further aspect, the invention provides methods for treating a c-fms-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal c-fms activity (e.g. kinase activity). Invention methods involve administering to the subject suffering from or at risk of a c-fms-mediated disease or condition an effective amount of compound of Formula I, Formula Ia, Formula Ib, or Formula Ig, and all sub-embodiments thereof. In one embodiment, the c-fms mediated disease is selected from the group consisting of immune disorders, including rheumatoid arthritis, systemic lupus erythematosis (SLE), Wegener's granulomatosis, and transplant rejection, inflammatory diseases including Chronic Obstructive Pulmonary Disease (COPD), emphysema, and atherosclerosis, metabolic disorders, including insulin resistance, hyperglycemia, and lipolysis, disorders of bone structure or mineralization, including osteoporosis, increased risk of fracture, hypercalcemia, and bone metastases, kidney diseases, including nephritis (e.g. glomerulonephritis, interstitial nephritis, Lupus nephritis), tubular necrosis, diabetes-associated renal complications, and hypertrophy and cancers, including multiple myeloma, acute myeloid leukemia, chronic myeloid leukemia (CML), breast cancer, and ovarian cancer.

In a related aspect, compounds of Formula I, Formula Ia, Formula Ib, or Formula Ig, and all sub-embodiments thereof, can be used in the preparation of a medicament for the treatment of a c-fms-mediated disease or condition selected from the group consisting of immune disorders, including rheumatoid arthritis, systemic lupus erythematosis (SLE), Wegener's granulomatosis, and transplant rejection, inflammatory diseases including Chronic Obstructive Pulmonary Disease (COPD), emphysema, and atherosclerosis, metabolic disorders, including insulin resistance, hyperglycemia, and lipolysis, disorders of bone structure or mineralization, including osteoporosis, increased risk of fracture, hypercalcemia, and bone metastases, kidney diseases, including nephritis (e.g. glomerulonephritis, interstitial nephritis, Lupus nephritis), tubular necrosis, diabetes-associated renal complications, and hypertrophy and cancers, including multiple myeloma, acute myeloid leukemia, chronic myeloid leukemia (CML), breast cancer, and ovarian cancer.

In a further aspect, the invention provides methods for treating a c-fms-mediated and/or c-kit-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal c-fms activity and/or c-kit activity (e.g. kinase activity). Invention methods involve administering to the subject suffering from or at risk of a c-fms-mediated and/or c-kit mediated disease or condition an effective amount of compound of Formula I, Formula Ia, Formula Ib, or Formula Ig, and all sub-embodiments thereof. In one embodiment, the c-fms and/or c-kit mediated disease is selected from the group consisting of mast cell tumors, small cell lung cancer, testicular cancer, gastrointestinal stromal tumors, glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myeloid leukemia, acute lymphocytic leukemia, chronic myelogenous leukemia, multiple myeloma, mastocytosis, melanoma, breast cancer, ovarian cancer, canine mast cell tumors, hypertrophy, asthma, rheumatoid arthritis, allergic rhinitis, multiple sclerosis, inflammatory bowel syndrome, transplant rejection, systemic lupus erythematosis, Wegener's granulomatosis, Chronic Obstructive Pulmonary Disease, emphysema, atherosclerosis, insulin resistance, hyperglycemia, lipolysis, hypereosinophilia, osteoporosis, increased risk of fracture, hypercalcemia, bone metastases, glomerulonephritis, interstitial nephritis, Lupus nephritis, tubular necrosis, and diabetes-associated renal complications.

In a related aspect, compounds of Formula I, Formula Ia, Formula Ib, or Formula Ig, and all sub-embodiments thereof, can be used in the preparation of a medicament for the treatment of a c-fms-mediated and/or c-kit mediated disease or condition selected from the group consisting of mast cell tumors, small cell lung cancer, testicular cancer, gastrointestinal stromal tumors, glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myeloid leukemia, acute lymphocytic leukemia, chronic myelogenous leukemia, multiple myeloma, mastocytosis, melanoma, breast cancer, ovarian cancer, canine mast cell tumors, hypertrophy, asthma, rheumatoid arthritis, allergic rhinitis, multiple sclerosis, inflammatory bowel syndrome, transplant rejection, systemic lupus erythematosis, Wegener's granulomatosis, Chronic Obstructive Pulmonary Disease, emphysema, atherosclerosis, insulin resistance, hyperglycemia, lipolysis, hypereosinophilia, osteoporosis, increased risk of fracture, hypercalcemia, bone metastases, glomerulonephritis, interstitial nephritis, Lupus nephritis, tubular necrosis, and diabetes-associated renal complications.

In another aspect, the invention provides methods of using compounds of Formula I, Formula Ia, Formula Ib, or Formula Ig, and all sub-embodiments thereof, as described herein (e.g. compounds that have advantageous levels of activity and/or selectivity on c-kit, c-fms or both c-kit and c-fms). In certain embodiments, the compounds are substituted at the 3-position of the core bicyclic ring structure (azaindole core) with a substituent group that in order includes a first linker bound to a first aryl or heteroaryl group, which is bound to a linker of 1 to 3 atoms bound to a second aryl or heteroaryl group. In certain embodiments including the just-described 3-position substituent group, the first linker is methylene, ethylene, —C(O)—, —C(S)—, —O—, —S—, or —S(O)$_2$—; the first aryl or heteroaryl group is pyridinyl, pyrimidinyl, pyrazinyl, pyridazinyl, pyrrolyl, imidazolyl, triazolyl, thiazolyl, or oxazolyl; the second linker is methyl amino (NHCH$_2$), ethyl amino (NHCH$_2$CH$_2$), amide (NHC(O)), or sulfonamide (NHSO$_2$); the second aryl or heteroaryl group is phenyl, pyridinyl, pyrimidinyl, pyrazinyl, pyridazinyl, pyrrolyl, imidazolyl, triazolyl, thiazolyl, furanyl, or oxazolyl; the second aryl or heteroaryl group is optionally substituted with a lower alkyl group (e.g. a methyl group, an ethyl group, a propyl group, or a butyl group), an alkoxy group (e.g. a methoxy group, an ethoxy group, a propoxy group, or a butoxy group), a halo substituted lower alkyl (e.g. —CH$_2$F, —CHF$_2$, or —CF$_3$), or halo (e.g. F or Cl). In particular embodiments, the second aryl or heteroaryl group is a 6-membered ring; the 6-membered ring is substituted at the para position; the 6-membered ring is substituted at the meta position; the 6-membered ring is substituted at the ortho position; or the 6-membered ring is substituted at the meta and para positions. In particular embodiments, the second aryl or heteroaryl group is a 5-membered ring; the 5-membered ring is substituted at a position adjacent to the atom bound to the second linker; or the 5-membered ring is substituted at a position not adjacent to the atom bound to the second linker. In particular embodiments, the 3-position substitutent group is the only non-hydrogen substitutent on the azaindole core.

In particular embodiments, the compound has an IC$_{50}$ of less than 100 nM, less than 50 nM, less than 20 nM, less than 10 nM, or less than 5 nM as determined in a generally accepted kinase activity assay. In certain embodiments, the selectivity of the compound is such that the compound is at least 2-fold, 5-fold, 10-fold, or 100-fold more active on c-kit than on Ret, PDGF, or both Ret and PDGF. In certain embodiments, the selectivity of the compound is such that the compound is at least 2-fold, 5-fold, 10-fold, or 100-fold more active on c-kit than on c-fms. In certain embodiments, the selectivity of the compound is such that the compound is at least 2-fold, 5-fold, 10-fold, or 100-fold more active on c-fms than on c-kit. In certain embodiments, the compound has in combination each pairing of activity (e.g. IC$_{50}$) and/or selectivity as specified in this paragraph.

In particular embodiments, the compound has an IC$_{50}$ of less than 100 nM, less than 50 nM, less than 20 nM, less than 10 nM, or less than 5 nM as determined in a generally accepted kinase activity assay for c-kit, c-fms, or both c-kit and c-fms kinase activity. In certain embodiments, the selectivity of the compound is such that the compound is at least 2-fold, 5-fold, 10-fold, or 100-fold more active on c-kit, c-fms, or both c-kit and c-fms than on Ret, PDGF, or both Ret and PDGF.

An additional aspect of this invention relates to compositions that include a therapeutically effective amount of a compound of Formula I (including Formula Ia, Ib, Ig and all sub-embodiments thereof) and at least one pharmaceutically acceptable carrier, excipient, and/or diluent. The composition can include a plurality of different pharmacologically active compounds, which can include a plurality of compounds of Formula I (including Formula Ia, Ib, Ig and all sub-embodiments thereof).

In a related aspect, the invention provides kits that include a composition as described herein. In particular embodiments, the composition is packaged, e.g., in a vial, bottle, flask, which may be further packaged, e.g., within a box, envelope, or bag; the composition is approved by the U.S. Food and Drug Administration or similar regulatory agency for administration to a mammal, e.g., a human; the composition is approved for administration to a mammal, e.g., a human, for a c-kit- and/or c-fms-mediated disease or condition; the kit of the invention includes written instructions on use and/or other indication that the composition is suitable or approved for administration to a mammal, e.g., a human, for a c-kit- and/or c-fms-mediated disease or condition; the composition is packaged in unit dose or single dose form, e.g., single dose pills, capsules, or the like.

The invention also provides a method for identifying or developing additional compounds active on c-kit and c-fms, e.g., improved modulators, by determining whether any of a plurality of test compounds of Formula I, Formula Ia, Formula Ib, or Formula Ig, and all sub-embodiments thereof, active on c-kit and c-fms provides an improvement in one or more desired pharmacologic properties relative to a reference compound active on c-kit and c-fms, and selecting a compound if any, that has an improvement in the desired pharmacologic property, thereby providing an improved modulator.

In particular aspects of modulator development, the desired pharmacologic property is serum half-life longer than 2 hr or longer than 4 hr or longer than 8 hr, aqueous solubility, oral bioavailability more than 10%, or oral bioavailability more than 20%.

Furthermore, in particular aspects of modulator development, the process can be repeated multiple times, i.e., multiple rounds of preparation of derivatives and/or selection of additional related compounds and evaluation of such further derivatives of related compounds can be carried out, e.g., 1, 2, 3, 4, 5, 6, 7, 8, 9, 10 or more additional rounds.

In another aspect, the present invention also provides a method for modulating c-kit or c-fms activity by contacting c-kit or c-fms with an effective amount of a compound of Formula I (including Formula Ia, Ib, Ig and all sub-embodiments thereof) active on c-kit and/or c-fms (such as compounds developed using methods described herein). The compound is preferably provided at a level sufficient to modulate the activity of the c-kit or c-fms by at least 10%, more preferably at least 20%, 30%, 40%, 50%, 60%, 70%, 80%, 90%, or greater than 90%. In many embodiments, the compound will be at a concentration of about 1 µM, 100 µM, or 1 mM, or in a range of 1-100 nM, 100-500 nM, 500-1000 nM, 1-100 µM, 100-500 µM, or 500-1000 µM. In particular embodiments, the contacting is carried out in vitro.

Additional aspects and embodiments will be apparent from the following Detailed Description and from the claims.

DETAILED DESCRIPTION OF THE PREFERRED EMBODIMENTS

As used herein the following definitions apply:

"Halo" and "halogen" refer to all halogens, that is, chloro (Cl), fluoro (F), bromo (Br), or iodo (I).

"Hydroxyl" and "hydroxy" refer to the group —OH.

"Thiol" refers to the group —SH.

"Lower alkyl" alone or in combination means an alkane-derived radical containing from 1 to 6 carbon atoms (unless specifically defined) that includes a straight chain alkyl or branched alkyl. The straight chain or branched alkyl group is attached at any available point to produce a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. "Optionally substituted lower alkyl" denotes lower alkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^e$, —R$^f$, and —R$^g$. Further, possible substitutions include subsets of these substitutions, such as are indicated herein, for example, in the description of compounds of Formula I (including Formulae Ia, Ib, Ig and all sub-embodiments thereof), attached at any available atom to produce a stable compound. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as —OR, —NHR, —C(O)NHR, and the like, substitution of the alkyl R group is such that substitution of the alkyl carbon bound to any —O—, —S—, or —N— of the moiety (except where —N— is a heteroaryl ring atom) excludes substituents that would result in any —O—, —S—, or —N— of the substituent (except where —N— is a heteroaryl ring atom) being bound to the alkyl carbon bound to any —O—, —S—, or —N— of the moiety.

"Lower alkylene" refers to a divalent alkane-derived radical containing 1-6 carbon atoms, straight chain or branched, from which two hydrogen atoms are taken from the same carbon atom or from different carbon atoms. Examples of lower alkylene include, but are not limited to, methylene —CH$_2$—, ethylene —CH$_2$CH$_2$—, propylene —CH$_2$CH$_2$CH$_2$—, isopropylene —CH(CH$_3$)CH—, and the like. "Optionally substituted lower alkylene" denotes lower alkylene that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, NR$^a$C(S)R$^a$, —NHS(O)$_2$R$^a$, —NR$^a$S(O)$_2$R$^a$, —NHC(O)NHR$^a$, —NHC(S)

NHR$^a$, —NR$^a$C(O)NHR$^a$, —NR$^a$C(O)NH$_2$, —NR$^a$C(S) NH$_2$, —NR$^a$C(S)NHR$^a$, —NHC(O)NR$^a$R$^a$, —NHC(S) NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^e$, —R$^f$, and —R$^g$, or two substituents on any one carbon or a substituent on each of any two carbons in the alkylene chain may join to form a 3-7 membered monocyclic cycloalkyl or 5-7 membered monocyclic heterocycloalkyl wherein the monocyclic cycloalkyl or monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. Examples of lower alkenyl groups include ethenyl, propenyl, isopropenyl, butenyl, and the like. "Substituted lower alkenyl" denotes lower alkenyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S) R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^f$, and —R$^g$. Further, possible substitutions include subsets of these substitutions, such as are indicated herein, for example, in the description of compounds of Formula I (including Formulae Ia, Ib, Ig and all sub-embodiments thereof), attached at any available atom to produce a stable compound. For example "fluoro substituted lower alkenyl" denotes a lower alkenyl group substituted with one or more fluoro atoms, where preferably the lower alkenyl is substituted with 1, 2, 3, 4 or 5 fluoro atoms, also 1, 2, or 3 fluoro atoms. While it is understood that substitutions are attached at any available atom to produce a stable compound, substitution of alkenyl groups are such that —F, —C(O)—, —C(S)—, —C(NH)—, —S(O)—, —S(O)$_2$—, —O—, —S—, or —N— (except where —N— is a heteroaryl ring atom), are not bound to an alkene carbon thereof. Further, where alkenyl is a substituent of another moiety or an R group of a moiety such as —OR, —NHR, —C(O)R, and the like, substitution of the moiety is such that any —C(O)—, —C(S)—, —S(O)—, —S(O)$_2$—, —O—, —S—, or —N— thereof (except where —N— is a heteroaryl ring atom) are not bound to an alkene carbon of the alkenyl substituent or R group. Further, where alkenyl is a substituent of another moiety or an R group of a moiety such as —OR, —NHR, —C(O)NHR, and the like, substitution of the alkenyl R group is such that substitution of the alkenyl carbon bound to any —O—, —S—, or —N— of the moiety (except where —N— is a heteroaryl ring atom) excludes substituents that would result in any —O—, —S—, or —N— of the substituent (except where —N— is a heteroaryl ring atom) being bound to the alkenyl carbon bound to any —O—, —S—, or —N— of the moiety. An "alkenyl carbon" refers to any carbon within an alkenyl group, whether saturated or part of the carbon to carbon double bond. An "alkene carbon" refers to a carbon within an alkenyl group that is part of a carbon to carbon double bond.

"Lower alkynyl" alone or in combination means a straight or branched hydrocarbon containing 2-6 carbon atoms (unless specifically defined) containing at least one, preferably one, carbon to carbon triple bond. Examples of alkynyl groups include ethynyl, propynyl, butynyl, and the like. "Substituted lower alkynyl" denotes lower alkynyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S) R$^a$, —C(O)OR$^a$, —C(S)OR$^a$ —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, and —R$^g$. Further, possible substitutions include subsets of these substitutions, such as are indicated herein, for example, in the description of compounds of Formula I (including Formulae Ia, Ib, Ig and all sub-embodiments thereof), attached at any available atom to produce a stable compound. For example "fluoro substituted lower alkynyl" denotes a lower alkynyl group substituted with one or more fluoro atoms, where preferably the lower alkynyl is substituted with 1, 2, 3, 4 or 5 fluoro atoms, also 1, 2, or 3 fluoro atoms. While it is understood that substitutions are attached at any available atom to produce a stable compound, substitution of alkynyl groups are such that —F, —C(O)—, —C(S)—, —C(NH)—, —S(O)—, —S(O)$_2$—, —O—, —S—, or —N— (except where —N— is a heteroaryl ring atom), are not bound to an alkyne carbon thereof. Further, where alkynyl is a substituent of another moiety or an R group of a moiety such as —OR, —NHR, —C(O)R, and the like, substitution of the moiety is such that any —C(O)—, —C(S)—, —S(O)—, —S(O)$_2$—, —O—, —S—, or —N— thereof (except where —N— is a heteroaryl ring atom) are not bound to an alkyne carbon of the alkynyl substituent or R group. Further, where alkynyl is a substituent of another moiety or an R group of a moiety such as —OR, —NHR, —C(O)NHR, and the like, substitution of the alkynyl R group is such that substitution of the alkynyl carbon bound to any —O—, —S—, or —N— of the moiety (except where —N— is a heteroaryl ring atom) excludes substituents that would result in any —O—, —S—, or —N— of the substituent (except where —N— is a heteroaryl ring atom) being bound to the alkynyl carbon bound to any —O—, —S—, or —N— of the moiety. An "alkynyl carbon" refers to any carbon within an alkynyl group, whether saturated or part of the carbon to carbon triple bond. An "alkyne carbon" refers to a carbon within an alkynyl group that is part of a carbon to carbon triple bond.

"Cycloalkyl" refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, adamantyl, and the like. "Cycloalkylene" is a divalent cycloalkyl. A "substituted cycloalkyl" is a cycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, —R$^f$, and —R$^g$. "Substituted cycloalkylene" is a divalent substituted cycloalkyl.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which one of the ring carbons is oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl. "Heterocycloalkylene" is a divalent heterocycloalkyl. A "substituted heterocycloalkyl" is a heterocycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, —R$^f$, and —R$^g$. "Substituted heterocycloalkylene" is a divalent substituted heterocycloalkyl.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. "Arylene" is a divalent aryl. A "substituted aryl" is an aryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, —R$^f$, and —R$^g$. A "substituted arylene" is a divalent substituted aryl.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, and indolyl. "Nitrogen containing heteroaryl" refers to heteroaryl wherein any heteroatoms are N. "Heteroarylene" is a divalent heteroaryl. A "substituted heteroaryl" is a heteroaryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, —R$^f$, and —R$^g$. "Substituted heteroarylene" is a divalent substituted heteroaryl.

The variables R$^a$, R$^b$, R$^c$, —R$^d$, —R$^e$, —R$^f$ and —R$^g$ as used in the description of optional substituents for alkyl, alkylene, alkenyl, alkynyl, cycloalkyl, heterocycloalkyl, aryl and heteroaryl are defined as follows:

each $R^a$, $R^b$, and $R^c$ are independently selected from the group consisting of —$R^d$, —$R^e$, —$R^f$, and —$R^g$, or $R^b$ and $R^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —$NO_2$, —CN, —OH, —$NH_2$, —$OR^u$, —$SR^u$, —$NHR^u$, —$NR^uR^u$, —$R^x$, and —$R^y$;

each —$R^d$ is independently lower alkyl, wherein lower alkyl is optionally substituted with one or more, preferably 1, 2, 3, 4 or 5, also 1, 2 or 3 substituents selected from the group consisting of fluoro, —OH, —$NH_2$, —$NO_2$, —CN, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —$OR^k$, $SR^k$, —OC(O)$R^k$, —OC(S)$R^k$, —C(O)$R^k$, —C(S)$R^k$, —C(O)$OR^k$, —C(S)$OR^k$, —S(O)$R^k$, —S(O)$_2R^k$, —C(O)$NHR^k$, —C(S)$NHR^k$, —C(O)$NR^kR^k$, —C(S)$NR^kR^k$, —S(O)$_2NHR^k$, —S(O)$_2NR^kR^k$, —C(NH)$NHR^k$, —C(NH)$NR^mR^n$, —NHC(O)$R^k$, —NHC(S)$R^k$, —$NR^kC(O)R^k$, —$NR^kC(S)R^k$, —NHS(O)$_2R^k$, —$NR^kS(O)_2R^k$, —NHC(O)$NHR^k$, —NHC(S)$NHR^k$, —$NR^kC(O)NH_2$, —$NR^kC(S)NH_2$, —$NR^kC(O)NHR^k$, —$NR^kC(S)NHR^k$, —NHC(O)$NR^kR^k$, —NHC(S)$NR^kR^k$, —$NR^kC(O)NR^kR^k$, —$NR^kC(S)NR^kR^k$, —NHS(O)$_2NHR^k$, —$NR^kS(O)_2NH_2$, —$NR^kS(O)_2NHR^k$, —NHS(O)$_2NR^kR^k$, —$NR^kS(O)_2NR^kR^k$, —$NHR^k$, —$NR^kR^k$, —$R^i$, and —$R^j$;

each —$R^e$ is independently lower alkenyl, wherein lower alkenyl is optionally substituted with one or more, preferably 1, 2, 3, 4 or 5, also 1, 2 or 3 substituents selected from the group consisting of fluoro, —OH, —$NH_2$, —$NO_2$, —CN, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —$OR^k$, —$SR^k$, —OC(O)$R^k$, —OC(S)$R^k$, —C(O)$R^k$, —C(S)$R^k$, —C(O)$OR^k$, —C(S)$OR^k$, S(O)$R^k$, —S(O)$_2R^k$, —C(O)$NHR^k$, —C(S)$NHR^k$, —C(O)$NR^kR^k$, —C(S)$NR^kR^k$, —S(O)$_2NHR^k$, —S(O)$_2NR^kR^k$, —C(NH)$NHR^k$, —C(NH)$NR^mR^n$, —NHC(O)$R^k$, —NHC(S)$R^k$, —$NR^kC(O)R^k$, —$NR^kC(S)R^k$, —NHS(O)$_2R^k$, —$NR^kS(O)_2R^k$, —NHC(O)$NHR^k$, —NHC(S)$NHR^k$, —$NR^kC(O)NH_2$, —$NR^kC(S)NH_2$, —$NR^kC(O)NHR^k$, —$NR^kC(S)NHR^k$, —NHC(O)$NR^kR^k$, —NHC(S)$NR^kR^k$, —$NR^kC(O)NR^kR^k$, —$NR^kC(S)NR^kR^k$, —NHS(O)$_2NHR^k$, —$NR^kS(O)_2NH_2$, —$NR^kS(O)_2NHR^k$, —NHS(O)$_2NR^kR^k$, —$NR^kS(O)_2NR^kR^k$, —$NHR^k$, —$NR^kR^k$, —$R^h$, and —$R^j$;

each —$R^f$ is independently lower alkynyl, wherein lower alkynyl is optionally substituted with one or more, preferably 1, 2, 3, 4 or 5, also 1, 2 or 3 substituents selected from the group consisting of fluoro, —OH, —$NH_2$, —$NO_2$, —CN, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —$OR^k$, —$SR^k$, —OC(O)$R^k$, —OC(S)$R^k$, —C(O)$R^k$, —C(S)$R^k$, —C(O)$OR^k$, —C(S)$OR^k$, —S(O)$R^k$, —S(O)$_2R^k$, —C(O)$NHR^k$, —C(S)$NHR^k$, —C(O)$NR^kR^k$, —C(S)$NR^kR^k$, —S(O)$_2NHR^k$, —S(O)$_2NR^kR^k$, —C(NH)$NHR^k$, —C(NH)$NR^mR^n$, —NHC(O)$R^k$, —NHC(S)$R^k$, —$NR^kC(O)R^k$, —$NR^kC(S)R^k$, —NHS(O)$_2R^k$, —$NR^kS(O)_2R^k$, —NHC(O)$NHR^k$, —NHC(S)$NHR^k$, —$NR^kC(O)NH_2$, —$NR^kC(S)NH_2$, —$NR^kC(O)NHR^k$, —$NR^kC(S)NHR^k$, —NHC(O)$NR^kR^k$, —NHC(S)$NR^kR^k$, —$NR^kC(O)NR^kR^k$, —$NR^kC(S)NR^kR^k$, —NHS(O)$_2NHR^k$, —$NR^k S(O)_2NH_2$, —$NR^kS(O)_2NHR^k$, —NHS(O)$_2NR^kR^k$, —$NR^kS(O)_2NR^kR^k$, —$NHR^k$, —$NR^kR^k$, —$R^h$, and —$R^j$;

each —$R^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —$NH_2$, —$NO_2$, —CN, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —$OR^k$, —$SR^k$, —OC(O)$R^k$, —OC(S)$R^k$, —C(O)$R^k$, —C(S)$R^k$, —C(O)$OR^k$, —C(S)$OR^k$, —S(O)$R^k$, —S(O)$_2R^k$, —C(O)$NHR^k$, —C(S)$NHR^k$, —C(O)$NR^kR^k$, —C(S)$NR^kR^k$, —S(O)$_2NHR^k$, —S(O)$_2NR^kR^k$, —C(NH)$NHR^k$, —C(NH)$NR^mR^n$, —NHC(O)$R^k$, —NHC(S)$R^k$, —$NR^kC(O)R^k$, —$NR^kC(S)R^k$, —NHS(O)$_2R^k$, —$NR^kS(O)_2R^k$, —NHC(O)$NHR^k$, —NHC(S)$NHR^k$, —$NR^kC(O)NH_2$, —$NR^kC(S)NH_2$, —$NR^kC(O)NHR^k$, —$NR^kC(S)NHR^k$, —NHC(O)$NR^kR^k$, —NHC(S)$NR^kR^k$, —$NR^kC(O)NR^kR^k$, —$NR^kC(S)NR^kR^k$, —NHS(O)$_2NHR^k$, —$NR^kS(O)_2NH_2$, —$NR^kS(O)_2NHR^k$, —NHS(O)$_2NR^kR^k$, —$NR^kS(O)_2NR^kR^k$, —$NHR^k$, —$NR^kR^k$, —$R^h$, —$R^i$, and —$R^j$;

wherein $R^k$, $R^m$, and $R^n$ at each occurrence are independently selected from the group consisting of —$R^h$, —$R^i$, and —$R^j$, or $R^m$ and $R^n$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —$NO_2$, —CN, —OH, —$NH_2$, $OR^u$, —$SR^u$, —$NHR^u$, —$NR^uR^u$, —$R^x$, and —$R^y$;

wherein each —$R^h$ is independently lower alkyl optionally substituted with one or more, preferably 1, 2, 3, 4 or 5, also 1, 2, or 3 substituents selected from the group consisting of fluoro, —OH, —$NH_2$, —$NO_2$, —CN, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —$OR^r$, —$SR^r$, —OC(O)$R^r$, —OC(S)$R^r$, —C(O)$R^r$, —C(S)$R^r$, —C(O)$OR^r$, —C(S)$OR^r$, —S(O)$R^r$, —S(O)$_2R^r$, —C(O)$NHR^r$, —C(S)$NHR^r$, —C(O)$NR^rR^r$, —C(S)$NR^rR^r$, —S(O)$_2NHR^r$, —S(O)$_2NR^rR^r$, —C(NH)$NHR^r$, —C(NH)$NR^rR^r$, —NHC(O)$R^r$, —NHC(S)$R^r$, —$NR^rC(O)R^r$, $NR^rC(S)R^r$, —NHS(O)$_2R^r$, —$NR^rS(O)_2R^r$, —NHC(O)$NHR^r$, —NHC(S)$NHR^r$, —$NR^rC(O)NH_2$, —$NR^rC(S)NH_2$, —$NR^rC(O)NHR^r$, —$NR^rC(S)NHR^r$, —NHC(O)$NR^rR^r$, —NHC(S)$NR^rR^r$, —$NR^rC(O)NR^rR^r$, —$NR^rC(S)NR^rR^r$, —NHS(O)$_2NHR^r$, —$NR^rS(O)_2NH_2$, —$NR^rS(O)_2NHR^r$, —NHS(O)$_2NR^rR^r$, —$NR^rS(O)_2NR^rR^r$, —$NHR^r$, —$NR^rR^r$, —$R^i$, and —$R^j$;

wherein each —$R^i$ is independently selected from the group consisting of lower alkenyl and lower alkynyl, wherein lower alkenyl or lower alkynyl are optionally substituted with one or more, preferably 1, 2, 3, 4 or 5, also 1, 2 or 3 substituents selected from the group consisting of fluoro, —OH, —$NH_2$, —$NO_2$, —CN, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —$OR^r$, —$SR^r$, —OC(O)$R^r$, —OC(S)$R^r$, —C(O)$R^r$, —C(S)$R^r$, —C(O)$OR^r$, —C(S)$OR^r$, —S(O)$R^r$, —S(O)$_2R^r$, —C(O)$NHR^r$, —C(S)

NHR$^r$, —C(O)NR′R$^r$, —C(S)NR′R$^r$, —S(O)$_2$NHR$^r$, —S(O)$_2$NR′R$^r$, —C(NH)NHR$^r$, —C(NH)NR$^s$R$^r$, —NHC(O)R$^r$, —NHC(S)R$^r$, —NR′C(O)R$^r$, —NR′C(S)R$^r$, —NHS(O)$_2$R$^r$, —NR′S(O)$_2$R$^r$, —NHC(O)NHR$^r$, —NHC(S)NHR$^r$, —NR′C(O)NH$_2$, —NR′C(S)NH$_2$, —NHC(O)NR′R$^r$, —NHC(S)NR′R$^r$, —NR′C(O)NR′R$^r$, —NR′C(S)NR′R$^r$, —NHS(O)$_2$NHR$^r$, —NR′S(O)$_2$NH$_2$, —NR′S(O)$_2$NHR$^r$, —NHS(O)$_2$NR′R$^r$, —NR′S(O)$_2$NR′R$^r$, —NHR$^r$, —NR′R$^r$, and —R$^1$;

wherein each —R$^j$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$ R$^r$, —C(O)NHR$^r$, —C(S)NHR$^r$, —C(O)NR′R$^r$, —C(S)NR′R$^r$, —S(O)$_2$NHR$^r$, —S(O)$_2$NR′R$^r$, —C(NH)NHR$^r$, —C(NH)NR$^s$R$^r$, —NHC(O)R$^r$, —NHC(S)R$^r$, —NR′C(O)R$^r$, —NR′C(S)R$^r$, —NHS(O)$_2$R$^r$, —NR′S(O)$_2$R$^r$, —NHC(O)NHR$^r$, —NHC(S)NHR$^r$, —NR′C(O)NH$_2$, —NR′C(S)NH$_2$, —NR′C(O)NHR$^r$, —NR′C(S)NHR$^r$, —NHC(O)NR′R$^r$, —NHC(S)NR′R$^r$, —NR′C(O)NR′R$^r$, —NR′C(S)NR′R$^r$, —NHS(O)$_2$NHR$^r$, —NR′S(O)$_2$NH$_2$, —NR′S(O)$_2$NHR$^r$, —NHS(O)$_2$NR′R$^r$, —NR′S(O)$_2$NR′R$^r$, —NHR$^r$, —NR′R$^r$, cycloalkylamino, and —R$^x$;

wherein each R$^r$, R$^s$, and R$^t$ at each occurrence are independently selected from the group consisting of lower alkyl, C$_{3-6}$ alkenyl, C$_{3-6}$ alkynyl, cycloalkyl, heterocycloalkyl, aryl and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided that any substitution of the lower alkyl carbon bound to any —O—, —S—, or —N—, of —OR$^r$, —SR$^r$, —C(O)OR$^r$, —C(S)OR$^r$, —C(O)NHR$^r$, —C(S)NHR$^r$, —C(O)NR′R$^r$, —C(S)NR′R$^r$, —S(O)$_2$ NHR$^r$, —S(O)$_2$NR′R$^r$, —C(NH)NHR$^r$, —NR′R$^r$C(O)R$^r$, —NR′R$^r$C(S)R$^r$, —NR′S(O)$_2$R$^r$, —NHC(O)NHR$^r$, —NHC(S)NHR$^r$, —NR′C(O)NH$_2$, —NR′C(S)NH$_2$, —NR′C(O)NHR$^r$, —NR′C(S)NHR$^r$, —NHC(O)NR′R$^r$, —NHC(S)NR′R$^r$, —NR′C(O)NR′R$^r$, —NR′C(S)NR′R$^r$, —NHS(O)$_2$NHR$^r$, —NR′S(O)$_2$NH$_2$, —NR′S(O)$_2$NHR$^r$, —NHS(O)$_2$NR′R$^r$, —NR′S(O)$_2$NR′R$^r$, —NHR$^r$, or —NR′R$^r$ is selected from the group consisting of fluoro and —R$^y$, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided that any substitution of the C$_{3-6}$ alkenyl or C$_{3-6}$ alkynyl carbon bound to any —O—, —S—, or —N—, of —OR$^r$, —SR$^r$, —C(O)OR$^r$, —C(S)OR$^r$, C(O)NHR$^r$, —C(S)NHR$^r$, —C(O)NR′R$^r$, —C(S)NR′R$^r$, —S(O)$_2$NHR$^r$, S(O)$_2$NR′R$^r$, —C(NH)NHR$^r$, —NR′C(O)R$^r$, NR′C(S)R$^r$, —NR′S(O)$_2$R$^r$, —NHC(O)NHR$^r$, —NHC(S)NHR$^r$, —NR′C(O)NH$_2$, —NR′C(S)NH$_2$, —NR′C(O)NHR$^r$, —NR′C(S)NHR$^r$, —NHC(O)NR′R$^r$, —NHC(S)NR′R$^r$, —NR′C(O)NR′R$^r$, —NR′C(S)NR′R$^r$, —NHS(O)$_2$NHR$^r$, —NR′S(O)$_2$NH$_2$, —NR′S(O)$_2$NHR$^r$, —NHS(O)$_2$NR′R$^r$, —NR′S(O)$_2$NR′R$^r$, —NHR$^r$, or —NR′R$^r$ is selected from the group consisting of fluoro, lower alkyl, fluoro substituted lower alkyl, or —R$^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkyl amino, di-alkyl amino, and cycloalkylamino, or R$^s$ and R$^t$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, OR$^u$, —SR$^u$, —NHR$^u$, —NR$^u$R$^u$, —R$^x$, and —R$^y$;

wherein each R$^u$ is independently selected from the group consisting of lower alkyl, C$_{3-6}$ alkenyl, C$_{3-6}$ alkynyl, cycloalkyl, heterocycloalkyl, aryl, and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided that any substitution of the lower alkyl carbon bound to the —O— of —OR$^u$, —S— of —SR$^u$, or —N— of —NHR$^u$ is fluoro or —R$^y$, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided that any substitution of the C$_{3-6}$ alkenyl or C$_{3-6}$ alkynyl carbon bound to the —O— of —OR$^u$, —S— of —SR$^u$, or —N— of —NHR$^u$ is fluoro, lower alkyl, fluoro substituted lower alkyl, or —R$^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkyl amino, di-alkyl amino, and cycloalkylamino;

wherein each —R$^x$ is selected from the group consisting of lower alkyl, lower alkenyl and lower alkynyl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkyl amino, di-alkyl amino, and cycloalkylamino, and wherein lower alkenyl or lower alkynyl are optionally substituted with one or more, preferably 1, 2, 3, 4 or 5, also 1, 2, or 3 substituents selected from the group consisting of —$R^y$, fluoro, —OH, —$NH_2$, lower alkyl, fluoro substituted lower alkyl, lower alkoxy, fluoro substituted lower alkoxy, lower alkylthio, fluoro substituted lower alkylthio, mono-alkyl amino, di-alkyl amino, and cycloalkylamino;

wherein each —$R^y$ is selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —$NH_2$, —$NO_2$, —CN, lower alkyl, fluoro substituted lower alkyl, lower alkoxy, fluoro substituted lower alkoxy, lower alkylthio, fluoro substituted lower alkylthio, mono-alkyl amino, di-alkyl amino, and cycloalkylamino.

"Lower alkoxy" denotes the group —$OR^z$, where $R^z$ is lower alkyl. "Substituted lower alkoxy" denotes lower alkoxy in which $R^z$ is lower alkyl substituted with one or more substituents as indicated herein, for example, in the description of compounds of Formula I (including Formulae Ia, Ib, Ig and all sub-embodiments thereof), including descriptions of substituted cycloalkyl, cycloheteroalkyl, aryl and heteroaryl, attached at any available atom to produce a stable compound. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. While it is understood that substitutions on alkoxy are attached at any available atom to produce a stable compound, substitution of alkoxy is such that —O—, —S—, or —N— (except where N is a heteroaryl ring atom), are not bound to the alkyl carbon bound to the alkoxy —O—. Further, where alkoxy is described as a substituent of another moiety, the alkoxy oxygen is not bound to a carbon atom that is bound to an —O—, —S—, or —N— of the other moiety (except where N is a heteroaryl ring atom), or to an alkene or alkyne carbon of the other moiety.

"Lower alkylthio" denotes the group —$SR^{aa}$, where $R^{aa}$ is lower alkyl. "Substituted lower alkylthio" denotes lower alkylthio in which $R^{aa}$ is lower alkyl substituted with one or more substituents as indicated herein, for example, in the description of compounds of Formula I (including Formulae Ia, Ib, Ig and all sub-embodiments thereof), including descriptions of substituted cycloalkyl, cycloheteroalkyl, aryl and heteroaryl, attached at any available atom to produce a stable compound. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. While it is understood that substitutions on alkylthio are attached at any available atom to produce a stable compound, substitution of alkylthio is such that —O—, —S—, or —N— (except where N is a heteroaryl ring atom), are not bound to the alkyl carbon bound to the alkylthio —S—. Further, where alkylthio is described as a substituent of another moiety, the alkylthio sulfur is not bound to a carbon atom that is bound to an —O—, —S—, or —N— of the other moiety (except where N is a heteroaryl ring atom), or to an alkene or alkyne carbon of the other moiety.

"Amino" or "amine" denotes the group —$NH_2$. "Mono-alkylamino" denotes the group —$NHR^{bb}$ where $R^{bb}$ is lower alkyl. "Di-alkylamino" denotes the group —$NR^{bb}R^{cc}$, where $R^{bb}$ and $R^{cc}$ are independently lower alkyl. "Cycloalkylamino" denotes the group —$NR^{dd}R^{ee}$, where $R^{dd}$ and $R^{ee}$ combine with the nitrogen to form a 5-7 membered heterocycloalkyl, where the heterocycloalkyl may contain an additional heteroatom within the ring, such as —O—, —N—, or —S—, and may also be further substituted with lower alkyl. Examples of 5-7 membered heterocycloalkyl include, but are not limited to, piperidine, piperazine, 4-methylpiperazine, morpholine, and thiomorpholine. While it is understood that when mono-alkylamino, di-alkylamino, or cycloalkylamino are substituents on other moieties that are attached at any available atom to produce a stable compound, the nitrogen of mono-alkylamino, di-alkylamino, or cycloalkylamino as substituents is not bound to a carbon atom that is bound to an —O—, —S—, or —N— of the other moiety.

As used herein, the term c-kit-mediated disease or condition refers to a disease or condition in which the biological function of c-kit affects the development and/or course of the disease or condition, and/or in which modulation of c-kit alters the development, course, and/or symptoms. For example, mutations in the c-kit gene such as the W42, Wv, and W41 mutations reported by Herbst et al (J. Biol. Chem., 1992, 267: 13210-13216) confer severe, intermediate, and mild phenotypic characteristics, respectively. These mutations attenuate the intrinsic tyrosine kinase activity of the receptor to different degrees and are models for the effect of modulation of c-kit activity. A c-kit mediated disease or condition includes a disease or condition for which c-kit inhibition provides a therapeutic benefit, e.g. wherein treatment with c-kit inhibitors, including compounds described herein, provides a therapeutic benefit to the subject suffering from or at risk of the disease or condition.

As used herein, the term c-fms-mediated disease or condition refers to a disease or condition in which the biological function of c-fms affects the development and/or course of the disease or condition, and/or in which modulation of c-fms alters the development, course, and/or symptoms. For example, the Csflr⁻/Csflr⁻ mutant mouse of Dai et al (Blood, 2002, 99: 111-120) which lacks c-fms is an animal model for diseases or conditions wherein c-fms activity has been abolished. A c-fms mediated disease or condition includes a disease or condition for which c-fms inhibition provides a therapeutic benefit, e.g. wherein treatment with c-fms inhibitors, including compounds described herein, provides a therapeutic benefit to the subject suffering from or at risk of the disease or condition.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

In the present context, the terms "therapeutically effective" and "effective amount" indicate that the materials or amount of material is effective to prevent, alleviate, or ameliorate one or more symptoms of a disease or medical condition, and/or to prolong the survival of the subject being treated.

Reference to particular amino acid residues in human c-kit polypeptide is defined by the numbering corresponding to the Kit sequence in GenBark NP_000213 (SEQ ID NO:1). Reference to particular nucleotide positions in a nucleotide sequence encoding all or a portion of c-kit is defined by the numbering corresponding to the sequence provided in GenBank NM_000222 (SEQ ID NO:2). Reference to particular amino acid residues in human c-fms polypeptide is defined by the numbering corresponding to the FMS precursor sequence in GenBank NP 005202 (SEQ ID NO:3). Reference to particular nucleotide positions in a nucleotide sequence encoding all or a portion of c-fms is defined by the numbering corresponding to the sequence provided in GenBank NM 005211 (SEQ ID NO:4).

The terms "kit", "c-kit", and "c-Kit" mean an enzymatically active kinase that contains a portion with greater than 90% amino acid sequence identity to amino acid residues including the ATP binding site of full-length c-kit (e.g., human c-kit, e.g., the sequence NP_000213, SEQ ID NO:1), for a maximal alignment over an equal length segment; or that contains a portion with greater than 90% amino acid sequence identity to at least 200 contiguous amino acids of native c-kit and retains kinase activity. Preferably the sequence identity is at least 95, 97, 98, 99, or even 100%. Preferably the specified level of sequence identity is over a sequence at least 100-500, at least 200-400, or at least 300 contiguous amino acid residues in length. Unless indicated to the contrary, the term includes reference to wild-type c-kit, allelic variants, and mutated forms (e.g., having activating mutations).

The terms "fms", "c-fms", "FMS", and "c-Fms" mean an enzymatically active kinase that contains a portion with greater than 90% amino acid sequence identity to amino acid residues including the ATP binding site of full-length c-fms (e.g. human c-fms, e.g. residues 20-972 of GenBank sequence NP 005202, SEQ ID NO:3), for a maximal alignment over an equal length segment; or that contains a portion with greater than 90% amino acid sequence identity to at least 200 contiguous amino acids of native c-fms and retains kinase activity. Preferably the sequence identity is at least 95, 97, 98, 99, or 100%. Preferably the specified level of sequence identity is over a sequence at least 100-150, at least 200-400, or at least 300 contiguous amino acid residues in length. Unless indicated to the contrary, the term includes wild-type c-fms, allelic variants, and mutated forms (e.g. having activating mutations). The term "pFMS" refers to phosphorylated c-fms. The term "c-fms activity" refers to a biological activity of c-fms, particularly including kinase activity. The abbreviation "M-CSF" refers to the ligand for the c-fms RPTK, and the abbreviation "SCF" refers to the ligand for the c-Kit RPTK.

The term "c-kit kinase domain" refers to a reduced length c-kit (i.e., shorter than a full-length c-kit by at least 100 amino acids) that includes the kinase catalytic region in c-kit. The term "c-fms kinase domain" refers to a c-fms of reduced length (i.e., shorter than a full-length c-fms by at least 100 amino acids) that includes the kinase catalytic region of c-fms. Highly preferably for use in this invention, the kinase domain retains kinase activity, preferably at least 60, 70, 80, 90, or 100% of the native c-fms kinase activity. The term "the kinase" or terms of similar import relate to either c-kit or c-fms.

As used herein, the terms "ligand" and "modulator" are used equivalently to refer to a compound that changes (i.e., increases or decreases) the activity of a target biomolecule, e.g., an enzyme such as a kinase or kinase. Generally a ligand or modulator will be a small molecule, where "small molecule" refers to a compound with a molecular weight of 1500 daltons or less, or preferably 1000 daltons or less, 800 daltons or less, or 600 daltons or less.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. Preferably a binding compound interacts with a specified target with a dissociation constant ($K_D$) of 1 mM or less. A binding compound can bind with "low affinity", "very low affinity", "extremely low affinity", "moderate affinity", "moderately high affinity", or "high affinity" as described herein.

In the context of compounds binding to a target, the term "greater affinity" indicates that the compound binds more tightly than a reference compound, or than the same compound in a reference condition, i.e., with a lower dissociation constant. In particular embodiments, the greater affinity is at least 2, 3, 4, 5, 8, 10, 50, 100, 200, 400, 500, 1000, or 10,000-fold greater affinity.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of c-kit or c-fms, other tyrosine kinases or even other type of enzymes. In particular embodiments, the greater specificity is at least 2, 3, 4, 5, 8, 10, 50, 100, 200, 400, 500, or 1000-fold greater specificity.

As used herein in connection with binding compounds or ligands, the term "specific for c-kit kinase", "specific for c-kit", and terms of like import mean that a particular compound binds to c-kit to a statistically greater extent than to other kinases that may be present in a particular sample. Also, where biological activity other than binding is indicated, the term "specific for c-kit" indicates that a particular compound has greater biological effect associated with binding c-kit than to other tyrosine kinases, e.g., kinase activity inhibition. Preferably, the specificity is also with respect to other biomolecules (not limited to tyrosine kinases) that may be present in a particular sample. The term "specific for c-fms kinase", "specific for c-fms", and terms of like import mean that a particular compound binds to c-fms to a statistically greater extent than to other kinases that may be present in a particular sample. Also, where biological activity other than binding is indicated, the term "specific for c-fms" indicates that a particular compound has greater biological effect associated with binding c-fms than to other tyrosine kinases, e.g., kinase activity inhibition. Preferably, the specificity is also with respect to other biomolecules (not limited to tyrosine kinases) that may be present in a particular sample.

As used herein in connection with test compounds, binding compounds, and modulators (ligands), the term "synthesizing" and like terms means chemical synthesis from one or more precursor materials.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

As used herein, the term "modulating" or "modulate" refers to an effect of altering a biological activity, especially a biological activity associated with a particular biomolecule such as c-kit or c-fms. For example, an agonist or antagonist of a particular biomolecule modulates the activity of that biomolecule, e.g., an enzyme.

The term "c-kit activity" refers to a biological activity of c-kit, particularly including kinase activity. The term "c-fms activity" refers to a biological activity of c-fms, particularly including kinase activity.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the particular molecule constitutes a significantly greater proportion of the biomolecules in a composition than in a prior composition, e.g., in a cell culture. The greater proportion can be 2-fold, 5-fold, 10-fold or more greater.

I. General

In one aspect, the present invention concerns compounds of Formula I, Formula Ia, Formula Ib, or Formula Ig and all sub-embodiments thereof, that are inhibitors of c-kit, c-fms, or both c-kit and c-fms, and the use of the compounds in treating diseases that are mediated by c-kit, c-fms, or both c-kit and c-fms.

Exemplary compounds of Formula I, Formula Ia, Formula Ib or Formula Ig prepared following methods described in the Examples herein are as follows:
Benzyl-[5-(1H-pyrrolo[2,3-b]pyridin-3-ylmethyl)-pyridin-2-yl]-amine (P-0001),
(6-Benzylamino-pyridin-3-yl)-(1H-pyrrolo[2,3-b]pyridin-3-yl)-methanone (P-0002),
[5-(1H-Pyrrolo[2,3-b]pyridin-3-ylmethyl)-pyridin-2-yl]-(4trifluoromethyl-benzyl)-amine (P-0003),
(4-Methoxy-benzyl)-[5-(1H-pyrrolo[2,3-b]pyridin-3-ylmethyl)-pyridin-2-yl]-amine (P-0004),
(4-Chloro-benzyl)-[5-(1H-pyrrolo[2,3-b]pyridin-3-ylmethyl)-pyridin-2-yl]-amine (P-0005),
(4-Fluoro-benzyl)-[5-(1H-pyrrolo[2,3-b]pyridin-3-ylmethyl)-pyridin-2-yl]-amine (P-0006),
(4-Methyl-benzyl)-[5-(1H-pyrrolo[2,3-b]pyridin-3-ylmethyl)-pyridin-2-yl]-amine (P-0007),
[5-(1H-Pyrrolo[2,3-b]pyridin-3-ylmethyl)-pyridin-2-yl]-thiophen-2-ylmethyl-amine (P-0008),
(4-Chloro-benzyl)-[5-(4-chloro-1H-pyrrolo[2,3-b]pyridin-3-ylmethyl)-pyridin-2-yl]-amine (P-0009),
(4-Chloro-benzyl)-[5-(4-methoxy-1H-pyrrolo[2,3-b]pyridin-3-ylmethyl)-pyridin-2-yl]-amine (P-0010),
[5-(4-Methoxy-1H-pyrrolo[2,3-b]pyridin-3-ylmethyl)-pyridin-2-yl]-(4-trifluoromethyl-benzyl)-amine (P-0011),
[6-Methoxy-5-(1H-pyrrolo[2,3-b]pyridin-3-ylmethyl)-pyridin-2-yl]-(4-trifluoromethyl-benzyl)-amine (P-0012),
[6-Methyl-5-(1H-pyrrolo[2,3-b]pyridin-3-ylmethyl)-pyridin-2-yl]-(4-trifluoromethyl-benzyl)-amine (P-0013),
(4-Chloro-benzyl)-[6-methyl-5-(1H-pyrrolo[2,3-b]pyridin-3-ylmethyl)-pyridin-2-yl]-amine (P-0014),
[6-(4-Fluoro-benzylamino)-pyridin-3-yl]-(1H-pyrrolo[2,3-b]pyridin-3-yl)-methanone (P-0015),
[6-(3-Fluoro-benzylamino)-pyridin-3-yl]-(1H-pyrrolo[2,3-b]pyridin-3-yl)-methanone (P-0016),
H-Pyrrolo[2,3-b]pyridin-3-yl)-[6-(4-trifluoromethyl-benzylamino)-pyridin-3-yl]-methanone (P-0017),
H-Pyrrolo[2,3-b]pyridin-3-yl)-{6-[(thiophen-2-ylmethyl)-amino]-pyridin-3-yl}-methanone (P-0018),
3-(6-Isopropyl-pyridin-3-ylmethyl)-1H-pyrrolo[2,3-b]pyridine (P-0019), 3-(6-tert-Butoxy-pyridin-3-ylmethyl)-1H-pyrrolo[2,3-b]pyridine (P-0020),
Dimethyl-[5-(1H-pyrrolo[2,3-b]pyridin-3-ylmethyl)-pyridin-2-yl]-amine (P-0021),
3-(6-Methoxy-pyridin-3-ylmethyl)-4-thiophen-3-yl-1H-pyrrolo[2,3-b]pyridine (P-0022),
(6-Phenylamino-pyridin-3-yl)-(1H-pyrrolo[2,3-b]pyridin-3-yl)-methanone (P-0023),
(6-Isopropylamino-pyridin-3-yl)-(1H-pyrrolo[2,3-b]pyridin-3-yl)-methanone (P-0024),
(6-Isobutylamino-pyridin-3-yl)-(1H-pyrrolo[2,3-b]pyridin-3-yl)-methanone (P-0025),
[6-(3-Benzyloxy-phenylamino)-pyridin-3-yl]-(1H-pyrrolo[2,3-b]pyridin-3-yl)-methanone (P-0026),
[6-(3-Hydroxy-phenylamino)-pyridin-3-yl]-(1H-pyrrolo[2,3-b]pyridin-3-yl)-methanone (P-0027),
Isobutyl-[5-(1H-pyrrolo[2,3-b]pyridin-3-ylmethyl)-pyridin-2-yl]-amine (P-0028),
(6-Isobutylamino-pyridin-3-yl)-(1H-pyrrolo[2,3-b]pyridin-3-yl)-methanol (P-0029),
[6-(Cyclopropylmethyl-amino)-pyridin-3-yl]-(1H-pyrrolo[2,3-b]pyridin-3-yl)-methanone (P-0030),
[6-(Cyclohexylmethyl-amino)-pyridin-3-yl]-(1H-pyrrolo[2,3-b]pyridin-3-yl)-methanone (P-0031),
Cyclopropylmethyl-[5-(1H-pyrrolo[2,3-b]pyridin-3-ylmethyl)-pyridin-2-yl]-amine (P-0032),
Cyclohexylmethyl-[5-(1H-pyrrolo[2,3-b]pyridin-3-ylmethyl)-pyridin-2-yl]-amine (P-0033),
[6-(Cyclopropylmethyl-amino)-pyridin-3-yl]-(1H-pyrrolo[2,3-b]pyridin-3-yl)-methanol (P-0034),
[6-(Cyclohexylmethyl-amino)-pyridin-3-yl]-(1H-pyrrolo[2,3-b]pyridin-3-yl)-methanol (P-0035),
(1H-Pyrrolo[2,3-b]pyridin-3-yl)-[6-(4-trifluoromethyl-benzylamino)-pyridin-3-yl]-methanol (P-0036),
[6-(4-Chloro-benzylamino)-pyridin-3-yl]-(1H-pyrrolo[2,3-b]pyridin-3-yl)-methanol (P-0037),
[5-(5-Bromo-1H-pyrrolo[2,3-b]pyridin-3-ylmethyl)-pyridin-2-yl]-(4-chloro-benzyl)-amine (P-0038),
(4-Chloro-benzyl)-{5-[methoxy-(1H-pyrrolo[2,3-b]pyridin-3-yl)-methyl]-pyridin-2-yl}-amine (P-0039),
(4-Chloro-3-trifluoromethyl-benzyl)-{5-[methoxy-(1H-pyrrolo[2,3-b]pyridin-3-yl)-methyl]-pyridin-2-yl}-amine (P-0040),
(4-Chloro-benzyl)-{5-[methoxy-(5-pyridin-3-yl-1H-pyrrolo[2,3-b]pyridin-3-yl)-methyl]-pyridin-2-yl}-amine (P-0041),
(4-Chloro-benzyl)-(5-{[5-(3-methanesulfonyl-phenyl)-1H-pyrrolo[2,3-b]pyridin-3-yl]-methoxy-methyl}-pyridin-2-yl)-amine (P-0042),
{5-[Methoxy-(1H-pyrrolo[2,3-b]pyridin-3-yl)-methyl]-pyridin-2-yl}-(4-trifluoromethyl-benzyl)-amine (P-0043),
[6-(4-Chloro-benzylamino)-2-methyl-pyridin-3-yl]-(1H-pyrrolo[2,3-b]pyridin-3-yl)-methanol (P-0046),
[2-Chloro-6-(4-chloro-benzylamino)-pyridin-3-yl]-(1H-pyrrolo[2,3-b]pyridin-3-yl)-methanone (P-0048),
[2,6-Bis-(4-chloro-benzylamino)-pyridin-3-yl]-(1H-pyrrolo[2,3-b]pyridin-3-yl)-methanone (P-0049),

[2-Chloro-6-(4-chloro-benzylamino)-pyridin-3-yl]-(1H-pyrrolo[2,3-b]pyridin-3-yl)-methanol (P-0050),
6-(4-Chloro-benzylamino)-3-(1H-pyrrolo[2,3-b]pyridin-3-ylmethyl)-pyridin-2-ol (P-0051),
3-(2-Ethylsulfanyl-4,6-dimethyl-pyrimidin-5-ylmethyl)-1H-pyrrolo[2,3-b]pyridine (P-0052),
[5-(5-Methoxy-1H-pyrrolo[2,3-b]pyridin-3-ylmethyl)-pyridin-2-yl]-(4-trifluoromethyl-benzyl)-amine (P-0053),
[5-(5-Chloro-1H-pyrrolo[2,3-b]pyridin-3-ylmethyl)-pyridin-2-yl]-(4-trifluoromethyl-benzyl)-amine (P-0054),
3-[6-(3-Chloro-benzyloxy)-pyridin-3-ylmethyl]-1H-pyrrolo[2,3-b]pyridine (P-0055),
3-[6-(4-Chloro-benzyloxy)-pyridin-3-ylmethyl]-1H-pyrrolo[2,3-b]pyridine (P-0056),
3-[6-(3-Trifluoromethyl-benzyloxy)-pyridin-3-ylmethyl]-1H-pyrrolo[2,3-b]pyridine (P-0057),
(4-Chloro-benzyl)-[5-(5-methoxy-1H-pyrrolo[2,3-b]pyridin-3-ylmethyl)-pyridin-2-yl]-amine (P-0058),
(4-Chloro-benzyl)-[5-(5-chloro-1H-pyrrolo[2,3-b]pyridin-3-ylmethyl)-pyridin-2-yl]-amine (P-0059),
{5-[5-(2-Diethylamino-ethoxy)-1H-pyrrolo[2,3-b]pyridin-3-ylmethyl]-pyridin-2-yl}-(4-trifluoromethyl-benzyl)-amine (P-0060),
3-[6-(4-Trifluoromethyl-benzylamino)-pyridin-3-ylmethyl]-1H-pyrrolo[2,3-b]pyridin-5-ol (P-0061),
3-[6-(4-Chloro-benzylamino)-pyridin-3-ylmethyl]-1H-pyrrolo[2,3-b]pyridin-5-ol (P-0062),
(4-Chloro-benzyl)-{5-[5-(2-morpholin-4-yl-ethoxy)-1H-pyrrolo[2,3-b]pyridin-3-ylmethyl]-pyridin-2-yl}-amine (P-0063),
{5-[5-(2-Pyrrolidin-1-yl-ethoxy)-1H-pyrrolo[2,3-b]pyridin-3-ylmethyl]-pyridin-2-yl}-(4-trifluoromethyl-benzyl)-amine (P-0064),
{5-[5-(2-Morpholin-4-yl-ethoxy)-1H-pyrrolo[2,3-b]pyridin-3-ylmethyl]-pyridin-2-yl}-(4-trifluoromethyl-benzyl)-amine (P-0065),
{5-[5-(3-Diethylamino-propoxy)-1H-pyrrolo[2,3-b]pyridin-3-ylmethyl]-pyridin-2-yl}-(4-trifluoromethyl-benzyl)-amine (P-0066),
N-[5-(1H-Pyrrolo[2,3-b]pyridine-3-carbonyl)-pyridin-2-yl]-4-trifluoromethyl-benzamide (P-0067),
N-[5-(1H-Pyrrolo[2,3-b]pyridine-3-carbonyl)-pyridin-2-yl]-4-trifluoromethyl-benzenesulfonamide (P-0068),
(4-Chloro-benzyl)-{5-[5-(3-diethylamino-propoxy)-1H-pyrrolo[2,3-b]pyridin-3-ylmethyl]-pyridin-2-yl}-amine (P-0069),
[6-(4-Chloro-benzylamino)-2-trifluoromethyl-pyridin-3-yl]-(1H-pyrrolo[2,3-b]pyridin-3-yl)-methanone (P-0070),
N-[5-(1H-Pyrrolo[2,3-b]pyridin-3-ylmethyl)-pyridin-2-yl]-4-trifluoromethyl-benzenesulfonamide (P-0071),
N-[5-(1H-Pyrrolo[2,3-b]pyridin-3-ylmethyl)-pyridin-2-yl]-4-trifluoromethyl-benzamide (P-0072),
4-Fluoro-N-[5-(1H-pyrrolo[2,3-b]pyridin-3-ylmethyl)-pyridin-2-yl]-benzamide (P-0073),
4-Chloro-N-[5-(1H-pyrrolo[2,3-b]pyridin-3-ylmethyl)-pyridin-2-yl]-benzamide (P-0074),
[(S)-1-(4-Chloro-phenyl)-ethyl]-[5-(1H-pyrrolo[2,3-b]pyridin-3-ylmethyl)-pyridin-2-yl]-amine (P-0075),
5-(1H-Pyrrolo[2,3-b]pyridin-3-ylmethyl)-pyridine-2-carboxylic acid (4-chloro-phenyl)-amide (P-0076),
[2-(4-Chloro-benzylamino)-thiazol-5-yl]-(1H-pyrrolo[2,3-b]pyridin-3-yl)-methanone (P-0077),
(4-Chloro-phenyl)-[5-(1H-pyrrolo[2,3-b]pyridin-3-ylmethyl)-pyridin-2-ylmethyl]-amine (P-0078),
3-[(5-Chloro-3-methyl-1-phenyl-1H-pyrazol-4-yl)-methoxy-methyl]-1H-pyrrolo[2,3-b]pyridine (P-0079),
3-(5-Chloro-3-methyl-1-phenyl-1H-pyrazol-4-ylmethyl)-1H-pyrrolo[2,3-b]pyridine (P-0080),
(4-Chloro-benzyl)-[6-methoxy-5-(1H-pyrrolo[2,3-b]pyridin-3-ylmethyl)-pyridin-2-yl]-amine (P-0081),
(4-Chloro-benzyl)-[6-fluoro-5-(1H-pyrrolo[2,3-b]pyridin-3-ylmethyl)-pyridin-2-yl]-amine (P-0082), and
(4-Chloro-benzyl)-[4-chloro-5-(1H-pyrrolo[2,3-b]pyridin-3-ylmethyl)-thiazol-2-yl]-amine (P-0083),
3,5-Dimethyl-4-(1H-pyrrolo[2,3-b]pyridin-3-ylmethyl)-pyrazole-1-carboxylic acid benzylamide (P-0084),
3,5-Dimethyl-4-(1H-pyrrolo[2,3-b]pyridin-3-ylmethyl)-pyrazole-1-carboxylic acid phenylamide (P-0085),
[3,5-Dimethyl-4-(1H-pyrrolo[2,3-b]pyridin-3-ylmethyl)-pyrazol-1-yl]-phenyl-methanone (P-0086),
1-[3,5-Dimethyl-4-(1H-pyrrolo[2,3-b]pyridin-3-ylmethyl)-pyrazol-1-yl]-3-phenyl-propan-1-one (P-0087),
3-(3,5-Dimethyl-1-phenylmethanesulfonyl-1H-pyrazol-4-ylmethyl)-1H-pyrrolo[2,3-b]pyridine (P-0088),
3-[1-(Butane-1-sulfonyl)-3,5-dimethyl-1H-pyrazol-4-ylmethyl]-1H-pyrrolo[2,3-b]pyridine (P-0089), and
3,5-Dimethyl-4-(1H-pyrrolo[2,3-b]pyridin-3-ylmethyl)-pyrazole-1-carboxylic acid butylamide (P-0090).

Exemplary Diseases Associated with c-Kit.

The compounds described herein are useful for treating disorders related to c-kit e.g., diseases related to unregulated kinase signal transduction, including cell proliferative disorders, fibrotic disorders and metabolic disorders, among others. As described in more detail below and in Lipson et al., U.S. 20040002534 (U.S. application Ser. No. 10/600,868, filed Jun. 23, 2003) which is incorporated herein by reference in its entirety, cell proliferative disorders which can be treated by the present invention include cancers, and mast cell proliferative disorders.

The presence of c-kit has also been associated with a number of different types of cancers, as described below. In addition, the association between abnormalities in c-kit and disease are not restricted to cancer. As such, c-kit has been associated with malignancies, including mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including asthma, rheumatoid arthritis, allergic rhinitis, multiple sclerosis, inflammatory bowel syndrome, transplant rejection, and hypereosinophilia.

Exemplary Malignant Diseases Associated with c-kit

Aberrant expression and/or activation of c-kit has been implicated in a variety of cancers. Evidence for a contribution of c-kit to neoplastic pathology includes its association with leukemias and mast cell tumors, small cell lung cancer, testicular cancer, and some cancers of the gastrointestinal tract and central nervous system. In addition, c-kit has been implicated in playing a role in carcinogenesis of the female genital tract (Inoue, et al., 1994, Cancer Res. 54(11):3049-3053), sarcomas of neuroectodermal origin (Ricotti, et al., 1998, Blood 91:2397-2405), and Schwann cell neoplasia associated with neurofibromatosis (Ryan, et al., 1994, J. Neuro. Res. 37:415-432). It was found that mast cells are involved in modifying the tumor microenvironment and enhancing tumor growth (Yang et al., 2003, J Clin Invest. 112:1851-1861; Viskochil, 2003, J Clin Invest. 112:1791-1793). Thus, c-kit is a useful target in treating neurofibromatosis as well as malignant tumors.

Small cell lung carcinoma: c-kit kinase receptor has been found to be aberrantly expressed in many cases of small cell lung carcinoma (SCLC) cells (Hibi, et al., 1991, Oncogene 6:2291-2296). Thus, as an example, inhibition of c-kit kinase can be beneficial in treatment of SCLC, e.g., to improve the long term survival of patients with SCLC.

Leukemias: SCF binding to the c-kit protects hematopoietic stem and progenitor cells from apoptosis (Lee, et al., 1997, J. Immunol. 159:3211-3219), thereby contributing to colony formation and hematopoiesis. Expression of c-kit is frequently observed in acute myelocytic leukemia (AML), and in some cases of acute lymphocytic leukemia (ALL) (for reviews, see Sperling, et al., 1997, Haemat 82:617-621; Escribano, et al., 1998, Leuk. Lymph. 30:459-466). Although c-kit is expressed in the majority of AML cells, its expression does not appear to be prognostic of disease progression (Sperling, et al, 1997, Haemat 82:617-621). However, SCF protected AML cells from apoptosis induced by chemotherapeutic agents (Hassan, et al., 1996, Acta. Hem. 95:257-262). Inhibition of c-kit by the present invention will enhance the efficacy of these agents and can induce apoptosis of AML cells.

The clonal growth of cells from patients with myelodysplastic syndrome (Sawada, et al., 1996, Blood 88:319-327) or chronic myelogenous leukemia (CML) (Sawai, et al., 1996, Exp. Hem. 2:116-122) was found to be significantly enhanced by SCF in combination with other cytokines. CML is characterized by expansion of Philadelphia chromosome positive cells of the marrow (Verfaillie, et al., Leuk. 1998, 12:136-138), which appears to primarily result from inhibition of apoptotic death (Jones, Curr. Opin. One. 1997, 9:3-7). The product of the Philadelphia chromosome, $p210^{BCR-ABL}$, has been reported to mediate inhibition of apoptosis (Bedi, et al., Blood 1995, 86:1148-1158). Since $p210^{BCR-ABL}$ and c-kit both inhibit apoptosis and $p62^{dok}$ has been suggested as a substrate (Carpino, et al., Cell 1997, 88:197-204), clonal expansion mediated by these kinases may occur through a common signaling pathway. However, c-kit has also been reported to interact directly with $p210^{BCR-ABL}$ (Hallek, et al., Brit. J Haem. 1996, 94:5-16), which suggests that c-kit has a more causative role in CML pathology. Therefore, inhibition of c-kit will be useful in the treatment of the above disorders.

Gastrointestinal cancers: Normal colorectal mucosa does not express c-kit (Bellone, et al., 1997, J. Cell Physiol. 172: 1-11). However, c-kit is frequently expressed in colorectal carcinoma (Bellone, et al., 1997, J. Cell Physiol. 172: 1-11), and autocrine loops of SCF and c-kit have been observed in several colon carcinoma cell lines (Toyota, et al., 1993, Turn Biol 14:295-302; Lahm, et al., 1995, Cell Growth & Differ 6:1111-1118; Bellone, et al., 1997, J. Cell Physiol. 172:1-11). Furthermore, disruption of the autocrine loop by the use of neutralizing antibodies (Lahm, et al., 1995, Cell Growth & Differ. 6:1111-1118) and downregulation of c-kit and/or SCF significantly inhibits cell proliferation (Lahm, et al., 1995, Cell Growth & Differ 6:1111-1118; Bellone, et al., 1997, J. Cell Physiol. 172: 1-11).

SCF/c-kit autocrine loops have been observed in gastric carcinoma cell lines (Turner, et al., 1992, Blood 80:374-381; Hassan, et al., 1998, Digest. Dis. Science 43:8-14), and constitutive c-kit activation also appears to be important for gastrointestinal stromal tumors (GISTs). GISTs are the most common mesenchymal tumor of the digestive system. More than 90% of GISTs express c-kit, which is consistent with the putative origin of these tumor cells from interstitial cells of Cajal (ICCs) (Hirota, et al., 1998, Science 279:577-580). ICCs are thought to regulate contraction of the gastrointestinal tract, and patients lacking c-kit in their ICCs exhibited a myopathic form of chronic idiopathic intestinal pseudo-obstruction (Isozaki, et al., 1997, Amer. J. of Gast. 9 332-334). The c-kit expressed in GISTs from several different patients was observed to have mutations in the intracellular juxtamembrane domain leading to constitutive activation of c-kit (Hirota, et al., 1998, Science 279:577-580). Hence, inhibition of c-kit kinase will be an efficacious means for the treatment of these cancers.

Testicular cancers: Male germ cell tumors have been histologically categorized into seminomas, which retain germ cell characteristics, and nonseminomas which can display characteristics of embryonal differentiation. Both seminomas and nonseminomas are thought to initiate from a preinvasive stage designated carcinoma in situ (CIS) (Murty, et al., 1998, Sem. Oncol. 25:133-144). Both c-kit and SCF have been reported to be essential for normal gonadal development during embryogenesis (Loveland, et al., 1997, J. Endocrinol 153:337-344). Loss of either the receptor or the ligand resulted in animals devoid of germ cells. In postnatal testes, c-kit has been found to be expressed in Leydig cells and spermatogonia, while SCF was expressed in Sertoli cells (Loveland, et al., 1997, J. Endocrinol 153:337-344). Testicular tumors develop from Leydig cells with high frequency in transgenic mice expressing human papilloma virus 16 (HPV16) E6 and E7 oncogenes (Kondoh, et al., 1991, J. Virol. 65:3335-3339; Kondoh, et al., 1994, J. Urol. 152:2151-2154). These tumors express both c-kit and SCF, and an autocrine loop may contribute to the tumorigenesis (Kondoh, et al., 1995, Oncogene 10:341-347) associated with cellular loss of functional p53 and the retinoblastoma gene product by association with E6 and E7 (Dyson, et al., 1989, Science 243:934-937; Werness, et al., 1990, Science 248:76-79; Scheffner, et al., 1990, Cell 63:1129-1136). Defective signaling mutants of SCF (Kondoh, et al., 1995, Oncogene 10:341-347) or c-kit (Li, et al., 1996, Canc. Res. 56:4343-4346) inhibited formation of testicular tumors in mice expressing HPV16 E6 and E7. The c-kit kinase activation is pivotal to tumorigenesis in these animals and thus modulation of the c-kit kinase pathway by the present invention will prevent or treat such disorders.

Expression of c-kit in germ cell tumors shows that the receptor is expressed by the majority of carcinomas in situ and seminomas, but c-kit is expressed in only a minority of nonseminomas (Strohmeyer, et al., 1991, Canc. Res. 51:1811-1816; Rajpert-de Meyts, et al., 1994, Int. J. Androl. 17:85-92; Izquierdo, et al., 1995, J. Pathol. 177:253-258; Strohmeyer, et al., 1995, J. Urol. 153:511-515; Bokenmeyer, et al., 1996, J. Cancer Res. Clin. Oncol. 122:301-306; Sandlow, et al., 1996, J. Androl. 17:403-408). Therefore, inhibition of c-kit kinase provides a means for treating these disorders.

CNS cancers: SCF and c-kit are expressed throughout the CNS of developing rodents, and the pattern of expression indicates a role in growth, migration and differentiation of neuroectodermal cells. Expression of both receptor and ligand have also been reported in the adult brain (Hamel, et al., 1997, J. Neuro-Onc. 35:327-333). Expression of c-kit has also been observed in normal human brain tissue (Tada, et al. 1994, J. Neuro 80:1063-1073). Glioblastoma and astrocytoma, which define the majority of intracranial tumors, arise from neoplastic transformation of astrocytes (Levin, et al., 1997, Principles & Practice of Oncology:2022-2082). Expression of c-kit has been observed in glioblastoma cell lines and tissues (Berdel, et al., 1992, Canc. Res. 52:3498-3502; Tada, et al. 1994, J. Neuro 80:1063-1073; Stanulla, et al., 1995, Act Neuropath 89:158-165).

Cohen, et al., 1994, Blood 84:3465-3472 reported that all 14 neuroblastoma cell lines examined contained c-kit/SCF autocrine loops, and expression of both the receptor and ligand were observed in 45% of tumor samples examined. In two cell lines, anti-c-kit antibodies inhibited cell proliferation, suggesting that the SCF/c-kit autocrine loop contributed to growth (will Cohen, et al., 1994, Blood 84:3465-3472). Hence, c-kit kinase inhibitors can be used to treat these cancers.

Exemplary Mast Cell Diseases Involving c-Kit

Excessive activation of c-kit is also associated with diseases resulting from an over-abundance of mast cells. Mastocytosis is the term used to describe a heterogeneous group of disorders characterized by excessive mast cell proliferation (Metcalfe, 1991, J. Invest. Derm 93:2S-4S; Golkar, et al., 1997, Lancet 349:1379-1385). Elevated c-kit expression was reported on mast cells from patients with aggressive mastocytosis (Nagata, et al., 1998, Leukemia 12:175-181).

Additionally, mast cells and eosinophils represent key cells involved in allergy, inflammation and asthma (Thomas, et al., 1996, Gen. Pharmacol 27:593-597; Metcalfe, et al., 1997, Physiol Rev 77:1033-1079; Naclerio, et al., 1997, JAMA 278:1842-1848; Costa, et al., 1997, JAMA 278:1815-1822). SCF, and hence c-kit, directly and indirectly regulates activation of both mast cells and eosinophils, thereby influencing the primary cells involved in allergy and asthma through multiple mechanisms. Because of this mutual regulation of mast cell and eosinophil function, and the role that SCF can play in this regulation, inhibition of c-kit can be used to treat allergy-associated chronic rhinitis, inflammation and asthma.

Mastocytosis: SCF (also known as mast cell growth factor) stimulation of c-kit has been reported to be essential for the growth and development of mast cells (Hamel, et al., 1997, J. Neuro-Onc. 35:327-333; Kitamura, et al., 1995, Int. Arch. Aller. Immunol. 107:54-56). Mice with mutations of c-kit that attenuate its signaling activity have exhibited significantly fewer mast cells in their skin (Tsujimura, 1996, Pathol Int 46:933-938). Excessive activation of c-kit can be associated with diseases resulting from an over abundance of mast cells.

Mastocytosis is limited to the skin in the majority of patients, but can involve other organs in 15-20% of patients (Valent, 1996, Wein/Klin Wochenschr 108:385-397; Golkar, et al., 1997, Lancet 349:1379-1385). Even among patients with systemic mastocytosis, the disease can range from having a relatively benign prognosis to aggressive mastocytosis and mast cell leukemia. (Valent, 1996, Wein/Klin Wochenschr 108:385-397; Golkar, et al., 1997, Lancet 349:1379-1385). c-kit has been observed on malignant mast cells from canine mast cell tumors (London, et al., 1996, J. Compar. Pathol. 115:399-414), as well as on mast cells from patients with aggressive systemic mastocytosis (Baghestanian, et al., 1996, Leuk.:116-122; Castells, et al., 1996, J. Aller. Clin. Immunol. 98:831-840).

SCF has been shown to be expressed on stromal cells as a membrane-bound protein, and its expression can be induced by fibrogenic growth factors such as PDGF. It has also been shown to be expressed on keratinocytes as a membrane-bound protein in normal skin. However, in the skin of patients with mastocytosis, an increased amount of soluble SCF has been observed (Longley, et al., 1993, New Engl. J. Med. 328:1302-1307).

Mast cell chymase has been reported to cleave membrane-associated SCF to a soluble and biologically active form. This mast cell-mediated process can generate a feedback loop to enhance mast cell proliferation and function (Longley, et al., 1997, Proc. Natl. Acad. Sci. 94:9017-9021), and may be important for the etiology of mastocytosis. Transgenic mice overexpressing a form of SCF that could not be proteolytically released from keratinocytes did not develop mastocytosis, while similar animals expressing normal SCF in keratinocytes exhibited a phenotype resembling human cutaneous mastocytosis (Kunisada, et al., 1998, J. Exp. Med. 187:1565-1573). Formation of large amounts of soluble SCF can contribute to the pathology associated with mastocytosis in some patients and the present invention can treat or prevent such disorders by modulating the interaction between SCF and c-kit kinase. Several different mutations of c-kit that resulted in constitutive kinase activity have been found in human and rodent mast cell tumor cell lines (Furitsu, et al., 1993, J. Clin. Invest. 92:1736-1744; Tsujimura, et al., 1994, Blood 9:2619-2626; Tsujimura, et al., 1995, Int. Arch. Aller. Immunol 106: 377-385; Tsujimura, 1996, Pathol Int 46:933-938). In addition, activating mutations of the c-kit gene have been observed in peripheral mononuclear cells isolated from patients with mastocytosis and associated hematologic disorders (Nagata, et al., 1998, Mastocytosis Leuk 12:175-181), and in mast cells from a patient with urticaria pigmentosa and aggressive mastocytosis (Longley, et al., 1996, Nat. Gen. 12:312-314). Inhibition of c-kit kinase will therefore prove to have an excellent therapeutic role in the treatment of these disorders.

In some patients, activating mutations of c-kit may be responsible for the pathogenesis of the disease and these patients can be treated, or their diseases prevented, by modulation of the SCF interaction with c-kit kinase. SCF activation of c-kit as been shown to prevent mast cell apoptosis which may be critical for maintaining cutaneous mast cell homeostasis (Iemura, et al., 1994, Amer. J. Pathol 144:321-328; Yee, et al., 1994, J. Exp. Med. 179:1777-1787; Mekori, et al., 1994, J. Immunol 153:2194-2203; Mekori, et al., 1995, Int. Arch. Allergy Immunol. 107:137-138). Inhibition of mast cell apoptosis can lead to the mast cell accumulation associated with mastocytosis. Thus, observation of c-kit activation resulting from overexpression of the receptor, excessive formation of soluble SCF, or mutations of the c-kit gene that constitutively activate its kinase, provides a rationale that inhibition of the kinase activity of c-kit will decrease the number of mast cells and provide benefit for patients with mastocytosis.

For cells with activating c-kit mutations, it was found that inhibitors of c-kit inhibit or even kill the cells (Ma et al., 2000, J Invest Dermatol. 114:392-394), particularly for mutations in the regulatory region (Ma et al., 2002, Blood 99:1741-1744). Ma et al., 2002, also showed that for mutations in the catalytic region, inhibitors STI571 (Gleevec) and SU9529 did not inhibit the cells, such that additional types of c-kit inhibitors are useful. Thus, c-kit inhibitors can be used against both wild-type c-kit as well as c-kit having mutations, e.g., activating mutations in the regulatory region and/or catalytic region.

Asthma & Allergy: Mast cells and eosinophils represent key cells in parasitic infection, allergy, inflammation, and asthma (Thomas, et al., 1996, Gen. Pharmacol 27:593-597; Metcalfe, et al., 1997, Physiol Rev 77:1033-1079; Holgate, 1997, CIBA Found. Symp.; Naclerio, et al, 1997, JAMA 278:1842-1848; Costa, et al., 1997, JAMA 778:1815-1822). SCF has been shown to be essential for mast cell development, survival and growth (Kitamura, et al., 1995, Int. Arch. Aller. Immunol. 107:54-56; Metcalfe, et al., 1997, Physiol Rev 77:1033-1079). In addition, SCF cooperates with the eosinophil-specific regulator, IL-5, to increase the development of eosinophil progenitors (Metcalf, et al., 1998, Proc. Natl. Acad. Sci., USA 95:6408-6412). SCF has also been reported to induce mast cells to secrete factors (Okayama, et al., 1997, Int. Arch. Aller. Immunol. 114:75-77; Okayama, et al., 1998, Eur. J. Immunol. 28:708-715) that promote the survival of eosinophils (Kay, et al., 1997, Int. Arch. Aller.

Immunol. 113:196-199), which may contribute to chronic, eosinophil-mediated inflammation (Okayama, et al., 1997, Int. Arch. Aller. Immunol. 114:75-77; Okayama, et al., 1998, Eur. J. Immunol. 28:708-715). In this regard, SCF directly and indirectly regulates activation of both mast cells and eosinophils.

SCF induces mediator release from mast cells, as well as priming these cells for IgE-induced degranulation (Columbo, et al., 1992, J. Immunol 149:599-602) and sensitizing their responsiveness to eosinophil-derived granule major basic protein (Furuta, et al., 1998, Blood 92:1055-1061). Among the factors released by activated mast cells are IL-5, GM-CSF and TNF-α, which influence eosinophil protein secretion (Okayama, et al., 1997, Int. Arch. Aller. Immunol. 114:75-77; Okayama, et al., 1998, Eur. J. Immunol. 28:708-715). In addition to inducing histamine release from mast cells (Luckacs, et al., 1996, J. Immunol. 156:3945-3951; Hogaboam, et al., 1998, J. Immunol. 160:6166-6171), SCF promotes the mast cell production of the eosinophil chemotactic factor, eotaxin (Hogaboam, et al., 1998, J. Immunol. 160:6166-6171), and eosinophil infiltration (Luckacs, et al., 1996, J. Immunol. 156:3945-3951).

SCF also directly influences the adhesion of both mast cells (Dastych, et al., 1994, J. Immunol. 152:213-219; Kinashi, et al., 1994, Blood 83:1033-1038) and eosinophils (Yuan, et al., 1997, J. Exp. Med. 186:313-323), which in turn, regulates tissue infiltration. Thus, SCF can influence the primary cells involved in allergy and asthma through multiple mechanisms. Currently, corticosteroids are the most effective treatment for chronic rhinitis and inflammation associated with allergy (Naclerio, et al., 1997, JAMA 278:1842-1848; Meltzer, 1997, Aller. 52:33-40). These agents work through multiple mechanisms including reduction of circulating and infiltrating mast cells and eosinophils, and diminished survival of eosinophils associated with inhibition of cytokine production (Meltzer, 1997, Aller. 52:33-40). Steroids have also been reported to inhibit the expression of SCF by fibroblasts and resident connective tissue cells, which leads to diminished mast cell survival (Finotto, et al., 1997, J. Clin. Invest. 99 1721-1728). Because of the mutual regulation of mast cell and eosinophil function, and the role that SCF can play in this regulation, inhibition of c-kit kinase will provide a means to treat allergy-associated chronic rhinitis, inflammation and asthma.

Inflammatory arthritis (e.g. rheumatoid arthritis): Due to the association of mast cells with the arthritic process (Lee et al., 2002, Science 297:1689-1692), c-kit provides a useful target for prevention, delay, and/or treatment of inflammatory arthritis, such as rheumatoid arthritis.

Multiple sclerosis: Mast cells have been shown to play an extensive role in autoimmune diseases, as demonstrated in the mouse model of multiple sclerosis (MS), experimental allergic encephalomyelitis (EAE). Mast cells were indicated to be required for full manifestation of the disease. Secor et al., 2000, J Exp Med 191:813-821. Thus, c-kit also provides a useful target for the prevention, delay, and/or treatment of multiple sclerosis.

Exemplary Diseases Associated with c-fms

The presence of c-fms has been associated with a number of different types of diseases. As such, c-fms has been associated with immune disorders, including rheumatoid arthritis, systemic lupus erythematosis (SLE), Wegener's granulomatosis, and transplant rejection, inflammatory diseases including Chronic Obstructive Pulmonary Disease (COPD), emphysema, and atherosclerosis, metabolic disorders, including insulin resistance, hyperglycemia, and lipolysis, disorders of bone structure or mineralization, including osteoporosis, increased risk of fracture, hypercalcemia, and bone metastases, kidney diseases, including nephritis (e.g. glomerulonephritis, interstitial nephritis, Lupus nephritis), tubular necrosis, diabetes-associated renal complications, and hypertrophy and cancers, including multiple myeloma, acute myeloid leukemia, chronic myeloid leukemia (CML), breast cancer, and ovarian cancer.

Aberrant expression and/or activation of c-fms has been implicated in acute myeloid leukemia, AML (Ridge et al, Proc. Nat. Acad. Sci., 1990, 87:1377-1380). Mutations at codon 301 are believed to lead to neoplastic transformation by ligand independence and constitutive tyrosine kinase activity of the receptor. The tyrosine residue at codon 969 has been shown to be involved in a negative regulatory activity, which is disrupted by amino acid substitutions. Accordingly, c-fms mutations are most prevalent (20%) in chronic myelomonocytic leukemia and AML type M4 (23%), both of which are characterized by monocytic differentiation.

A condition related to AML is chronic myeloid leukemia (CML). During the myeloid blast crisis (BC) of CML, non-random additional chromosome abnormalities occur in over 80% of patients. However, these cytogenetic changes have been reported to precede the clinical signs of CML-BC by several months to years suggesting that other biological events may participate in the multistep process of acute transformation of CML. The autocrine production of growth factors has been shown to occur in several hematological malignancies and particularly in AML. Specchia et al [Br J Haematol. 1992 March; 80(3):310-6] have demonstrated that IL-1 beta gene is expressed in almost all cases of CML in myeloid blast crisis, and that a high proportion of cases showed constitutive expression of the M-CSF gene. Many of the same patients in the Specchia et al study demonstrated simultaneous co-expression of c-fms. After exposure of leukemic cells to phorbol myristate acetate (PMA), release of M-CSF protein was documented in three of five patients studied; however, no significant interleukin-3 (IL-3), granulocyte-macrophage colony-stimulating factor (GM-CSF) or granulocyte colony-stimulating factor (G-CSF), was detected in these patients. This demonstrates that different patterns of growth factors secretion exist in AML and CML, and that distinct molecular events are likely involved in the control of leukemic proliferation.

The observation that production of M-CSF, the major macrophage growth factor, is increased in tissues during inflammation (Le Meur et al, J. Leukocyte Biology. 2002; 72:530-537) provides a role for c-fms in certain diseases. For example, COPD is characterized by airflow limitation that is not fully reversible. The airflow limitation is usually progressive and associated with an abnormal inflammatory response of the lungs to noxious particles or gases. The chronic inflammation of COPD is observed through the airways, parenchyma, and pulmonary vasculature. The inflammatory cell population consists of neutrophils, macrophages, and T lymphocytes, along with eosinophils in some patients. Macrophages are postulated to play an orchestrating role in COPD inflammation by releasing mediators such as TNF-α, IL-8 and LTB4, which are capable of damaging lung structures and/or sustaining neutrophilic inflammation.

Further, M-CSF/Fms signaling is critical to osteoclast formation and survival of osteoclast precursors. For example, estrogen loss in menopause results in increased M-CSF and thus increased osteoclast number and bone resorption which leads to increased risk of fracture and osteoporosis. Accordingly, blockage of this signal is a target for the inhibition of bone resorption (Teitelbaum, Science. 2000; 289:1504; Rohan, Science. 2000; 289:1508.)

Atherosclerosis, an inflammatory disease of the vessel walls, is associated with significant morbidity and mortality. A effect for c-fms inhibition in the treatment and prevention of atherosclerosis depends on several observations (Libby, Nature. 2002; 420:868-874.) First, monocytes resident in the arterial intima increase expression of scavenger receptors and internalize modified lipoproteins. The resulting lipid-laden macrophages develop into foam cells characteristic of the atherosclerotic lesion. Macrophages in atheroma secrete cytokines and growth factors involved in lesion progression. Additionally, macrophages replicate within the intima. Through c-fms, M-CSF activates the transition from monocyte to lipid-laden macrophage and augments expression of scavenger receptor A. Indeed, atherosclerotic plaques overexpress M-CSF which is critical for atherosclerotic progression. Mice deficient in M-CSF have been found to experience less severe atherosclerosis than mice with normal M-CSF (Rajavashisth, et. al., J. Clin. Invest. 1998; 101:2702-2710; Qiao, et. al., Am. J. Path. 1997; 150:1687-1699). Accordingly, inhibitors of c-fms disrupt M-CSF signaling, compromising monocyte to macrophage foam cell progression, macrophage survival and replication, and cytokine signaling that participates in lesion progression.

Wegener's granulomatosis, also known as vasculitis, is characterized by granulomatous inflammation of the blood vessels with necrosis. This inflammation limits blood flow to organs with consequent damage. Although the disease can involve any organ system, Wegener's granulomatosis mainly affects the respiratory tract (i.e., sinuses, nose, trachea, and lungs) and the kidneys. The endothelium plays a central role in the immunopathology of several vascular disorders in many inflammatory conditions such as Wegener's granulomatosis in which use of intravenous immunoglobulin (IV Ig) has been shown to be beneficial (see e.g., Basta et al, J Clin Invest 1994, 94:1729-1735). It has been reported (Xu et al, Am. J. Path. 1998; 153:1257-1266) that IV Ig inhibits endothelial cell proliferation in a dose- and time-dependent manner and down-regulates the expression of adhesion molecule mRNA (ICAM-1 and VCAM-1), chemokine mRNA (MCP-1, M-CSF, and GM-CSF), and proinflammatory cytokine mRNA (TNF-α, IL-1β, and IL-6) induced by TNF-α or IL-1β. These results may explain, at least in part, the therapeutic effect of IV Ig in vascular and inflammatory disorders. Additionally, these results suggest that inhibition of M-CSF activity at the level of interaction with c-fms is an efficacious treatment strategy.

The role of M-CSF and c-fms in emphysema appears to involve the regulation of elastin metabolism through control of matrix metalloproteins. M-CSF has a role in the modulation of the accumulation and function of alveolar macrophages (AMs) in vivo (Shibata et al, Blood 2001, 98: pp. 2845-2852). Osteopetrotic (Op/Op) mice have no detectable M-CSF and show variable tissue-specific reductions in macrophage numbers. Accordingly, it was hypothesized that AMs would be decreased in number and have altered function in Op/Op mice because of the absence of M-CSF. Shibata et al found that lung macrophages identified in lung sections were decreased in number in 20-day-old Op/Op mice but not Op/Op mice older than 4 months compared with findings in age-matched littermate controls. The numbers of AMs recovered by bronchoalveolar lavage (BAL) were also reduced in young but not adult Op/Op mice compared with controls. Importantly, AMs of Op/Op mice spontaneously release higher levels of matrix metalloproteinases (MMPs) than AMs of controls. Consistent with an increased release of MMP, Op/Op mice have abnormal elastin deposition and spontaneously develop emphysema in the absence of molecular or cellular evidence of lung inflammation. Accordingly, the modulation of metalloelastase activity in macrophages by M-CSF may control the degradation of elastin fibers in lungs or blood vessels.

Metastatic cancer cells cause bone destruction, with associated fracture, pain, deformation, and hypercalcaemia, due to production of osteoclasticogenic factors including M-CSF by tumor cells (Clohisy et al, Clin. Orthop. 2000, 373:104-14). Binding of M-CSF to the c-fms product stimulates formation of osteoclasts and osteolytic activity (Kodama et al, J. Exp. Med. 1991, 173:269-72; Feng et al, Endocrinology 2002, 143: 4868-74). Accordingly, inhibition of osteoclast activity at the level of c-fms offers a compelling target for amelioration of bone metastasis.

Macrophage accumulation is a prominent feature in many forms of glomerulonephritis. Local proliferation of macrophages within the kidney has been described in human and experimental glomerulonephritis and may have an important role in augmenting the inflammatory response. Isbel et al (Nephrol Dial Transplant 2001, 16: 1638-1647) examined the relationship between local macrophage proliferation and renal expression of M-CSF. Glomerular and tubulointerstitial M-CSF expression was found to be up-regulated in human glomerulonephritis, being most prominent in proliferative forms of disease. Because this correlates with local macrophage proliferation, it suggests that increased renal M-CSF production plays an important role in regulating local macrophage proliferation in human glomerulonephritis. In a model of renal inflammation (UUO—unilateral ureteric obstruction) anti-c-fms antibody treatment reduced macrophage accumulation (Le Meur et. al., J Leukocyte Biology, 2002, 72:530-537). Accordingly, inhibition of c-fms offers a target for therapeutic intervention in glomerulonephritis.

Insulin resistance and obesity are hallmark of type II diabetes and there is a strong correlation between insulin resistance and abdominal visceral fat accumulation (Bjorntrop, Diabetes Metab. Res. Rev., 1999, 15:427-441). Current evidence indicates that macrophages accumulating in adipose tissue release TNF-a and other factors that cause adipocyte changes (hypertrophy, lipolysis, reduced insulin sensitivity) and also promote insulin resistance in surrounding tissues. Therefore, macrophage accumulation in type 2 diabetes is important for disease progression. Accordingly, inhibition of c-fms has potential in preventing the development of insulin resistance and hyperglycemia.

Dewar et al. have recently demonstrated that the kinase inhibitor imatinib also specifically targets the macrophage colony stimulating factor receptor, c-fms, at therapeutic concentrations. Although this finding has important implications with regard to potential side effects in patients currently receiving imatinib therapy, these results suggest that imatinib may also be useful in the treatment of diseases where c-fms is implicated. This includes breast and ovarian cancer and inflammatory conditions such as rheumatoid arthritis. Dewar et al. also speculate that imatinib may be used in diseases where bone destruction occurs due to excessive osteoclast activity, such as in the haematologic malignancy, multiple myeloma (Dewar et al., Cell Cycle 2005, 4(7):851-3).

To determine the importance of M-CSF in driving macrophage proliferation during acute rejection, Jose et al. blocked the M-CSF receptor, c-fms, in a mouse model of acute renal allograft rejection. They observed that the severity of tubulointerstitial rejection was reduced in the treatment group as shown by decreased tubulitis and tubular cell proliferation. Macrophage proliferation during acute allograft rejection is dependent on the interaction of M-CSF with its receptor c-fms. They indicate that this pathway plays a significant and specific role in the accumulation of macrophages within a rejecting renal allograft (Jose et al., Am J Transplant 2003, 3(3):294-300).

Further, modulators of both c-fms and c-kit function can be used against diseases such as those indicated above, where in some instances, the dual activity of the modulator for both c-fms and c-kit provides distinct advantages in treating such diseases. The complementary activities provided by a single compound would provide added benefits over compounds targeting one or the other activity, or separate compounds targeting these activities. For example, by attenuating release of macrophage chemo-attractants by mast cells or mast cell chemoattractants by macrophages, these anti-inflammatory effects would synergize with the concomitant inhibition of intrinsic cellular function. Limitations in co-administration are absent in a dual inhibitor. Further, the dual activity may result in much lower effective doses for treatment.

II. Production of c-kit and c-fms Related Polypeptides

The native and mutated kinase polypeptides described herein may be chemically synthesized in whole or part using techniques that are well-known in the art (see, e.g., Creighton (1983) Biopolymers 22(1):49-58).

Alternatively, methods which are well known to those skilled in the art can be used to construct expression vectors containing the native or mutated kinase polypeptide coding sequence and appropriate transcriptional/translational control signals. These methods include in vitro recombinant DNA techniques, synthetic techniques and in vivo recombination/genetic recombination. See, for example, the techniques described in Maniatis, T (1989). *Molecular cloning: A laboratory Manual*. Cold Spring Harbor Laboratory, New York. Cold Spring Harbor Laboratory Press; and Ausubel, F. M. et al. (1994) *Current Protocols in Molecular Biology*. John Wiley & Sons, Secaucus, N.J.

A variety of host-expression vector systems may be utilized to express the kinase coding sequence. These include but are not limited to microorganisms such as bacteria transformed with recombinant bacteriophage DNA, plasmid DNA or cosmid DNA expression vectors containing the kinase domain coding sequence; yeast transformed with recombinant yeast expression vectors containing the kinase domain coding sequence; insect cell systems infected with recombinant virus expression vectors (e.g. baculovirus) containing the kinase domain coding sequence; plant cell systems infected with recombinant virus expression vectors (e.g. cauliflower mosaic virus, CaMV; tobacco mosaic virus, TMV) or transformed with recombinant plasmid expression vectors (e.g. Ti plasmid) containing the kinase domain coding sequence; or animal cell systems. The expression elements of these systems vary in their strength and specificities.

Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g. heat shock promoters; the promoter for the small subunit of RUBISCO; the promoter for the chlorophyll a/b binding protein) or from plant viruses (e.g. the 35S RNA promoter of CaMV; the coat protein promoter of TMV) may be used; when cloning in mammalian cell systems, promoters derived from the genome of mammalian cells (e.g. metallothionein promoter) or from mammalian viruses (e.g. the adenovirus late promoter; the vaccinia virus 7.5K promoter) may be used; when generating cell lines that contain multiple copies of the kinase domain DNA, SV4O-, BPV- and EBV-based vectors may be used with an appropriate selectable marker.

Exemplary methods describing methods of DNA manipulation, vectors, various types of cells used, methods of incorporating the vectors into the cells, expression techniques, protein purification and isolation methods, and protein concentration methods are disclosed in detail in PCT publication WO 96/18738. This publication is incorporated herein by reference in its entirety, including any drawings. Those skilled in the art will appreciate that such descriptions are applicable to the present invention and can be easily adapted to it.

III. Binding Assays

The methods of the present invention can involve assays that are able to detect the binding of compounds to a target molecule. Such binding is at a statistically significant level, preferably with a confidence level of at least 90%, more preferably at least 95, 97, 98, 99% or greater confidence level that the assay signal represents binding to the target molecule, i.e., is distinguished from background. Preferably controls are used to distinguish target binding from non-specific binding. A large variety of assays indicative of binding are known for different target types and can be used for this invention.

Binding compounds can be characterized by their effect on the activity of the target molecule. Thus, a "low activity" compound has an inhibitory concentration ($IC_{50}$) or effective concentration ($EC_{50}$) of greater than 1 µM under standard conditions. By "very low activity" is meant an $IC_{50}$ or $EC_{50}$ of above 100 µM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 µM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ or $EC_{50}$ is defined as the concentration of compound at which 50% of the activity of the target molecule (e.g. enzyme or other protein) activity being measured is lost or gained relative to the range of activity observed when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, Methods in Molecular Biology. 121: 313-21; Liparoto et al., (1999) Biosensor analysis of the interleukin-2 receptor complex, Journal of Molecular Recognition. 12:316-21; Lipschultz et al., (2000) Experimental design for analysis of complex kinetics using surface plasmon resonance, Methods. 20(3):310-8; Malmqvist., (1999) BIACORE: an affinity biosensor system for characterization of biomolecular interactions, Biochemical Society Transactions 27:335-40; Alfthan, (1998) Surface plasmon resonance biosensors as a tool in antibody engineering, Biosensors & Bioelectronics. 13:653-63; Fivash et al., (1998) BIAcore for macromolecular interaction, Current Opinion in Biotechnology. 9:97-101; Price et al.; (1998) Summary report on the ISOBM TD-4 Workshop: analysis of 56 monoclonal antibodies against the MUC1 mucin. Tumour Biology 19 Suppl 1:1-20; Malmqvist et al, (1997) Biomolecular interaction analysis: affinity biosensor technologies for functional analysis of proteins, Current Opinion in Chemical Biology. 1:378-83; O'Shannessy et al., (1996) Interpretation of deviations from pseudo-first-order kinetic behavior in the characterization of ligand binding by biosensor technology, Analytical Biochemistry. 236:275-83; Malmborg et al., (1995) BIAcore as a tool in antibody engineering, Journal of Immunological Methods. 183:7-13; Van Regenmortel, (1994) Use of biosensors to characterize recombinant proteins, Developments in Biological Standardization. 83:143-51; and O'Shannessy, (1994) Determination of kinetic rate and equilibrium binding constants for macromolecular interactions: a critique of the surface plasmon resonance literature, Current Opinions in Biotechnology. 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g. by ligand binding to the bound protein) a shift occurs in the resonance angle. This angle shift can be measured and is expressed as resonance units (RUs) such that 1000 RUs is equivalent to a change in surface protein concentration of 1 ng/mm$^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100, 000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., (1972) *The Chemist's Companion: A Handbook Of Practical Data, Techniques, And References*, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) *Spectrophotometry and Spectrofluorometry: A Practical Approach*, pp. 91-114, IRL Press Ltd.; and Bell, (1981) *Spectroscopy In Biochemistry*, Vol. I, pp. 155-194, CRC Press.

In spectrofluorometric methods, enzymes are exposed to substrates that change their intrinsic fluorescence when processed by the target enzyme. Typically, the substrate is non-fluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owicki et al., (1997), Application of Fluorescence Polarization Assays in High-Throughput Screening, Genetic Engineering News, 17:27.

FP is particularly desirable since its readout is independent of the emission intensity (Checovich, W. J., et al., (1995) Nature 375:254-256; Dandliker, W. B., et al., (1981) Methods in Enzymology 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, J Biomol Screen 5:77-88.

Fluorophores derived from sphingolipids that may be used in FP assays are commercially available. For example, Molecular Probes (Eugene, Oreg.) currently sells sphingomyelin and one ceramide flurophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan AG, Hombrechtikon, Switzerland). General multiwell plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) Curr. Biol. 6:178-182; Mitra et al., (1996) Gene 173:13-17; and Selvin et al., (1995) Meth. Enzymol. 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) J. Lipid Res. 38:2365-2373; Kahl et al., (1996) Anal. Biochem. 243:282-283; Undenfriend et al., (1987) Anal. Biochem. 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

The target molecule can be bound to the scintillator plates by a variety of well known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) Anal. Biochem. 257:112-119).

IV. Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases described assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phospho-specific antibody.

V. Organic Synthetic Techniques

A wide array of organic synthetic techniques exist in the art to meet the challenge of constructing potential modulators. Many of these organic synthetic methods are described in detail in standard reference sources utilized by those skilled in the art. One example of such a reference is March, 1994, *Advanced Organic Chemistry; Reactions, Mechanisms and Structure*, New York, McGraw Hill. Thus, the techniques useful to synthesize a potential modulator of kinase function are readily available to those skilled in the art of organic chemical synthesis.

Regarding the synthetic examples described herein, solvents include polar and non-polar solvents known to those of skill in the art, including polar aprotic and polar protic solvents. Polar solvents include, without limitation, protic solvents such as methanol, ethanol, isopropyl alcohol, t-butanol, n-butanol, acetic acid, formic acid or water, or aprotic solvents such as tetrahydrofuran (THF), acetonitrile, dioxane, methylene chloride, dimethylsulfoxide (DMSO), acetone, N,N-dimethylformamide (DMF), N,N-dimethylacetamide (DMA), ethyl acetate, 1,2-dimethoxyethane, 1,2-dichloroethane, chloroform, 1,2-dichloroethane, or pyridine. Polar solvents include a mixture of water with any of the above, or a mixture of any two or more of the above. Apolar solvents include, without limitation, toluene, benzene, chlorobenzene, xylenes and hexanes.

Regarding the synthetic examples described herein, reducing agent includes, without limitation, a reducing agent such as catalytic reducing agents using hydrogen and transition metal catalysts such as palladium, platinum, rhodium, etc. (e.g. Pt/acetic acid/$H_2$); a mixture of trifluoroacetic acid and triethylsilane, borane tetrahydrofuran complex, diborane, borane dimethylsulfide complex, and a combination of sodium borohydride and boron trifluoride; metals such as reduced iron, zinc powder, magnesium etc.; metal hydrogen complex compounds such as alkali metal borohydrides (for example, potassium borohydride, sodium borohydride, lithium borohydride, zinc borohydride, sodium triacetoxyborohydride, etc.), aluminum lithium hydride, etc.; metal hydrides such as sodium hydride, etc.; organic tin compounds (triphenyltin hydride, etc.); and metal salts such as nickel compounds, zinc compounds, tin compounds (for example tin(II) chloride), and samarium iodide/pivalic acid/hexamethylphorphoric triamide.

Regarding the synthetic examples described herein, oxidizing agent includes, without limitation, an oxidizing agent such as Dess-Martin reagent, TEMPO (2,2,6,6-tetramethylpiperidine-N-oxide), DDQ (2,3-Dichloro-5,6-dicyano-1,4-benzoquinone), PDC (pyridinium dichromate), PCC (pyridinium chlorochromate), Pyridine.SO3, Chromium trioxide, p-nitroperbenzoic acid, magnesium monoperoxyphthalate, sodium periodate, potassium periodate, hydrogen peroxide, urea peroxide, alkali metal bromates, cumene hydroperoxide, tert-butyl peroxide, peracids such as performic acid, peracetic acid, pertrifluoroacetic acid, perbenzoic acid, m-chloroperbenzoic acid, o-carboxyperbenzoic acid and the like; sodium metaperiodate, bichromic acid; bichromates such as sodium bichromate, potassium bichromate; permanganic acid; permanganates such as potassium permanganate, sodium permanganate; and lead salts such as lead tetraacetate.

VI. Alternative Compound Forms or Derivatives (a) Isomers, Prodrugs, and Active Metabolites Compounds contemplated herein are described with reference to both generic formulae and specific compounds. In addition, the invention compounds may exist in a number of different forms or derivatives, all within the scope of the present invention. These include, for example, tautomers, stereoisomers, racemic mixtures, regioisomers, salts, prodrugs (e.g. carboxylic acid esters), solvated forms, different crystal forms or polymorphs, and active metabolites.

(b) Tautomers, Stereoisomers, Regioisomers, and Solvated Forms

It is understood that certain compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. they have the same sequence of covalently bonded atoms and differ in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such steroisomeric forms are included within the formulae provided herein.

In certain embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In certain embodiments, the compound is present in optically pure form.

For compounds in which synthesis involves addition of a single group at a double bond, particularly a carbon-carbon double bond, the addition may occur at either of the double bond-linked atoms. For such compounds, the present invention includes both such regioisomers.

Additionally, the formulae are intended to cover solvated as well as unsolvated forms of the identified structures. For example, the indicated structures include both hydrated and non-hydrated forms. Other examples of solvates include the structures in combination with isopropanol, ethanol, methanol, DMSO, ethyl acetate, acetic acid, or ethanol amine.

(c) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Typically, the prodrug is inactive, or less active than the active compound, but may provide advantageous handling, administration, or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

Oxidative reactions: Oxidative reactions are exemplified without limitation to reactions such as oxidation of alcohol, carbonyl, and acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation to reactions such as reduction of carbonyl groups, reduction of hydroxyl groups and carbon-carbon double bonds, reduction of nitrogen-containing functions groups, and other reduction reactions.

Reactions without change in the oxidation state: Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 2004/0077595, Ser. No. 10/656,838, incorporated herein by reference.) Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g. stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, *The Practice of Medicinal Chemistry*, Ch. 31-32, Ed. Wermuth, Academic Press, San Diego, Calif., 2001.

Prodrugs may proceed from prodrug form to active form in a single step or may have one or more intermediate forms which may themselves have activity or may be inactive.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject or patient. Of these, active metabolites are such pharmacologically active derivative compounds. For prodrugs, the prodrug compounds is generally inactive or of lower activity than the metabolic product. For active metabolites, the parent compound may be either an active compound or may be an inactive prodrug.

Prodrugs and active metabolites may be identified using routine techniques known in the art. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, *The Practice of Medicinal Chemistry*, Ch. 31-32, Academic Press, San Diego, Calif., 2001.

(d) Pharmaceutically Acceptable Salts

Compounds can be formulated as or be in the form of pharmaceutically acceptable salts. Pharmaceutically acceptable salts are non-toxic salts in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical Sciences*, 19$^{th}$ ed., Mack Publishing Co., Easton, Pa., Vol. 2, p. 1457, 1995. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

Thus, for example, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Unless specified to the contrary, specification of a compound herein includes pharmaceutically acceptable salts of such compound.

(e) Polymorphic Forms

In the case of agents that are solids, it is understood by those skilled in the art that the compounds and salts may exist in different crystal or polymorphic forms, all of which are intended to be within the scope of the present invention and specified formulae.

VII. Administration

The methods and compounds will typically be used in therapy for human patients. However, they may also be used to treat similar or identical diseases in other vertebrates, e.g., mammals such as other primates, animals of commercial significance, e.g., sports animals, farm animals, e.g., bovines, equines, porcines, and ovines, and pets such as dogs and cats.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in Remington: The Science and Practice of Pharmacy, 21$^{st}$ edition, Lippincott, Williams and Wilkins, Philadelphia, Pa., 2005 (hereby incorporated by reference herein).

Compounds of the present invention (i.e. Formula I, including Formulae Ia, Ib, Ig and all sub-embodiments disclosed herein) can be formulated as pharmaceutically acceptable salts.

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, transdermal, or inhalant. In some embodiments, oral administration is preferred. For oral administration, for example, the compounds can be formulated into conventional oral dosage forms such as capsules, tablets, and liquid preparations such as syrups, elixirs, and concentrated drops.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the invention are formulated in sterile liquid solutions, preferably in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this invention are formulated preferably as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount solvent (e.g. an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

For inhalants, compounds of the invention may be formulated as dry powder or a suitable solution, suspension, or aerosol. Powders and solutions may be formulated with suitable additives known in the art. For example, powders may include a suitable powder base such as lacatose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the invention may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The compounds of the invention may also be used in combination with other therapies for treating the same disease. Such combination use includes administration of the compounds and one or more other therapeutics at different times, or co-administration of the compound and one or more other therapies. In certain embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present invention, or at the same time as a compound of the invention. Use in combination also includes use with a therapy or medical procedure that is administered once or infrequently, such as surgery, along with a compound of the invention administered within a short time or longer time before or after the other therapy or procedure. In certain embodiments, the present invention provides for delivery of compounds of the invention and one or more other drug therapeutics delivered by a different route of administration or by the same route of administration. The use in combination for any route of administration includes delivery of compounds of the invention and one or more other drug therapeutics delivered by the same route of administration together in any formulation, including formulations where the two compounds are chemically linked in such a way that they maintain their therapeutic activity when administered. In one aspect, the other drug therapy may be co-administered with one or more compounds of the invention. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of compounds of the invention and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

The amounts of various compound to be administered as an effective amount can be determined by standard procedures taking into account factors such as the compound $IC_{50}$, the biological half-life of the compound, the age, size, and weight of the subject, and the disorder associated with the subject. The importance of these and other factors are well known to those of ordinary skill in the art. Generally, a dose will be between about 0.01 and 50 mg/kg, preferably 0.1 and 20 mg/kg of the subject being treated. Multiple doses may be used.

VIII. Manipulation of c-kit and c-fms

As the full-length coding sequence and amino acid sequence of c-kit and c-fms from various mammals including human is known, cloning, construction of recombinant c-kit and c-fms, production and purification of recombinant protein, introduction of c-kit or c-fms into other organisms, and other molecular biological manipulations of c-kit and c-fms are readily performed.

Techniques for the manipulation of nucleic acids, such as, e.g., subcloning, labeling probes (e.g. random-primer labeling using Klenow polymerase, nick translation, amplification), sequencing, hybridization and the like are well disclosed in the scientific and patent literature, see, e.g., Sambrook, ed., Molecular Cloning: a Laboratory Manual (2nd ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993).

Nucleic acid sequences can be amplified as necessary for further use using amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4):852-6, 858, 860 passim.

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g. SDS-PAGE), nucleic acid or target or signal amplification methods, radiolabeling, scintillation counting, and affinity chromatography.

Obtaining and manipulating nucleic acids used to practice the methods of the invention can be performed by cloning from genomic samples, and, if desired, screening and re-cloning inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The nucleic acids of the invention can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The nucleic acids of the invention can also be provided in expression vectors and cloning vehicles, e.g., sequences encoding the polypeptides of the invention. Expression vectors and cloning vehicles of the invention can comprise viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, *Aspergillus* and yeast). Vectors of the invention can include chromosomal, non-chromosomal and synthetic DNA sequences. Large numbers of suitable vectors are known to those of skill in the art, and are commercially available.

The nucleic acids of the invention can be cloned, if desired, into any of a variety of vectors using routine molecular biological methods; methods for cloning in vitro amplified nucleic acids are disclosed, e.g., U.S. Pat. No. 5,426,039. To facilitate cloning of amplified sequences, restriction enzyme sites can be "built into" a PCR primer pair. Vectors may be introduced into a genome or into the cytoplasm or a nucleus of a cell and expressed by a variety of conventional techniques, well described in the scientific and patent literature. See, e.g., Roberts (1987) Nature 328:731; Schneider (1995) Protein Expr. Purif. 6435:10; Sambrook, Tijssen or Ausubel. The vectors can be isolated from natural sources, obtained from such sources as ATCC or GenBank libraries, or prepared by synthetic or recombinant methods. For example, the nucleic acids of the invention can be expressed in expression cassettes, vectors or viruses which are stably or transiently expressed in cells (e.g. episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids of the invention are administered in vivo for in situ expression of the peptides or polypeptides of the invention. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, preferably selected from baculoviridiae, parvoviridiae, picornoviridiae, herpesveridiae, poxviridae, adenoviridiae, or picornnaviridiae. Chimeric vectors may also be employed which exploit advantageous merits of each of the parent vector properties (See e.g., Feng (1997) Nature Biotechnology 15:866-870). Such viral genomes may be modified by recombinant DNA techniques to include the nucleic acids of the invention; and may be further engineered to be replication deficient, conditionally replicating or replication competent. In alternative aspects, vectors are derived from the adenoviral (e.g. replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher (1992) J. Virol. 66:2731-2739; Johann (1992) *J. Virol.* 66:1635-1640). Adeno-associated virus (AAV)-based vectors can be used to transduce cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada (1996) *Gene Ther.* 3:957-964.

The present invention also relates to fusion proteins, and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. In one aspect, a nucleic acid encoding a polypeptide of the invention is assembled in appropriate phase with a leader sequence capable of directing secretion of the translated polypeptide or fragment thereof. Technology pertaining to vectors encoding fusion proteins and application of fusion proteins are well disclosed in the scientific and patent literature, see e.g., Kroll (1993) DNA Cell. Biol. 12:441-53.

The nucleic acids and polypeptides of the invention can be bound to a solid support, e.g., for use in screening and diagnostic methods. Solid supports can include, e.g., membranes (e.g. nitrocellulose or nylon), a microtiter dish (e.g. PVC, polypropylene, or polystyrene), a test tube (glass or plastic), a dip stick (e.g. glass, PVC, polypropylene, polystyrene, latex and the like), a microfuge tube, or a glass, silica, plastic, metallic or polymer bead or other substrate such as paper. One solid support uses a metal (e.g. cobalt or nickel)-comprising column which binds with specificity to a histidine tag engineered onto a peptide.

Adhesion of molecules to a solid support can be direct (i.e., the molecule contacts the solid support) or indirect (a "linker" is bound to the support and the molecule of interest binds to this linker). Molecules can be immobilized either covalently (e.g. utilizing single reactive thiol groups of cysteine residues (see, e.g., Colliuod (1993) Bioconjugate Chem. 4:528-536) or non-covalently but specifically (e.g. via immobilized antibodies (see, e.g., Schuhmann (1991) Adv. Mater. 3:388-391; Lu (1995) Anal. Chem. 67:83-87; the biotin/strepavidin system (see, e.g., Iwane (1997) Biophys. Biochem. Res. Comm. 230:76-80); metal chelating, e.g., Langmuir-Blodgett films (see, e.g., Ng (1995) Langmuir 11:4048-55); metal-chelating self-assembled monolayers (see, e.g., Sigal (1996) Anal. Chem. 68:490-497) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl(4-iodoacetyl)aminobenzoate (SIAB) and the sulfosuccinimidyl derivatives such as sulfosuccinimidyl(4-iodoacetyl)aminobenzoate (sulfo-SIAB) (Pierce). Another group of coupling agents is the heterobifunctional and thiol cleavable agents such as N-succinimidyl 3-(2-pyridyidithio)propionate (SPDP) (Pierce Chemicals, Rockford, Ill.).

Antibodies can also be used for binding paolypeptides and peptides of the invention to a solid support. This can be done directly by binding peptide-specific antibodies to the column or it can be done by creating fusion protein chimeras comprising motif-containing peptides linked to, e.g., a known epitope (e.g. a tag (e.g. FLAG, myc) or an appropriate immunoglobulin constant domain sequence (an "immunoadhesin," see, e.g., Capon (1989) Nature 377:525-531 (1989).

Nucleic acids or polypeptides of the invention can be immobilized to or applied to an array. Arrays can be used to screen for or monitor libraries of compositions (e.g. small molecules, antibodies, nucleic acids, etc.) for their ability to bind to or modulate the activity of a nucleic acid or a polypeptide of the invention. For example, in one aspect of the invention, a monitored parameter is transcript expression of a gene comprising a nucleic acid of the invention. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface. In practicing the methods of the invention, any known array and/or method of making and using arrays can be incorporated in whole or in part, or variations thereof, as disclosed, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Host Cells and Transformed Cells

The invention also provides a transformed cell comprising a nucleic acid sequence of the invention, e.g., a sequence encoding a polypeptide of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

Vectors may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g. temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in E. coli.

For transient expression in mammalian cells, cDNA encoding a polypeptide of interest may be incorporated into a mammalian expression vector, e.g. pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes, incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

The cDNA insert may be first released from the above phagemid incorporated at appropriate restriction sites in the pcDNAI polylinker. Sequencing across the junctions may be performed to confirm proper insert orientation in pcDNAI. The resulting plasmid may then be introduced for transient expression into a selected mammalian cell host, for example, the monkey-derived, fibroblast like cells of the COS-1 lineage (available from the American Type Culture Collection, Rockville, Md. as ATCC CRL 1650).

For transient expression of the protein-encoding DNA, for example, COS-1 cells may be transfected with approximately 8 µg DNA per $10^6$ COS cells, by DEAE-mediated DNA transfection and treated with chloroquine according to the procedures described by Sambrook et al, Molecular Cloning: A Laboratory Manual, 1989, Cold Spring Harbor Laboratory Press, Cold Spring Harbor N.Y., pp. 16.30-16.37. An exemplary method is as follows. Briefly, COS-1 cells are plated at a density of $5 \times 10^6$ cells/dish and then grown for 24 hours in FBS-supplemented DMEM/F12 medium. Medium is then removed and cells are washed in PBS and then in medium. A transfection solution containing DEAE dextran (0.4 mg/ml), 100 µM chloroquine, 10% NuSerum, DNA (0.4 mg/ml) in DMEM/F12 medium is then applied on the cells 10 ml volume. After incubation for 3 hours at 37° C., cells are washed in PBS and medium as just described and then shocked for 1 minute with 10% DMSO in DMEM/F12 medium. Cells are allowed to grow for 2-3 days in 10% FBS-supplemented medium, and at the end of incubation dishes are placed on ice, washed with ice cold PBS and then removed by scraping. Cells are then harvested by centrifugation at 1000 rpm for 10 minutes and the cellular pellet is frozen in liquid nitrogen, for subsequent use in protein expression. Northern blot analysis of a thawed aliquot of frozen cells may be used to confirm expression of receptor-encoding cDNA in cells under storage.

In a like manner, stably transfected cell lines can also prepared, for example, using two different cell types as host: CHO K1 and CHO Pro5. To construct these cell lines, cDNA coding for the relevant protein may be incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

An exemplary protocol to introduce plasmids constructed as described above is as follows. The host CHO cells are first seeded at a density of $5 \times 10^5$ in 10% FBS-supplemented MEM medium. After growth for 24 hours, fresh medium is added to the plates and three hours later, the cells are transfected using the calcium phosphate-DNA co-precipitation procedure (Sambrook et al, supra). Briefly, 3 µg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2-3 weeks later, clonally selected and then propagated for assay purposes.

EXAMPLES

A number of examples illustrative of the present invention are described below. In most cases, alternative techniques could also be used. The examples are intended to be illustrative and are not limiting or restrictive to the scope of the invention. Unless specifically noted to the contrary, in cases where a compound number is not preceded by a "P-" (e.g., "P-0001") in the Examples section, compound naming and/or enumeration is not related to naming and/or enumeration employed in other sections of this application. Similarly, structure and substituent naming and enumeration within the Examples are independent of structure and substituent naming and enumeration in above sections of this application unless clearly indicated otherwise.

Example 1

Synthesis of Compound of Formula I, where $X_1$, $X_2$, $Y_1$ and $Y_2$ are CH and $L^1$ is —$CH_2$—

Compounds of Formula I where $X_1$, $X_2$, $Y_1$ and $Y_2$ are CH and $L^1$ is —$CH_2$— or —CO— may be synthesized from 7-azaindole according to one of the following Schemes 1-3, where $R^{24}$ is consistent with $Ar_1$, which can be further substituted to provide compounds where $R^{24}$ is $Ar_1$-$L^2$-$R^1$ as described for Formula I.

Step-1

Synthesis of Compound 2

Compound 2 is synthesized from commercially available 7-azaindole following the literature procedure (Robinson, *J. Am. Chem. Soc.*, 1955, 77, p. 457).

Step-2

Synthesis of Compound of Formula II

Compound of Formula II is synthesized by deprotonation using base (e.g. BuLi, NaH) in aprotic solvent like tetrahydrofuran or ether and reacting the anion with a silyl chloride (e.g. TIPS) or an anhydride (e.g. Boc anhydride). The compound is isolated by following standard procedure (quenching with ice-cold brine, work up, and purification by flash silica gel chromatography).

Steps-3 and 4

Synthesis of Compound of Formula I

Compounds of Formula I, wherein $R^{24}$ is $Ar_1$ as defined in Formula I, is synthesized through the reaction of compounds of Formula II with isopropyl chloroformate (or ethyl chloroformate) at room temperature in toluene to give a 3-chloromethyl intermediate. This intermediate is cooled to −78° C. and immediately reacted with an organocopper reagent, which is generated from the reaction between a Grignard reagent (or organolithium reagent) and a solution of copper cyanide and LiCl. The mixture is stirred at −78° C. for one hour and allowed to warm to room temperature. The reaction is quenched with a solution of 4:1 ammonium chloride:ammonium hydroxide. The reaction is worked up in the usual manner and purified by flash silica gel chromatography to give the nitrogen-protected compound. The final compound can be realized through the deprotection of the protecting group (Boc, TIPS) using standard conditions (TFA or $NH_4F$) at room temperature.

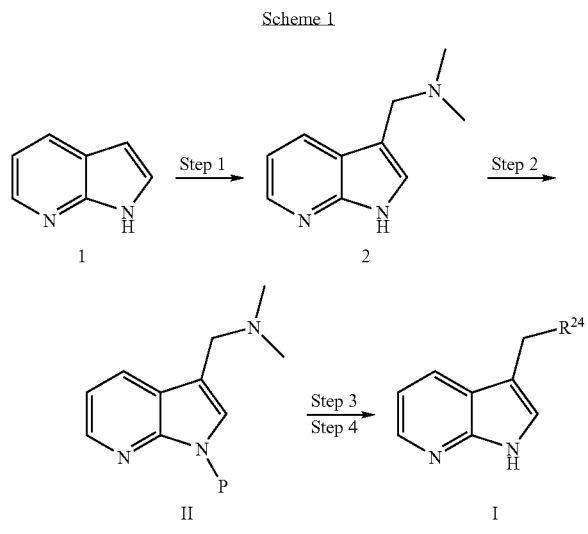

Scheme 1

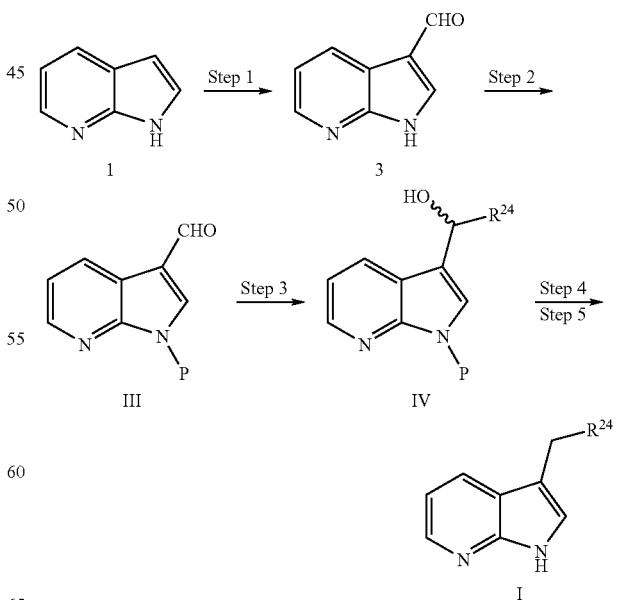

Scheme 2

Step-1

Synthesis of Compound 3

Compound 3 is synthesized by reacting commercially available 7-azaindole, compound 1, with hexamethyltetramine and acetic acid in water with heating to reflux for two hours. After cooling, the desired compound is precipitated and collected by filtration.

Step-2

Synthesis of Compound of Formula III

Compound of Formula III, where P is a protecting group, is synthesized by reacting compound 3 with an appropriate reagent to introduce a protecting group (e.g. tert-butyloxycarbonyl dianhydride) and a base (e.g. sodium hydride) in an appropriate solvent (e.g. tetrahydrofuran) typically at room temperature for 12-18 hours. The compound can be isolated by conventional means (e.g. extraction).

Step-3

Synthesis of Compound of Formula IV

Compound of Formula IV, wherein $R^{24}$ is $Ar_1$, is synthesized by reacting compound of Formula III in an appropriate solvent (e.g. 1,2-dimethoxyethane) with a Grignard reagent of the formula $R^{24}MgCl$ or $R^{24}MgBr$ (e.g. pyridinyl magnesium bromide) or an equivalent nucleophile in an appropriate solvent (e.g. tetrahydrofuran) under inert atmosphere cooled typically to $-10°$ C. The reaction is typically allowed to warm to room temperature and stirred for 12-18 hours. The desired compound is purified by reverse phase high pressure liquid chromatography.

Steps-4 and 5

Synthesis of an Intermediate of Compound of Formula I

An intermediate of compound of Formula I is synthesized by reacting compound of Formula IV with a reducing agent (e.g. sodium borohydride) in a polar solvent (e.g. ethanol) typically with heating to 80° C. for 1-4 hours. The reaction is quenched with the addition of methanol and concentrated and purified by reverse phase high performance liquid chromatography. Compound of Formula I where $R^{24}$ is $Ar_1$ is synthesized by reacting this intermediate with an appropriate reagent to remove the protecting group, P, (e.g. hydrochloric acid) in an apolar solvent (e.g. dioxane). The final compound is isolated by standard procedures (e.g. reverse phase preparative high pressure liquid chromatography).

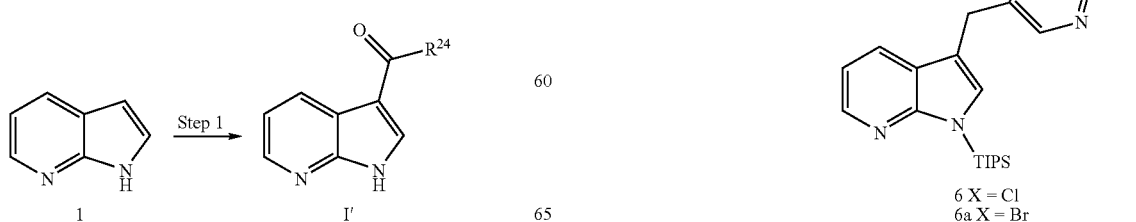

Scheme 3

Step 1

Synthesis of Compound of Formula I'

Compound of Formula I' where $R^{24}$ is $Ar_1$, is synthesized by reacting compound 1 with an activating agent (e.g. methyl magnesium bromide and zinc dichloride or anhydrous aluminum chloride) and a heteroaryl acid chloride (e.g. nicotinic acid chloride) in a non-reactive solvent (e.g. dichloromethane), under inert atmosphere (e.g. argon), at room temperature or with heating up to reflux for 18-24 hours. The compound is isolated by standard procedures (e.g. extraction and silica-gel chromatography).

Example 2

Synthesis of Intermediate 3-(6-Chloro-pyridin-3-ylmethyl)-1-triisopropylsilanyl-1H-pyrrolo[2,3-b]pyridine (6) and (3-(6-Bromo-pyridin-3-ylmethyl)-1-triisopropylsilanyl-1H-pyrrolo[2,3-b]pyridine) (6a)

Compound 6, an intermediate to compounds of Formula I where $X_1$, $X_2$, $Y_1$ and $Y_2$ are CH, n is 1, P, Q and T are CH and $L^1$ is —$CH_2$—, may be synthesized in four steps from 7-azaindole according to the following Scheme 4.

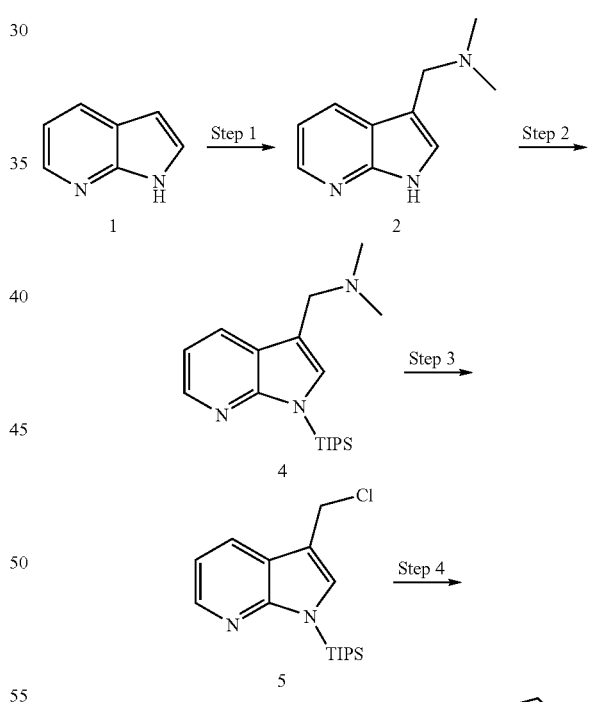

Step-1

Synthesis of dimethyl-(1H-pyrrolo[2,3-b]pyridin-3-ylmethyl)-amine (2)

Into a 3-neck round bottom flask was added Isopropyl alcohol (320.0 mL) followed by the addition of 1H-pyrrolo[2,3-b]pyridine 1 (7.10 g, 60.1 mmol), dimethylamine hydrochloride (5.4 g, 0.066 mol), and formaldehyde (2.0 g, 0.066 mol). The reaction mixture was stirred at room temperature for 12 hours, and then refluxed for 30 minutes. The suspension solution was evaporated to dryness in vacuo. To the residue was added water (60.0 mL, 3.33 mol) and concentrated hydrochloric acid (6.0 mL, 0.20 mol). The water layer was extracted with ether and the aqueous layer was neutralized with potassium carbonate. The aqueous layer was extracted with dichloromethane, dried over sodium sulfate and concentrated to give the compound, which was then further washed with ether and dried to afford compound 2 (7.1 g, yield=67.4%), as a white solid.

Step-2

Synthesis of dimethyl-(1-triisopropylsilanyl-1H-pyrrolo[2,3-b]pyridin-3-ylmethyl)-amine (4)

Into a round bottom flask 7-Azagramine 2 (5.38 g, 30.7 mmol), N,N-dimethylformamide (25.0 mL), and sodium hydride (1.35 g, 33.8 mol) were combined. Into the reaction was added triisopropylsilyl chloride (6.8 mL, 0.032 mol). The reaction was stirred at 20° C. for 12 hours. The reaction mixture was poured into water and extracted with ethyl acetate. The organic layer was washed with brine, dried over sodium sulfate, concentrated and purified with biotage to give compound 4 (6.0 g, yield=58.8%) as a colorless oil.

Step-3

Synthesis of 3-chloromethyl-1-triisopropylsilanyl-1H-pyrrolo[2,3-b]pyridine (5)

Into a round bottom flask was added compound 4 (500.0 mg, 1.51 mmol) and toluene (5.0 mL, 0.047 mol) under an atmosphere of nitrogen. Into the reaction mixture 1.0 M isopropyl chloroformate in toluene (1.6 mL) was added slowly at room temperature. The reaction mixture was stirred for another 2 hours to give desired compound 5 used for next step without purification.

Step-4

Synthesis of 3-(6-Chloro-pyridin-3-ylmethyl)-1-triisopropylsilanyl-1H-pyrrolo[2,3-b]pyridine (6)

Into a round bottom flask was added 5-iodo-2-chloro-pyridine (315.0 mg, 1.32 mmol) and tetrahydrofuran (12.0 mL, 0.15 mol) at −40° C. under an atmosphere of nitrogen. Into the reaction 2.0 M of isopropylmagnesium chloride in tetrahydrofuran (0.72 mL, 1.44 mmol) was added. The reaction mixture was stirred for 40 minutes at −40° C. TLC (hexane/ethyl acetate 2:1) indicated no starting material. Into the reaction mixture 0.6 M of CuCN.2LiCl in tetrahydrofuran (2.4 mL, 1.44 mmol) was added. The reaction mixture was allowed to come to room temperature for 5 minutes and trimethyl phosphite (0.29 mL, 2.4 mmol) was added. After 10 minutes, this solution was added into a round bottom flask containing compound 5 (315.0 mg) and toluene (8.0 mL). The reaction was stirred at 20° C. for 40 hours. The reaction mixture was poured into water and the compound extracted with ethyl acetate. The organic layer was washed with brine, dried over sodium sulfate, concentrated and purified with biotage (dichloromethane/methanol 1:10) to give compound 6 (230 mg, yield=59.0%) as a white solid. Compound 6a (3-(6-Bromo-pyridin-3-ylmethyl)-1-triisopropylsilanyl-1H-pyrrolo[2,3-b]pyridine) (MS (ESI) [M+H$^+$]$^+$=288.1, 290.1) was prepared substituting 5-iodo-2-chloro-pyridine with 5-iodo-2-bromo-pyridine in Step 4, with reaction conditions and work up procedure the same as that for the synthesis of compound 6.

Example 3

Synthesis of Intermediate (6-Chloro-pyridin-3-yl)-(1H-pyrrolo[2,3-b]pyridin-3-yl)-methanone (7)

Compound 7, an intermediate to compounds of Formula I where $X_1$, $X_2$, $Y_1$ and $Y_2$ are CH, n is 1, P, Q and T are CH and $L^1$ is —CO—, may be synthesized in one step from 7-azaindole according to the following Scheme 5.

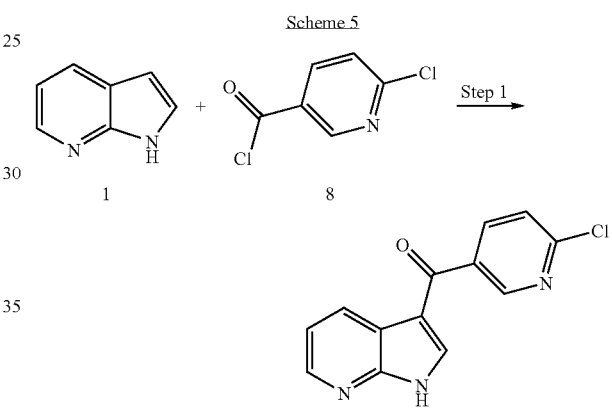

Into a round bottom flask was added aluminum trichloride (16.0 g, 0.12 mol) and dichloromethane (100.0 mL) under an atmosphere of nitrogen. Into the reaction mixture 1H-Pyrrolo[2,3-b]pyridine 1 (3.2 g, 0.027 mol) in dichloromethane (20.0 mL) was added. The reaction was stirred at room temperature for 70.0 minutes and 6-Chloropyridine-3-carbonyl chloride 8 (5.4 g, 0.031 mol) in dichloromethane (10.0 mL) was added. The reaction mixture was stirred at room temperature for 3 hours. Methanol (10 mL) was added to the reaction mixture and the solvent was evaporated in vacuo. The residue was poured into water and the precipitated compound was removed by filtration. The aqueous layer was extracted with ethyl acetate and the organic layer was dried and concentrated and combined with the solid isolated by filtration to give 7 (6.2 g, yield=88.6%) as a white solid. MS (ESI) [M+H$^+$]$^+$=258.

Example 4

Synthesis of benzyl-[5-(1H-pyrrolo[2,3-b]pyridin-3-ylmethyl)-pyridin-2-yl]-amine (P-0001)

Benzyl-[5-(1H-pyrrolo[2,3-b]pyridin-3-ylmethyl)-pyridin-2-yl]-amine (P-0001) was prepared in two steps from 3-(6-Chloro-pyridin-3-ylmethyl)-1-triisopropylsilanyl-1H-pyrrolo[2,3-b]pyridine (6) according to Scheme 6.

Scheme 6

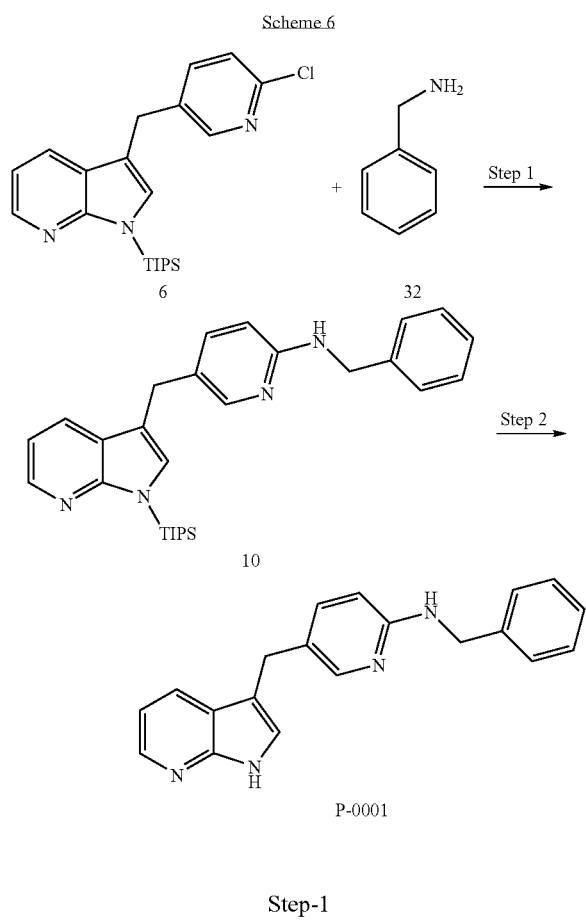

Step-1

Synthesis of benzyl-[5-(1-triisopropylsilanyl-1H-pyrrolo[2,3-b]pyridin-3-ylmethyl)-pyridin-2-yl]-amine (10)

Into a round bottom flask was added 3-(6-Chloro-pyridin-3-ylmethyl)-1-triisopropylsilanyl-1H-pyrrolo[2,3-b]pyridine 6 (160.0 mg, 0.40 mmol, prepared as described in Example 2), benzylamine (32, 0.1 mL, 0.90 mmol), palladium acetate (17.0 mg, 0.076 mmol), toluene (10.0 mL), potassium tert-butoxide (80.0 mg, 0.71 mmol) and 2-(di-t-butylphosphino)biphenyl (31.4 mg, 0.11 mmol) under an atmosphere of nitrogen. The reaction was stirred under reflux for 3 hours. TLC and MS indicated no starting material. The reaction mixture was poured into water and extracted with ethyl acetate. The organic layer was washed with brine, dried over sodium sulfate, concentrated and purified with biotage (dichloromethane/methanol 1:20) to give compound 10 (110 mg, yield=58.5%) as a white solid. MS (ESI) [M+H$^+$]$^+$=471.

Step-2

Synthesis of benzyl-[5-(1H-pyrrolo[2,3-b]pyridin-3-ylmethyl)-pyridin-2-yl]-amine (P-0001)

Into a round bottom flask was added benzyl-[5-(1-triisopropylsilanyl-1H-pyrrolo[2,3-b]pyridin-3-ylmethyl)-pyridin-2-yl]-amine 10 (400.0 mg, 0.85 mmol), tetrahydrofuran (20.0 mL) and tetra-n-butylammonium fluoride (240 mg, 0.93 mmol). The reaction mixture was stirred at 20° C. for 30 minutes. TLC indicated no starting material. The reaction mixture was poured into water and extracted with ethyl acetate. The organic layer was washed with brine, dried over sodium sulfate, concentrated and purified with biotage (dichloromethane/methanol 1:10) to give compound P-0001 (220 mg, Yield=82.4%) as a white solid. MS (ESI) [M+H$^+$]$^+$=315.

Additional compounds were prepared following the protocol of Scheme 6, substituting benzyl amine with a suitable amine in Step 1, and using either 3-(6-Chloro-pyridin-3-ylmethyl)-1-triisopropylsilanyl-1H-pyrrolo[2,3-b]pyridine 6 or 3-(6-Bromo-pyridin-3-ylmethyl)-1-triisopropylsilanyl-1H-pyrrolo[2,3-b]pyridine 6a, in Step 1. The following compounds were made following this procedure:
Dimethyl-[5-(1H-pyrrolo[2,3-b]pyridin-3-ylmethyl)-pyridin-2-yl]-amine (P-0021), (4-methoxy-benzyl)-[5-(1H-pyrrolo[2,3-b]pyridin-3-ylmethyl)-pyridin-2-yl]-amine (P-0004),
(4-chloro-benzyl)-[5-(1H-pyrrolo[2,3-b]pyridin-3-ylmethyl)-pyridin-2-yl]-amine (P-0005),
(4-fluoro-benzyl)-[5-(1H-pyrrolo[2,3-b]pyridin-3-ylmethyl)-pyridin-2-yl]-amine (P-0006),
(4-methyl-benzyl)-[5-(1H-pyrrolo[2,3-b]pyridin-3-ylmethyl)-pyridin-2-yl]-amine (P-0007), and
[5-(1H-pyrrolo[2,3-b]pyridin-3-ylmethyl)-pyridin-2-yl]-thiophen-2-ylmethyl-amine (P-0008).

The following table indicates the amine used in Step 1 in place of benzyl amine in Column 2, and whether 3-(6-Chloro-pyridin-3-ylmethyl)-1-triisopropylsilanyl-1H-pyrrolo[2,3-b]pyridine or 3-(6-Bromo-pyridin-3-ylmethyl)-1-triisopropylsilanyl-1H-pyrrolo[2,3-b]pyridine was used in Step 1 in Column 3 (Cl or Br, respectively), with the compound structure in Column 4, experimental mass spectrometry result in Column 5, and compound number in Column 1.

| | Starting azaindole | Amine | Compound | MS (ESI) [M + H$^+$]$^+$ observed |
|---|---|---|---|---|
| P-0021 | Cl | ![amine] | ![compound] | 253 |

-continued
| | Starting azaindole | Amine | Compound | MS (ESI) [M + H⁺]⁺ observed |
|---|---|---|---|---|
| P-0004 | Br | 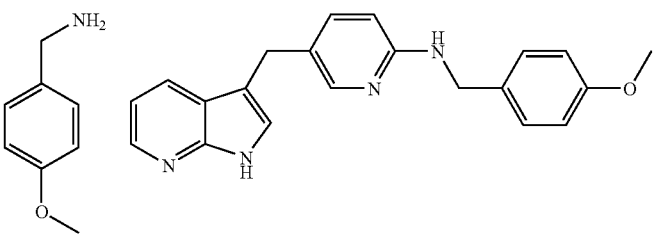 | | 344.4 |
| P-0005 | Br | 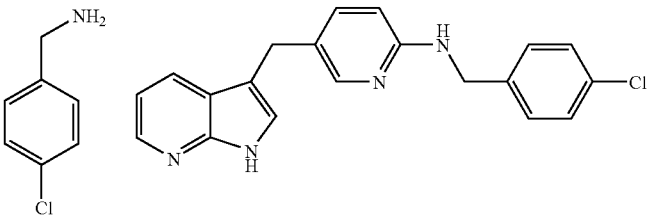 | | 348.8 |
| P-0006 | Br | 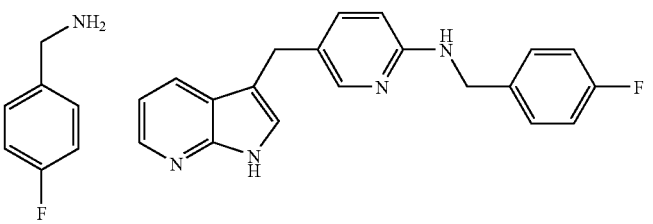 | | 332.4 |
| P-0007 | Br | 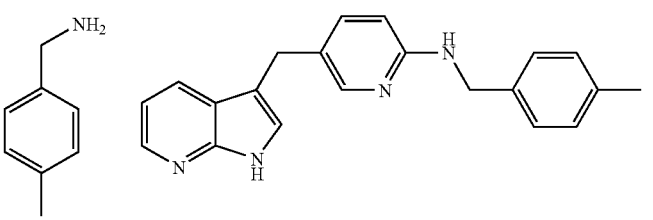 | | 328.4 |
| P-0008 | Br | 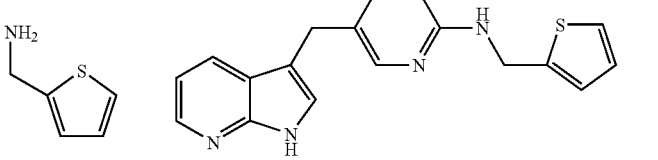 | | 330.4 |

Example 5

Synthesis of (6-Benzylamino-pyridin-3-yl)-(1H-pyrrolo[2,3-b]pyridin-3-yl)-methanone (P-0002)

(6-Benzylamino-pyridin-3-yl)-(1H-pyrrolo[2,3-b]pyridin-3-yl)-methanone (P-0002) was prepared in one step from (6-Chloro-pyridin-3-yl)-(1H-pyrrolo[2,3-b]pyridin-3-yl)-methanone (7) according to Scheme 7.

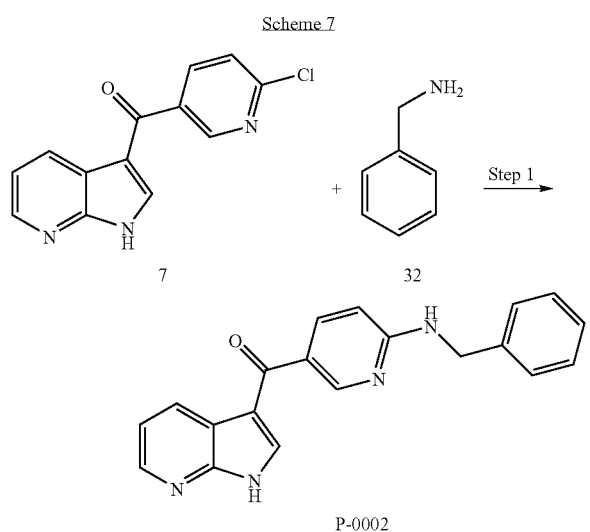

Scheme 7

P-0002

Into a pressure tube was added (6-Chloro-pyridin-3-yl)-(1H-pyrrolo[2,3-b]pyridin-3-yl)-methanone 7 (270.0 mg, 1.05 mmol, prepared as described in Example 3), and benzylamine (32, 0.7 mL, 0.006 mol) and tetrahydrofuran (25.0 mL) under an atmosphere of nitrogen. The reaction mixture was heated to 185° C. for 60 hours. The reaction mixture was concentrated to remove most of the solvent and the residue was poured into water and extracted with ethyl acetate. The organic layer was dried over sodium sulfate, concentrated and purified with biotage (dichloromethane/methanol 1:20) to give compound P-0002 (30 mg, yield=8.7%) as a white solid. MS (ESI) [M+H$^+$]$^+$=329.

Additional compounds were prepared following the protocol of Scheme 7, replacing benzylamine with a suitable amine. The following compounds were made following this procedure:

[6-(4-Fluoro-benzylamino)-pyridin-3-yl]-(1H-pyrrolo[2,3-b]pyridin-3-yl)-methanone (P-0015),
[6-(3-Fluoro-benzylamino)-pyridin-3-yl]-(1H-pyrrolo[2,3-b]pyridin-3-yl)-methanone (P-0016),
(1H-Pyrrolo[2,3-b]pyridin-3-yl)-[6-(4-trifluoromethyl-benzylamino)-pyridin-3-yl]-methanone (P-0017),
(1H-Pyrrolo[2,3-b]pyridin-3-yl)-{6-[(thiophen-2-ylmethyl)-amino]-pyridin-3-yl}-methanone (P-0018),
(6-Phenylamino-pyridin-3-yl)-(1H-pyrrolo[2,3-b]pyridin-3-yl)-methanone (P-0023),
(6-Isopropylamino-pyridin-3-yl)-(1H-pyrrolo[2,3-b]pyridin-3-yl)-methanone (P-0024),
(6-Isobutylamino-pyridin-3-yl)-(1H-pyrrolo[2,3-b]pyridin-3-yl)-methanone (P-0025),
[6-(3-Benzyloxy-phenylamino)-pyridin-3-yl]-(1H-pyrrolo[2,3-b]pyridin-3-yl)-methanone (P-0026),
[6-(Cyclopropylmethyl-amino)-pyridin-3-yl]-(1H-pyrrolo[2,3-b]pyridin-3-yl)-methanone (P-0030),
[6-(Cyclohexylmethyl-amino)-pyridin-3-yl]-(1H-pyrrolo[2,3-b]pyridin-3-yl)-methanone (P-0031), The following table indicates the amine substituted in place of benzylamine in column 2, to provide these compounds, shown by structure in column 3. Column 1 provides the compound number and column 4 gives the experimental mass spectrometry result.

| | Amine | Compound | MS (ESI) [M + H$^+$]$^+$ observed |
|---|---|---|---|
| P-0015 | (4-fluorobenzylamine structure) | (structure) | 347.0 |
| P-0016 | (3-fluorobenzylamine structure) | (structure) | 347.1 |

-continued

| Amine | Compound | MS (ESI) [M + H⁺]⁺ observed |
|---|---|---|
| P-0017 (4-CF₃-benzylamine) | 7-azaindole-3-yl-(6-(4-trifluoromethylbenzylamino)pyridin-3-yl)methanone | 396.9 |
| P-0018 (2-thienylmethylamine) | 7-azaindole-3-yl-(6-(2-thienylmethylamino)pyridin-3-yl)methanone | 335.0 |
| P-0023 (aniline) | 7-azaindole-3-yl-(6-phenylaminopyridin-3-yl)methanone | 315.1 |
| P-0024 (isopropylamine) | 7-azaindole-3-yl-(6-isopropylaminopyridin-3-yl)methanone | 279 [M − H⁺]⁻ |
| P-0025 (isobutylamine) | 7-azaindole-3-yl-(6-isobutylaminopyridin-3-yl)methanone | 293 [M − H⁺]⁻ |
| P-0026 (3-benzyloxyaniline) | 7-azaindole-3-yl-(6-(3-benzyloxyphenylamino)pyridin-3-yl)methanone | 419 [M − H⁺]⁻ |
| P-0030 (cyclopropylmethylamine) | 7-azaindole-3-yl-(6-(cyclopropylmethylamino)pyridin-3-yl)methanone | 293.1 |

| Amine | Compound | MS (ESI) [M + H+]+ observed |
|---|---|---|
| P-0031 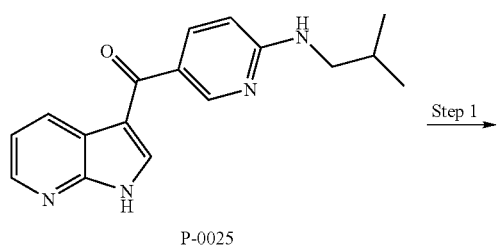 | 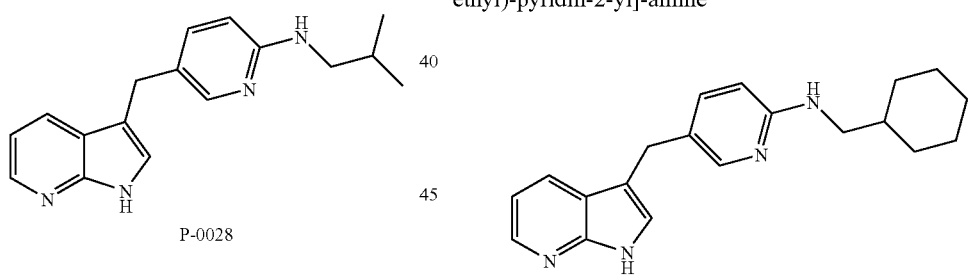 | 335.2 |

Example 6

Synthesis of Isobutyl-[5-(1H-pyrrolo[2,3-b]pyridin-3-ylmethyl)-pyridin-2-yl]-amine P-0028

Compound P-0028 was synthesized in 1 step from 6-Isobutylamino-pyridin-3-yl)-(1H-pyrrolo[2,3-b]pyridin-3-yl)-methanone P-0025 as shown in Scheme 8.

Scheme 8

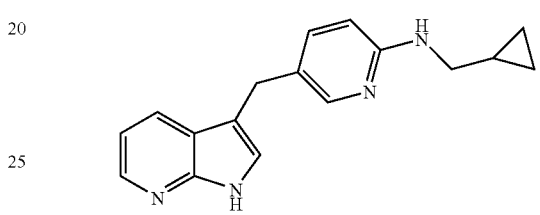

Step-1

Synthesis of Isobutyl-[5-(1H-pyrrolo[2,3-b]pyridin-3-ylmethyl)-pyridin-2-yl]-amine (P-0028)

To (6-Isobutylamino-pyridin-3-yl)-(1H-pyrrolo[2,3-b]pyridin-3-yl)-methanone (P-0025, 60.0 mg, 0.20 mmol, prepared as described in Example 5) in 1,2-ethanediol (5.0 mL) was added hydrazine (1.0 mL, 0.032 mol) and potassium hydroxide (200.0 mg, 3.56 mmol). The reaction mixture was heated to 180° C. overnight. The reaction mixture was poured into water and extracted with ethyl acetate. The organic layer was washed with brine, dried over sodium sulfate, concentrated and purified by silica gel column chromatography eluting with 10% methanol in dichloromethane to give compound (P-0028, 10 mg, 16.7%). MS (ESI) [M+H+]+=281.

Cyclopropylmethyl-[5-(1H-pyrrolo[2,3-b]pyridin-3-ylmethyl)-pyridin-2-yl]-amine (P-0032)

was prepared following the protocol of Scheme 8, substituting (6-Isobutylamino-pyridin-3-yl)-(1H-pyrrolo[2,3-b]pyridin-3-yl)-methanone P-0025 with [6-(Cyclopropylmethylamino)-pyridin-3-yl]-(1H-pyrrolo[2,3-b]pyridin-3-yl)-methanone P-0030 (prepared as described in Example 5). MS (ESI) [M+H+]+=279.

Cyclohexylmethyl-[5-(1H-pyrrolo[2,3-b]pyridin-3-ylmethyl)-pyridin-2-yl]-amine was prepared following the protocol of Scheme 8, substituting (6-Isobutylamino-pyridin-3-yl)-(1H-pyrrolo[2,3-b]pyridin-3-yl)-methanone P-0025 with [6-(Cyclohexylmethylamino)-pyridin-3-yl]-(1H-pyrrolo[2,3-b]pyridin-3-yl)-methanone P-0031, (prepared as described in Example 5). MS (ESI) [M+H+]+=321.

Example 7

3-(6-Isopropyl-pyridin-3-ylmethyl)-1H-pyrrolo[2,3-b]pyridine P-0019

3-(6-Isopropyl-pyridin-3-ylmethyl)-1H-pyrrolo[2,3-b]pyridine P-0019 was synthesized in 2 steps from 3-(6-Chloro-pyridin-3-ylmethyl)-1-triisopropylsilanyl-1H-pyrrolo[2,3-b]pyridine 6 as shown in Scheme 9.

89 / 90 and purified by silica gel column chromatography eluting with 10% methanol in dichloromethane to give compound (P-0019, 18.0 mg, 81.9%). MS (ESI) [M+H$^+$]$^+$=252.

Example 8

Synthesis of [5-(1H-Pyrrolo[2,3-b]pyridin-3-ylmethyl)-pyridin-2-yl]-(4-trifluoromethyl-benzyl)-amine (P-0003)

[5-(1H-Pyrrolo[2,3-b]pyridin-3-ylmethyl)-pyridin-2-yl]-(4-trifluoromethyl-benzyl)-amine (P-0003) was prepared in three steps from (6-Chloro-pyridin-3-yl)-(1H-pyrrolo[2,3-b]pyridin-3-yl)-methanone (7) according to Scheme 10.

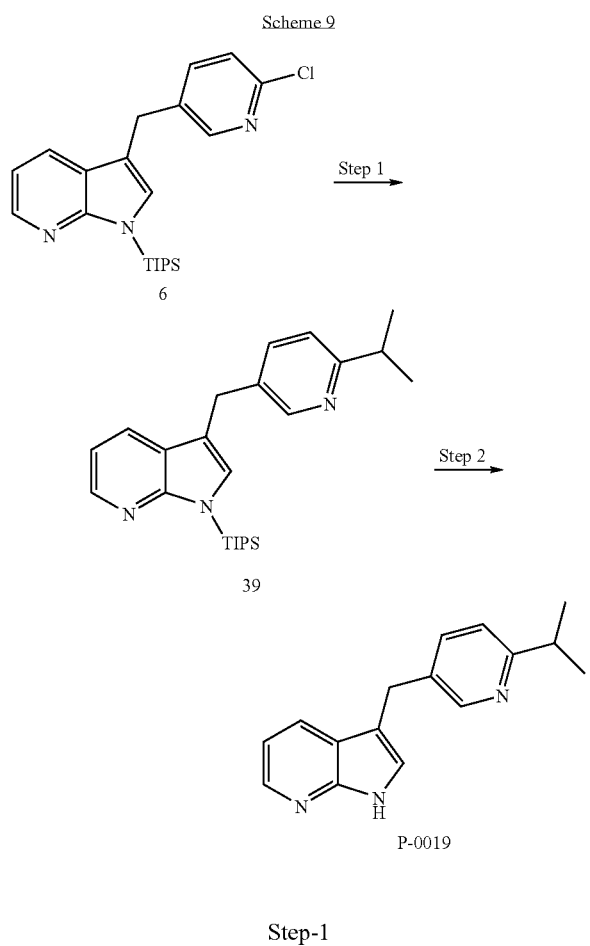

Scheme 9

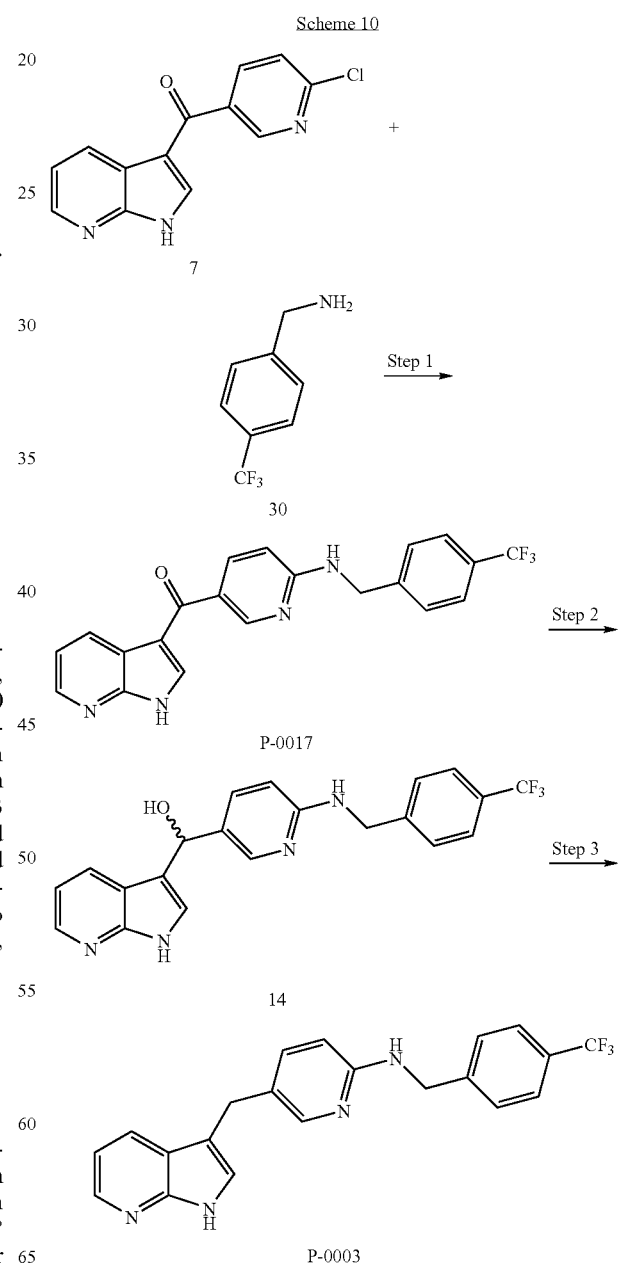

Scheme 10

Step-1

Synthesis of 3-(6-Isopropyl-pyridin-3-ylmethyl)-1-triisopropylsilanyl-1H-pyrrolo[2,3-b]pyridine (39)

To 3-(6-Chloro-pyridin-3-ylmethyl)-1-triisopropylsilanyl-1H-pyrrolo[2,3-b]pyridine (6, 54.0 mg, 0.000135 mol, prepared as described in Example 2) in Tetrahydrofuran (4.0 mL) were added [1,1'-bis(diphenylphosphino)ferrocene]-dichloropalladium(II) (23.0 mg) and Isopropylmagnesium Chloride (0.15 mL, 2.0 M in Tetrahydrofuran). The reaction was stirred at 20° C. under an atmosphere of Nitrogen for 3 hours. The reaction mixture was poured into water and extracted with ethyl acetate. The organic layer was washed with brine, dried over sodium sulfate, concentrated and purified by silica gel column chromatography eluting with 10% methanol in dichloromethane to give compound 39 (38 mg, 70.4%).

Step-2

Synthesis of 3-(6-Isopropyl-pyridin-3-ylmethyl)-1H-pyrrolo[2,3-b]pyridine (P-0019)

To 3-(6-Isopropyl-pyridin-3-ylmethyl)-1-triisopropylsilanyl-1H-pyrrolo[2,3-b]pyridine (39, 35.0 mg, 0.086 mmol) in tetrahydrofuran (3.0 mL) was added tetra-n-butylammonium fluoride (29 mg, 0.11 mmol). The reaction was stirred at 20° C. for 30 minutes. The reaction mixture was poured into water and extracted with ethyl acetate. The organic layer was washed with brine, dried over sodium sulfate, concentrated

Step-1

Synthesis of (1H-Pyrrolo[2,3-b]pyridin-3-yl)-[6-(4-trifluoromethyl-benzylamino)-pyridin-3-yl]-methanone (P-0017)

Into a pressure flask was added (6-Chloro-pyridin-3-yl)-(1H-pyrrolo[2,3-b]pyridin-3-yl)-methanone 7 (3.5 g, 0.014 mol, prepared as described in Example 3), 4-(trifluoromethyl)benzylamine (30, 9.0 g, 0.051 mol), tetrahydrofuran (30.0 mL, 0.37 mol), palladium acetate (200.0 mg, 0.890 mmol) and 2-(di-t-butylphosphino)biphenyl (200.0 mg, 0.67 mmol). The reaction mixture was stirred at 180° C. overnight, poured into water and extracted with ethyl acetate. The organic layer was washed with brine, dried over sodium sulfate and concentrated. To the residue was added acetic acid (15.0 mL) and H$_2$O (5.0 mL). The reaction mixture was stirred at 100° C. for 5 hours and concentrated to remove the acetic acid. The residue was then treated with aqueous Na$_2$HCO$_3$ and extracted with ethyl acetate. The organic layer was washed, dried, concentrated and purified to give compound P-0017 (1.0 g, yield=18.5%) as a light yellow solid. MS (ESI) [M+H$^+$]$^+$=397.

Step-2

Synthesis of (1H-Pyrrolo[2,3-b]pyridin-3-yl)-[6-(4-trifluoromethyl-benzylamino)-pyridin-3-yl]-methanol (14)

Into a round bottom flask was added (1H-Pyrrolo[2,3-b]pyridin-3-yl)-[6-(4-trifluoromethyl-benzylamino)-pyridin-3-yl]-methanone P-0017 (210.0 mg, 0.53 mmol) and sodium tetrahydroborate (80.0 mg, 2.11 mmol), dissolved in N,N-dimethylformamide (5.0 mL) and ethanol (20.0 mL). The reaction was stirred at room temperature overnight, poured into water and extracted with ethyl acetate. The organic layer was washed with brine, dried over sodium sulfate, concentrated and purified with biotage (dichloromethane/methanol 1:20) to give compound 14 (63 mg, yield=30%) as a white solid. MS (ESI) [M+H$^+$]$^+$=399.

Step-3

Synthesis of [5-(1H-Pyrrolo[2,3-b]pyridin-3-ylmethyl)-pyridin-2-yl]-(4-trifluoromethyl-benzyl)-amine (P-0003)

Into a round bottom flask was added (1H-Pyrrolo[2,3-b]pyridin-3-yl)-[6-(4-trifluoromethyl-benzylamino)-pyridin-3-yl]-methanol 14 (200.0 mg, 0.50 mmol), trifluoroacetic acid (5.0 mL, 0.065 mol) and triethylsilane (3.0 mL, 0.019 mol). The reaction was stirred at room temperature for 30 min, poured into aqueous sodium bicarbonate, and extracted with ethyl acetate. The organic layer was washed with brine, dried over sodium sulfate, concentrated and purified to give pure compound P-0003 (120.0 mg, yield=62.8%) as a white solid. MS (ESI) [M+H$^+$]$^+$=383.

Example 9

Synthesis of Compounds of Formula I where n is 1, P, Q and T are CH X$_1$, X$_2$ and Y$_2$ are CH, Y$_1$ is CR$^4$, L$^1$ is —CH2—, L$^2$ is —NHCH$_2$—, and R$^1$ is 4 Substituted Phenyl (Formula Ic)

Compounds of Formula Ic, where R$^4$ is as defined for Formula I and Z is a substituent as defined for optionally substituted aryl, can be synthesized in five Steps from 2-amino-5-bromopyridines as shown in the following general Scheme 11.

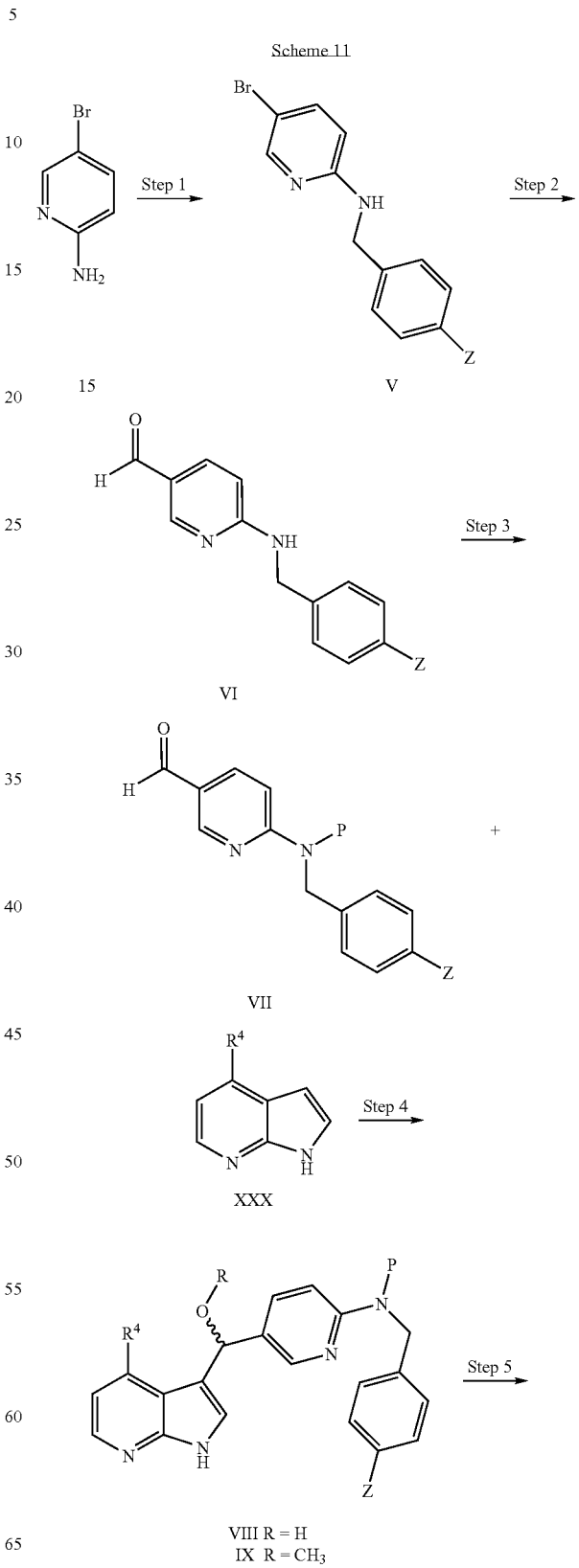

93

-continued

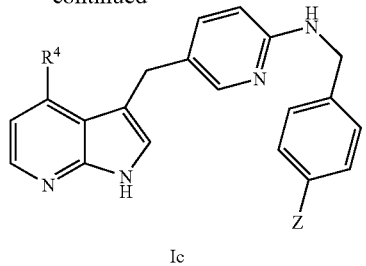

Ic

Step-1

Preparation of Compounds of Formula V

To a solution of an appropriately substituted benzaldehyde (e.g. p-trifluoromethyl benzaldehyde) in a non-reactive solvent (e.g. tetrahydrofuran) is added an appropriate 2-amino-5-bromo-pyridine 15, followed by appropriate reagents to effect the reduction (e.g. dibutyltin dichloride and phenylsilane). Typically the reaction is heated (e.g. 50° C.) overnight. The solvent is removed at reduced pressure after heating to 50° C. overnight. Isolation by conventional means (e.g. extraction) affords compounds of Formula V.

Step-2

Preparation of Compounds of Formula VI

Compound of Formula V is dissolved in a non-reactive solvent (e.g. tetrahydrofuran) and typically cooled at −78° C. under an inert atmosphere. To this mixture is added an organo lithium reagent (e.g. methyl lithium). The reaction mixture is typically stirred at −78° C. for several hours. To this mixture is added an organo lithium reagent (e.g. tert-butyl lithium), and the mixture is stirred for several hours. The reaction mixture is maintained at −78° C., and an appropriate formylating reagent (e.g. 1-piperidine carboxaldehyde) is added. Typically, the reaction is allowed to stir at −78° C. for an additional several hours and slowly warmed to room temperature. Isolation by conventional means (e.g. extraction) affords compounds of Formula VI.

Step-3

Preparation of Compounds of Formula VII

Compound of Formula VI is dissolved in a non-reactive solvent (e.g. tetrahydrofuran) and stirred under an inert atmosphere. To this solution is added a base (e.g. triethylamine) and typically a catalyst (e.g. 4-dimethylaminopyridine). Typically, the mixture is stirred for a few minutes and then a reagent appropriate for the introduction of a protecting group (e.g. di-tert-butyldicarbonate) is added. Typically, the reaction is stirred overnight. Isolation by conventional means (e.g. extraction) affords compounds of Formula VII.

Step-4

Preparation of Compounds of Formula VIII and IX

4-Substituted 1H-pyrrolo[2,3-b]pyridine XXX is added to a stirring solution of base (e.g. potassium hydroxide) in an appropriate polar protic solvent (e.g. methanol). Compound of Formula VII is added, and the mixture is typically stirred at room temperature for several days. The solvent is evaporated, and 1 M HCl is added to the residue. Isolation by conventional means (e.g. extraction, silica gel chromatography) affords compounds of Formula VIII and IX.

Step-5

Preparation of Compounds of Formula Ic

Typically, compounds of Formula VIII and IX is combined and dissolved in an appropriate polar aprotic solvent (e.g. acetonitrile). Reagents appropriate to effect the reduction (e.g. triethylsilane and trifluoroacetic acid) are added. Typically, the reactions are stirred at room temperature for several days. Isolation by conventional means (e.g. extraction, silica gel chromatography) affords compounds of Formula Ic.

Example 10

Synthesis of [5-(4-Methoxy-1H-pyrrolo[2,3-b]pyridin-3-ylmethyl)-pyridin-2-yl]-(4-trifluoromethyl-benzyl)-amine (P-0011)

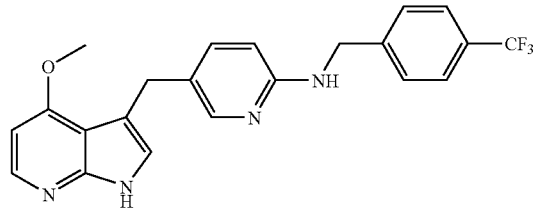

[5-(4-Methoxy-1H-pyrrolo[2,3-b]pyridin-3-ylmethyl)-pyridin-2-yl]-(4-trifluoromethyl-benzyl)-amine P-0011 was synthesized as shown in Scheme 12:

Scheme 11

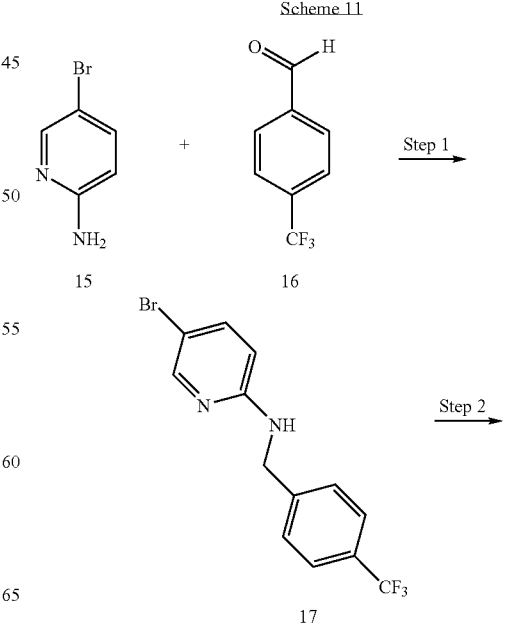

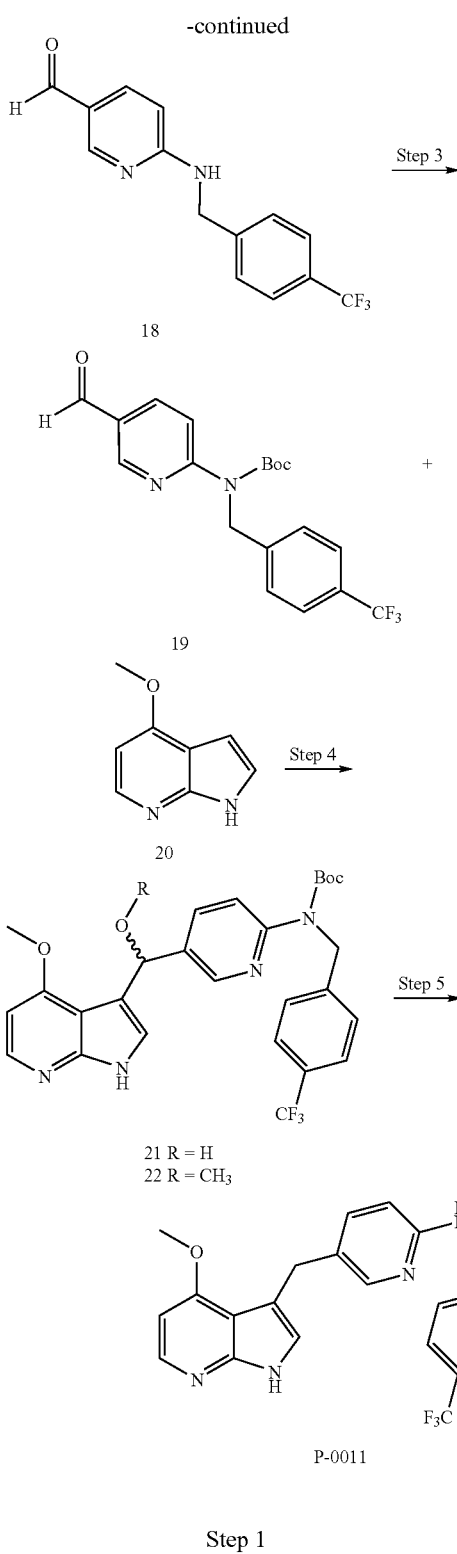

triethylsilane (825 mL) and acetonitrile (7500 mL). The reaction was heated to reflux overnight (24 hours). Solvents were removed and the residue was poured into aqueous $K_2CO_3$ and extracted with ethyl acetate. The organic layer was washed with brine, dried over sodium sulfate, and concentrated. The crude compound was crystallized with diethyl ether/hexane to afford compound 17, 420 g (73.6%) as off white solid. MS (ESI) $[M+H^+]^+$=331.1 and 333.1 (1:1 ratio).

Step 2

Preparation of 6-(4-Trifluoromethyl-benzylamino)-pyridine-3-carbaldehyde (18)

Into a 5 L round bottom flask was added compound 17 (0.6 mol, 198.6 g,) and tetrahydrofuran (2.5 L) under an atmosphere of argon at −78° C. Into the reaction mixture was added 1.7 M tert-butyllithium in pentane (800 mL) over 60 mins. Two hours after the addition of tert-butyllithium, N,N-dimethylformamide (100 mL) was added. The reaction mixture was stirred at −78° C. for 2 hours, then allowed to stand at room temperature for another 1 hour. The reaction mixture was poured into saturated ammonium chloride solution and extracted with ethyl acetate. The organic layer was washed with brine, dried over sodium sulfate, concentrated and triturated with hexane/isopropyl ether (1:1) to give aldehyde compound 18.

Step 3

Preparation of (5-Formyl-pyridin-2-yl)-(4-trifluoromethyl-benzyl)-carbamic acid tert-butyl ester (19)

Into a 2 L round bottom flask was added di-tert-butyldicarbonate (90 g), aldehyde 18 (75 g), diisopropyl ethyl amine (60 g), 4-dimethylaminopyridine (2.0 g,) and dichloromethane (1000.0 mL). The reaction was stirred at room temperature overnight (18 hours) and the solvent was evaporated to give compound 19 (94 g).

Steps 4 and 5

Preparation of [5-(4-Methoxy-1H-pyrrolo[2,3-b]pyridin-3-ylmethyl)-pyridin-2-yl]-(4-trifluoromethyl-benzyl)-amine (P-0011)

Step 4: Into a solution of methanol (20 mL, 0.5 mol) was added sodium hydroxide (0.62 g, 0.016 mol), followed by 4-methoxy-7-azaindole (20, 600 mg, 4 mmol, prepared as described in Example 12). Once the mixture was homogeneous, compound 19 (1.7 g, 4.46 mmol) was added and the mixture was stirred at room temperature for 48 hours. The solvent was evaporated and dilute HCl was added to the residue. The residue was extracted with ethyl acetate and washed with 10% sodium bicarbonate, followed by brine. The organic layer was dried over $MgSO_4$, filtered and evaporated to give a mixture of crude compounds 21 and 22, which was used in the next step.

Step 5: The mixture of 21 and 22 from Step 4 (2.36 g, 4.46 mmol) was dissolved in dichloromethane (60 mL, 0.9 mol) to which triethylsilane (3.6 mL, 0.022 mol) and trifluoroacetic Acid (2.1 mL, 0.027 mol) were added. The resulting mixture was stirred for 48 hours at room temperature. The solvent was evaporated and the mixture was extracted with dichloromethane:methanol (3:1). The organic layer was washed with saturated bicarbonate followed by brine. The organic layer was dried over $MgSO_4$, filtered and evaporated to give Step 1

Preparation of (5-Bromo-pyridin-2-yl)-(4-trifluoromethyl-benzyl)-amine (17)

Into a round bottom flask fitted with stirrer and reflux condenser was added 2-amino-5-bromopyridine (15, 1.73 mol, 300 g) and p-trifluoromethylbenzaldehyde (16, 1.723 mol, 300 g) to a solution of trifluoroacetic acid (400 mL), crude compound as a residue. The residue was purified by flash silica gel chromatography to give 1.15 g of solid P-0011 for a 60% yield. MS (ESI) [M+H$^+$]$^+$=413.24.

[5-(4-Methoxy-1H-pyrrolo[2,3-b]pyridin-3-ylmethyl)-pyridin-2-yl]-(4-chloro-benzyl)-amine P-0010

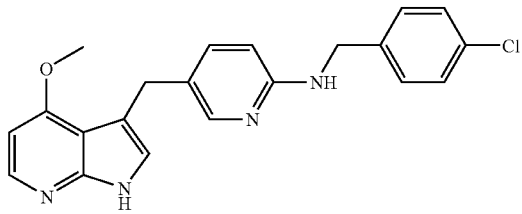

was prepared following the protocol of Scheme 12, substituting 4-trifluoro-benzylamine with 4-chloro-benzylamine in Step 1. MS (ESI) [M+H$^+$]$^+$=379.2 and 381.2 (3:1 ratio).

[5-(4-chloro-1H-pyrrolo[2,3-b]pyridin-3-ylmethyl)-pyridin-2-yl]-(4-chloro-benzyl)-amine P-0009

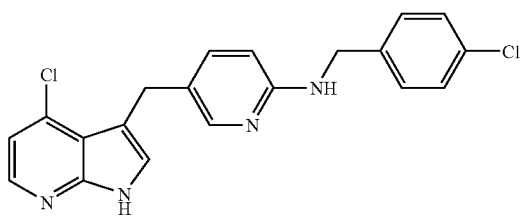

was prepared following the protocol of Scheme 12, substituting 4-trifluoro-benzylamine with 4-chloro-benzylamine in Step 1 and 4-methoxy-7-azaindole with 4-chloro-7-azaindole (24, prepared as described in Example 11) in Step 4. MS (ESI) [M+H$^+$]$^+$=381.1 and 383.0.

Example 11

Synthesis of 4-chloro-7-azaindole (24)

4-chloro-7-azaindole 24 was synthesized in two Steps from 7-azaindole according to the protocol of Scheme 13.

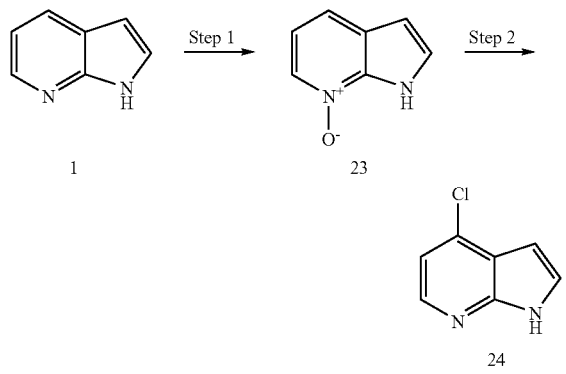

Step-1

Synthesis of 1H-Pyrrolo[2,3-b]pyridine 7-oxide (23)

1H-Pyrrolo[2,3-b]pyridine 7-oxide 23 was synthesized by reacting commercially available 7-azaindole 1 with an oxidizing agent (e.g. m-CPBA) in a non-reactive solvent (e.g. dimethoxyethane) as described by Schneller, S. W.; Luo, Jiann-Kuan. J. Org. Chem. 1980, 45:4045-4048. The compound was isolated by filtration of the resulting solid that forms upon standing at 5° C. for typically 1-3 h.

Step-2

Synthesis of 4-chloro-7-azaindole (24)

4-chloro-7-azaindole 24 was synthesized by reacting 1H-Pyrrolo[2,3-b]pyridine 7-oxide 23 with a chlorinating agent (e.g. POCl$_3$) neat as described by Schneller, S. W.; Luo, Jiann-Kuan. J. Org. Chem. 1980, 45:4045-4048. The resulting solution after heating for 3-5 h at elevated temperatures (100-150° C.) was neutralized with a base (e.g. NH$_4$OH) until a solid precipitated. The solid was isolated by filtration.

Example 12

Synthesis of 4-methoxy-7-azaindole (20)

4-methoxy-7-azaindole 20 was synthesized in one Step from 4-chloro-7-azaindole according to the protocol of Scheme 14.

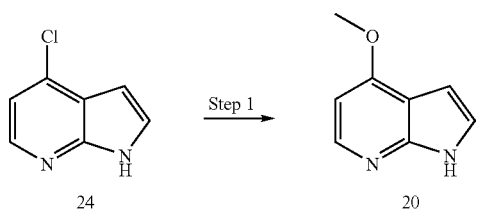

4-methoxy-7-azaindole 20 was prepared by reacting 4-chloro-7-azaindole 24 (prepared as described in Example 9) with sodium hydroxide in methanol as described by Girgis, N. et. al., J. Heterocyclic. Chem. 1989, 26:317-325.

Example 13

Synthesis of Compounds of Formula I where n is 1, P is CR$^{30}$, Q, T, X$_1$, X$_2$, Y$_1$ and Y$_2$ are CH, L$^1$ is —CH2—, L$^2$ is —NHCH$_2$—, and R$^1$ is Substituted Phenyl (Formula Id)

Compounds of Formula Id, where R$^{30}$ is a substituent as defined for optionally substituted heteroarylene (further defined in Scheme 13 below) and R$^{31}$ is a substituent as defined for optionally substituted aryl, can be synthesized in six Steps from appropriately substituted 2-halopyridines as shown in the following general Scheme 15.

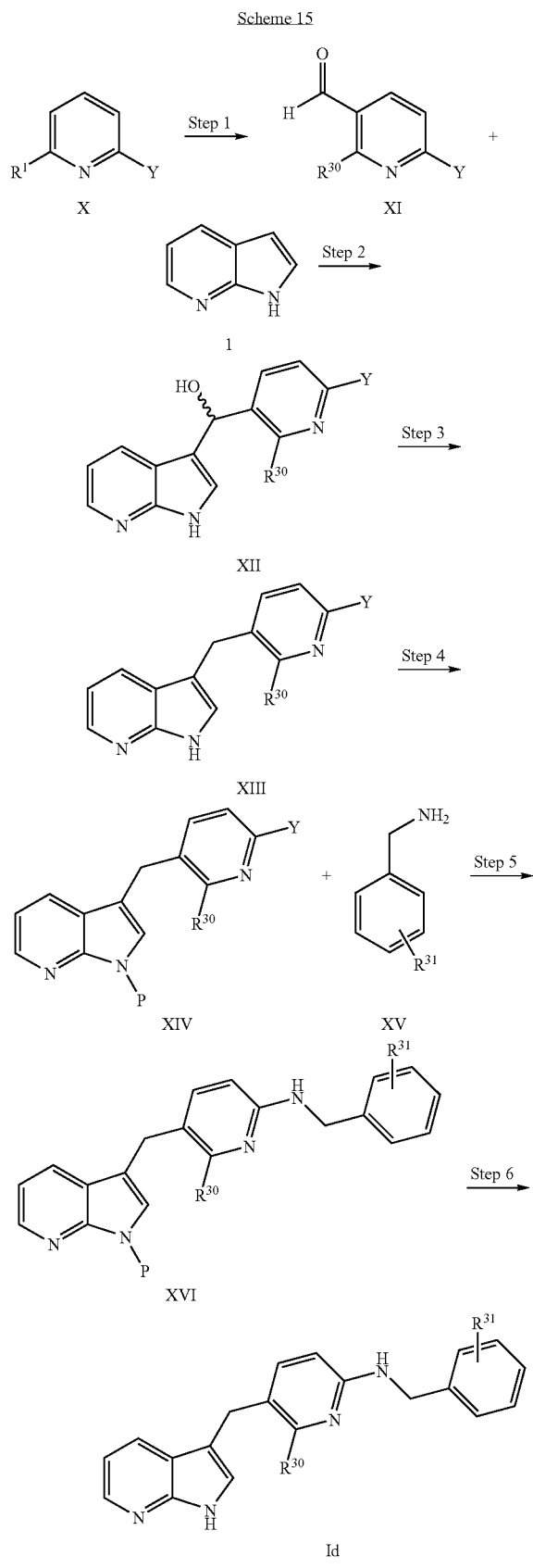

Step 1

Preparation of Compounds of Formula XI

To an appropriately substituted 2-halopyridine X (e.g. 2-chloro-6-methoxypyridine), where Y is a halogen, preferably chlorine or bromine, and $R^{30}$ is a group appropriate to direct the following lithiation to the 5-position (e.g. $R^{30}$=methoxy), in a non-reactive solvent (e.g. tetrahydrofuran) typically cooled in a −78° C. acetone/dry ice bath is added a solution of organolithium reagent (e.g. tert-butyllithium). The reaction is allowed to stir for a period, typically 1 hour. An appropriate formylating agent (e.g. dimethylformamide) is added and the reaction is allowed to stir cooled for a period and then warmed to room temperature for a period, typically 30 minutes. The reaction can be placed back in the dry-ice bath and quenched with 6 N HCl (1.5 mL) followed by water and allowed to warm to room temperature. Isolation by conventional means (e.g. extraction) provides compounds of Formula XI.

Step 2

Preparation of Compounds of Formula XII

To 1H-pyrrolo[2,3-b]pyridine 1 and a compound of Formula XI is added an appropriate polar solvent (e.g. methanol) followed by an appropriate base (e.g. potassium hydroxide). The reaction is typically allowed to stir at room temperature overnight. Isolation by convention means (e.g. extraction, washing and filtering) affords compounds of Formula XII.

Step 3

Preparation of Compounds of Formula XIII

To a compound of Formula XII in an appropriate polar solvent (e.g. acetonitrile) is added a reducing agent (e.g. trifluoroacetic acid and triethylsilane). Typically, the reaction is allowed to stir at room temperature overnight. Isolation by conventional means (e.g. extraction and silica gel chromatography) affords compounds of Formula XIII.

Step 4

Preparation of Compounds of Formula XIV

To a solution of compound of Formula XIII in an appropriate polar solvent (e.g. dimethylformamide) is added a base (e.g. sodium hydride). Typically, the reaction is stirred at room temperature for 30 minutes, and then an appropriate reagent to introduce a protecting group ("P") is added (e.g. triisopropylsilyl chloride). The reaction typically is stirred at room temperature for several hours. Isolation by conventional means (e.g. extraction and silica gel chromatography) affords compounds of Formula XIV.

Step 5

Preparation of Compounds of Formula XVI

To a compound of Formula XIV, an appropriately substituted benzylamine XV (e.g. 4-(trifluoromethyl)benzylamine), a base (e.g. sodium tert-butoxide), a catalyst (e.g. tris(dibenzylideneacetone)dipalladium(0)), and ligand (e.g. 2,2'-Bis(diphenylphosphino)-1,1'-binaphthyl) are added a non-reactive solvent (e.g. toluene) under an inert atmosphere. Typically, the reaction is heated (e.g. 80° C.) for several hours. Isolation by conventional means (e.g. extraction and silica gel chromatography) affords compounds of Formula XVI.

Step 6

Preparation of Compounds of Formula Id

To compound of Formula XVI is added an appropriate polar solvent (e.g. tetrahydrofuran) followed by an appropriate reagent to remove the protecting group (e.g. tetra-n-butylammonium fluoride). Typically, the reaction is allowed to stir at room temperature for several hours. Isolation by conventional means (e.g. extraction and silica gel chromatography) affords compounds of Formula Id.

Example 14

Synthesis of Compounds of Formula I where n is 1, P is $CR^{32}$, Q, T, $X_1$, $X_2$, $Y_1$ and $Y_2$ are CH, $L^1$ is —CH2—, $L^2$ is —NHCH$_2$—, and $R^1$ is Substituted Phenyl (Formula Ie)

Compounds of Formula Id, where $R^{32}$ is a substituent as defined for optionally substituted heteroarylene and $R^{33}$ is a substituent as defined for optionally substituted aryl, can be synthesized in five Steps from appropriately substituted 2-amino-5-bromopyridines as shown in the following general Scheme 16.

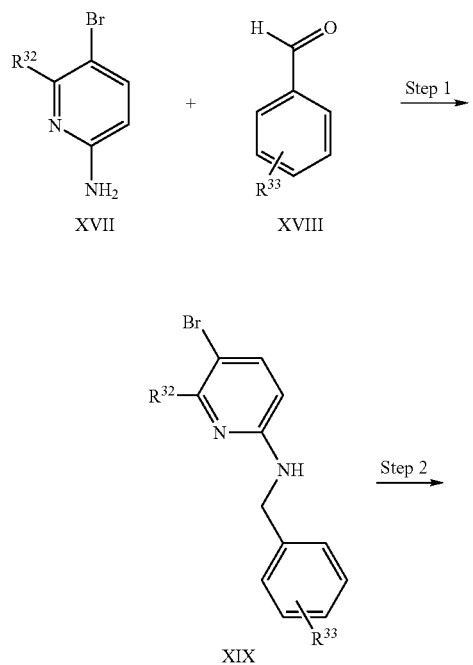

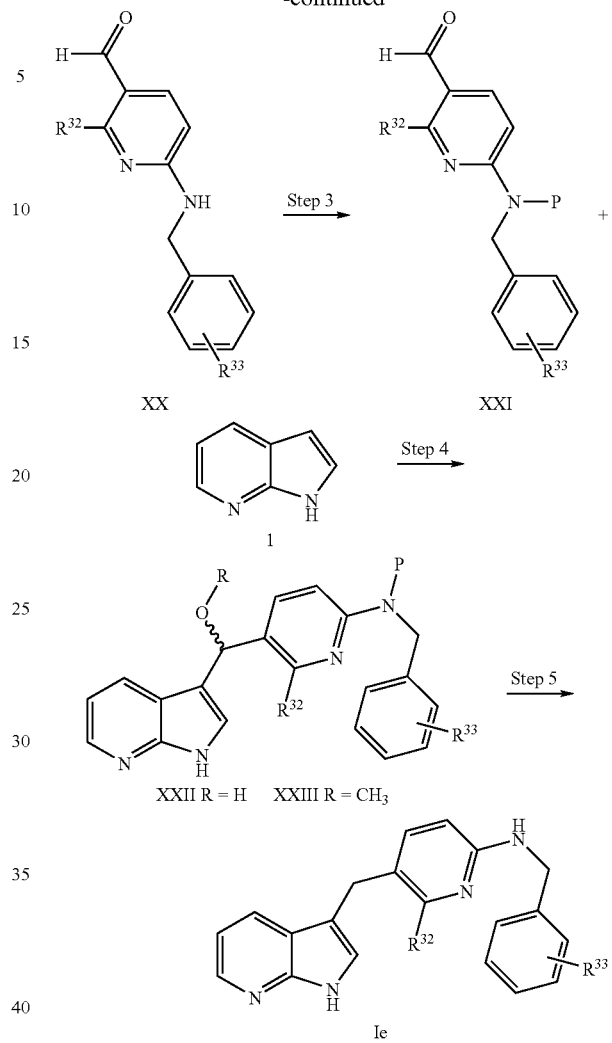

Step-1

Preparation of Compounds of Formula XIX

To a solution of an appropriately substituted benzaldehyde XVIII (e.g. p-trifluoromethyl benzaldehyde) in a non-reactive solvent (e.g. tetrahydrofuran) can be added an appropriate 2-amino-5-bromo-pyridine XVII (e.g. 2-amino-5-bromo-6-methylpyridine), followed by appropriate reagents to effect the reduction (e.g. dibutyltin dichloride and phenylsilane). Typically the reaction is heated (e.g. 50° C.) overnight. Isolation by conventional means (e.g. extraction) affords compounds of Formula XIX.

Step-2

Preparation of Compounds of Formula XX

Compound of Formula XIX is dissolved in a non-reactive solvent (e.g. tetrahydrofuran) and typically cooled at −78° C. under an inert atmosphere. To this mixture is added an organolithium reagent (e.g. methyllithium). The reaction mixture is typically stirred at −78° C. for several hours. To this mixture is added an organolithium reagent (e.g. tert-butyllithium) and the mixture is stirred for several hours. The reaction mixture is maintained at −78° C., and an appropriate formylating reagent (e.g. 1-piperidine carboxaldehyde) is added. Typically, the reaction is allowed to stir at −78° C. for an additional several hours and slowly warmed to room temperature. Isolation by conventional means (e.g. extraction) affords compounds of Formula XX.

Step-3

Preparation of Compounds of Formula XXI

Compound of Formula XX is dissolved in a non-reactive solvent (e.g. tetrahydrofuran) and stirred under an inert atmosphere. To this solution is added a base (e.g. triethylamine) and typically a catalyst (e.g. 4-dimethylaminopyridine). Typically, the mixture is stirred for a few minutes, and then a reagent appropriate for the introduction of a protecting group (e.g. di-tert-butyldicarbonate) is added. Typically, the reaction is stirred overnight. Isolation by conventional means (e.g. extraction) affords compounds of Formula XXI.

Step-4

Preparation of Compounds of Formula XXII and XXIII

1H-Pyrrolo[2,3-b]pyridine 1 is added to a stirred solution of base (e.g. potassium hydroxide) in an appropriate polar solvent (e.g. methanol). Compound of Formula XXI is added, and the mixture is typically stirred at room temperature for several days. The solvent is evaporated and 1 M HCl is added to the residue. Isolation by conventional means (e.g. extraction, silica gel chromatography) affords compounds of Formula XXII and XXIII.

Step-5

Preparation of Compounds of Formula XIV of Scheme 14

Typically, compounds of Formula XII and XIII are combined and dissolved in an appropriate polar aprotic solvent (e.g. acetonitrile). Reagents appropriate to effect the reduction (e.g. triethylsilane and trifluoroacetic acid) are added. Typically, the reaction is stirred at room temperature for several days. Isolation by conventional means (e.g. extraction, silica gel chromatography) affords compounds of Formula Ie.

Example 15

Synthesis of [6-Methoxy-5-(1H-pyrrolo[2,3-b]pyridin-3-ylmethyl)-pyridin-2-yl]-(4-trifluoromethyl-benzyl)-amine (P-0012)

[6-Methoxy-5-(1H-pyrrolo[2,3-b]pyridin-3-ylmethyl)-pyridin-2-yl]-(4-trifluoromethyl-benzyl)-amine P-0012 was synthesized in five steps from commercially available 2-chloro-6-methoxypyridine and 7-azaindole as shown in Scheme 17.

Scheme 17

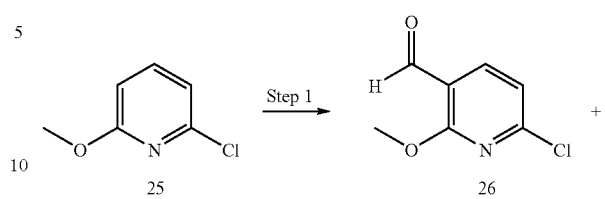

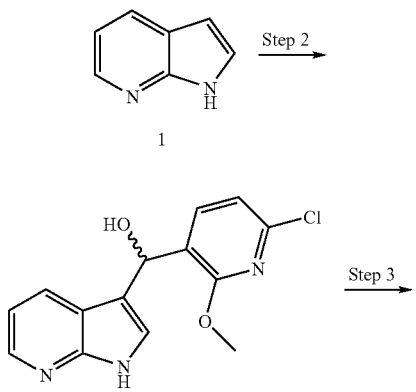

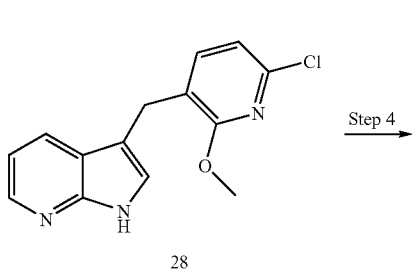

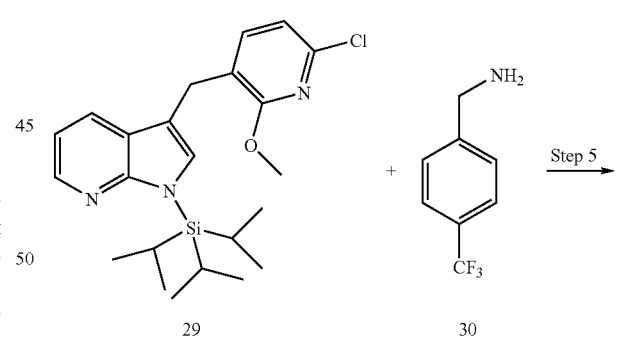

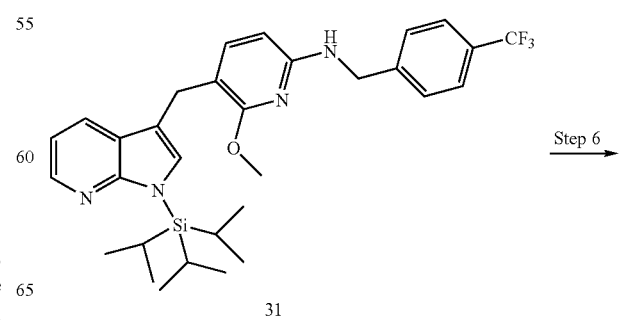

-continued

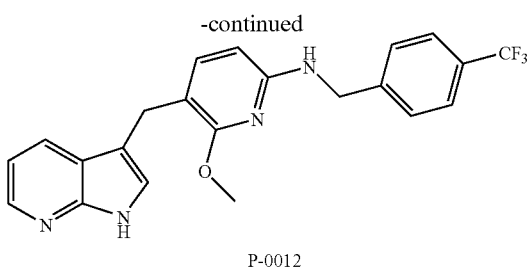

P-0012

Step 1

Preparation of 6-chloro-2-methoxypyridine-3-carbaldehyde (26)

To 2-Chloro-6-methoxypyridine (25, 0.511 g, 3.56 mmol) in tetrahydrofuran (10 mL) cooled in a −78° C. acetone/dry ice bath was added tert-butyllithium (1.7 M in pentane, 5.0 mL, 7.66 mmol). The reaction was allowed to stir for 1 hour. Dimethylformamide (0.673 mL, 17.4 mmol) was added and the reaction was allowed to continue for an additional 30 minutes at −78° C., then stirred for 30 minutes outside of the dry-ice bath. The reaction was placed back in the dry-ice bath and quenched with 6 N HCl (1.5 mL) followed by water and allowed to warm to room temperature. The reaction was extracted with diethyl ether and aqueous (1 M) sodium bicarbonate. The organic layer was separated, dried with anhydrous magnesium sulfate, filtered and volatiles removed by rotary evaporation, and the resulting yellow solid was dried under vacuum to provide 561 mg of compound 26 (3.27 mmol, 92% yield). MS (ESI) $[M+H^+]^+=172.0$.

Step 2

Preparation of (6-chloro-2-methoxypyridin-3-yl)(1H-pyrrolo[2,3-b]pyridin-3-yl)methanol (27)

To 1H-Pyrrolo[2,3-b]pyridine (1, 0.455 g, 3.85 mmol) and 6-chloro-2-methoxypyridine-3-carbaldehyde (26, 0.661 g, 3.85 mmol) was added methanol (10 mL) followed by potassium hydroxide (0.310 g, 5.52 mmol). The reaction was allowed to stir at room temperature overnight. The reaction was extracted with diethyl ether/ethyl acetate and water. The organic layer was separated, dried over anhydrous magnesium sulfate, filtered and volatiles were removed by rotary evaporation to provide a solid that was treated with dichloromethane and stored in a freezer overnight. The white solid was collected by vacuum filtration and dried in vacuo to give 613 mg of compound 27 (2.12 mmol, 55%). MS (ESI) $[M+H^+]^+=290.1$.

Step 3

Preparation 3-(6-chloro-2-methoxypyridin-3-ylmethyl)-1H-pyrrolo[2,3-b]pyridine (28)

To (6-chloro-2-methoxypyridin-3-yl)(1H-pyrrolo[2,3-b]pyridin-3-yl)methanol (27, 0.613 g, 2.12 mmol) in acetonitrile (10 mL) was added trifluoroacetic acid (0.82 mL, 10.0 mmol) followed by triethylsilane (1.69 mL, 10.6 mmol). The reaction was allowed to stir at room temperature for 2 days, then 60° C. for 4 hours. The reaction was extracted with diethyl ether and aqueous sodium bicarbonate. The organic layer was dried over anhydrous magnesium sulfate and filtered. The desired material was isolated from the filtrate by silica gel column chromatography eluting with 1% methanol in dichloromethane to give 516 mg of a white solid compound 28 (1.88 mmol, 89%). MS (ESI) $[M+H^+]^+=274.1$.

Step 4

Preparation 3-(6-chloro-2-methoxypyridin-3-ylmethyl)-1-(triisopropylsilyl)-1H-pyrrolo[2,3-b]pyridine (29)

To a clear solution of 3-(6-chloro-2-methoxypyridin-3-ylmethyl)-1H-pyrrolo[2,3-b]pyridine (28, 0.516 g, 1.88 mmol) in dimethylformamide (10 mL) was added sodium hydride (60% dispersion, 0.113 g, 2.82 mmol). After stirring at room temperature for 30 minutes, triisopropylsilyl chloride (600 µL, 2.83 mmol) was added. The reaction was stirred at room temperature for 2 hours, then poured into aqueous (1 M) sodium bicarbonate and extracted with ethyl acetate. The organic layer was separated, dried (magnesium sulfate), filtered and volatiles were removed by rotary evaporation to give a crude solid. The compound was purified by silica gel column chromatography eluting with 2% ethyl acetate in hexanes. This provided 732 mg of the desired compound as a white, crystalline solid (29, 1.70 mmol, 90%). MS (ESI) $[M+H^+]^+=430.2$.

Step 5

Preparation of [6-Methoxy-5-(1-triisopropylsilanyl-1H-pyrrolo[2,3-b]pyridin-3-ylmethyl)-pyridin-2-yl]-(4-trifluoromethyl-benzyl)-amine (31)

3-(6-chloro-2-methoxypyridin-3-ylmethyl)-1-(triisopropylsilyl)-1H-pyrrolo[2,3-b]pyridine (29, 0.104 g, 0.242 mmol), 4-(Trifluoromethyl)benzylamine (30, 0.047 g, 0.266 mmol), sodium tert-butoxide (0.0325 g, 0.338 mmol), Tris(dibenzylideneacetone)-dipalladium (0) (0.00062 g, 0.0006 mmol), and 2,2'-Bis(diphenylphosphino)-1,1'-binaphthyl (0.0011 g, 0.0018 mmol) were added to toluene (2 mL) under nitrogen. The reaction vial was placed in an oil bath at 80° C. for 3 hours. The reaction was poured into water and extracted with ethyl acetate. The organic layer was dried (magnesium sulfate), filtered, and volatiles were removed by rotary evaporation. The residue was purified by silica gel column chromatography eluting with 2% ethyl acetate in hexanes. This provided 34 mg of the desired compound 31 (0.060 mmol, 25%). MS (ESI) $[M+H^+]^+=569.3$.

Step 6

Preparation of [6-Methoxy-5-(1H-pyrrolo[2,3-b]pyridin-3-ylmethyl)-pyridin-2-yl]-(4-trifluoromethyl-benzyl)-amine (P-0012)

To [6-Methoxy-5-(1-triisopropylsilanyl-1H-pyrrolo[2,3-b]pyridin-3-ylmethyl)-pyridin-2-yl]-(4-trifluoromethyl-benzyl)-amine (31, 0.0340 g, 0.0598 mmol) was added tetrahydrofuran (5 mL) followed by tetra-n-butylammonium fluoride (1M solution in tetrahydrofuran, 66 µL, 0.0658 mmol). The reaction was allowed to stir at room temperature for 2 hours, then poured into 1:1 water:saturated sodium bicarbonate and extracted with ethyl acetate. The organic layer was separated, dried over magnesium sulfate, filtered and the volatiles were removed by rotary evaporation. The resulting residue was purified by silica gel column chromatography, eluting with dichloromethane followed by 1% methanol in dichloromethane and finally 3% methanol in dichloromethane. This provided 20 mg of the desired compound as a white solid (P-0012, 0.048 mmol, 81%). MS (ESI) [M+H⁺]⁺=413.2.

Example 16

Synthesis of [6-Methyl-5-(1H-pyrrolo[2,3-b]pyridin-3-ylmethyl)-pyridin-2-yl]-(4-trifluoromethyl-benzyl)-amine (P-0013)

[6-Methyl-5-(1H-pyrrolo[2,3-b]pyridin-3-ylmethyl)-pyridin-2-yl]-(4-trifluoromethyl-benzyl)-amine (P-0013) was synthesized in five steps from commercially available 2-amino-5-bromo-6-methylpyridine and 7-azaindole as shown in Scheme 18.

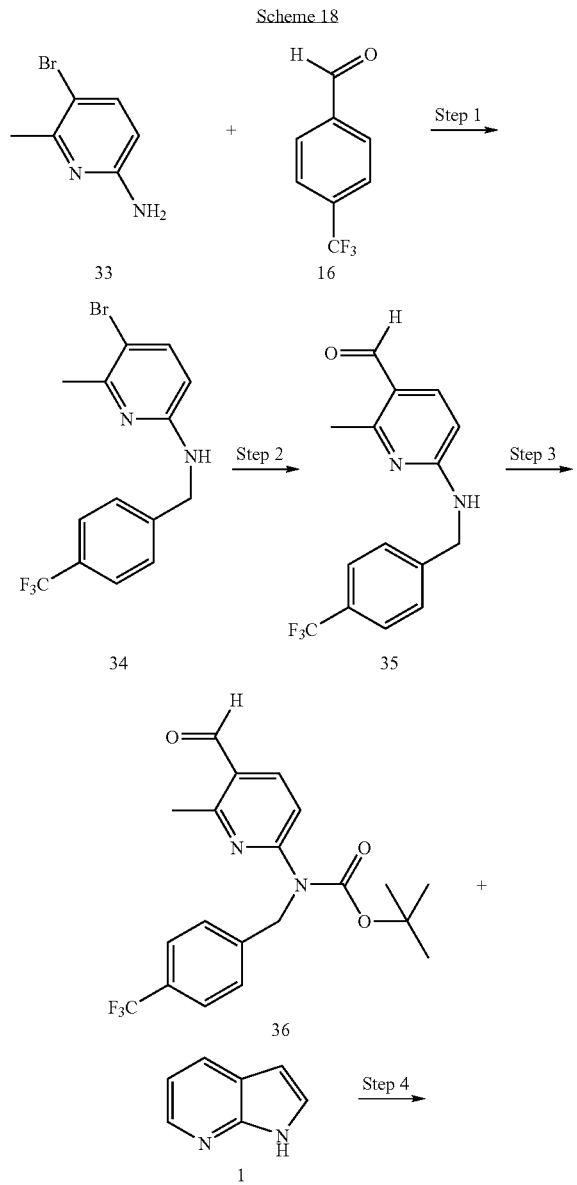

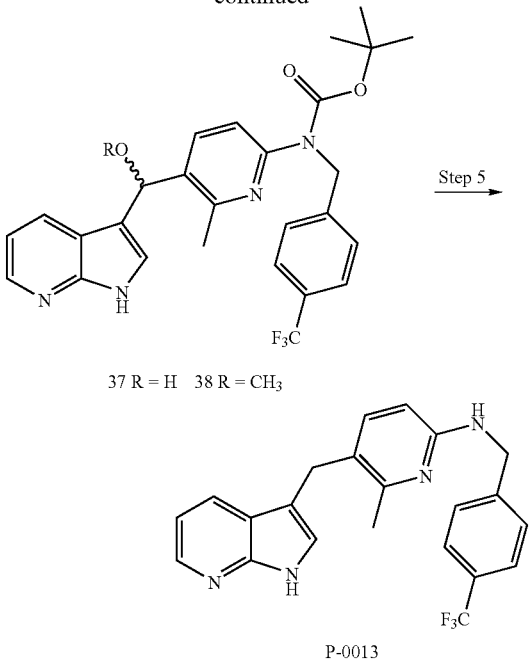

Step-1

Preparation of (5-Bromo-6-methyl-pyridin-2-yl)-(4-trifluoromethyl-benzyl)-amine (34)

To a solution of p-trifluoromethylbenzaldehyde (16, 1.00 g, 5.74 mmol) in tetrahydrofuran (9 mL) was added 2-amino-5-bromo-6-methylpyridine (33, 1.08 g, 5.77 mmol), followed by dibutyltin dichloride (40 mg, 0.13 mmol). The mixture was stirred for 5 minutes at 25° C. and phenylsilane (0.69 g, 6.4 mmol) was added. The reaction was heated at 50° C. overnight, then the solvent was removed at reduced pressure. Ethyl acetate was added to the resulting solid which was washed with saturated sodium carbonate, dried over magnesium sulfate and filtered. Concentration under reduced pressure afforded a light yellow solid (34, 1.7 g, 4.93 mmol). MS (ESI) [M+H⁺]⁺=345.1.

Step-2

Preparation of 2-Methyl-6-(4-trifluoromethyl-benzylamino)-pyridine-3-carbaldehyde (35)

(5-Bromo-6-methyl-pyridin-2-yl)-(4-trifluoromethyl-benzyl)-amine (34, 1.7 g, 4.93 mmol) was dissolved in tetrahydrofuran (40 mL) and cooled at −78° C. under a nitrogen atmosphere. To this mixture was added methyllithium (1.6 M in diethyl ether, 5.91 mmol) dropwise over 20 minutes. After the addition of methyllithium was completed, the reaction mixture was stirred at −78° C. for 2 hours. To this mixture was added tert-butyllithium (1.7 M in pentane, 10.85 mmol) and the mixture was stirred for 4 hours. The reaction mixture was maintained at −78° C., and 1-piperidinecarboxaldehyde (0.60 mL, 5.42 mmol) was added dropwise. The reaction was allowed to stir at −78° C. for an additional 2 hours and warming to 25° C. was achieved from the slow evaporation of the dry ice/acetone cooling bath. The reaction was quenched with ice cold saturated sodium chloride and the resulting mixture was extracted with ethyl acetate. The organic layer was dried over magnesium sulfate and filtered. Concentration under reduced pressure afforded an orange oil (35, 1.4 g, 4.93 mmol). MS (ESI) [M+H$^+$]$^+$=295.1.

Step-3

Preparation of (5-Formyl-6-methyl-pyridin-2-yl)-(4-trifluoromethyl-benzyl)-carbamic acid tert-butyl ester (36)

2-Methyl-6-(4-trifluoromethyl-benzylamino)-pyridine-3-carbaldehyde (35, 1.4 g, 4.9 mmol) was dissolved in tetrahydrofuran (22 mL) and was stirred under an atmosphere of nitrogen. To this solution was added 4-dimethylaminopyridine (150 mg, 1.23 mmol) and triethylamine (0.66 mL, 4.9 mmol). The mixture was stirred for 5 minutes before solid di-tert-butyldicarbonate (1.0 g, 4.9 mmol) was added directly to the reaction mixture. The mixture was stirred overnight at 25° C. and was diluted with ethyl acetate and washed with sodium bicarbonate, followed by washing with saturated sodium chloride. The resulting organic layer was dried over magnesium sulfate, filtered and evaporated to give a beige solid (36, 1.8 g, 4.6 mmol). MS (ESI) [M+H$^+$]$^+$=395.2.

Step-4

Preparation of {5-[Hydroxy-(1H-pyrrolo[2,3-b]pyridin-3-yl)-methyl]-6-methyl-pyridin-2-yl}-(4-trifluoromethyl-benzyl)-carbamic acid tert-butyl ester (37) and {5-[Methoxy-(1H-pyrrolo[2,3-b]pyridin-3-yl)-methyl]-6-methyl-pyridin-2-yl}-(4-trifluoromethyl-benzyl)-carbamic acid tert-butyl ester (38)

1H-Pyrrolo[2,3-b]pyridine (1, 540 mg, 4.57 mmol) was added to a stirring solution of potassium hydroxide (868 mg, 10.08 mmol) in methanol (33 mL). Once the mixture was homogeneous, (5-formyl-6-methyl-pyridin-2-yl)-(4-trifluoromethyl-benzyl)-carbamic acid tert-butyl ester (36, 1.8 g, 4.6 mmol) was added and the mixture was stirred at 25° C. for 72 hours. The solvent was evaporated and 1 M HCl was added to the residue. The organic material was extracted with ethyl acetate and washed with 10% sodium bicarbonate, followed by washing with saturated sodium chloride. The organic layer was dried over magnesium sulfate. Concentration under reduced pressure afforded the crude material, which was purified by silica gel column chromatography (0-5% methanol in dichloromethane) to yield the desired compounds as a light yellow solid (37 and 38 as a mixture, 294 mg; 13% yield). MS (ESI) [M+H$^+$]$^+$=511.2 for 37 and MS (ESI) [M+H$^+$]$^+$=525.2 for 38.

Step-5

Preparation of [6-Methyl-5-(1H-pyrrolo[2,3-b]bipyridin-3-ylmethyl)-pyridin-2-yl]-(4-trifluoromethyl-benzyl)-amine (P-0013)

The combined materials of {5-[Hydroxy-(1H-pyrrolo[2,3-b]pyridin-3-yl)-methyl]-6-methyl-pyridin-2-yl}-(4-trifluoromethyl-benzyl)-carbamic acid tert-butyl ester (37) and {5-[Methoxy-(1H-pyrrolo[2,3-b]pyridin-3-yl)-methyl]-6-methyl-pyridin-2-yl}-(4-trifluoromethyl-benzyl)-carbamic acid tert-butyl ester (38) (194 mg, 0.378 mmol) were dissolved in acetonitrile (3 mL) and triethylsilane (0.30 mL, 1.9 mmol) and trifluoroacetic acid (0.17 mL, 2.3 mmol) were added. After stirring at 25° C. for overnight, TLC analysis indicated that the reaction was about 50% complete. To the reaction mixture was added triethylsilane (0.30 mL, 1.9 mmol), and trifluoroacetic acid (0.17 mL, 2.3 mmol). The mixture was allowed to stir for another 48 hours at 25° C. and the solvent, excess triethylsilane and trifluoroacetic acid were removed by evaporation. Ethyl acetate was added and washed with saturated sodium bicarbonate. The organic layer was dried over magnesium sulfate, filtered and concentrated at reduced pressure to afford a brown oil. Purification of 80 mg of the crude material was carried out using preparatory chromatography (50% ethyl acetate in hexanes) to afford the compound as an off-white solid (P-0013, 10 mg, 0.025 mmol). MS (ESI) [M+H$^+$]$^+$=397.2.

(4-Chloro-benzyl)-[6-methyl-5-(1H-pyrrolo[2,3-b]pyridin-3-ylmethyl)-pyridin-2-yl]-amine P-0014

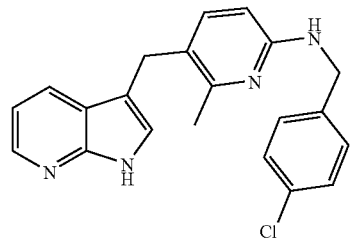

was prepared following the protocol of Scheme 18, substituting 4-trifluoromethyl benzaldehyde with 4-chlorobenzaldehyde (40) in Step 1. MS (ESI) [M+H$^+$]$^+$=363.1.

Example 17

Synthesis of [5-(5-Bromo-1H-pyrrolo[2,3-b]pyridin-3-ylmethyl)-pyridin-2-yl]-(4-chloro-benzyl)-amine (P-0038)

[5-(5-Bromo-1H-pyrrolo[2,3-b]pyridin-3-ylmethyl)-pyridin-2-yl]-(4-chloro-benzyl)-amine P-0038 was synthesized in 5 steps from commercially available 2-Amino-5-bromopyridine 15 as shown in Scheme 19.

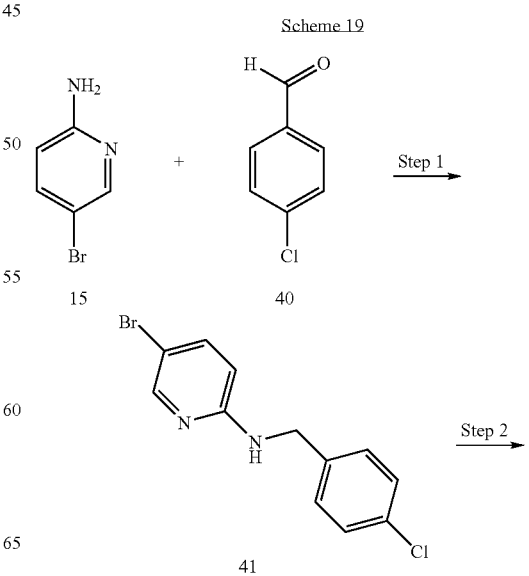

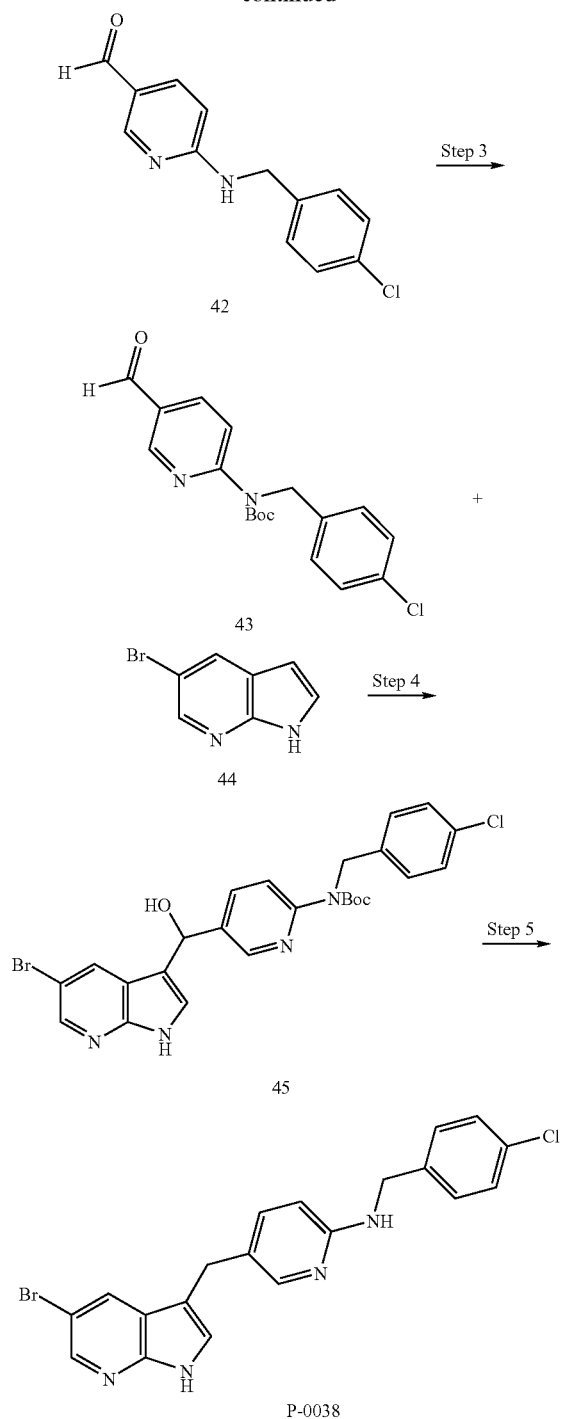

and triethylsilane (16.5 mL, 0.103 mol). The reaction was heated to reflux for 48 hours. The reaction was concentrated, poured into aqueous potassium carbonate and extracted with ethyl acetate. The organic layer was washed with brine, dried over sodium sulfate and concentrated. The crude residue was crystallized with ethyl acetate to give compound (41, 6.8 g, 65.4%).

Step 2

Synthesis of 6-(4-Chloro-benzylamino)-pyridine-3-carbaldehyde (42)

To (5-Bromo-pyridin-2-yl)-(4-chloro-benzyl)-amine (41, 10.00 g, 0.03360 mol) in tetrahydrofuran (400.0 mL) under an atmosphere of nitrogen at −78° C. was added n-butyllithium (17.5 mL, 2.00 M in cyclohexane). After 90 minutes, tert-butyllithium (42.00 mL, 1.70 M in hexane) was added to the reaction. After 80 minutes, N,N-dimethylformamide (6.9 mL, 0.089 mol) was added to the reaction. The reaction mixture was stirred at −78° C. for 2 hours, then allowed to warm to room temperature for 1 hour. The reaction mixture was poured into water and extracted with ethyl acetate. The organic layer was washed with brine, dried over sodium sulfate and concentrated to give the crude compound, which was crystallized from tert-butoxyl methyl ether to provide compound (42, 7.66 g, 92.2%).

Step 3

Synthesis of (4-Chloro-benzyl)-(5-formyl-pyridin-2-yl)-carbamic acid tert-butyl ester (43)

To 6-(4-Chloro-benzylamino)-pyridine-3-carbaldehyde (42, 2.00 g, 8.11 mmol) in dichloromethane (20.0 mL) were added triethylamine (1.70 mL, 12.2 mmol), di-tert-butyldicarbonate (2.00 g, 9.16 mmol) and 4-dimethylaminopyridine (52.3 mg, 0.43 mmol). The reaction was stirred at room temperature for 48 hours. The reaction was concentrated and purified by silica gel column chromatography eluting with 20% ethyl acetate in hexane to give compound (43, 2.50 g, 89.3%).

Step 4

Synthesis of {5-[(5-Bromo-1H-pyrrolo[2,3-b]pyridin-3-yl)-hydroxy-methyl]-pyridin-2-yl}-(4-chlorobenzyl)-carbamic acid tert-butyl ester (45)

To 5-bromo-7-azaindole (44, 198.0 mg, 1.01 mmol) in methanol (30.0 mL, 0.741 mol) were added (4-Chloro-benzyl)-(5-formyl-pyridin-2-yl)-carbamic acid tert-butyl ester (43, 355.0 mg, 1.02 mmol) and potassium hydroxide (80.0 mg, 1.42 mmol). The reaction was stirred at room temperature 48 hours. The reaction mixture was poured into water and extracted with ethyl acetate. The organic layer was washed with brine, dried over sodium sulfate, concentrated and purified by silica gel column chromatography eluting with 8% methanol in dichloromethane to give compound (45, 200.0 mg, 36.8%).

Step 1

Synthesis of (5-Bromo-pyridin-2-yl)-(4-chloro-benzyl)-amine (41)

To 2-Amino-5-bromopyridine (15, 6.10 g, 0.0352 mol) in toluene (90.0 mL) were added 4-chlorobenzaldehyde (40, 5.00 g, 0.0356 mol), trifluoroacetic acid (8.0 mL, 0.10 mol)

Step 5

Synthesis of [5-(5-Bromo-1H-pyrrolo[2,3-b]pyridin-3-ylmethyl)-pyridin-2-yl]-(4-chloro-benzyl)-amine (P-0038)

To {5-[(5-Bromo-1H-pyrrolo[2,3-b]pyridin-3-yl)-hydroxy-methyl]-pyridin-2-yl}-(4-chloro-benzyl)-carbamic acid tert-butyl ester (45, 180.0 mg, 0.33 mmol) in acetonitrile (30.0 mL) were added trifluoroacetic acid (2.0 mL, 0.026 mol) and triethylsilane (4.0 mL, 0.025 mol). The reaction was heated to reflux for 4 hours. The reaction mixture was poured into water and extracted with ethyl acetate. The organic layer was washed with brine, dried over sodium sulfate, concentrated and purified by silica gel column chromatography eluting with 10% methanol in dichloromethane to give compound (P-0038, 120 mg, 85.2%). MS (ESI)[M+H$^+$]$^+$=427.2, 429.2.

Example 18

Synthesis of 1-triisopropylsilanyl-1H-pyrrolo[2,3-b]pyridine-3-carbaldehyde 47

Compound 47 was synthesized in 2 steps from 7-azaindole 1 as described in Scheme 20.

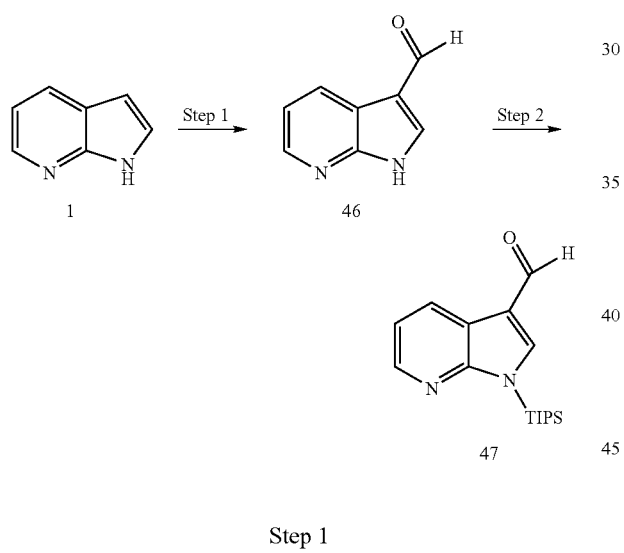

Scheme 20

Step 1

Preparation of 1H-pyrrolo[2,3-b]pyridine-3-carbaldehyde (46)

To 1H-Pyrrolo[2,3-b]pyridine (1, 16.0 g, 135 mmol) in water (110 mL), were added hexamethylenetetramine (26.0 g, 185 mmol), and acetic acid (55.0 mL, 967 mmol). The reaction was refluxed for 12 hours. Water (329 mL) was added and the reaction was cooled to room temperature. The reaction was filtrated and washed with water to give compound (46, 15.0 g, 76%). MS (ESI)[M+H$^+$]$^+$=147.

Step 2

Preparation of 1-triisopropylsilanyl-1H-pyrrolo[2,3-b]pyridine-3-carbaldehyde (47)

To 1H-Pyrrolo[2,3-b]pyridine-3-carbaldehyde (46, 4.05 g, 27.71 mmol) in tetrahydrofuran (30.0 mL) were added sodium hydride (60% in mineral oil, 1.5 g, 38 mmol) and triisopropylsilyl chloride (8.0 mL, 38 mmol) under an atmosphere of nitrogen. The reaction was stirred for 2 hours at room temperature. The reaction was poured into water and extracted with ethyl acetate. The organic layer was washed with brine, dried over anhydrous sodium sulfate and filtered. The filtrate was concentrated and purified by silica gel column chromatography eluting with 10% ethyl acetate in hexane to give compound (47, 3.0 g, 36%). MS (ESI) [M+H$^+$]$^+$=303.

1-(tert-Butyl-dimethyl-silanyl)-3-iodo-1H-pyrrolo[2,3-b]pyridine 66

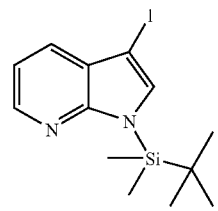

was prepared following the protocol of Scheme 20 Step 2, substituting 1H-Pyrrolo[2,3-b]pyridine-3-carbaldehyde 46 with 3-iodo-1H-pyrrolo[2,3-b]pyridine and triisopropylsilyl chloride with tert-Butyl-dimethyl-silyl chloride.

1-benzenesulfonyl-1H-pyrrolo[2,3-b]pyridine-3-carbaldehyde 55

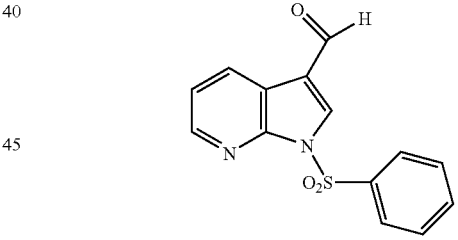

was prepared following the protocol of Scheme 20, substituting triisopropylsilyl chloride with benzenesulfonyl chloride in Step 2.

Example 19

Synthesis of N-[5-(1H-Pyrrolo[2,3-b]pyridin-3-ylmethyl)-pyridin-2-yl]-4-trifluoromethyl-benzenesulfonamide (P-0071)

N-[5-(1H-Pyrrolo[2,3-b]pyridin-3-ylmethyl)-pyridin-2-yl]-4-trifluoromethyl-benzenesulfonamide P-0071 was synthesized in 3 steps from 2-Amino-5-bromopyridine 15 as shown in Scheme 21.

Scheme 21

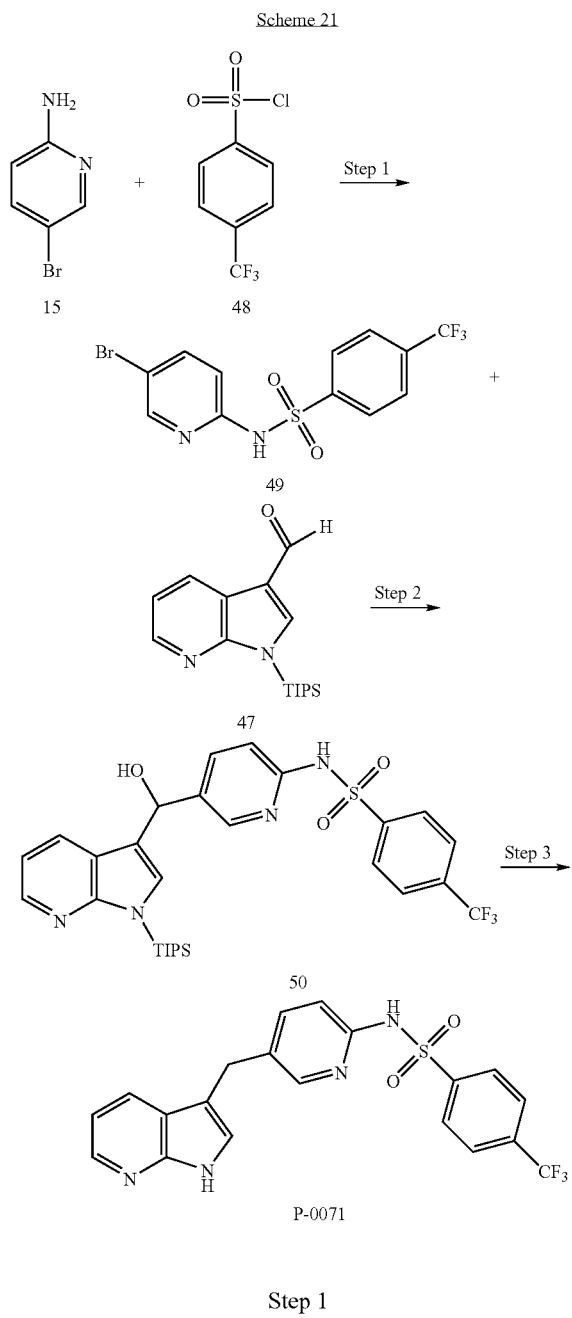

Step 1

Synthesis of N-(5-Bromo-pyridin-2-yl)-4-trifluoromethyl-benzenesulfonamide (49)

To 2-Amino-5-bromopyridine (15, 1.50 g, 8.67 mmol) in acetonitrile (20.0 mL) were added pyridine (6.0 mL, 0.074 mol), 4-dimethylaminopyridine (0.10 g, 0.82 mmol) and 4-trifluoromethyl-benzenesulfonyl chloride (48, 2.14 g, 8.75 mmol). The reaction mixture was stirred at room temperature overnight. The reaction was concentrated, poured into water, acidified with 1N HCl to pH=2, and extracted with ethyl acetate. The organic layer was washed with brine, dried over anhydrous sodium sulfate and concentrated. The residue was washed with ethyl acetate to give a white solid as desired compound (49, 2.80 g, 84.8%). MS (ESI) [M+H$^+$]$^+$=381.0, 383.0.

Step 2

Synthesis of N-5-[Hydroxy-(1-triisopropylsilanyl-1H-pyrrolo[2,3-b]pyridin-3-yl)-methyl]-pyridin-2-yl-4-trifluoromethyl-benzenesulfonamide (50)

To N-(5-Bromo-pyridin-2-yl)-4-trifluoromethyl-benzenesulfonamide (49, 0.96 g, 2.5 mmol) in tetrahydrofuran (50.0 mL) under an atmosphere of nitrogen at −78° C., tert-butyllithium (4.62 mL, 1.70 M in hexane) was added slowly. After 15 minutes, 1-triisopropylsilanyl-1H-pyrrolo[2,3-b]pyridine-3-carbaldehyde (47, 0.30 g, 0.99 mmol, prepared as described in Example 18) in tetrahydrofuran (15.0 mL) was added to the reaction. After 30 minutes, the reaction was allowed to come to room temperature for 10 minutes. The reaction was poured into water, acidified with 1N HCl to pH around 2, and extracted with ethyl acetate. The organic layer was dried over anhydrous sodium sulfate and filtered. The filtrate was concentrated and purified by silica gel column chromatography eluting with 20% ethyl acetate in hexane to give a white solid compound (50, 0.55 g, 90.1%). MS (ESI) [M+H$^+$]$^+$=605.3.

Step 3

Synthesis of N-[5-(1H-Pyrrolo[2,3-b]pyridin-3-ylmethyl)-pyridin-2-yl]-4-trifluoromethyl-benzenesulfonamide (P-0071)

To N-5-[Hydroxy-(1-triisopropylsilanyl-1H-pyrrolo[2,3-b]pyridin-3-yl)-methyl]-pyridin-2-yl-4-trifluoromethyl-benzenesulfonamide (50, 0.27 g, 0.45 mmol) in acetonitrile (15.0 mL) were added trifluoroacetic acid (1.0 mL, 0.013 mol) and triethylsilane (2.0 mL, 0.012 mol). The reaction was heated to 85° C. for 1 hour. The reaction was concentrated, poured into water and extracted with ethyl acetate. The organic layer was purified with silica gel column chromatography eluting with 50% ethyl acetate in hexane to give a white solid compound (P-0071, 28.5 mg, 14.7%). MS (ESI) [M+H$^+$]$^+$=433.2.

4-Chloro-N-[5-(1H-pyrrolo[2,3-b]pyridin-3-ylmethyl)-pyridin-2-yl]-benzamide P-0074

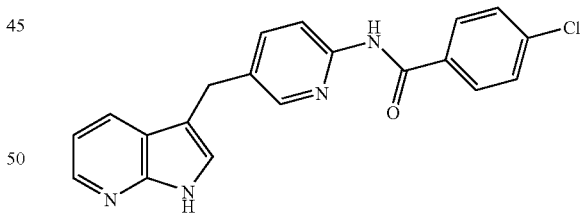

was prepared following the protocol of Scheme 21, substituting 4-trifluoromethyl-benzenesulfonyl chloride 48 with 4-chloro-benzoyl chloride in step 1. MS (ESI) [M+H$^+$]$^+$=363.2.

Example 20

Synthesis of N-[5-(1H-Pyrrolo[2,3-b]pyridin-3-ylmethyl)-pyridin-2-yl]-4-trifluoromethyl-benzamide (P-0072)

N-[5-(1H-Pyrrolo[2,3-b]pyridin-3-ylmethyl)-pyridin-2-yl]-4-trifluoromethyl-benzamide P-0072 was synthesized in one step from (3-(6-Bromo-pyridin-3-ylmethyl)-1-triisopropylsilanyl-1H-pyrrolo[2,3-b]pyridine 6a as shown in Scheme 22.

Scheme 22

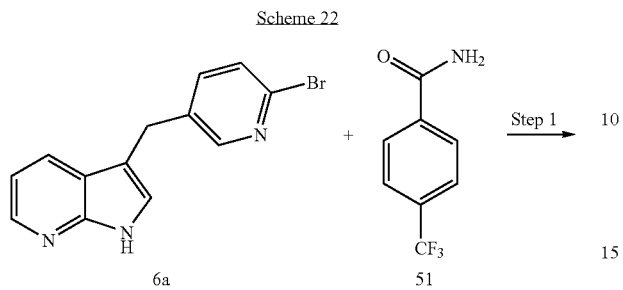

Step 1

Synthesis of N-[5-(1H-Pyrrolo[2,3-b]pyridin-3-ylmethyl)-pyridin-2-yl]-4-trifluoromethyl-benzamide (P-0072)

To 3-(6-Bromo-pyridin-3-ylmethyl)-1H-pyrrolo[2,3-b]pyridine (6a, 50.0 mg, 0.000174 mol, prepared as described in Example 2) in 1,4-dioxane (4.0 mL) were added 4-trifluoromethyl-benzamide (51, 70.0 mg, 0.37 mmol), Xanthphos (15.0 mg, 0.026 mmol), cesium carbonate (130.0 mg, 0.40 mmol) and Tris(dibenzylideneacetone)-dipalladium(0) (25.0 mg, 0.024 mmol) under an atmosphere of nitrogen. The reaction was heated to 120° C. for 10 minutes in a CEM Discover microwave instrument. The reaction was poured into water and extracted with ethyl acetate. The organic layer was dried over anhydrous sodium sulfate and filtered. The filtrate was concentrated and purified by silica gel column chromatography eluting with 50% ethyl acetate in hexane to give a white solid (P-0072, 4.7 mg, 6.8%). MS (ESI) [M+H$^+$]$^+$=397.2.

4-Fluoro-N-[5-(1H-pyrrolo[2,3-b]pyridin-3-ylmethyl)-pyridin-2-yl]-benzamide P-0073

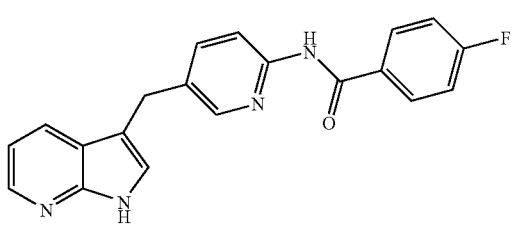

was prepared following the protocol of Scheme 22, substituting 4-trifluoromethyl-benzamide with 4-fluoromethyl-benzamide. MS (ESI) [M+H$^+$]$^+$=347.2.

Example 21

Synthesis of (4-Chloro-phenyl)-[5-(1H-pyrrolo[2,3-b]pyridin-3-ylmethyl)-pyridin-2-ylmethyl]-amine (P-0078)

(4-Chloro-phenyl)-[5-(1H-pyrrolo[2,3-b]pyridin-3-ylmethyl)-pyridin-2-ylmethyl]-amine P-0078 was synthesized in 3 steps from 5-Bromo-pyridine-2-carbaldehyde 52 as shown in Scheme 23.

Scheme 23

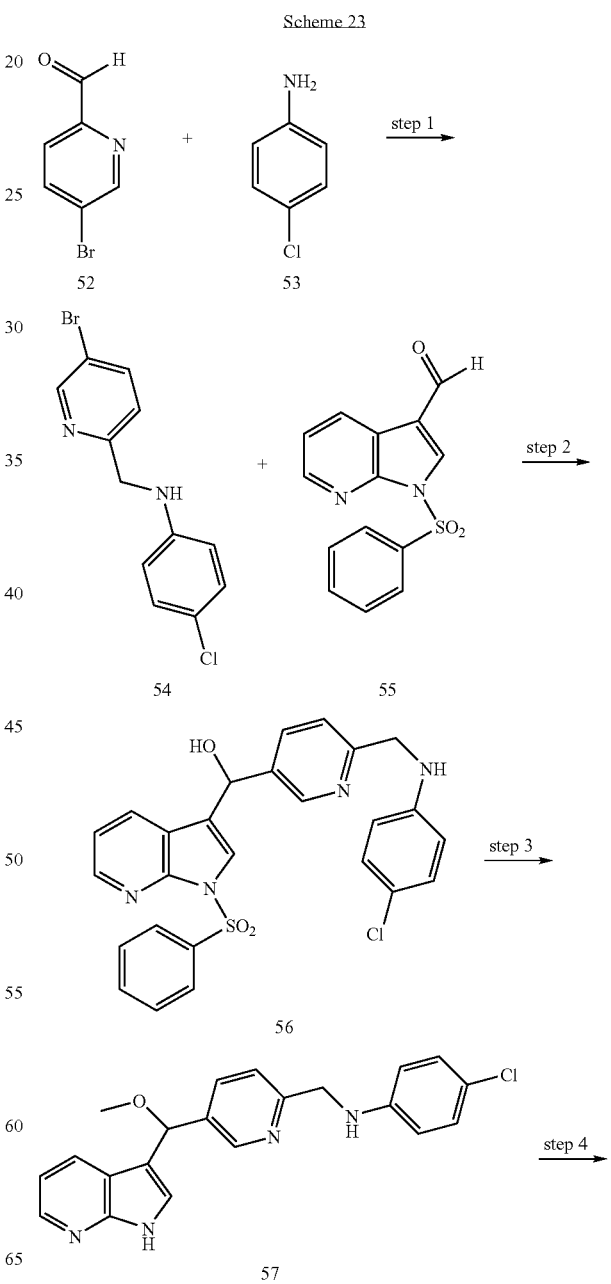

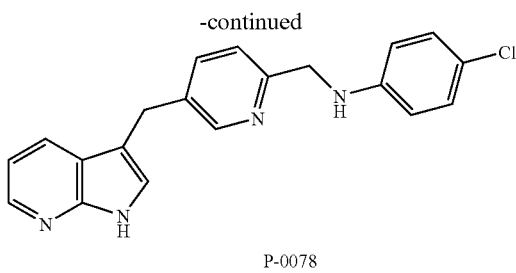

P-0078

Step 1

Synthesis of (5-Bromo-pyridin-2-ylmethyl)-(4-chloro-phenyl)-amine (54)

To 5-Bromo-pyridine-2-carbaldehyde (52, 1.00 g, 5.38 mmol) in acetonitrile (50.0 mL) were added p-chloroaniline (53, 0.686 g, 5.38 mmol), triethylsilane (6.00 mL, 0.0376 mol) and trifluoroacetic acid (3.00 mL, 0.0389 mol). The reaction was heated to reflux for 3 hours. The reaction was concentrated, poured into water and then extracted with ethyl acetate. The organic layer was dried over anhydrous sodium sulfate and filtered. The filtrate was concentrated and purified by silica gel column chromatography eluting with 20% ethyl acetate in hexane to give a white solid (54, 0.75 g, 47.0%).

Step 2

Synthesis of (1-Benzenesulfonyl-1H-pyrrolo[2,3-b]pyridin-3-yl)-6-[(4-chloro-phenylamino)-methyl]-pyridin-3-yl-methanol (56)

To (5-Bromo-pyridin-2-ylmethyl)-(4-chloro-phenyl)-amine (54, 0.380 g, 1.28 mmol) in tetrahydrofuran (15.0 mL) under an atmosphere of nitrogen at −78° C. was added n-butyllithium (0.850 mL, 1.60 M in hexane). After 10 minutes, 1,2-bis-(chloro-dimethyl-silanyl)-ethane (0.135 g, 0.627 mmol) in tetrahydrofuran (5.0 mL) was added to the reaction. The reaction was allowed to warm to room temperature for 40 minutes. The reaction was cooled to −78° C., followed by addition of 1.70 M tert-butyllithium in hexane (1.58 mL). After 30 minutes, 1-benzenesulfonyl-1H-pyrrolo[2,3-b]pyridine-3-carbaldehyde (55, 0.380 g, 1.33 mmol, prepared as described in Example 18) in tetrahydrofuran (10.0 mL) was added to the reaction. After 20 minutes, the reaction was allowed to warm to room temperature. The reaction was poured into water and extracted with ethyl acetate. The organic layer was dried over anhydrous sodium sulfate and filtered. The filtrate was concentrated and purified by silica gel column chromatography eluting with 50% ethyl acetate in hexane to give compound (56, 0.30 g, 46.0%). MS (ESI) $[M+H^+]^+=505.3$.

Step 3

(4-Chloro-phenyl)-5-[methoxy-(1H-pyrrolo[2,3-b]pyridin-3-yl)-methyl]-pyridin-2-ylmethyl-amine (57)

To (1-Benzenesulfonyl-1H-pyrrolo[2,3-b]pyridin-3-yl)-6-[(4-chloro-phenylamino)-methyl]-pyridin-3-yl-methanol (56, 120.0 mg, 0.24 mmol) in methanol (20.0 mL) were added potassium hydroxide (0.400 g, 7.13 mmol) and water (5.0 mL, 0.28 mol). The reaction was heated to 50° C. for 10 hours. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give compound (57, 30 mg, 33.0%). MS (ESI) $[M+H^+]^+=379.4$.

Step 4

Synthesis of (4-Chloro-phenyl)-[5-(1H-pyrrolo[2,3-b]pyridin-3-ylmethyl)-pyridin-2-ylmethyl]-amine (P-0078)

To (4-Chloro-phenyl)-5-[methoxy-(1H-pyrrolo[2,3-b]pyridin-3-yl)-methyl]-pyridin-2-ylmethyl-amine (57, 20.8 mg, 0.055 mmol) in acetonitrile (10.0 mL) were added trifluoroacetic acid (0.50 mL, 6.5 mmol) and triethylsilane (1.00 mL, 6.26 mmol). The reaction was heated to reflux for 3 hours, then poured into water and extracted with ethyl acetate. The organic layer was dried over anhydrous sodium sulfate and filtered. The filtrate was concentrated and purified by silica gel column chromatography eluting with 10% methanol in dichloromethane to give compound (P-0078, 6.1 mg, 32.0%). MS (ESI) $[M+H^+]^+=349.4$.

Example 22

Synthesis of (4-Chloro-benzyl)-[6-fluoro-5-(1H-pyrrolo[2,3-b]pyridin-3-ylmethyl)-pyridin-2-yl]-amine (P-0082)

(4-Chloro-benzyl)-[6-fluoro-5-(1H-pyrrolo[2,3-b]pyridin-3-ylmethyl)-pyridin-2-yl]-amine P-0082 was synthesized in 8 steps from 2,6-Difluoropyridine 58 as shown in Scheme 24.

Scheme 24

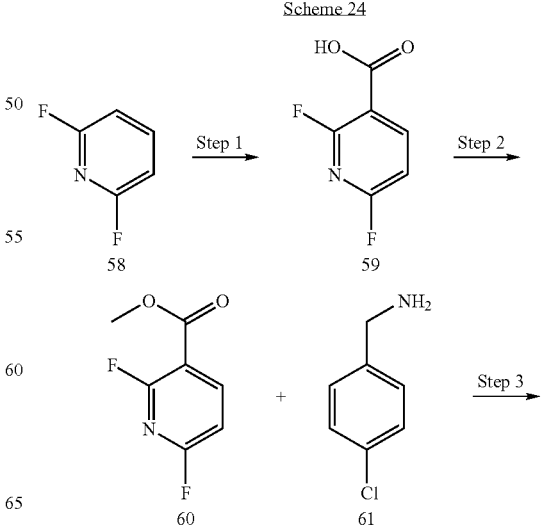

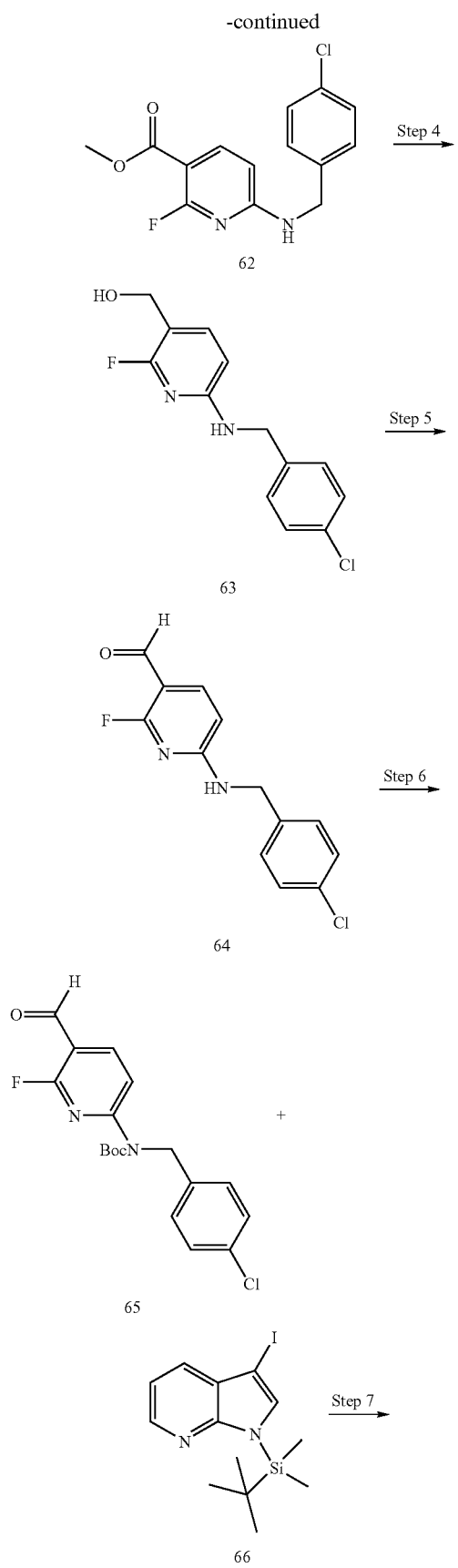

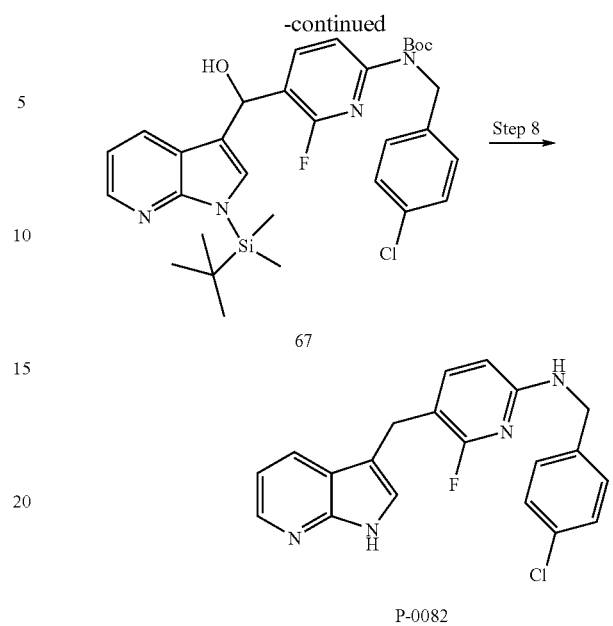

Step 1

Synthesis of 2,6-Difluoro-nicotinic acid (59)

To 2,6-difluoropyridine (58, 7.10 g, 0.0617 mol) in tetrahydrofuran (150.0 mL) under an atmosphere of nitrogen at −78° C., n-butyllithium (26.0 mL, 2.50 M in hexane) was added slowly. After 30 minutes, dry ice (3.0 g) was added to the reaction. After 1 hour, the reaction was allowed to warm to room temperature, then poured into water and extracted with ethyl acetate. The aqueous layer was acidified with 1 N HCl to pH=4-5 and extracted with ethyl acetate. The organic layer was dried over anyhydrous sodium sulfate, filtered and concentrated to give the crude compound as a light yellow solid (59, 5.6 g, 57.0%).

Step 2

Synthesis of 2,6-Difluoro-nicotinic acid methyl ester (60)

To 2,6-difluoro-nicotinic acid (59, 5.60 g, 0.0352 mol) in methanol (60.0 mL) was added concentrated sulfuric acid (1.0 mL, 0.019 mol). The reaction was heated to reflux overnight, then poured into water, basified with 1M potassium carbonate to pH around 9, and extracted with ethyl acetate. The organic layer was dried over anhydrous sodium sulfate and concentrated to give a yellow oil (60, 3.5 g, 57.0%).

Step 3

Synthesis of 6-(4-Chloro-benzylamino)-2-fluoro-nicotinic acid methyl ester (62)

To 2,6-difluoro-nicotinic acid methyl ester (60, 2.00 g, 0.0116 mol) in N,N-dimethylformamide (20.0 mL), under an atmosphere of nitrogen at −40° C., was added p-chlorobenzylamine (61, 2.60 mL, 0.0214 mol). The reaction was stirred at −40° C. to −20° C. for 2 hours, then poured into water and extracted with ethyl acetate. The organic layer was dried over anhydrous sodium sulfate and filtered. The filtrate was concentrated and purified by silica gel column chromatography eluting with 25% ethyl acetate in hexane to give compound (62, 2.0 g, 58.7%).

Step 4

Synthesis of [6-(4-Chloro-benzylamino)-2-fluoro-pyridin-3-yl]-methanol (63)

To 6-(4-Chloro-benzylamino)-2-fluoro-nicotinic acid methyl ester (62, 2.00 g, 6.79 mmol) in tetrahydrofuran (100.0 mL) was added lithium tetrahydroaluminate (13.6 mL, 1.00 M in Tetrahydrofuran) under an atmosphere of nitrogen. The reaction was stirred at room temperature overnight. To the reaction was added an excessive amount of $NaSO_4.10H_2O$, and then stirred for 1 hour. Filtration, concentration and purification with silica gel column chromatography eluting with 30% ethyl acetate in hexane provided compound 63 (1.0 g, 55.0%).

Step 5

Synthesis of 6-(4-Chloro-benzylamino)-2-fluoro-pyridine-3-carbaldehyde (64)

To [6-(4-Chloro-benzylamino)-2-fluoro-pyridin-3-yl]-methanol (63, 1.0 g, 3.7 mmol) in tetrahydrofuran (50.0 mL) was added Dess-Martin periodinane (1.75 g, 4.12 mmol). The reaction was stirred at room temperature for 10 minutes, then poured into water and extracted with ethyl acetate. The organic layer was dried over anhydrous sodium sulfate and filtered. The filtrate was concentrated and purified by silica gel column chromatography eluting with 20% ethyl acetate in hexane to give a white solid (64, 0.67 g, 68.0%).

Step 6

Synthesis of (4-Chloro-benzyl)-(6-fluoro-5-formyl-pyridin-2-yl)-carbamic acid tert-butyl ester (65)

To 6-(4-Chloro-benzylamino)-2-fluoro-pyridine-3-carbaldehyde (64, 670.0 mg, 2.53 mmol) in dichloromethane (16.2 mL) were added di-tert-butyldicarbonate (1.23 g, 5.65 mmol) and 4-dimethylaminopyridine (16.2 mg, 0.133 mmol). The reaction was stirred at room temperature overnight. The reaction was concentrated and purified by silica gel column chromatography eluting with 30% ethyl acetate in hexane to give a white solid (65, 0.63 g, 68.0%).

Step 7

Synthesis of (5-[1-(tert-Butyl-dimethyl-silanyl)-1H-pyrrolo[2,3-b]pyridin-3-yl]-hydroxy-methyl-6-fluoro-pyridin-2-yl)-(4-chloro-benzyl)-carbamic acid tert-butyl ester (67)

To 1-(tert-butyl-dimethyl-silanyl)-3-iodo-1H-pyrrolo[2,3-b]pyridine (66, 0.53 g, 0.0015 mol) and tetrahydrofuran (15.0 mL), under an atmosphere of nitrogen at −20° C., was added isopropylmagnesium chloride (0.78 mL, 2.0 M in tetrahydrofuran). The reaction was allowed to warm to 0° C. (around 80 minutes), then cooled to −20° C., followed by addition of (4-Chloro-benzyl)-(6-fluoro-5-formyl-pyridin-2-yl)-carbamic acid tert-butyl ester (65, 0.200 g, 0.55 mmol) in tetrahydrofuran (6.0 mL). The reaction was allowed to warm to room temperature in 1 hour, then poured into water and extracted with ethyl acetate. The organic layer was dried over anhydrous sodium sulfate, and filtered. The filtrate was concentrated and purified by silica gel column chromatography eluting with 20% ethyl acetate in hexane to give a yellow solid (67, 0.20 g, 61.1%). MS (ESI) $[M+H^+]^+$=597.4.

Step 8

Synthesis of (4-Chloro-benzyl)-[6-fluoro-5-(1H-pyrrolo[2,3-b]pyridin-3-ylmethyl)-pyridin-2-yl]-amine (P-0082)

To (5-[1-(tert-Butyl-dimethyl-silanyl)-1H-pyrrolo[2,3-b]pyridin-3-yl]-hydroxy-methyl-6-fluoro-pyridin-2-yl)-(4-chloro-benzyl)-carbamic acid tert-butyl ester (67, 0.10 g, 0.17 mmol) in acetonitrile (10.0 mL) were added triethylsilane (1.00 mL, 6.26 mmol) and trifluoroacetic acid (0.50 mL, 6.5 mmol). The reaction was heated to reflux for 2 hours, then poured into aqueous potassium carbonate, and extracted with ethyl acetate. The organic layer was dried over anhydrous sodium sulfate, and filtered. The filtrate was concentrated and purified by silica gel column chromatography eluting with 30% ethyl acetate in hexane to give a white solid (P-0082, 43.2 mg, 70.0%).

MS (ESI) $[M+H^+]^+$=367.4.

Example 23

Synthesis of (4-Chloro-benzyl)-[6-methoxy-5-(1H-pyrrolo[2,3-b]pyridin-3-ylmethyl)-pyridin-2-yl]-amine (P-0081)

(4-Chloro-benzyl)-[6-methoxy-5-(1H-pyrrolo[2,3-b]pyridin-3-ylmethyl)-pyridin-2-yl]-amine P-0081 was synthesized in 2 steps from (4-Chloro-benzyl)-(6-fluoro-5-formyl-pyridin-2-yl)-carbamic acid tert-butyl ester 65 as shown in Scheme 25.

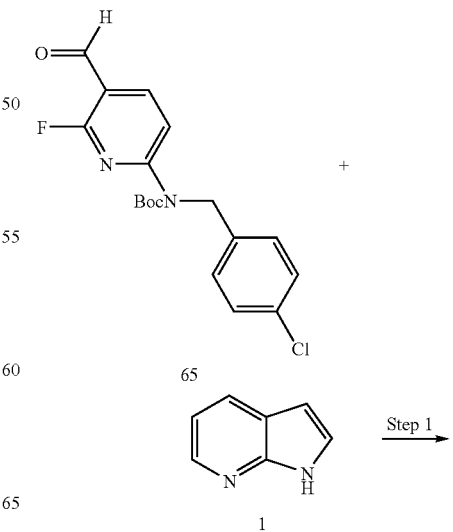

Scheme 25

-continued

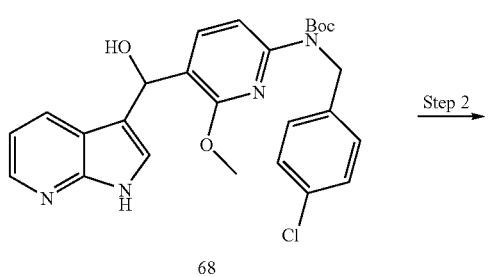

68

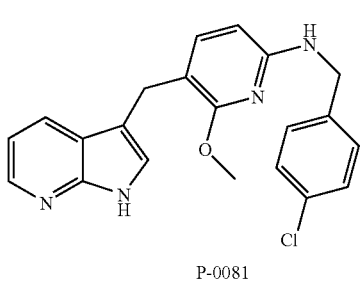

P-0081

Step 1

Synthesis of (4-Chloro-benzyl)-5-[hydroxy-(1H-pyrrolo[2,3-b]pyridin-3-yl)-methyl]-6-methoxy-pyridin-2-yl-carbamic acid tert-butyl ester (68)

To 1H-Pyrrolo[2,3-b]pyridine (1, 90.0 mg, 0.76 mmol) in methanol (30.0 mL) were added (4-chloro-benzyl)-(6-fluoro-5-formyl-pyridin-2-yl)-carbamic acid tert-butyl ester (65, 300.0 mg, 0.82 mmol) and potassium hydroxide (720.0 mg, 12.83 mmol) under an atmosphere of nitrogen. The reaction was stirred at room temperature for 2 hours, then poured into water and extracted with ethyl acetate. The organic layer was dried over anhydrous sodium sulfate and filtered. The filtrate was concentrated and purified by silica gel column chromatography eluting with 20% ethyl acetate in hexane to give the compound (68, 60 mg, 15.9%). MS (ESI) [M+H$^+$]$^+$=495.3.

Step 2

Synthesis of (4-Chloro-benzyl)-[6-methoxy-5-(1H-pyrrolo[2,3-b]pyridin-3-ylmethyl)-pyridin-2-yl]-amine (P-0081)

To (4-Chloro-benzyl)-5-[hydroxy-(1H-pyrrolo[2,3-b]pyridin-3-yl)-methyl]-6-methoxy-pyridin-2-yl-carbamic acid tert-butyl ester (68, 40.0 mg, 0.081 mmol) in acetonitrile (10.0 mL) were added trifluoroacetic acid (0.30 mL, 0.0039 mol) and triethylsilane (0.60 mL, 0.0038 mol). The reaction was heated to reflux for 3 hours. The reaction was concentrated to remove the solvents, then purified with silica gel column chromatography eluting with 40% ethyl acetate in hexane to give compound (P-0081, 10 mg, 32.7%). MS (ESI) [M+H$^+$]$^+$=379.4.

Example 24

Synthesis of 5-(1H-Pyrrolo[2,3-b]pyridin-3-ylmethyl)-pyridine-2-carboxylic acid (4-chloro-phenyl)-amide (P-0076)

5-(1H-Pyrrolo[2,3-b]pyridin-3-ylmethyl)-pyridine-2-carboxylic acid (4-chloro-phenyl)-amide P-0076 was synthesized in 3 Steps from 5-Bromo-pyridine-2-carbonyl chloride 69 as shown in Scheme 26.

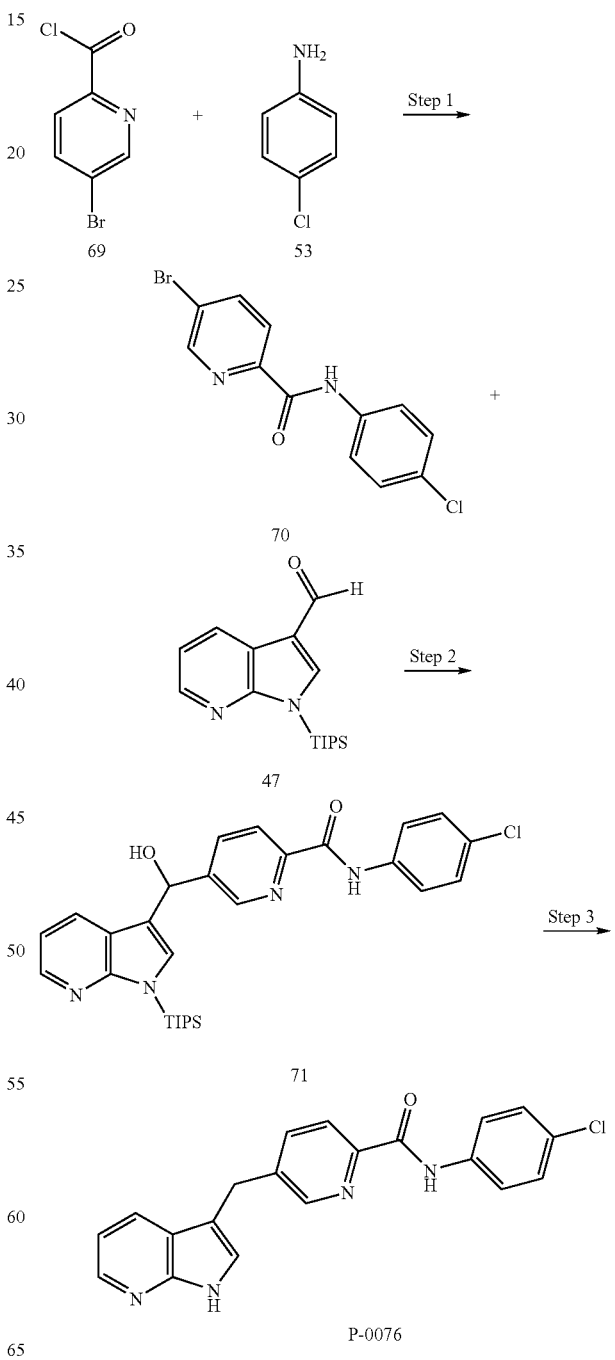

Step 1

Synthesis of 5-Bromo-pyridine-2-carboxylic acid (4-chloro-phenyl)-amide (70)

To 5-Bromo-pyridine-2-carbonyl chloride (69, 0.76 g, 3.4 mmol) in acetonitrile (29.0 mL) were added p-chloroaniline (53, 0.702 g, 5.50 mmol), 4-dimethylamino-pyridine (0.12 g, 0.96 mmol) and pyridine (2.9 mL, 0.036 mol). The reaction was stirred at 68° C. overnight, then poured into water, acidified with 1 N HCl to pH around 1 and extracted with ethyl acetate. The organic layer was dried over anhydrous sodium sulfate and filtered. The filtrate was concentrated and purified by silica gel column chromatography eluting with dichloromethane to give a white solid (70, 0.75 g, 70.0%).

Step 2

Synthesis of 5-[Hydroxy-(1-triisopropylsilanyl-1H-pyrrolo[2,3-b]pyridin-3-yl)-methyl]-pyridine-2-carboxylic acid (4-chloro-phenyl)-amide (71)

To 5-Bromo-pyridine-2-carboxylic acid (4-chloro-phenyl)-amide (70, 0.50 g, 1.60 mmol) in tetrahydrofuran (20.0 mL), under an atmosphere of nitrogen at −78° C., tert-butyllithium (3.02 mL, 1.70 M in Hexane) was added. After 20 minutes, 1-triisopropylsilanyl-1H-pyrrolo[2,3-b]pyridine-3-carbaldehyde (47, 0.39 g, 1.3 mmol, prepared as described in Example 18) in tetrahydrofuran (10.0 mL) was added to the reaction. The reaction was stirred at −78° C. for 1 hour, then allowed to warm to room temperature for 10 minutes. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give the compound as colorless oil (71, 100 mg, 14%). MS (ESI) [M+H$^+$]$^+$=535.3.

Step 3

Synthesis of 5-(1H-Pyrrolo[2,3-b]pyridin-3-ylmethyl)-pyridine-2-carboxylic acid (4-chloro-phenyl)-amide (P-0076)

To 5-[Hydroxy-(1-triisopropylsilanyl-1H-pyrrolo[2,3-b]pyridin-3-yl)-methyl]-pyridine-2-carboxylic acid (4-chloro-phenyl)-amide (71, 100.0 mg, 0.19 mmol) in acetonitrile (10.0 mL) were added trifluoroacetic acid (0.20 mL, 2.6 mmol) and triethylsilane (0.40 mL, 2.5 mmol). The reaction was stirred at 80° C. for 2 hours. The reaction was concentrated and purified by silica gel column chromatography eluting with 20% ethyl acetate in hexane to give a yellow solid compound (P-0076, 5.5 mg, 8.1%). MS (ESI) [M−H$^+$]$^-$=361.1.

Example 25

Synthesis of [6-(3-Hydroxy-phenylamino)-pyridin-3-yl]-(1H-pyrrolo[2,3-b]pyridin-3-yl)-methanone (P-0027)

[6-(3-Hydroxy-phenylamino)-pyridin-3-yl]-(1H-pyrrolo[2,3-b]pyridin-3-yl)-methanone P-0027 was synthesized in 1 Step from [6-(3-Benzyloxy-phenylamino)-pyridin-3-yl]-(1H-pyrrolo[2,3-b]pyridin-3-yl)-methanone P-0026 as shown in Scheme 27.

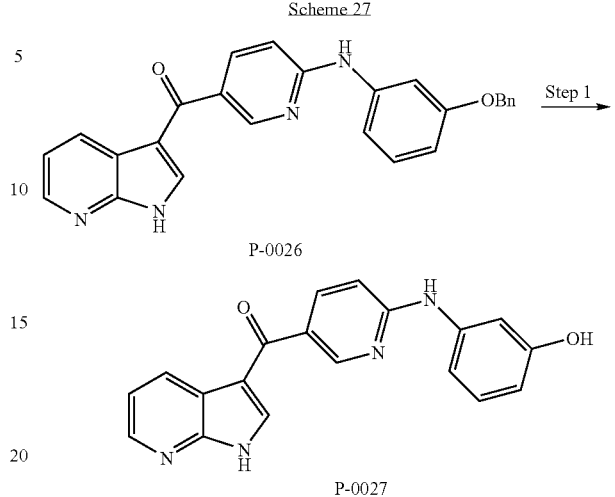

Scheme 27

To [6-(3-Benzyloxy-phenylamino)-pyridin-3-yl]-(1H-pyrrolo[2,3-b]pyridin-3-yl)-methanone (P-0026, 12.0 mg, 0.0285 mmol) in methanol (5.0 mL) was added 20% palladium hydroxide on carbon (10.0 mg) under an atmosphere of hydrogen. The reaction was stirred at room temperature for 5 hours. Filtration and concentration gave compound (P-0027, 3.5 mg, 37%). MS (ESI) [M+H$^+$]$^+$=331.

Example 26

Synthesis of 3-[6-(3-Trifluoromethyl-benzyloxy)-pyridin-3-ylmethyl]-1H-pyrrolo[2,3-b]pyridine P-0057

3-[6-(3-Trifluoromethyl-benzyloxy)-pyridin-3-ylmethyl]-1H-pyrrolo[2,3-b]pyridine P-0057 was synthesized in 4 steps from commercially available 7-azaindole as shown in Scheme 28.

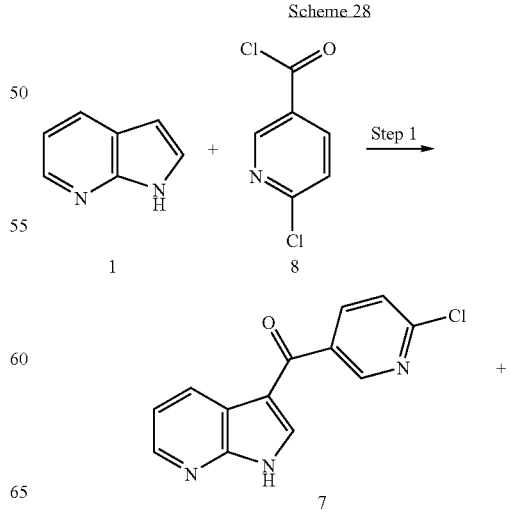

Scheme 28

-continued

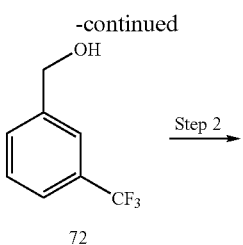
72

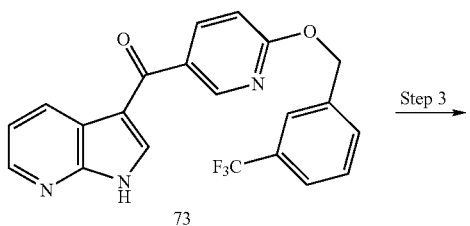
73

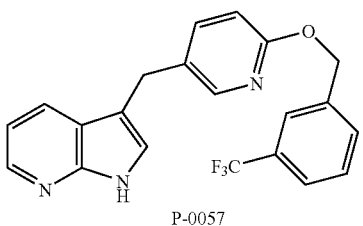
74

[structure]
P-0057

Step 1

Preparation of (6-Chloro-pyridin-3-yl)-(1H-pyrrolo[2,3-b]pyridin-3-yl)-methanone (7)

To 7-azaindole 1 in dichloromethane was added 6-chloronicotinoyl chloride 8, followed by aluminum chloride, under an atmosphere of nitrogen at −10° C. The reaction was stirred and allowed to warm to room temperature overnight. The reaction was quenched with 3 N hydrochloric acid and concentrated hydrochloric acid was added until all solids dissolved. The mixture was extracted with dichloromethane and the combined organic portions were dried with magnesium sulfate, filtered, and the filtrate was concentrated. The resulting solid material was recrystallized from chloroform/hexane to provide (6-Chloro-pyridin-3-yl)-(1H-pyrrolo[2,3-b]pyridin-3-yl)-methanone 7 and used in the next step without further purification.

Step 2

Preparation of (1H-pyrrolo[2,3-b]pyridin-3-yl)-[6-(3-trifluoromethyl-benzyloxy)-pyridin-3-yl]-methanone (73)

To (6-Chloro-pyridin-3-yl)-(1H-pyrrolo[2,3-b]pyridin-3-yl)-methanone 7 in DMSO was added (3-trifluoromethyl-phenyl)-methanol 72. Sodium hydride was added and the reaction was heated to 60° C. for two hours. The reaction was quenched with water and extracted with ethyl acetate. The organic portion was dried with magnesium sulfate and concentrated to provide (1H-pyrrolo[2,3-b]pyridin-3-yl)-[6-(3-trifluoromethyl-benzyloxy)-pyridin-3-yl]-methanone 73, which was used in the next step without additional purification.

Step 3

Preparation (1H-Pyrrolo[2,3-b]pyridin-3-yl)-[6-(3-trifluoromethyl-benzyloxy)-pyridin-3-yl]-methanol (74)

To (1H-pyrrolo[2,3-b]pyridin-3-yl)-[6-(3-trifluoromethyl-benzyloxy)-pyridin-3-yl]-methanone 73 in ethanol was added sodium borohydride. After one hour, the reaction was quenched with water and extracted with ethyl acetate. The organic portion was dried with magnesium sulfate and concentrated to provide (1H-Pyrrolo[2,3-b]pyridin-3-yl)-[6-(3-trifluoromethyl-benzyloxy)-pyridin-3-yl]-methanol 74, which was used in the next step without additional purification.

Step 4

Preparation of 3-[6-(3-Trifluoromethyl-benzyloxy)-pyridin-3-ylmethyl]-1H-pyrrolo[2,3-b]pyridine, P-0057

(1H-Pyrrolo[2,3-b]pyridin-3-yl)-[6-(3-trifluoromethyl-benzyloxy)-pyridin-3-yl]-methanol 74 was dissolved in 9:1 trifluoroacetic acid: triethylsilane. The reaction was stirred at room temperature for 15 hours. The reaction was diluted with water and extracted with ethyl acetate and concentrated. The crude material was purified by reverse phase HPLC to provide 3-[6-(3-Trifluoromethyl-benzyloxy)-pyridin-3-ylmethyl]-1H-pyrrolo[2,3-b]pyridine P-0057. MS (ESI) [M+H$^+$]$^+$=384.3.

Additional compounds may be prepared using steps 2-4 of Scheme 28, replacing (3-trifluoromethyl-phenyl)-methanol with an appropriate benzyl alcohol. The following compounds were made following this procedure:

3-[6-(4-Chloro-benzyloxy)-pyridin-3-ylmethyl]-1H-pyrrolo[2,3-b]pyridine (P-0056)

3-[6-(3-Chloro-benzyloxy)-pyridin-3-ylmethyl]-1H-pyrrolo[2,3-b]pyridine (P-0055)

The benzyl alcohols used in step 2 of this procedure are indicated in column 2 of the following table, with the compound structure indicated in column 3. Column 1 provides the compound number and Column for the measured mass spectrometry result.

| Benzyl alcohol | Compound | MS (ESI) [M + H⁺]⁺ observed |
|---|---|---|
| P-0056 | | 350.3 |
| P-0055 | | 350.3 |

Example 27

Synthesis of [2-Chloro-6-(4-chloro-benzylamino)-pyridin-3-yl]-(1H-pyrrolo[2,3-b]pyridin-3-yl)-methanone P-0048

[2-Chloro-6-(4-chloro-benzylamino)-pyridin-3-yl]-(1H-pyrrolo[2,3-b]pyridin-3-yl)-methanone P-0048 was synthesized in 3 steps from commercially available 2,6-dichloropyridine-3-carboxylic acid 75 as shown in Scheme 29.

Scheme 29

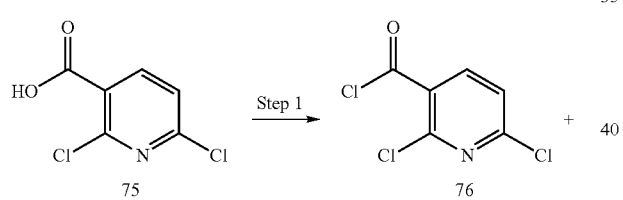

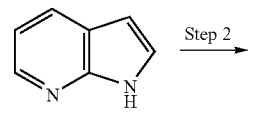

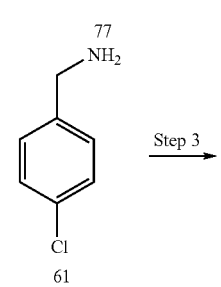

-continued

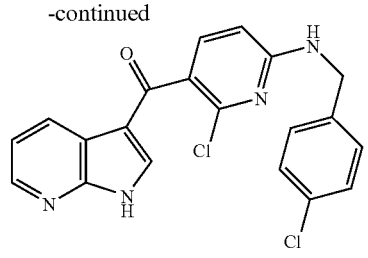

P-0048

Step 1

Preparation of 2,6-dichloropyridine-3-carbonyl chloride (76)

To 2,6-dichloropyridine-3-carboxylic acid (75, 1.00 g, 0.00521 mol) in dichloromethane (75 mL) was added 2 M Oxalyl chloride (2.61 mL, 0.727 g, 0.00573 mol). The solution began to show vigorous gas evolution, which slowed but continued for about 2 hours. The reaction was allowed to continue at room temperature for an additional 3 hours. The reaction was concentrated to give the compound as a brown oil that crystallized on standing (76, 1.09 g, 99%).

Step 2

Preparation of (2,6-dichloropyridin-3-yl)(1H-pyrrolo[2,3-b]pyridin-3-yl)methanone (77)

To Aluminum trichloride (4.18 g, 0.0314 mol) and dichloromethane (97.5 mL, 1.52 mol) under an atmosphere of nitrogen was added 1H-Pyrrolo[2,3-b]pyridine (1, 828.5 mg, 0.0070 mol) in dichloromethane (5.0 mL). The reaction was stirred at room temperature for 60 minutes, then added 2,6-dichloropyridine-3-carbonyl chloride (76, 1.09 g, 0.00523 mol) in dichloromethane (6.0 mL). The reaction was stirred at room temperature for 2 hours. A precipitate formed, and nitromethane was added in ~1 mL portions until almost all solid dissolved (8 mL). After an additional 60 minutes at room temperature, the reaction was slowly poured into water and extracted with ethyl acetate. The organic layer was dried over anhydrous magnesium sulfate and filtered. The filtrate was concentrated to give 1.54 g of solid, which turned dark purple on sitting overnight. The solid was treated with dichloromethane, and the insoluble material was collected by vacuum filtration to give compound (77, 863 mg, 57%). MS (ESI) [M+H⁺]⁺=292.2.

Step 3

Preparation of [2-Chloro-6-(4-chloro-benzylamino)-pyridin-3-yl]-(1H-pyrrolo[2,3-b]pyridin-3-yl)-methanone (P-0048)

To (2,6-dichloropyridin-3-yl)(1H-pyrrolo[2,3-b]pyridin-3-yl)methanone (77, 0.0570 g, 0.195 mmol) was added 2-propanol (1.5 mL) followed by p-chlorobenzylamine (61, 49.8 μL, 0.410 mmol). The reaction was microwaved at 300 watts, 100° C. for 10 minutes, at 120° C. for 10 minutes, and finally at 150° C. for 10 minutes. Additional p-chlorobenzylamine (50 μL, 0.410 mmol) was added and the reaction continued at 150° C. for 20 minutes. The reaction was extracted with ethyl acetate and 1 M sodium bicarbonate. The organic layer was dried over anhydrous magnesium sulfate and filtered. The filtrate was concentrated and purified by silica gel column chromatography eluting with dichloromethane followed by 1% methanol to give compound (P-0048, 47 mg, 61%). MS (ESI) [M+H⁺]⁺=397.3.

Additional compounds may be prepared according to Scheme 29, replacing 2,6-dichloropyridine-3-carboxylic acid with an appropriate carboxylic acid. (6-(4-chlorobenzylamino)-2-(trifluoromethyl)pyridin-3-yl)(1H-pyrrolo[2,3-b]pyridin-3-yl)methanone P-0070

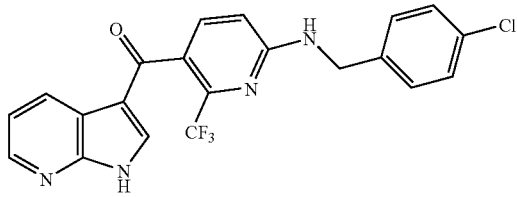

was made following this protocol, using 6-Chloro-2-trifluoromethyl-nicotinic acid as the carboxylic acid (prepared in two steps from commercially available 2-chloro-6-(trifluoromethyl)pyridine according to Cottet, F. and Schlosser, M. Eur. J. Org. Chem. 2004, 3793-3798). MS (ESI) [M+H⁺]⁺=431.2.

Example 28

Synthesis of 3-((1H-pyrrolo[2,3-b]pyridin-3-yl)methyl)-6-(4-chlorobenzylamino)pyridin-2-ol P-0051

3-((1H-pyrrolo[2,3-b]pyridin-3-yl)methyl)-6-(4-chlorobenzylamino)pyridin-2-ol P-0051 was synthesized in 2 steps from [2-Chloro-6-(4-chloro-benzylamino)-pyridin-3-yl]-(1H-pyrrolo[2,3-b]pyridin-3-yl)-methanone P-0048 as shown in Scheme 30.

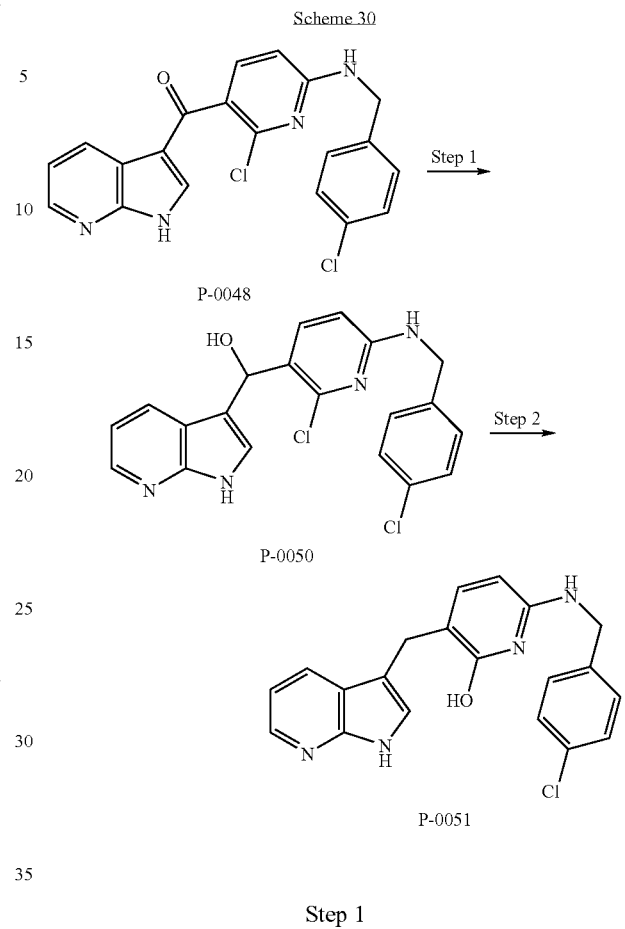

Step 1

Preparation of (6-(4-chlorobenzylamino)-2-chloropyridin-3-yl)(1H-pyrrolo[2,3-b]pyridin-3-yl)methanol (P-0050)

To [2-Chloro-6-(4-chloro-benzylamino)-pyridin-3-yl]-(1H-pyrrolo[2,3-b]pyridin-3-yl)-methanone (P-0048, 0.045 g, 0.00011 mol, prepared as described in Example 27) was added methanol (10 mL) and sodium borohydride (0.00428 g, 0.000113 mol). The reaction was allowed to stir at 50° C. overnight. The volatiles were removed from the reaction, and the resulting material was extracted with ethyl acetate and 1 M aqueous sodium bicarbonate. The organic layer was dried over magnesium sulfate and filtered. The filtrate was concentrated and purified by silica gel column chromatography eluting with dichloromethane followed by 1% methanol in dichloromethane to give the compound (P-0050, 31 mg, 68%). MS (ESI) [M+H⁺]⁺=399.2.

Step 2

Preparation of 3-((1H-pyrrolo[2,3-b]pyridin-3-yl)methyl)-6-(4-chlorobenzylamino)pyridin-2-ol (P-0051)

To (6-(4-chlorobenzylamino)-2-chloropyridin-3-yl)(1H-pyrrolo[2,3-b]pyridin-3-yl)methanol (P-0050, 0.028 g, 0.000070 mol) dissolved in acetonitrile (1 mL) was added triethylsilane (42.6 uL, 0.000266 mol) and trifluoroacetic acid (28.4 uL, 0.000368 mol). The reaction was heated at 85°

C. overnight. The reaction was extracted with ethyl acetate and saturated sodium bicarbonate. The organic layer was separated, dried over magnesium sulfate and filtered. The filtrate was concentrated and purified by silica gel column chromatography eluting with dichloromethane, 3%, 5% and finally 10% methanol in dichloromethane to give the compound as a white solid (P-0051, 20 mg, 78%). MS (ESI) [M+H$^+$]$^+$=365.3.

Example 29

Synthesis of 5 substituted 7-azaindole Intermediates 5-(2-Morpholin-4-yl-ethoxy)-1H-pyrrolo[2,3-b]pyridine 79 was synthesized in 1 Step from commercially available 5-bromo-azaindole as shown in Scheme 31.

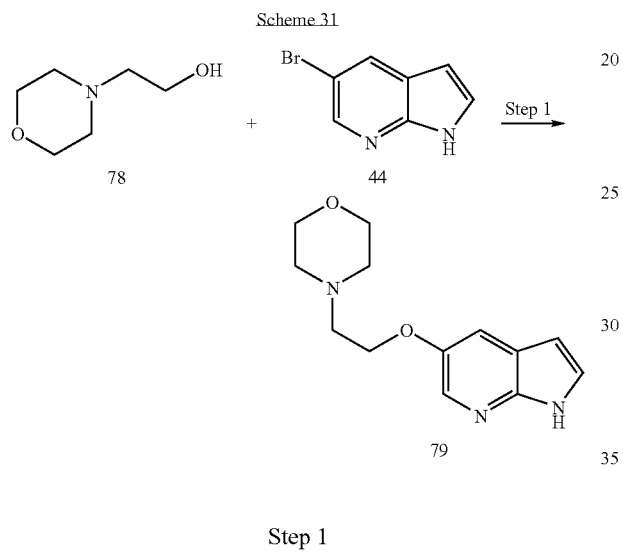

Step 1

5-(2-Morpholin-4-yl-ethoxy)-1H-pyrrolo[2,3-b]pyridine (79)

To 4-morpholineethanol (30 mL, 0.2 mol) in N,N-dimethylformamide (30 mL) was slowly added sodium hydride (7 g, 60% dispersion in mineral oil, 0.2 mol). After the solution turned clear, a solution of 5-bromo-7-azaindole (44, 1.0 g, 0.0051 mol) in N,N-dimethylformamide (5 mL) and copper (I) bromide (1.4 g, 0.0098 mol) were added. The reaction mixture was stirred at 120° C. under nitrogen for 2 hours. The reaction mixture was concentrated and the residue was dissolved in ethyl acetate and water. The organic layer was collected, washed with a solution of ammonium chloride and ammonium hydroxide (4:1), brine, and dried over magnesium sulfate. After removal of solvent, the residue was purified by silica gel column chromatography eluting with ethyl acetate in hexane to provide the compound as an off-white solid (79, 0.62 g, 50%). MS (ESI) [M+H$^+$]$^+$=248.25.

Additional 5-substituted 7-azaindoles were prepared following the protocol of Scheme 31, replacing 4-morpholineethanol with either 2-diethylamino-ethanol, 3-diethylamino-propan-1-ol, 2-piperidin-1-yl-ethanol, or 2-pyrrolidin-1-yl-ethanol to provide diethyl-[2-(1H-pyrrolo[2,3-b]pyridin-5-yloxy)-ethyl]-amine, Diethyl-[3-(1H-pyrrolo[2,3-b]pyridin-5-yloxy)-propyl]-amine, 5-(2-piperidin-1-yl-ethoxy)-1H-pyrrolo[2,3-b]pyridine, and 5-(2-pyrrolidin-1-yl-ethoxy)-1H-pyrrolo[2,3-b]pyridine, respectively.

Example 30

Synthesis of {5-[5-(2-Morpholin-4-yl-ethoxy)-1H-pyrrolo[2,3-b]pyridin-3-ylmethyl]-pyridin-2-yl}-(4-trifluoromethyl-benzyl)-amine P-0065

{5-[5-(2-Morpholin-4-yl-ethoxy)-1H-pyrrolo[2,3-b]pyridin-3-ylmethyl]-pyridin-2-yl}-(4-trifluoromethyl-benzyl)-amine P-0065 was synthesized in 4 Steps from (5-bromo-pyridin-2-yl)-(4-trifluoromethylbenzyl)-amine 17 as shown in Scheme 32.

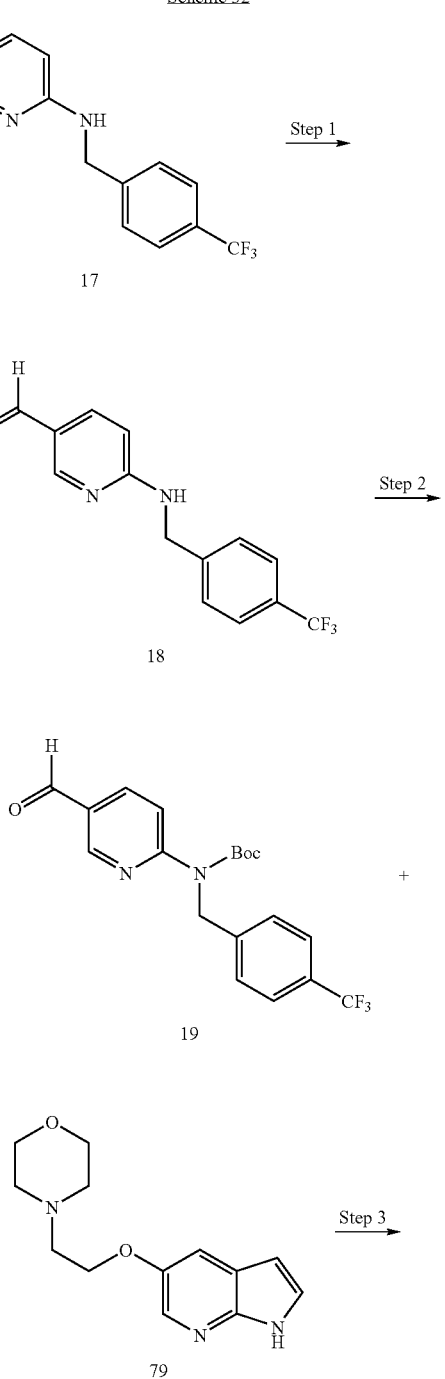

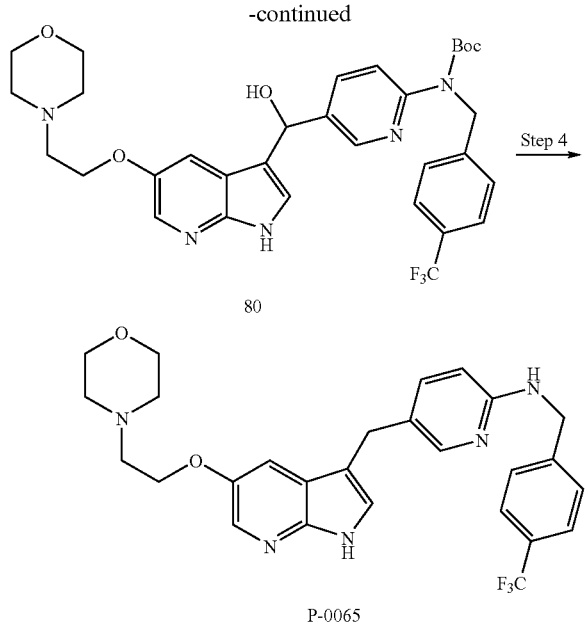

80

P-0065

Step 1

Preparation of 6-(4-Trifluoromethyl-benzylamino)-pyridine-3-carbaldehyde (18)

To a solution of (5-bromo-pyridin-2-yl)-(4-trifluoromethyl-benzyl)-amine (17, 3.55 g, 0.0107 mol, commercially available, or prepared as described in Example 10) in tetrahydrofuran (150 mL) was added tert-butyllithium (13.2 mL, 1.70 M in pentane, 0.0224 mol) slowly under an atmosphere of nitrogen at −78° C. over 10 minutes. The reaction mixture was stirred at −78° C. for 90 minutes. N,N-Dimethylformamide (2.2 mL, 0.028 mol) was added slowly into the reaction mixture. The reaction mixture was stirred at −78° C. for 2 hours, then allowed to warm to room temperature. After stirring at room temperature for 2 hours, the reaction mixture was poured into ice water and extracted with ethyl acetate. The organic phase was washed with saturated sodium bicarbonate, brine, and dried over magnesium sulfate. After removal of solvent, the residue was purified by silica gel column chromatography eluting with ethyl acetate in hexane to provide the compound as a light yellow solid (18, 1.67 g, 56%).

Step 2

Preparation of (5-Formyl-pyridin-2-yl)-(4-trifluoromethyl-benzyl)-carbamic acid tert-butyl ester (19)

To a solution of 6-(4-tifluoromethyl-benzylamino)-pyridine-3-carbaldehyde (18, 3.7 g, 0.013 mol) and di-tert-butyl-dicarbonate (3.4 g, 0.016 mol) in dichloromethane (100 mL) was added N,N-diisopropylethylamine (4.6 mL, 0.026 mol) and 4-diethylaminopyridine (0.2 g, 0.002 mol). The reaction mixture was stirred at room temperature overnight. The reaction mixture was concentrated and then dissolved in ethyl acetate. The solution was washed with hydrochloric acid (10%), saturated sodium bicarbonate, brine, and dried over magnesium sulfate. After removal of solvent, the residue was purified by silica gel column chromatography eluting with ethyl acetate in hexane to provide the compound as a white solid (19, 4.38 g, 87%).

Step 4

Preparation of (5-{Hydroxy-[5-(2-morpholin-4-yl-ethoxy)-1H-pyrrolo[2,3-b]pyridin-3-yl]-methyl}-pyridin-2-yl)-(4-trifluoromethyl-benzyl)-carbamic acid tert-butyl ester (80)

A mixture of (5-Formyl-pyridin-2-yl)-(4-trifluoromethyl-benzyl)-carbamic acid tert-butyl ester (19, 315 mg, 0.828 mmol), 5-(2-morpholin-4-yl-ethoxy)-1H-pyrrolo[2,3-b]pyridine (79, 205 mg, 0.829 mmol, prepared as described in Example 29), and potassium hydroxide (70 mg, 1 mmol) in methanol (25 mL) was stirred at room temperature overnight. The reaction mixture was poured into ice water, extracted with ethyl acetate, washed with brine, and dried over sodium sulfate. After removal of solvent, the residue was purified by silica gel column chromatography eluting with methanol in dichloromethane to provide the compound as a yellow solid (80, 0.2 g, 40%). MS (ESI) [M+H$^+$]$^+$=628.42.

Step 5

Preparation of {5-[5-(2-Morpholin-4-yl-ethoxy)-1H-pyrrolo[2,3-b]pyridin-3-ylmethyl]-pyridin-2-yl}-(4-trifluorom ethyl-benzyl)-amine (P-0065)

A mixture of (5-{Hydroxy-[5-(2-morpholin-4-yl-ethoxy)-1H-pyrrolo[2,3-b]pyridin-3-yl]-methyl}-pyridin-2-yl)-(4-trifluoromethyl-benzyl)-carbamic acid tert-butyl ester (80, 0.2 g, 0.3 mmol), triethylsilane (4 mL, 0.02 mol), and trifluoroacetic acid (2 mL, 0.02 mol) in acetonitrile (30 mL) was refluxed for 2 hours. After removal of solvent, the residue was dissolved in ethyl acetate, washed with saturated sodium bicarbonate, brine, and dried over magnesium sulfate. After removal of solvent, the residue was purified by silica gel column chromatography eluting with methanol in dichloromethane to provide the compound as a light yellow solid (P-0065, 17 mg, 10%). MS (ESI) [M+H$^+$]$^+$=512.42.

Additional compounds may be prepared using steps 3 and 4 of Scheme 32, using (5-Formyl-pyridin-2-yl)-(4-trifluoromethyl-benzyl)-carbamic acid tert-butyl ester 19 or replacing it with (5-Formyl-pyridin-2-yl)-(4-chloro-benzyl)-carbamic acid tert-butyl ester (43, prepared as described in Example 17) and replacing 5-(2-Morpholin-4-yl-ethoxy)-1H-pyrrolo[2,3-b]pyridine 79 with an appropriate azaindole, prepared as in Example 29 or 5-methoxy-7-azaindole (prepared as described in Example 31) or with commercially available 5-chloro-7-azaindole. The following compounds were made following this procedure:

[5-(5-Methoxy-1H-pyrrolo[2,3-b]pyridin-3-ylmethyl)-pyridin-2-yl]-(4-trifluoromethyl-benzyl)-amine (P-0053),

[5-(5-Chloro-1H-pyrrolo[2,3-b]pyridin-3-ylmethyl)-pyridin-2-yl]-(4-trifluoromethyl-benzyl)-amine (P-0054), (4-Chloro-benzyl)-[5-(5-methoxy-1H-pyrrolo[2,3-b]pyridin-3-ylmethyl)-pyridin-2-yl]-amine (P-0058), (4-Chloro-benzyl)-[5-(5-chloro-1H-pyrrolo[2,3-b]pyridin-3-ylmethyl)-pyridin-2-yl]-amine (P-0059), {5-[5-(2-Diethylamino-ethoxy)-1H-pyrrolo[2,3-b]pyridin-3-ylmethyl]-pyridin-2-yl}-(4-trifluoromethyl-benzyl)-amine (P-0060), (4-Chloro-benzyl)-{5-[5-(2-morpholin-4-yl-ethoxy)-1H-pyrrolo[2,3-b]pyridin-3-ylmethyl]-pyridin-2-yl}-amine (P-0063), {5-[5-(2-Pyrrolidin-1-yl-ethoxy)-1H-pyrrolo[2,3-b]pyridin-3-ylmethyl]-pyridin-2-yl}-(4-trifluoromethyl-benzyl)-amine (P-0064), {5-[5-(3-Diethylamino-propoxy)-1H-pyrrolo[2,3-b]pyridin-3-ylmethyl]-pyridin-2-yl}-(4-trifluoromethyl-benzyl)-amine (P-0066),
(4-Chloro-benzyl)-{5-[5-(3-diethylamino-propoxy)-1H-pyrrolo[2,3-b]pyridin-3-ylmethyl]-pyridin-2-yl}-amine (P-0069), The aldehyde and azaindole used in step 4 of this procedure are indicated in columns 2 and 3 of the following table, respectively, with the compound structure indicated in column 4. Column 1 provides the compound reference number and Column 5 the experimental mass spectrometry result.

| | Aldehyde | Azaindole | Compound | MS (ESI) [M + H$^+$]$^+$ observed |
|---|---|---|---|---|
| P-0053 | 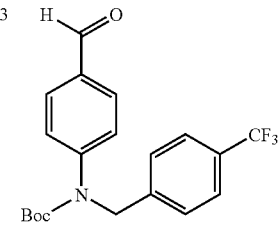 | 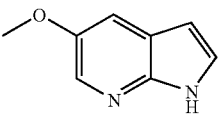 | 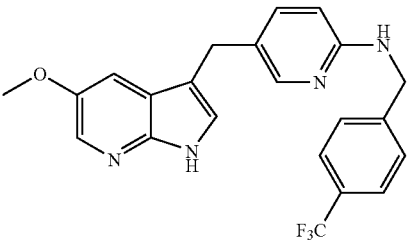 | 413.2 |
| P-0054 | 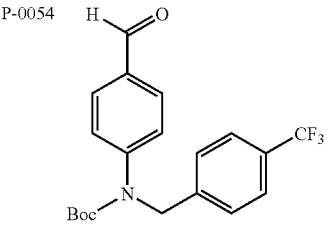 | 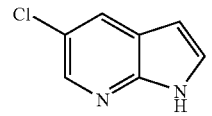 | 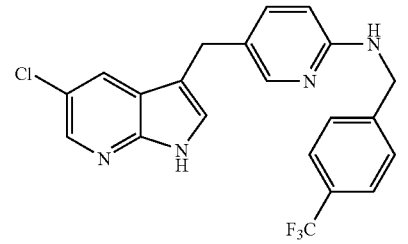 | 417.2 |
| P-0058 | 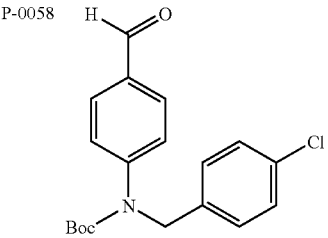 | 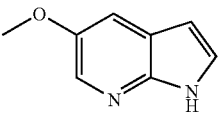 | 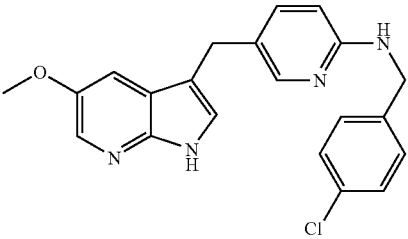 | 379.2 |
| P-0059 | 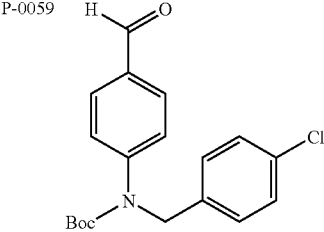 | 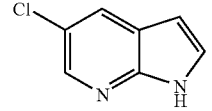 | 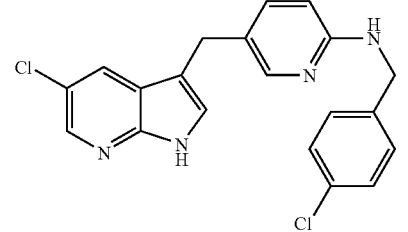 | 383.2 |
| P-0060 | 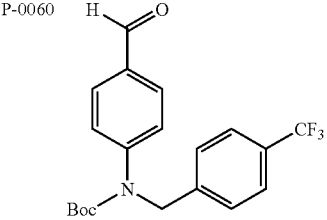 | 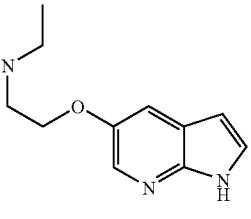 | 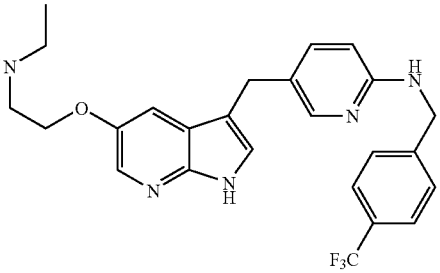 | 498.4 |

| Aldehyde | Azaindole | Compound | MS (ESI) [M + H⁺]⁺ observed |
|---|---|---|---|
| P-0063 | | | 478.3 |
| P-0064 | | | 496.3 |
| P-0066 | | | 512.3 |
| P-0069 | | | 478.3 |
Example 31
Synthesis of 3-[6-(4-Trifluoromethyl-benzylamino)-pyridin-3-ylmethyl]-1H-pyrrolo[2,3-b]pyridin-5-ol P-0061
3-[6-(4-Trifluoromethyl-benzylamino)-pyridin-3-ylmethyl]-1H-pyrrolo [2,3-b]pyridin-5-ol P-0061 was synthesized in 6 Steps from 5-bromo-7-azaindole 44 as described in Scheme 33.
Scheme 33
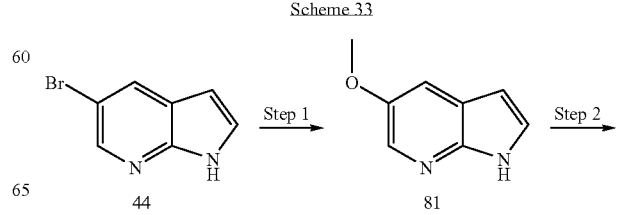

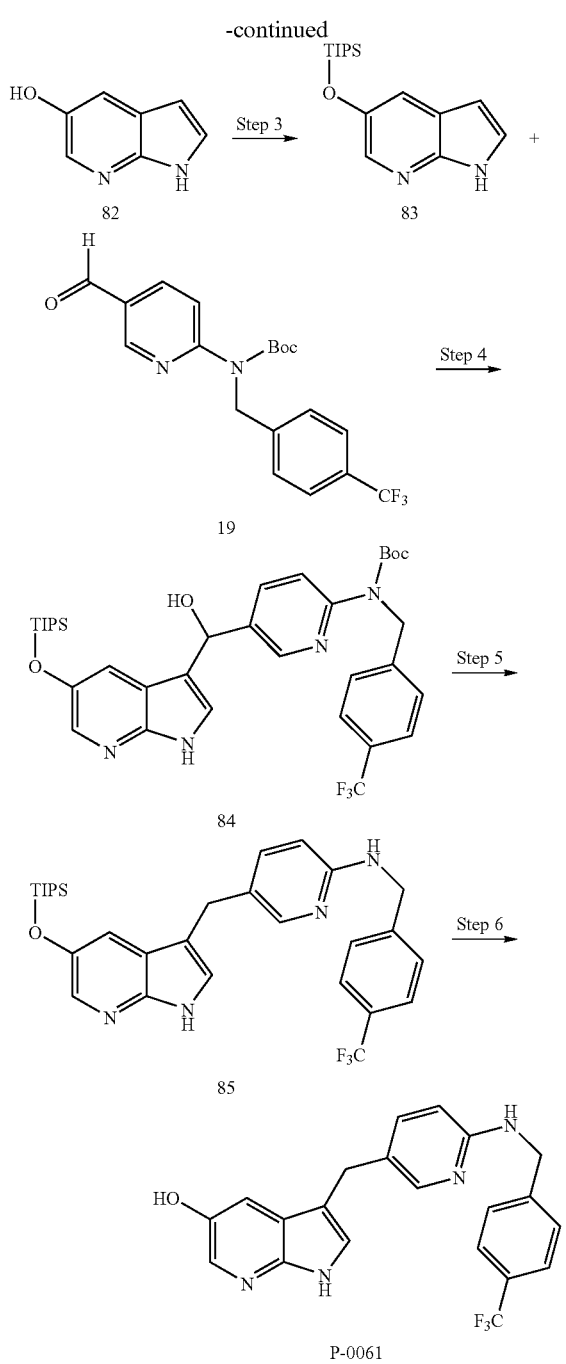

and ammonium hydroxide (4:1), brine, and dried over magnesium sulfate. After removal of solvent, the residue was purified by silica gel column chromatography eluting with ethyl acetate in hexane to provide the compound as a white solid (81, 0.4 g, 50%). MS (ESI) [M+H$^+$]$^+$=149.09.

Step 2

Preparation of 1H-Pyrrolo[2,3-b]pyridin-5-ol (82)

To a solution of 5-methoxy-1H-pyrrolo[2,3-b]pyridine (81, 0.5 g, 3 mmol) in tetrahydrofuran (20 mL) was added boron tribromide (1.5 g, 6.0 mmol) at 0° C. The reaction mixture was allowed to warm to room temperature, then stirred at room temperature for 3 hours. The reaction mixture was quenched by methanol. After repeated addition of methanol and removal of solvent, the concentrated reaction mixture was dissolved in ethyl acetate and water. The organic layer was collected, washed with brine, and dried over magnesium sulfate. After removal of solvent, the residue was purified by silica gel column chromatography eluting with ethyl acetate in hexane to provide the compound as an off-white solid (82, 0.18 g, 40%).

Step 3

Preparation of 5-Triisopropylsilanyloxy-1H-pyrrolo[2,3-b]pyridine (83)

To a solution of 1H-Pyrrolo[2,3-b]pyridin-5-ol (0.5 g, 0.004 mol) and 1H-imidazole (0.98 g, 0.014 mol) in N,N-dimethylformamide (5 mL) was added triisopropylsilyl chloride (1 mL, 0.005 mol). The reaction mixture was stirred at room temperature overnight. Dichloromethane (10 mL) was added and the solution was washed with brine and dried over sodium sulfate. After removal of solvent, the residue was purified by silica gel column chromatography eluting with ethyl acetate in hexane to provide the compound as a viscous liquid (83, 0.4 g, 40%).

Step 4

Preparation of {5-[Hydroxy-(5-triisopropylsilanyloxy-1H-pyrrolo[2,3-b]pyridin-3-yl)-methyl]-pyridin-2-yl}-(4-trifluoromethyl-benzyl)-carbamic acid tert-butyl ester (84)

A mixture of (5-Formyl-pyridin-2-yl)-(4-trifluoromethyl-benzyl)-carbamic acid tert-butyl ester (19, 41 mg, 0.11 mmol, prepared as described in Example 30), 5-triisopropylsilanyloxy-1H-pyrrolo[2,3-b]pyridine (83, 34 mg, 0.12 mmol) and potassium hydroxide (9.8 mg, 0.17 mmol) in methanol (10 mL) was stirred at room temperature overnight. The reaction mixture was poured into water, extracted with ethyl acetate, washed with brine and dried over sodium sulfate. After removal of solvent, the residue was purified by silica gel column chromatography eluting with ethyl acetate in hexane to provide the compound as a viscous liquid (84, 0.05 g, 70%). MS (ESI) [M+H$^+$]$^+$=671.38.

Step 1

Preparation of 5-Methoxy-1H-pyrrolo[2,3-b]pyridine (81)

To a mixture of 5-bromo-7-azaindole (1 g, 0.005 mol) in N,N-Dimethylformamide (20 mL) and methanol (20 mL) were added sodium methoxide (13 g, 0.24 mol) and Copper (I) bromide (0.7 g, 0.0048 mol) at room temperature. The reaction mixture was stirred at 120° C. under nitrogen for 3 hours. The reaction mixture was concentrated and the residue was dissolved in ethyl acetate and water. The organic layer was collected, washed with a solution of ammonium chloride

Step 5

Preparation of (4-Trifluoromethyl-benzyl)-[5-(5-triisopropylsilanyloxy-1H-pyrrolo[2,3-b]pyridin-3-ylmethyl)-pyridin-2-yl]-amine (85)

A mixture of {5-[hydroxy-(5-triisopropylsilanyloxy-1H-pyrrolo[2,3-b]pyridin-3-yl)-methyl]-pyridin-2-yl}-(4-trifluoromethyl-benzyl)-carbamic acid tert-butyl ester (84, 0.05 g, 0.07 mmol), trifluoroacetic acid (0.5 mL, 0.006 mol), and triethylsilane (1 mL, 0.006 mol) in acetonitrile (10 mL) was refluxed for 2 hours. The reaction mixture was poured into ice water, extracted with ethyl acetate, washed with saturated sodium bicarbonate, brine, and dried over sodium sulfate. After removal of solvent, the residue was purified by silica gel column chromatography eluting with ethyl acetate in hexane to provide the compound as a viscous liquid (85, 0.04 g, 97%). MS (ESI) $[M+H^+]^+=555.38$.

Step 6

Preparation of 3-[6-(4-Trifluoromethyl-benzylamino)-pyridin-3-ylmethyl]-1H-pyrrolo[2,3-b]pyridin-5-ol (P-0061)

To (4-Trifluoromethyl-benzyl)-[5-(5-triisopropylsilanyloxy-1H-pyrrolo[2,3-b]pyridin-3-ylmethyl)-pyridin-2-yl]-amine (85, 0.13 g, 0.23 mmol) in tetrahydrofuran (10 mL) was added tetrabutylammonium fluoride (3 mL, 1.0 M in tetrahydrofuran, 3 mmol). The reaction mixture was stirred at room temperature overnight, and then was stirred at 65° C. for 48 hours. The reaction mixture was concentrated and purified by silica gel column chromatography eluting with ethyl acetate in hexane to provide the compound as a viscous liquid (P-0061, 0.062 g, 66%). MS (ESI) $[M+H^+]^+=399.19$.

3-[6-(4-Chloro-benzylamino)-pyridin-3-ylmethyl]-1H-pyrrolo[2,3-b]pyridin-5-ol P-0062

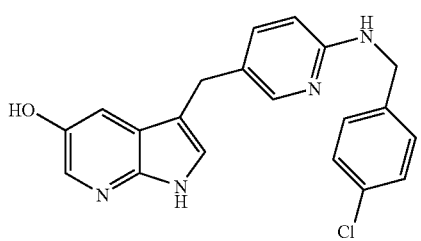

was prepared following the protocol of Scheme 33, replacing (5-Formyl-pyridin-2-yl)-(4-trifluoromethyl-benzyl)-carbamic acid tert-butyl ester 19 with (5-Formyl-pyridin-2-yl)-(4-chloro-benzyl)-carbamic acid tert-butyl ester (43, prepared as described in Example 17). MS (ESI) $[M+H^+]^+=365.2$.

Example 32

Synthesis of N-[5-(1H-Pyrrolo[2,3-b]pyridine-3-carbonyl)-pyridin-2-yl]-4-trifluoromethyl-benzamide P-0067

N-[5-(1H-Pyrrolo[2,3-b]pyridine-3-carbonyl)-pyridin-2-yl]-4-trifluoromethyl-benzamide P-0067 was synthesized in 2 Steps from 7-azaindole 1 as described in Scheme 34.

Scheme 34

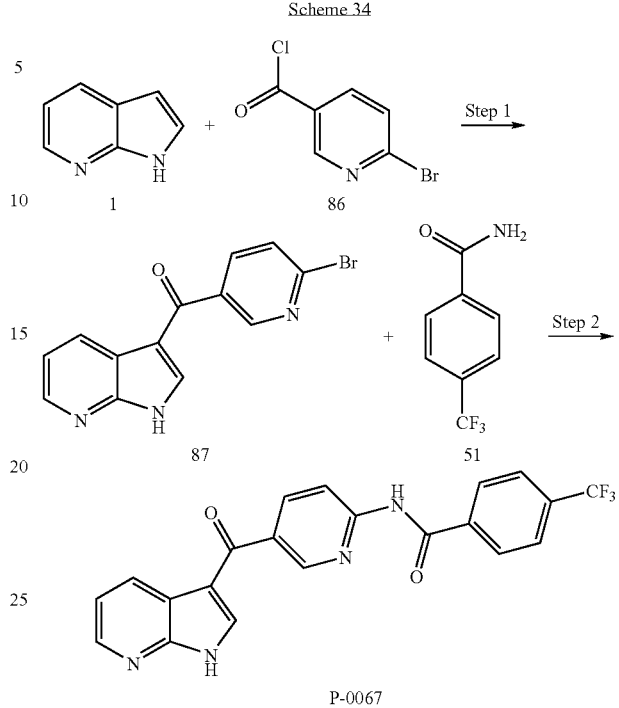

Step 1

Preparation of (6-Bromo-pyridin-3-yl)-(1H-pyrrolo[2,3-b]pyridin-3-yl)-methanone (87)

To a solution of 1H-Pyrrolo[2,3-b]pyridine (1, 1.2 g, 0.010 mol) in dichloromethane (50 mL) was added 6-bromo-nicotinoyl chloride (86, 2.6 g, 0.012 mol) at −10° C. After the solution turned clear, aluminum trichloride (10.2 g, 0.0765 mol) was added in one portion with vigorous stirring. The reaction mixture was stirred at −10° C. for 30 minutes, then was allowed to warm to room temperature and stirred at room temperature overnight. The reaction was quenched with ice water and neutralized with sodium bicarbonate. The solution was extracted with dichloromethane, washed with brine, and dried over sodium sulfate. After removal of solvent, the residue was purified by silica gel column chromatography eluting with methanol in dichloromethane to provide the compound as a white solid (87, 0.35 g, 11%).

Step 2

Preparation of N-[5-(1H-Pyrrolo[2,3-b]pyridine-3-carbonyl)-pyridin-2-yl]-4-trifluoromethyl-benzamide (P-0067)

A mixture of (6-bromo-pyridin-3-yl)-(1H-pyrrolo[2,3-b]pyridin-3-yl)-methanone (87,160 mg, 0.53 mmol), 4-trifluoromethyl benzamide (51, 130 mg, 0.69 mmol), xanthphos (9 mg, 0.02 mmol), cesium carbonate (245 mg, 0.752 mmol), and tris(dibenzylideneacetone)dipalladium (0) (5 mg, 0.005 mmol) in toluene (2 mL) in a sealed tube was stirred at 110° C. for 1 hour. The reaction was quenched with water and extracted with dichloromethane. The organic layer was collected, washed with brine and dried over sodium sulfate. After removal of the solvent, the residue was purified with silica gel column chromatography eluting with ethyl acetate in hexane to provide the compound as an off-white solid (P-0067, 0.42 mg, 19%). MS (ESI) [M+H$^+$]$^+$=411.17.

N-[5-(1H-Pyrrolo[2,3-b]pyridine-3-carbonyl)-pyridin-2-yl]-4-trifluoromethyl-benzenesulfonamide P-0068

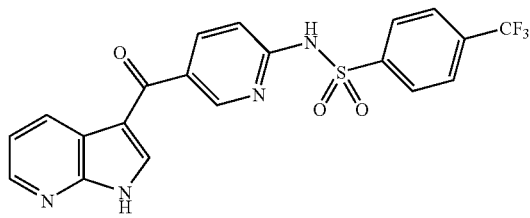

was prepared following the protocol of Scheme 34, replacing 4-trifluoromethyl benzamide 51 with 4-trifluoromethyl-benzenesulfonamide in Step 2. MS (ESI) [M+H$^+$]$^+$=445.1.

Example 33

Synthesis of [(S)-1-(4-Chloro-phenyl)-ethyl]-[5-(1H-pyrrolo[2,3-b]pyridin-3-ylmethyl)-pyridin-2-yl]-amine P-0075

[(S)-1-(4-Chloro-phenyl)-ethyl]-[5-(1H-pyrrolo[2,3-b]pyridin-3-ylmethyl)-pyridin-2-yl]-amine P-0075 was synthesized in 3 Steps from 7-azaindole 1 as described in Scheme 35.

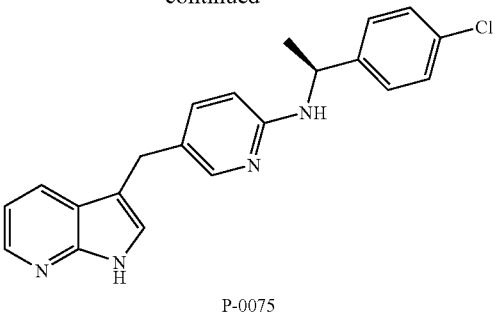

Step 1

Preparation of (6-Bromo-pyridin-3-yl)-(1H-pyrrolo[2,3-b]pyridin-3-yl)-methanol (89)

A mixture of 1H-Pyrrolo[2,3-b]pyridine (1, 1.2 g, 0.010 mol), 6-bromo-pyridine-3-carbaldehyde (88, 1.8 g, 0.0097 mol), and potassium hydroxide (1.8 g, 0.032 mol) in methanol (25 mL) was stirred at room temperature overnight. The reaction mixture was poured into ice water, extracted with ethyl acetate, washed with brine, and dried over sodium sulfate. After removal of solvent, the residue was purified by silica gel column chromatography eluting with methanol in dichloromethane to provide the compound as a white solid (89, 1.4 g, 45%), or may be used as mixture of 89 and 90 in Step 2.

Step 2

Preparation of 3-(6-Bromo-pyridin-3-ylmethyl)-1H-pyrrolo[2,3-b]pyridine (91)

A mixture of (6-bromo-pyridin-3-yl)-(1H-pyrrolo[2,3-b]pyridin-3-yl)-methanol (89, 1 g, 0.003 mol) and 3-[(6-bromo-pyridin-3-yl)-methoxy-methyl]-1H-pyrrolo[2,3-b]pyridine (90, 2 g, 0.006 mol), triethylsilane (1 mL, 0.006 mol), and trifluoroacetic acid (0.5 mL, 0.006 mol) in acetonitrile (25 mL) was refluxed for 2 hours. The reaction mixture was concentrated and the residue was dissolved in ethyl acetate and water. The organic layer was collected, washed with saturated sodium bicarbonate, brine, and dried over sodium sulfate. After removal of the solvent, the residue was purified with silica gel column chromatography eluting with ethyl acetate in hexane to provide the compound as an off-white solid (91, 0.75 g, 60%). MS (ESI) [M+H$^+$]$^+$=288.06, 290.00.

Step 3

Preparation of [(S)-1-(4-Chloro-phenyl)-ethyl]-[5-(1H-pyrrolo[2,3-b]pyridin-3-ylmethyl)-pyridin-2-yl]-amine P-0075

A mixture of 3-(6-bromo-pyridin-3-ylmethyl)-1H-pyrrolo[2,3-b]pyridine (91, 100 mg, 0.0003 mol) and (S)-1-(4-chloro-phenyl)-ethylamine (92, 0.5 g, 0.003 mol) in N-methylpyrrolidine (3 mL) was stirred at 150° C. in microwave for 100 minutes. The reaction mixture was concentrated under vacuum and the residue was purified with silica gel column chromatography eluting with ethyl acetate in hexane to provide the compound as a white solid (P-0075, 0.03 g, 20%). MS (ESI) [M+H$^+$]$^+$=363.18.

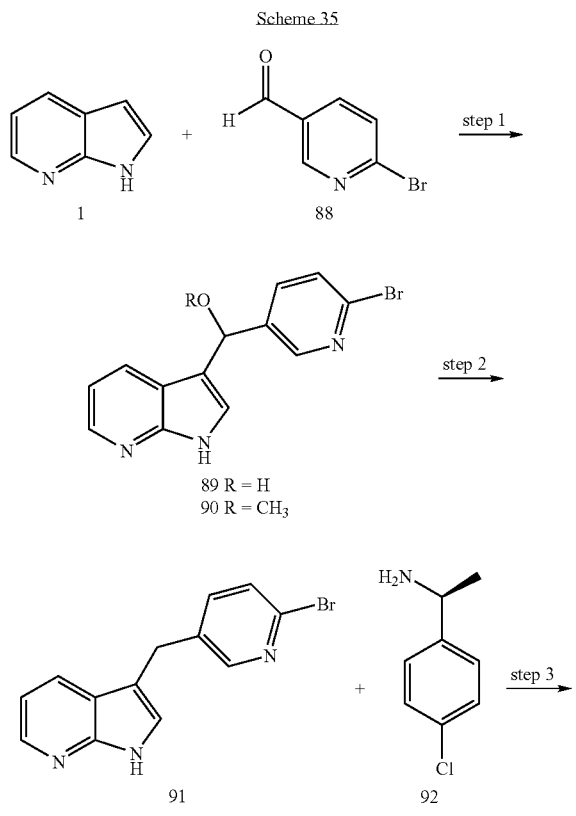

Example 34

Synthesis of (4-Chloro-benzyl)-[4-chloro-5-(1H-pyrrolo[2,3-b]pyridin-3-ylmethyl)-thiazol-2-yl]-amine P-0083

(4-Chloro-benzyl)-[4-chloro-5-(1H-pyrrolo[2,3-b]pyridin-3-ylmethyl)-thiazol-2-yl]-amine P-0083 was synthesized in 4 steps from 2,4-Dichloro-thiazole-5-carbaldehyde 93 as described in Scheme 36.

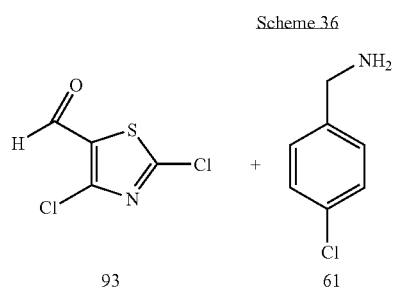

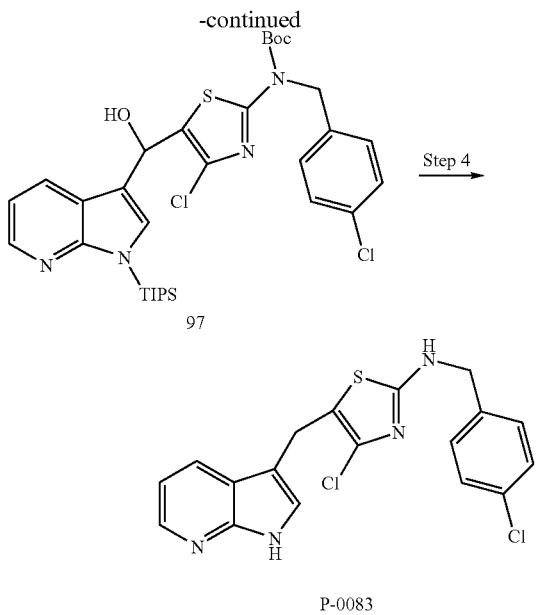

Step 1

Preparation of 4-Chloro-2-(4-chloro-benzylamino)-thiazole-5-carbaldehyde (94)

To a solution of p-chlorobenzylamine (61, 283 mg, 2.00 mmol) and N,N-Diisopropylethylamine (0.697 mL) in tetrahydrofuran (20 mL) was slowly added 2,4-Dichloro-thiazole-5-carbaldehyde (93, 364 mg, 2.00 mmol) in tetrahydrofuran (10 mL) at room temperature. The reaction was stirred at room temperature overnight. The reaction mixture was poured into iced water, extracted with ethyl acetate, washed with brine, and dried over sodium sulfate. After removal of solvent, the residue was purified by silica gel column chromatography eluting with ethyl acetate in hexane to provide the compound as a yellow solid (94, 0.3 g, 50%). MS (ESI) [M−H+]=286.97.

Step 2

Preparation of (4-Chloro-benzyl)-(4-chloro-5-formyl-thiazol-2-yl)-carbamic acid tert-butyl ester (95)

To a solution of 4-Chloro-2-(4-chloro-benzylamino)-thiazole-5-carbaldehyde (94, 0.32 g, 0.0011 mol) in dichloromethane (20 mL) was slowly added N,N-diisopropylethylamine (0.4 mL, 0.002 mol), 4-dimethylaminopyridine (27 mg, 0.22 mmol), and a solution of di-tert-Butyldicarbonate (290 mg, 0.0013 mol) in dichloromethane (5 mL) at room temperature. The reaction mixture was stirred at room temperature overnight, then poured into iced water, extracted with dichloromethane, washed with brine, and dried over sodium sulfate. After removal of solvent, the residue was purified by silica gel column chromatography eluting with ethyl acetate in hexane to provide the compound as a light brown solid (95, 0.32 g, 74%). MS (ESI) [M+H+]=387.26.

Step 3

Preparation of (4-Chloro-benzyl)-{4-chloro-5-[hydroxy-(1-triisopropylsilanyl-1H-pyrrolo[2,3-b]pyridin-3-yl)-methyl]-thiazol-2-yl}-carbamic acid tert-butyl ester (97)

To a solution of 3-Iodo-1-triisopropylsilanyl-1H-pyrrolo[2,3-b]pyridine (96, 99 mg, 0.25 mmol) in tetrahydrofuran (5 ml) at −20° C. under nitrogen was added 2.0 M solution isopropylmagnesium chloride in tetrahydrofuran (0.2 ml, 0.31 mmol). The reaction mixture was stirred for 1.5 hours, then allowed to warm to 5° C. After the reaction mixture was cooled down to −20° C., a solution of (4-Chloro-benzyl)-(4-chloro-5-formyl-thiazol-2-yl)-carbamic acid tert-butyl ester (95, 80 mg, 0.2 mmol) in tetrahydrofuran (5 mL) was slowly added. The reaction mixture was stirred for 2.5 hrs, then allowed to warm to 5° C. The reaction mixture was poured into iced water, extracted with ethyl acetate, washed with brine, and dried over magnesium sulfate. After removal of solvent, the residue was purified by silica gel column chromatography eluting with ethyl acetate in hexane to provide the compound as an off-white solid (97, 76 mg, 50%). MS (ESI) [M+H+]=661.32, 663.32.

Step 4

Preparation of (4-Chloro-benzyl)-[4-chloro-5-(1H-pyrrolo[2,3-b]pyridin-3-ylmethyl)-thiazol-2-yl]-amine (P-0083)

A mixture of (4-Chloro-benzyl)-{4-chloro-5-[hydroxy-(1-triisopropylsilanyl-1H-pyrrolo[2,3-b]pyridin-3-yl)-methyl]-thiazol-2-yl}-carbamic acid tert-butyl ester (97, 76 mg, 0.11 mmol), triethylsilane (0.5 mL, 3 mmol), and trifluoroacetic acid (0.25 mL, 3.2 mmol) in acetonitrile (5 mL) was refluxed for 3 hours. The reaction mixture was poured into iced water, extracted with ethyl acetate, washed with sodium bicarbonate, brine, and dried over sodium sulfate. After removal of solvent, the residue was purified by silica gel column chromatography eluting with ethyl acetate in hexane to provide the compound as a yellow solid (P-0083, 5.6 mg, 14%). MS (ESI) [M+H+]=389.35, 390.36.

Example 35

Synthesis of [2-(4-Chloro-benzylamino)-thiazol-5-yl]-(1H-pyrrolo[2,3-b]pyridin-3-yl)-methanone P-0077

[2-(4-Chloro-benzylamino)-thiazol-5-yl]-(1H-pyrrolo[2,3-b]pyridin-3-yl)-methanone P-0077 was synthesized in 2 steps from 2-Bromo-thiazole-5-carboxylic acid 98 and 1H-pyrrolo[2,3-b]pyridine 1 as shown in Scheme 37.

Scheme 37

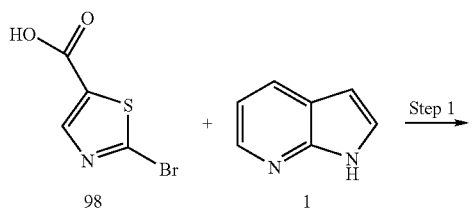

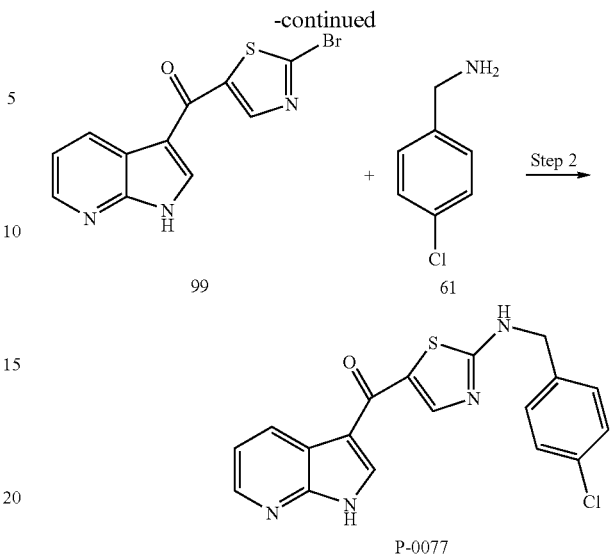

Step 1

Preparation of (2-Bromo-thiazol-5-yl)-(1H-pyrrolo[2,3-b]pyridin-3-yl)-methanone (99)

A suspension of 2-Bromo-thiazole-5-carboxylic acid (98, 0.5 g, 0.002 mol) in oxalyl chloride (3 mL) was stirred at room temperature until it turned into a clear solution. Solvent was removed and the residue was dried over vacuum. A light yellow solid was obtained and was dissolved in dichloromethane (10 mL) and slowly added to a solution of 1H-Pyrrolo[2,3-b]pyridine (1, 0.34 g, 0.0029 mol) in dichloromethane (30 mL) at −10° C. To the mixture was then added aluminum trichloride (2.6 g, 0.019 mol) in one portion with vigorous stirring. The reaction was held at −10° C. for 30 minutes, then allowed to warm to room temperature. The reaction mixture was stirred at ambient temperature overnight. The reaction was quenched with ice-water and acidified with hydrochloric acid (10%) to pH 4. The solution was then extracted with dichloromethane. The organic layer was collected, washed with brine, and dried over magnesium sulfate. After removal of solvent, the residue was purified by silica gel column chromatography eluting with ethyl acetate in hexane to provide the compound as a white solid (99, 12 mg, 2%). MS (ESI) [M−H+]=369.09.

Step 2

Preparation of [2-(4-Chloro-benzylamino)-thiazol-5-yl]-(1H-pyrrolo[2,3-b]pyridin-3-yl)-methanone (P-0077)

A mixture of (2-Bromo-thiazol-5-yl)-(1H-pyrrolo[2,3-b]pyridin-3-yl)-methanone (99, 5 mg, 0.02 mmol), p-chlorobenzylamine (61, 10 mg, 0.08 mmol), and N,N-Diisopropylethylamine (10 µL, 0.08 mmol) in tetrahydrfuran (10 mL), in a sealed reaction vessel, was stirred room temperature overnight. The reaction mixture was poured into iced water, extracted with ethyl acetate, washed with brine, and dried over magnesium sulfate. After removal of solvent, the residue was purified by silica gel column chromatography eluting with ethyl acetate in hexane to provide the compound as a light yellow solid (P-0077, 2 mg, 30%). MS (ESI) [M+H+]=305.90, 307.88.

Example 36

Synthesis of 3-((5-chloro-3-methyl-1-phenyl-1H-pyrazol-4-yl)methyl)-1H-pyrrolo[2,3-b]pyridine P-0080

3-((5-chloro-3-methyl-1-phenyl-1H-pyrazol-4-yl)methyl)-1H-pyrrolo[2,3-b]pyridine P-0080 was synthesized in 2 steps from 5-chloro-3-methyl-1-phenyl-1H-pyrazole-4-carbaldehyde 100 and 7-azaindole 1 as shown in Scheme 38.

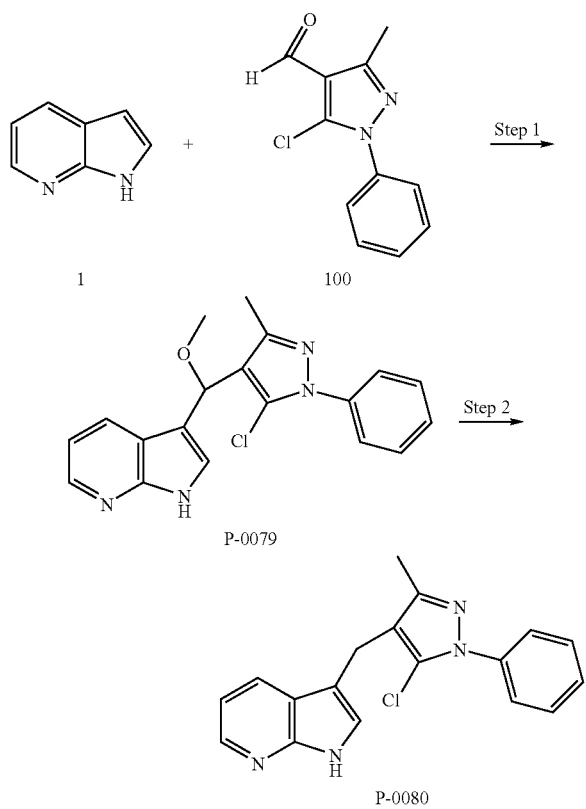

Scheme 38

Step 1

Preparation of 3-((5-chloro-3-methyl-1-phenyl-1H-pyrazol-4-yl)(methoxy)methyl)-1H-pyrrolo[2,3-b]pyridine (P-0079)

To 1H-Pyrrolo[2,3-b]pyridine (1, 0.100 g, 0.846 mmol) and 5-chloro-3-methyl-1-phenyl-1H-pyrazole-4-carbaldehyde (100, 0.205 g, 0.931 mmol) was added 2 mL of methanol to give a solution. Potassium hydroxide (0.0475 g, 0.846 mmol) was added and the reaction was allowed to stir at room temperature for 48 hours. The reaction was extracted with ethyl acetate and water. The organic layer was dried over anhydrous magnesium sulfate and filtered. The filtrate was concentrated and purified by silica gel column chromatography eluting with a gradient of 0-5% methanol in dichloromethane to give the compound (P-0079, 32 mg, 11%). MS (ESI) [M+H+]+=353.2.

Step 2

Preparation of 3-((5-chloro-3-methyl-1-phenyl-1H-pyrazol-4-yl)methyl)-1H-pyrrolo[2,3-b]pyridine (P-0080)

To 3-((5-chloro-3-methyl-1-phenyl-1H-pyrazol-4-yl)(methoxy)methyl)-1H-pyrrolo[2,3-b]pyridine (P-0079, 0.030 g, 0.085 mmol) was added acetonitrile (10 mL, 0.2 mol). Trifluoroacetic acid (500 uL, 0.006 mol) and triethylsilane (500 uL, 0.003 mol) were added and the reaction allowed to stir at room temperature for 16 hours. The reaction was extracted with ethyl acetate and water. The organic layer was dried over anhydrous magnesium sulfate and filtered. The filtrate was concentrated and purified by silica gel column chromatography eluting with dichloromethane followed 5% methanol in dichloromethane to give the compound as a yellowish foam (P-0080, 29 mg, 98%). MS (ESI) [M+H+]+=323.2.

Example 37 cKit Kinase Domain and Construction of c-Kit Sequences c-Kit cDNA sequence is available from NCBI, e.g., as GenBank accession number NM_000222. Using this sequence, c-kit DNA sequences can be cloned from commercially available libraries (e.g. cDNA libraries) or can be synthesized by conventional cloning methods.

Using conventional cloning methods, constructs encoding three c-kit polypeptides were prepared, and used to express c-kit kinase domain polypeptides. One such active c-kit kinase domain sequence included residues P551-S948, with the deletion of residues Q694-T753.

Example 38

Expression and Purification of c-Kit Kinase Domain

Purified c-kit kinase domain can be obtained using conventional expression and purification methods. Exemplary methods are described, for example, in Lipson et al., U.S. 20040002534 (U.S. application Ser. No. 10/600,868, filed Jun. 23, 2003), which is incorporated herein by reference in its entirety.

Example 39

Binding Assays

Binding assays can be performed in a variety of ways, including a variety of ways known in the art. For example, as indicated above, binding assays can be performed using fluorescence resonance energy transfer (FRET) format, or using an AlphaScreen Alternatively, any method which can measure binding of a ligand to the ATP-binding site can be used. For example, a fluorescent ligand can be used. When bound to c-kit, the emitted fluorescence is polarized. Once displaced by inhibitor binding, the polarization decreases.

Determination of $IC_{50}$ for compounds by competitive binding assays. (Note that $K_I$ is the dissociation constant for inhibitor binding; $K_D$ is the dissociation constant for substrate binding.) For this system, the IC50, inhibitor binding constant and substrate binding constant can be interrelated according to the following Formula:

When using radiolabeled substrate $$K_I = \frac{IC50}{1 + [L^*]/K_D},$$

the $IC_{50} \sim K_I$ when there is a small amount of labeled substrate.

Example 40

Cell-Based Assays of c-fms Kinase Activity or c-kit Kinase Activity

M-CSF dependent RAW264.7 cells were seeded on a 12 well plate, $2.5 \times 10^5$ cells/well and the cells were allowed to attach overnight at 37° C., 5% $CO_2$. The cells were then starved in serum-free medium overnight at 37° C., 5% $CO_2$. The cells were treated with compound for 1 hour in serum-free media (1% DMSO final concentration); and then stimulated with 20 ng/ml M-CSF for 5 minutes. After stimulation, the cells were lysed on ice, and the lysates were centrifuged at 13,000 rpm for 1 minute. The amount of protein in the sample was quantitated, sample buffer was added, and the samples were boiled at 95° C. for 10 minutes. The samples were then centrifuged at 13,000 rpm for 1 minute. The samples (15-20 µg/lane) were loaded and run on 4-12% tris-glycine gel at 75V, and then transferred onto a PVDF membrane. The membrane was blocked for 1 hour with 5% BSA in PBS/1% Tween-20 (PBST); or 5% milk, depending on the primary antibody used. Then the blots were incubated with primary antibody overnight at 4 degrees with gentle shaking. After incubation with the capture antibody, the membranes were washed 3×10 minutes with PBST; then incubated with detection antibody Goat Anti-Rabbit-HRP for 1 hour, with gentle shaking. The membranes were washed again 3×10 minutes with PBST. ECL Plus substrate was then added to the blots, the image captured with chemiluminescence camera, and the bands quantitated for pFMS and FMS levels.

The Fms inhibitors may also be assessed using M-NFS-60 mouse myelogenous leukemia cell line (ATCC catalog #CRL-1838). This cell line proliferation is stimulated by M-CSF, which binds and activates the fms tyrosine kinase receptor. Inhibitors of fms kinase activity reduce or eliminate the M-CSF stimulated kinase activity, resulting in reduced cell proliferation. This inhibition is measured as a function of compound concentration to assess $IC_{50}$ values. M-NFS-60 cells were seeded at $5 \times 10^4$ cells per well of a 96 well cell culture plate in 50 µl of cell culture medium of RPMI 1640 (CellGro Mediatech catalog #10-040-CV) supplemented with 10% FBS (HyClone catalog #SH30071.03). Compounds were dissolved in DMSO at a concentration of 1 mM and were serially diluted 1:3 for a total of eight points and added to the cells to final concentrations of 10, 3.3, 1.1, 0.37, 0.12, 0.041, 0.014 and 0.0046 µM in 100 µl cell culture medium (final concentration 0.2% DMSO). Cells were also treated with staurosporine as a positive control. The cells were stimulated by adding 20 µl of 372 ng/ml M-CSF to a final concentration of 62 ng/ml (R&D Systems catalog #216-MC). The cells were incubated at 37° C., 5% $CO_2$ for three days. CellTiter-Glo Buffer (Promega Cell Viability Assay catalog #G7573) and substrate were equilibrated to room temperature, and enzyme/substrate Recombinant Firefly Luciferase/Beetle Luciferin was reconstituted. The cell plates were equilibrated to room temperature for 30 minutes, then lysed by addition of an equivalent volume of the Celltiter-Glo Reagent. The plate was mixed for 2 minutes on a plate shaker to lyse the cells, then incubated for 10 minutes at room temperature. The plates were read on a Victor Wallac II using Luminescence protocol modified to read 0.1 s per well. The luminescence reading assesses the ATP content, which correlates directly with cell number such that the reading as a function of compound concentration was used to determine the $IC_{50}$ value.

The c-Kit inhibitors were assessed using M-07e cell line (DSMZ catalog #ACC 104). The M-07e proliferation is stimulated by SCF (Stem Cell Factor), which binds and activates c-Kit tyrosine kinase receptor. Inhibitors of c-Kit kinase reduce or eliminate the SCF mediated kinase activation, resulting in reduced cell proliferation of SCF stimulated cells. This inhibition is measured by the effect of compound concentration on cell growth to assess $IC_{50}$ values. M-07e cells were seeded at $5 \times 10^4$ cells per well of a 96 well cell culture plate in 50 µl of cell culture medium of Iscove's Medium 1× (MOD, CellGro Mediatech catalog #15-016-CV) supplemented with 10% FBS (HyClone catalog #SH30071.03). Compounds were dissolved in DMSO at a concentration of 0.1 mM and were serially diluted 1:3 for a total of eight points and added to the cells to final concentrations of 1, 0.33, 0.11, 0.037, 0.012, 0.0041, 0.0014 and 0.00046 µM in 100 µl cell culture medium (final concentration 0.2% DMSO). Cells were also treated with staurosporine as a positive control. Cells were stimulated by adding 20 µl of 600 ng/ml SCF to a final concentration of 100 ng/ml (Biosource International SCF kit ligand catalog #PHC2115) in cell culture medium. The cells were incubated at 37° C., 5% $CO_2$ for three days. CellTiter-Glo Buffer (Promega Cell Viability Assay catalog #G7573) and substrate were equilibrated to room temperature, and enzyme/substrate Recombinant Firefly Luciferase/Beetle Luciferin was reconstituted. The cell plates were equilibrated to room temperature for 30 minutes, then lysed by addition of an equivalent volume of the Celltiter-Glo Reagent. The plate was mixed for 2 minutes on a plate shaker to lyse the cells, then incubated for 10 minutes at room temperature. The plates were read on a Victor Wallac II using Luminescence protocol modified to read 0.1 s per well. The luminescence reading assesses the ATP content, which correlates directly with cell number such that the reading as a function of compound concentration is used to determine the $IC_{50}$ value.

This cell based assay was also used to assess phosphorylation. Samples were prepared with compounds as described for the growth inhibition assay only M-07e cells were seeded at $2 \times 10^5$ cells per well in a 96 well filter plate. Cells were incubated for 1 hour at 37° C. with the compounds as described above, and then stimulated by adding SCF to a final concentration of 50 ng/ml and incubated for 10 minutes at 37° C. The culture medium was removed by centrifugation and the cells were lysed by addition of 30 µl lysis buffer (25 mM Tris HCl pH 7.5, 150 mM NaCl, 5 mM EDTA, 1% Triton X100, 5 mM NaF, 1 mM Na Vanadate, 10 mM Beta-glycerophosphate, no EDTA (Boehringer-Roche catalog #1873580) and placed on ice for 30 minutes. A 15 µl aliquot of the lysate was taken and assayed according to Biosource Immunoassay Kit: Human c-Kit [pY823] (Catalog # KHO0401) by diluting the aliquot with 85 µl dilution buffer in the assay plate, incubating for 2 hours at room temperature and washing the plate 4 times with wash buffer. Detection antibody (100 µl) was added to the plate and samples incubated for 1 hour at room temperature, then washed 4 times with wash buffer. HRP anti-rabbit antibody (100 μl) was added and samples incubated for 30 minutes at room temperature, then washed 4 times with wash buffer. Stabilized chromogen (100 μl) was added and samples incubated for 15-25 minutes at room temperature, then washed 4 times with wash buffer. Stop solution (100 μl) was added and the samples read on a Wallac Victor reader at 450 nm. The absorbance was plotted against the compound concentration and the $IC_{50}$ concentration was determined.

Example 41 c-Kit and c-Fms Activity Assays

The effect of potential modulators of kinase activity of c-kit and other kinases can be measured in a variety of different assays known in the art, e.g., biochemical assays, cell-based assays, and in vivo testing (e.g. model system testing). Such in vitro and/or in vivo assays and tests can be used in the present invention. As an exemplary kinase assay, the kinase activity of c-kit or Fms is measured in AlphaScreening (Packard BioScience).

Exemplary c-kit Biochemical Assay

The c-kit (or kinase domain thereof) is an active kinase in AlphaScreen. $IC_{50}$ values are determined with respect to inhibition of c-Kit kinase activity, where inhibition of phosphorylation of a peptide substrate is measured as a function of compound concentration. Compounds to be tested were dissolved in DMSO to a concentration of 20 mM. These were diluted 30 μl into 120 μl of DMSO (4 mM) and 1 μl was added to an assay plate. These were then serially diluted 1:3 (50 μl to 100 μl DMSO) for a total of 8 points. Plates were prepared such that each kinase reaction is 20 μl in 1× kinase buffer (50 mM HEPES, pH 7.2, 5 mM $MgCl_2$, 5 mM $MnCl_2$, 0.01% NP-40, 0.2% BSA), 5% DMSO and 10 μM ATP. Substrate was 100 nM biotin-(E4Y)3 (Open Source Biotech, Inc.). C-kit kinase was at 0.1 ng per sample. After incubation of the kinase reaction for 1 hour at room temperature, 5 μl of donor beads (Streptavidin coated beads (Perkin Elmer Life Science) final concentration 1 μg/ml) in stop buffer (50 mM EDTA in 1× kinase buffer) was added, the sample was mixed and incubated for 20 minutes at room temperature before adding 5 μl of acceptor beads (PY20 coated beads (Perkin Elmer Life Science) final concentration 1 μg/ml) in stop buffer. The samples were incubated for 60 minutes at room temperature and the signal per well was read on AlphaQuest reader. Phosphorylated substrate results in binding of the PY20 antibody and association of the donor and acceptor beads such that signal correlates with kinase activity. The signal vs. compound concentration was used to determine the $IC_{50}$.

Compounds were also tested using a similar assay with a 10-fold higher ATP concentration. For these samples, compounds to be tested were dissolved in DMSO to a concentration of 20 mM. These were diluted 30 μl into 120 μl of DMSO (4 mM) and 1 μl was added to an assay plate. These were then serially diluted 1:3 (50 μl to 100 μl DMSO) for a total of 8 points. Plates were prepared such that each kinase reaction is 20 μl in 1× kinase buffer (8 mM MOPS pH 7.0, 1 mM $MgCl_2$, 2 mM $MnCl_2$, 0.01% Tween-20, 1 mM DTT, and 0.001% BSA), 5% DMSO and 100 μM ATP. Substrate was 30 nM biotin-(E4Y)10 (Upstate Biotech, Cat# 12-440). C-kit kinase was at 1 ng per sample. After incubation of the kinase reaction for 1 hour at room temperature, 5 μl of donor beads (Streptavidin coated beads (Perkin Elmer Life Science) final concentration 10 μg/ml) in stop buffer (8 mM MOPS pH 7.0, 100 mM EDTA, 0.3% BSA) was added, the sample was mixed and incubated for 20 minutes at room temperature before adding 5 μl of acceptor beads (PY20 coated beads (Perkin Elmer Life Science) final concentration 10 μg/ml) in stop buffer. The samples were incubated for 60 minutes at room temperature and the signal per well was read on AlphaQuest reader. Phosphorylated substrate results in binding of the PY20 antibody and association of the donor and acceptor beads such that signal correlates with kinase activity. The signal vs. compound concentration was used to determine the $IC_{50}$.

The c-kit enzyme used in the above assay was either obtained from Cell Signaling Technology (Cat. #7754) or was prepared as follows: A plasmid encoding kit (DNA and encoded protein sequences shown below) was engineered using common polymerase chain reaction (PCR) methods. Complementary DNA cloned from various human tissues were purchased from Invitrogen, and these were used as substrates in the PCR reactions. Specific custom synthetic oligonucleotide primers were designed to initiate the PCR product, and also to provide the appropriate restriction enzyme cleavage sites for ligation with the plasmids. The entire sequence encoding the enzyme was made through a gene synthesis procedure, using custom synthetic oligonucleotides covering the entire coding sequence (Invitrogen, see below).

The plasmid used for ligation with the kinase-encoding inserts was derivative of pET (Novagen) for expression using E. coli. The Kit kinase was engineered to include a Histidine tag for purification using metal affinity chromatography. The kinase-encoding plasmid was engineered as bicistronic mRNA to co-express a second protein that modifies the kinase protein during its expression in the host cell. Protein tyrosine phosphatase 1B (PTP), was co-expressed for dephosphorylation of the phospho-Tyrosines.

For protein expression, the plasmid containing the Kit gene was transformed into E. coli strains BL21(DE3)RIL and transformants selected for growth on LB agar plates containing appropriate antibiotics. Single colonies were grown overnight at 37° C. in 200 ml TB (Terrific broth) media. 16×1 L of fresh TB media in 2.8 L flasks were inoculated with 10 ml of overnight culture and grown with constant shaking at 37° C. Once cultures reached an absorbance of 1.0 at 600 nm, IPTG was added and cultures were allowed to grow for a further 12 to 18 hrs at temperatures ranging from 12-30° C. Cells were harvested by centrifugation and pellets frozen at −80° C. until ready for lysis.

For protein Purification; frozen E. coli cell pellets were resuspended in lysis buffer and lysed using standard mechanical methods. Protein was purified via poly-Histidine tags using immobilized metal affinity purification IMAC. The Kit kinase was purified using a 3 step purification process utilizing; IMAC, size exclusion chromatography and ion exchange chromatography. The poly-Histidine tag was removed using Thrombin (Calbiochem).

Compounds were assayed using a similar assay to that described above, using in a final reaction volume of 25 μl: c-Kit (h) (5-10 mU) in 8 mM MOPS pH 7.0, 0.2 mM EDTA, 10 mM $MnCl_2$, 0.1 mg/ml poly (Glu, Tyr) 4:1, 10 mM MgAcetate and $\gamma$-$^{33}$P-ATP (approximately 500 cpm/pmol), with appropriate concentrations of compound. Incubated for 40 minutes at room temperature and stopped by addition of 5 μl of 3% phosphoric acid. Spotted 10 μl of each sample onto Filtermat A and washed 3× with 75 mM phosphoric acid, once with methanol, dried and measured on scintillation counter (performed at Upstate USA, Charlottesville, Va.).

Compounds P-0001, P-0002, P-0003, P-0004, P-0005, P-0006, P-0007, P-0008, P-0009, P-0010, P-0011, P-0012, P-0013, P-0014, P-0015, P-0016, P-0017, P-0018, P-0020, P-0022, P-0024, P-0025, P-0026, P-0027, P-0028, P-0030, P-0031, P-0032, P-0033, P-0038, P-0053, P-0054, P-0055, P-0056, P-0057, P-0058, P-0059, P-0060, P-0061, P-0062, P-0063, P-0064, P-0065, P-0066, P-0069, P-0071, P-0072, P-0073, P-0074, P-0075, P-0078, and P-0082 had $IC_{50}$ of less than 1 μM in at least one of the c-kit assays described above in Examples 40 and 41.

| | Kit PCR primers | |
|---|---|---|
| KIT 8K1A | ATGTACGAAGTTCAGTGGAAAGTTGTTGAAGAAATCAACGG (SEQ ID NO:5) | 1776 |
| 8K1B | GGTCGATGTAAACGTAGTTGTTACCGTTGATTTCTTCAACAACTTT (SEQ ID NO:6) | 1777 |
| 8K2A | AACAACTACGTTTACATCGACCCGACCCAGCTGCCGTACGAC (SEQ ID NO:7) | 1779 |
| 8K2B | GTTACGCGGGAACTCCCATTTGTGGTCGTACGGCAGCTGGGTC (SEQ ID NO:8) | 1781 |
| 8K3A | AAATGGGAGTTCCCGCGTAACCGTCTGTCTTTCGGTAAAACCC (SEQ ID NO:9) | 1782 |
| 8K3B | ACCGAACGCACCCGCACCCAGGGTTTTACCGAAAGACAGAC (SEQ ID NO:10) | 1783 |
| 8K4A | GGTGCGGGTGCGTTCGGTAAAGTTGTTGAAGCGACCGCGTACG (SEQ ID NO:11) | 1784 |
| 8K4B | GCCGCGTCAGATTTGATCAGACCGTACGCGGTCGCTTCAAC (SEQ ID NO:12) | 1785 |
| 8K5A | CTGATCAAATCTGACGCGGCGATGACCGTTGCGGTTAAAATGC (SEQ ID NO:13) | 1786 |
| 8K5B | GTCAGGTGCGCAGACGGTTTCAGCATTTTAACCGCAACGGTCA (SEQ ID NO:14) | 1787 |
| 8K6A | AAACCGTCTGCGCACCTGACCGAACGTGAAGCGCTGATGTCTG (SEQ ID NO:15) | 1788 |
| 8K6B | CCAGGTAAGACAGAACTTTCAGTTCAGACATCAGCGCTTCACGT (SEQ ID NO:16) | 1789 |
| 8K7A | CTGAAAGTTCTGTCTTACCTGGGTAACCACATGAACATCGTTAA (SEQ ID NO:17) | 1791 |
| 8K7B | GGTGCACGCACCCAGCAGGTTAACGATGTTCATGTGGTTAC (SEQ ID NO:18) | 1792 |
| 8K8A | CTGCTGGGTGCGTGCACCATCGGTGGTCCGACCCTGGTTATCA (SEQ ID NO:19) | 1793 |
| 8K8B | GTCACCGTAGCAGCAGTATTCGGTGATAACCAGGGTCGGACCA (SEQ ID NO:20) | 1794 |
| 8K9A | GAATACTGCTGCTACGGTGACCTGCTGAACTTCCTGCGTCGTA (SEQ ID NO:21) | 1795 |
| 8K9B | AGAGCAGATGAAAGAGTCACGTTTACGACGCAGGAAGTTCAGC (SEQ ID NO:22) | 1796 |
| 8K10A | CGTGACTCTTTCATCTGCTCTAAACAGGAAGACCACGCGGAAG (SEQ ID NO:23) | 1797 |
| 8K10B | CAGCAGGTTTTTGTACAGCGCCGCTTCCGCGTGGTCTTCCTGT (SEQ ID NO:24) | 1798 |
| 8K11A | GCGCTGTACAAAAACCTGCTGCACTCTAAAGAATCTTCTTGCTC (SEQ ID NO:25) | 1799 |
| 8K11B | CCATGTATTCGTTGGTAGAGTCAGAGCAAGAAGATTCTTTAGAGT (SEQ ID NO:26) | 1811 |
| 8K11A | GACTCTACCAACGAATACATGGACATGAAACCGGGTGTTTCTTA (SEQ ID NO:27) | 1812 |

-continued

| Kit PCR primers | | |
|---|---|---|
| 8K11B | TCCGCTTTGGTCGGAACAACGTAAGAAACACCCGGTTTCATGT (SEQ ID NO:28) | 1813 |
| 8K12A | GTTGTTCCGACCAAAGCGGACAAACGTCGTTCTGTTCGTATCG (SEQ ID NO:29) | 1814 |
| 8K12B | TAACGTCACGTTCGATGTAAGAACCGATACGAACAGAACGACGTTT (SEQ ID NO:30) | 1815 |
| 8K13A | TCTTACATCGAACGTGACGTTACCCCGGCGATCATGGAAGACG (SEQ ID NO:31) | 1816 |
| 8K13B | CCAGGTCCAGCGCCAGTTCGTCGTCTTCCATGATCGCCGG (SEQ ID NO:32) | 1817 |
| 8K14A | GAACTGGCGCTGGACCTGGAAGACCTGCTGTCTTTCTCTTACC (SEQ ID NO:33) | 1818 |
| 8K14B | GAACGCCATACCTTTCGCAACCTGGTAAGAGAAAGACAGCAGGT (SEQ ID NO:34) | 1819 |
| 8K15A | GTTGCGAAAGGTATGGCGTTCCTGGCGTCTAAAAACTGCATCCA (SEQ ID NO:35) | 1821 |
| 8K15B | CGCGCCGCCAGGTCACGGTGGATGCAGTTTTTAGACGCC (SEQ ID NO:36) | 1822 |
| 8K16A | CGTGACCTGGCGGCGCGTAACATCCTGCTGACCCACGGTCG (SEQ ID NO:37) | 1823 |
| 8K16B | ACCGAAGTCGCAGATTTTGGTGATACGACCGTGGGTCAGCAGG (SEQ ID NO:38) | 1824 |
| 8K17A | ACCAAAATCTGCGACTTCGGTCTGGCGCGTGACATCAAAAACG (SEQ ID NO:39) | 1825 |
| 8K17B | GTTACCTTTAACAACGTAGTTAGAGTCGTTTTTGATGTCACGCGCC (SEQ ID NO:40) | 1826 |
| 8K18A | TCTAACTACGTTGTTAAAGGTAACGCGCGTCTGCCGGTTAAATG (SEQ ID NO:41) | 1827 |
| 8K18B | GAAGATAGATTCCGGCGCCATCCATTTAACCGGCAGACGCGC (SEQ ID NO:42) | 1829 |
| 8K19A | ATGGCGCCGGAATCTATCTTCAACTGCGTTTACACCTTCGAATC (SEQ ID NO:43) | 1831 |
| 8K19B | GATACCGTAAGACCAAACGTCAGATTCGAAGGTGTAAACGCAG (SEQ ID NO:44) | 1832 |
| 8K20A | GACGTTTGGTCTTACGGTATCTTCCTGTGGGAACTGTTCTCTC (SEQ ID NO:45) | 1833 |
| 8K20B | CCTGTGGGAACTGTTCTCTCTGGGTTCTTCTCCGTACCCGG (SEQ ID NO:46) | 1834 |
| 8K21A | GGTTCTTCTCCGTACCCGGGTATGCCGGTTGACTCTAAATTCTAT (SEQ ID NO:47) | 1835 |
| 8K21B | CGGAAACCTTCTTTGATCATTTTGTAGAATTTAGAGTCAACCGGC (SEQ ID NO:48) | 1836 |
| 8K22A | AAAATGATCAAAGAAGGTTTCCGTATGCTGTCTCCGGAACACG (SEQ ID NO:49) | 1837 |
| 8K22B | ATGTCGTACATTTCCGCCGGCGCGTGTTCCGGAGACAGCATA (SEQ ID NO:50) | 1838 |
| 8K23A | CCGGCGGAAATGTACGACATCATGAAAACCTGCTGGGACGCG (SEQ ID NO:51) | 1839 |
| 8K23B | AAGGTCGGACGTTTCAGCGGGTCCGCGTCCCAGCAGGTTTTC (SEQ ID NO:52) | 1841 |

-continued

| Kit PCR primers | | |
|---|---|---|
| 8K24A | CCGCTGAAACGTCCGACCTTCAAACAGATCGTTCAGCTGATCG (SEQ ID NO:53) | 1842 |
| 8K24B | TTGGTAGATTCAGAGATCTGTTTTTCGATCAGCTGAACGATCTGTT (SEQ ID NO:54) | 1843 |
| 8K25A | AAACAGATCTCTGAATCTACCAACCACATCTACTCTAACCTGGC (SEQ ID NO:55) | 1844 |
| 8K25B | TGACGGTTCGGAGAGCAGTTCGCCAGGTTAGAGTAGATGTGG (SEQ ID NO:56) | 1845 |
| 8K26A | AACTGCTCTCCGAACCGTCAGAAACCGGTTGTTGACCACTCTG (SEQ ID NO:57) | 1846 |
| 8K26B | GTAGAACCAACAGAGTTGATACGAACAGAGTGGTCAACAACCGGT (SEQ ID NO:58) | 1847 |
| 8K27A | CGTATCAACTCTGTTGGTTCTACCGCGTCTTCTTCTCAGCCG (SEQ ID NO:59) | 1848 |
| 8K27B | AACGTCGTCGTGAACCAGCAGCGGCTGAGAAGAAGACGCG (SEQ ID NO:60) | 1849 |
| 8K-F | GTTGTTTCATATGTACGAAGTTCAGTGGAAAG (SEQ ID NO:61) | 1851 |
| 8K-R | GTTGTTTGTCGACTAAACGTCGTCGTGAACCAGCAG (SEQ ID NO:62) | 1852 |
| KIT COD-K948X | GTTCTTGTCGACTAtttctgacggttcggagagc (SEQ ID NO:63) | 3411 |

P1332.N6 BI PTP KIT M552-K948-X COD
(Nucleic Acid SEQ ID NO:64) (Protein SEQ ID NO:65)
taatacgactcactataggggaattgtgagcggataacaattcccctctagaaataattt tgtttaactttaagaaggagatataccatgggtcaccaccatcaccatcatatgtacgaa

M  G  H  H  H  H  H  H  M  Y  E gttcagtggaaagttgttgaagaaatcaacggtaacaactacgtttacatcgacccgacc

V  Q  W  K  V  V  E  E  I  N  G  N  N  Y  V  Y  I  D  P  T cagctgccgtacgaccacaaatgggagttcccgcgtaaccgtctgtctttcggtaaaacc

Q  L  P  Y  D  H  K  W  E  F  P  R  N  R  L  S  F  G  K  T ctgggtgcgggtgcgttcggtaaagttgttgaagcgaccgcgtacggtctgatcaaatct

L  G  A  G  A  F  G  K  V  V  E  A  T  A  Y  G  L  I  K  S gacgcggcgatgaccgttgcggttaaaatgctgaaaccgtctgcgcacctgaccgaacgt

D  A  A  M  T  V  A  V  K  M  L  K  P  S  A  H  L  T  E  R gaagcgctgatgtctgaactgaaagttctgtcttacctgggtaaccacatgaacatcgtt

E  A  L  M  S  E  L  K  V  L  S  Y  L  G  N  H  M  N  I  V aacctgctgggtgcgtgcaccatcggtggtccgaccctggttatcaccgaatactgctgc

N  L  L  G  A  C  T  I  G  G  P  T  L  V  I  T  E  Y  C  C tacggtgacctgctgaacttcctgcgtcgtaaacgtgactcttttcatctgctctaaacag

Y  G  D  L  L  N  F  L  R  R  K  R  D  S  F  I  C  S  K  Q gaagaccacgcggaagcggcgctgtacaaaaacctgctgcactctaaagaatcttcttgc

E  D  H  A  E  A  A  L  Y  K  N  L  L  H  S  K  E  S  S  C

-continued

```
tctgactctaccaacgaatacatggacatgaaacgggtgtttcttacgttgttccgacc
 S   D   S   T   N   E   Y   M   D   M   K   P   G   V   S   Y   V   V   P   T aaagcggacaaacgtcgttctgttcgtatcggttcttacatcgaacgtgacgttaccccg
 K   A   D   K   R   R   S   V   R   I   G   S   Y   I   E   R   D   V   T   P gcgatcatggaagacgacgaactggcgctggacctggaagacctgctgtctttctcttac
 A   I   M   E   D   D   E   L   A   L   D   L   E   D   L   L   S   F   S   Y caggttgcgaaaggtatggcgttcctggcgtctaaaaactgcatccaccgtgacctggcg
 Q   V   A   K   G   M   A   F   L   A   S   K   N   C   I   H   R   D   L   A gcgcgtaacatcctgctgacccacggtcgtatcaccaaaatctgcgacttcggtctggcg
 A   R   N   I   L   L   T   H   G   R   I   T   K   I   C   D   F   G   L   A cgtgacatcaaaaacgactctaactacgttgttaaaggtaacgcgcgtctgccggttaaa
 R   D   I   K   N   D   S   N   Y   V   V   K   G   N   A   R   L   P   V   K tggatggcgccggaatctatcttcaactgcgtttacaccttcgaatctgacgtttggtct
 W   M   A   P   E   S   I   F   N   C   V   Y   T   F   E   S   D   V   W   S tacggtatcttcctgtgggaactgttctctctgggttcttctccgtacccgggtatgccg
 Y   G   I   F   L   W   E   L   F   S   L   G   S   S   P   Y   P   G   M   P gttgactctaaattctacaaaatgatcaaagaaggtttccgtatgctgtctccggaacac
 V   D   S   K   F   Y   K   M   I   K   E   G   F   R   M   L   S   P   E   H gcgccggcggaaatgtacgacatcatgaaaacctgctgggacgcggacccgctgaaacgt
 A   P   A   E   M   Y   D   I   M   K   T   C   W   D   A   D   P   L   K   R ccgaccttcaaacagatcgttcagctgatcgaaaaacagatctctgaatctaccaaccac
 P   T   F   K   Q   I   V   Q   L   I   E   K   Q   I   S   E   S   T   N   H atctactctaacctggcgaactgctctccgaaccgtcagaaatagtcgactgaaaaagga
 I   Y   S   N   L   A   N   C   S   P   N   R   Q   K   - agagt
```

Additional Biochemical and Cell-Based Assays

In general, any protein kinase assay can be adapted for use with c-kit. For example, assays (e.g. biochemical and cell-based assays) as described in Lipson et al., U.S. Patent Publ. 20040002534 (incorporated herein by reference in its entirety) can be used in the present invention.

In Vivo Model System Testing

For in vivo testing, a suitable animal model system can be selected for use. For example, for multiple scerosis, the rodent experimental allergic encephalomyelitis (EAE) is commently used. This system is well-known, and is described, for example, in Steinman, 1996, Cell 85:299-302 and Secor et al., 2000, J. Exp. Med 5:813-821, which are incorporated herein by reference in their entireties.

Similarly, other model systems can be selected and used in the present invention.

Exemplary Fms Biochemical Assay $IC_{50}$ values were determined with respect to inhibition of Fms kinase activity, where inhibition of phosphorylation of a peptide substrate is measured as a function of compound concentration. Compounds to be tested, dissolved in DMSO (1 µL), were added to a white 384-well plate (Costar #3705). Working stocks of Fms kinase (Upstate Biotech, #14-551), biotin-$(E4Y)_{10}$ substrate (Upstate Biotech, Cat# 12-440), and ATP (Sigma, Cat#A-3377) were prepared in 8 mM MOPS pH 7.4, 2 mM $MgCl_2$, 8 mM $MnCl_2$, 2 mM DTT, and 0.01% Tween-20. All components were added to the 384-well plate for a final concentration of 0.5 ng/well Fms, 30 nM biotin-$(E4Y)_{10}$ (Upstate Biotechnology) and 10 µM ATP in a volume of 20 µL. Each sample was at 5% DMSO. The plate was then incubated for 60 minutes at room temperature. Just before use, working stocks of donor and acceptor beads from the AlphaScreen PY20 Detection Kit (PerkinElmer, Cat#676601M) were prepared in 8 mM MOPS, pH 7.4, 100 mM EDTA, 0.3% BSA. To stop the reaction, the plate was uncovered in the dark and 5 µl of Donor Beads solution (Streptavidin beads) was added to each well. The plate was incubated at room temperature for 20 minutes. Five microliters of Acceptor Beads solution (PY20 coated beads) were then added to each well. The final concentration of each bead was 20 µg/mL. The plates were incubated at room temperature for 60 minutes. Fluorescence signal was recorded on the Fusion Alpha reader or AlphaQuest reader. Phosphorylated substrate results in binding of the PY20 antibody and association of the donor and acceptor beads such that signal correlates with kinase activity. The signal vs. compound concentration was used to determine the $IC_{50}$.

Compounds were also tested using a similar assay with a 10-fold higher ATP concentration. Compounds to be tested, dissolved in DMSO (1 μL), were added to a white 384-well plate (Costar #3705). Working stocks of Fms kinase (Upstate Biotech, #14-551), biotin-$(E4Y)_{10}$ substrate (Upstate Biotech, Cat# 12-440), and ATP (Sigma, Cat#A-3377) were prepared in 8 mM MOPS pH 7.0, 2 mM $MgCl_2$, 8 mM $MnCl_2$, 2 mM DTT, 50 mM NaCl, 0.01% BSA, and 0.01% Tween-20. All components were added to the 384-well plate for a final concentration of 0.5 ng/well Fms, 30 nM biotin-$(E4Y)_{10}$ (Upstate Biotechnology) and 100 μM ATP in a volume of 20 μL. Each sample was at 5% DMSO. The plate was then incubated for 20 minutes at 30° C. Just before use, working stocks of donor and acceptor beads from the AlphaScreen PY20 Detection Kit (PerkinElmer, Cat#676601M) were prepared in 8 mM MOPS, pH 7.0, 100 mM EDTA, 0.01% BSA. To stop the reaction, the plate was uncovered in the dark and 5 μl of Donor Beads solution (Streptavidin beads) was added to each well. The plate was incubated at room temperature for 20 minutes. Five microliters of Acceptor Beads solution (PY20 coated beads) were then added to each well. The final concentration of each bead was 10 μg/mL. The plates were incubated at room temperature for 60 minutes. Fluorescence signal was recorded on the Fusion Alpha reader or AlphaQuest reader. Phosphorylated substrate results in binding of the PY20 antibody and association of the donor and acceptor beads such that signal correlates with kinase activity. The signal vs. compound concentration was used to determine the $IC_{50}$.

Compounds were assayed using a similar assay to that described above, using in a final reaction volume of 25 μl: Fms (h) (5-10 mU) in 8 mM MOPS pH 7.0, 0.2 mM EDTA, 250 mM KKKSPGEYVNIEFG (SEQ ID NO: 66), 10 mM MgAcetate and $\gamma$-$^{33}$P-ATP (approximately 500 cpm/pmol), with appropriate concentrations of compound. Samples were incubated for 40 minutes at room temperature and stopped by addition of 5 μl of 3% phosphoric acid. 10 μl of each sample is spotted onto a P30 filtermat and washed 3× with 75 mM phosphoric acid, once with methanol, dried and measured on scintillation counter (Upstate USA, Charlottesville, Va.).

Compounds P-0001, P-0002, P-0003, P-0004, P-0005, P-0006, P-0007, P-0008, P-0009, P-0010, P-0011, P-0013, P-0014, P-0015, P-0016, P-0028, P-0032, P-0033, P-0038, P-0053, P-0054, P-0055, P-0056, P-0057, P-0058, P-0059, P-0060, P-0061, P-0062, P-0063, P-0064, P-0065, P-0066, P-0069, P-0072, P-0073, P-0074, P-0075, P-0076, P-0078, P-0081, and P-0082 had $IC_{50}$ of less than 1 μM in at least one of the Fms assays described above in Examples 40 or 41.

Example 42

Site-Directed Mutagenesis of c-Kit, c-Fms and Other Kinases

Mutagenesis of c-kit and other kinases (as well as other sequences of interest) can be carried out according to the following procedure as described in Molecular Biology: Current Innovations and Future Trends. Eds. A. M. Griffin and H. G. Griffin. (1995) ISBN 1-898486-01-8, Horizon Scientific Press, PO Box 1, Wymondham, Norfolk, U.K., among others.

In vitro site-directed mutagenesis is an invaluable technique for studying protein structure-function relationships, gene expression and vector modification. Several methods have appeared in the literature, but many of these methods require single-stranded DNA as the template. The reason for this, historically, has been the need for separating the complementary strands to prevent reannealing. Use of PCR in site-directed mutagenesis accomplishes strand separation by using a denaturing step to separate the complementing strands and allowing efficient polymerization of the PCR primers. PCR site-directed methods thus allow site-specific mutations to be incorporated in virtually any double-stranded plasmid; eliminating the need for M13-based vectors or single-stranded rescue.

It is often desirable to reduce the number of cycles during PCR when performing PCR-based site-directed mutagenesis to prevent clonal expansion of any (undesired) second-site mutations. Limited cycling which would result in reduced product yield, is offset by increasing the starting template concentration. A selection is used to reduce the number of parental molecules coming through the reaction. Also, in order to use a single PCR primer set, it is desirable to optimize the long PCR method. Further, because of the extendase activity of some thermostable polymerases it is often necessary to incorporate an end-polishing step into the procedure prior to end-to-end ligation of the PCR-generated product containing the incorporated mutations in one or both PCR primers.

The following protocol provides a facile method for site-directed mutagenesis and accomplishes the above desired features by the incorporation of the following steps: (i) increasing template concentration approximately 1000-fold over conventional PCR conditions; (ii) reducing the number of cycles from 25-30 to 5-10; (iii) adding the restriction endonuclease DpnI (recognition target sequence: 5-Gm6ATC-3, where the A residue is methylated) to select against parental DNA (note: DNA isolated from almost all common strains of E. coli is Dam-methylated at the sequence 5-GATC-3); (iv) using Taq Extender in the PCR mix for increased reliability for PCR to 10 kb; (v) using Pfu DNA polymerase to polish the ends of the PCR product, and (vi) efficient intramolecular ligation in the presence of T4 DNA ligase.

Plasmid template DNA (approximately 0.5 pmole) is added to a PCR cocktail containing, in 25 ul of 1× mutagenesis buffer: (20 mM Tris HCl, pH 7.5; 8 mM MgCl2; 40 ug/ml BSA); 12-20 pmole of each primer (one of which must contain a 5-prime phosphate), 250 uM each dNTP, 2.5 U Taq DNA polymerase, 2.5 U of Taq Extender (Stratagene).

The PCR cycling parameters are 1 cycle of: 4 min at 94 C, 2 min at 50 C and 2 min at 72° C.; followed by 5-10 cycles of 1 min at 94° C., 2 min at 54 C and 1 min at 72° C. (step 1).

The parental template DNA and the linear, mutagenesis-primer incorporating newly synthesized DNA are treated with DpnI (10 U) and Pfu DNA polymerase (2.5 U). This results in the DpnI digestion of the in vivo methylated parental template and hybrid DNA and the removal, by Pfu DNA polymerase, of the Taq DNA polymerase-extended base(s) on the linear PCR product.

The reaction is incubated at 37° C. for 30 min and then transferred to 72° C. for an additional 30 min (step 2).

Mutagenesis buffer (1×, 115 ul, containing 0.5 mM ATP) is added to the DpnI-digested, Pfu DNA polymerase-polished PCR products.

The solution is mixed and 10 ul is removed to a new microfuge tube and T4 DNA ligase (2-4 U) added.

The ligation is incubated for greater than 60 min at 37° C. (step 3).

The treated solution is transformed into competent E. coli (step 4).

In addition to the PCR-based site-directed mutagenesis described above, other methods are available. Examples include those described in Kunkel (1985) Proc. Natl. Acad. Sci. 82:488-492; Eckstein et al. (1985) Nucl. Acids Res. 13:8764-8785; and using the GeneEditor™ Site-Directed Mutageneis System from Promega.

In the following Examples, as well as in Examples 1-36 above, it is understood that the solvents and reagents used or suggested are not limiting, and can be substituted appropriately with solvents and reagents known to those of skill in the art. Reaction products may be isolated by means known in the art, such as extraction with a suitable solvent, precipitation from a suitable solvent, chromatography using a suitable solvent system, including silica gel column chromatography, HPLC, preparative TLC, and the like.

Synthetic routes available to Formula I

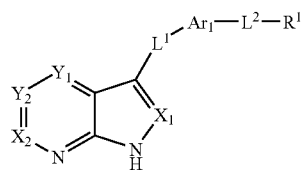

Formula I wherein $X_1$, $X_2$, $Y_1$, $Y_2$, $L_1$, $Ar_1$, $L^2$ and $R^1$ are as defined in Formula I of [0012] or Formula Ib

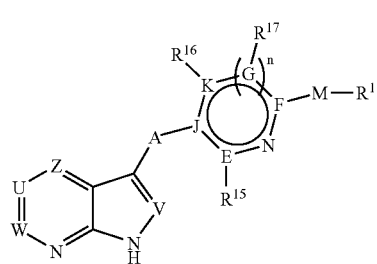

Formula Ib wherein U, V, W, Z, $R^1$, $R^{15}$, $R^{16}$, $R^{17}$, A, M, E, G, J, K, F and n are as defined in Formula Ib of [0026] are described in the schemes and examples below. While the methods described below are shown in terms of Formula Ib, it would be clear to one skilled in the art that the methods may be used to prepare compounds of either Formula I or Formula Ib. With reference to the schemes and examples below, unless clearly specified to the contrary, Formula and compound enumeration are defined for each scheme or example independently of such enumeration in the specification above, although general reference to Formula I and Ib indicate the Formulae above described in [0012] and [0026], respectively.

Compounds of Formula Ib can be prepared from compounds of Formula III and Formula X as described in Scheme 39.

Scheme 39:

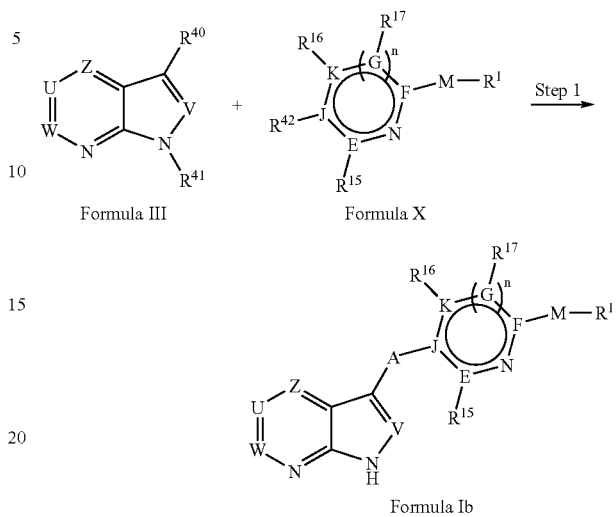

Compound of Formula III, where $R^{41}$ is either hydrogen or a protecting group P (e.g. phenylsulfone, t-butyloxycarbonyl, triisopropylsilyl) and $R^{40}$ is either hydrogen or a functional group appropriate for the coupling (e.g. Br, SH, OH, CHO etc.) is reacted with compound of Formula X where $R^{42}$ is a functional group appropriately chosen, based on $R^{40}$, to form the linkage A using standard coupling conditions known to one skilled in the art to provide a compound of Formula Ib.

Compounds of Formula Ib can be prepared from compounds of Formula III and Formula Xa, where $R^{43}$ is a functional group appropriate for introduction of M—$R^1$, is described in Scheme 40.

Scheme 40:

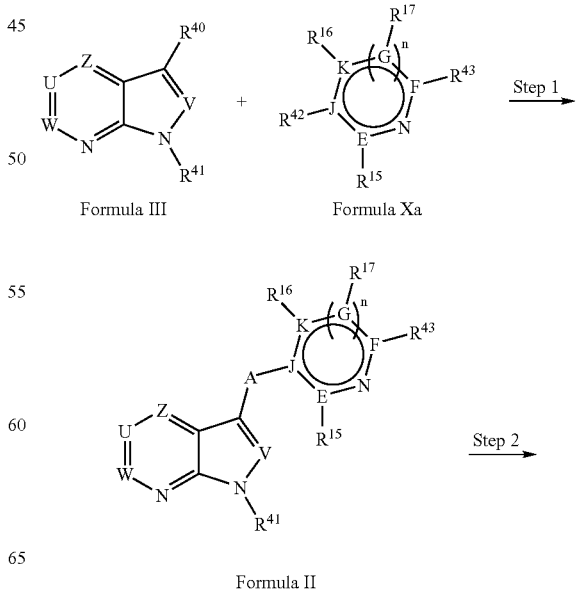

-continued

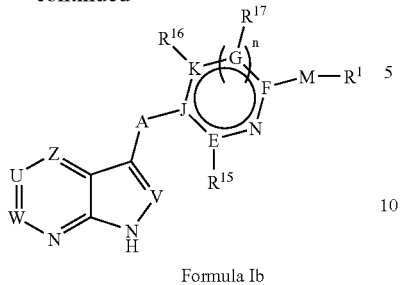

Formula Ib

Compound of Formula III, where $R^{41}$ is either hydrogen or a protecting group P (e.g. phenylsulfone, t-butyloxycarbonyl, triisopropylsilyl) and $R^{40}$ is either hydrogen or a functional group appropriate for the coupling (e.g. Br, SH, OH, CHO etc.,) is reacted with compound of Formula Xa where $R^{42}$ is a functional group appropriately chosen, based on $R^{40}$, and $R^{43}$ is a functional group appropriate to introduce M—$R^1$, to form the linkage A using standard coupling conditions known to one skilled in the art to provide compound of Formula II. Compound of Formula II is further functionalized to introduce M—$R^1$ using conditions known to one skilled in the art to provide compound of Formula Ib.

Steps 1 and 2 of Scheme 40 may be reversed such that compounds of Formula X are prepared from compounds of Formula Xa by methods of Step 2, followed by coupling of the resulting compounds of Formula X with compounds of Formula III following the methods of Step 1.

Many compounds of Formula X or Xa of Scheme 39 or 40 are commercially available or may be prepared in many different routes known in the literature, depending upon the specific ring system and substitution pattern that is desired, including substitution of nitrogen containing heterocycles, as well as de novo synthesis of the aromatic heterocycle.

General synthesis of compound of Formula III of Scheme 39 or 40 where $R^{40}$ is H or a functional group appropriate for coupling to compounds of Formula X or Xa (e.g. aldehyde, carboxylic acid, amine) is described in Scheme 41.

Scheme 41:

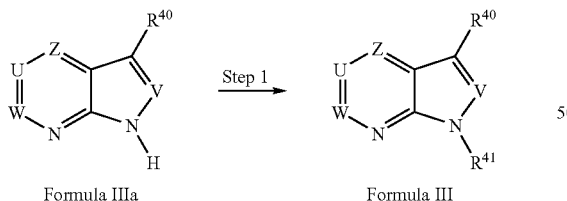

Formula IIIa          Formula III

Compounds of Formula IIIa, where U or Z is C—Br, C—Cl, C—NO$_2$ or C—NH$_2$, can be generally prepared from commercially available appropriate single heterocyclic ring or fused two ring heterocyclic compounds using methods known to one skilled in the art. Compound of Formula IIIa is further subjected to modification to provide appropriately substituted compounds of Formula III, where U or Z is C—Br, C—Cl, C—NO$_2$ or C—NH$_2$, and $R^{41}$ is H or protecting group P, using methods known to one skilled in the art.

General synthesis of compound of Formula III of Scheme 39 or 40 from compound of Formula IIIb, where $R^{40}$ is H, is described in Scheme 42.

Scheme 42:

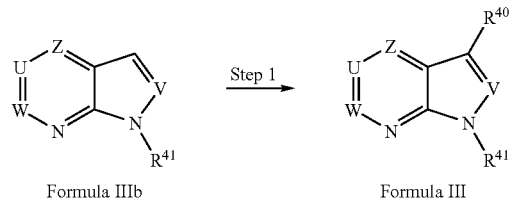

Formula IIIb          Formula III

Compounds of Formula III, where $R^{41}$ is either hydrogen or a protecting group P and $R^{40}$ is appropriate for coupling to compounds of Formula X or Xa of Scheme 39 or 40 (e.g. aldehyde, carboxylic acid, amine) or appropriate for modification to such substituents (e.g. ester, nitro) may also be prepared from compounds of Formula IIIb (here $R^{40}$ is H) using synthetic methods known to one skilled in the art, for example as described by Merour and Joseph in Curr. Org. Chem. 2001, 5:471-506.

In addition to these schemes, the reactions shown in the following Examples may be combined in different sequences to provide compounds of Formula Ib. The transformations shown in Schemes 39-42 and the following Schemes and Examples as a single step should be considered to represent the general overall transformation, as some specific cases may require more than one reaction step to realize the desired compound.

In the preparation of compounds of Formula Ib, Formula II and Formula III it may frequently be advantageous to substitute the hydrogen of the N—H in the 7-azaindole or its analog with a protecting group as exemplified in Scheme 43, Step 1. The protecting group can then be removed when appropriate to reveal the N—H according to Step 2.

Scheme 43:

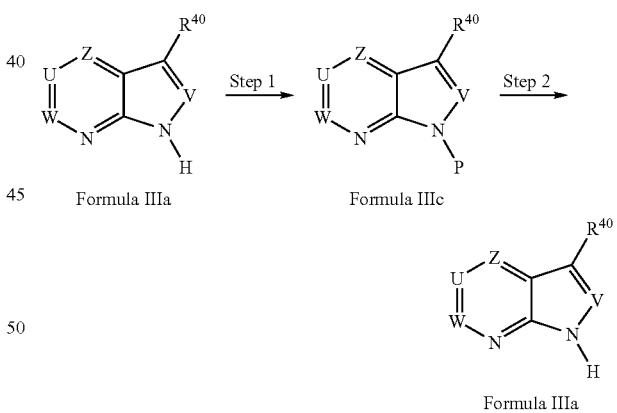

Formula IIIa          Formula IIIc

Formula IIIa

Step 1

Preparation of Formula IIIc where $R^{41}$ is a Protecting Group P

Compound of Formula IIIc where $R^{41}$ is a protecting group P may be prepared by dissolving compound of Formula IIIa where $R^{41}$ is hydrogen in a non-reactive solvent (e.g. dimethylformamide, tetrahydrofuran) and adding a base (e.g. aqueous sodium hydroxide, sodium hydride) and possibly a catalyst (e.g. tetrabutylammonium hydrogen sulfate). A reagent appropriate for the introduction of the protecting group (e.g.

phenylsulfonyl chloride, triisopropylsilyl chloride, Boc anhydride) is then added and the reaction is allowed to stir for one to several hours. Isolation and purification by conventional means (e.g. extraction, silica gel chromatography) provides compounds of Formula IIIc where $R^{43}$ is a protecting group.

Step 2

Preparation of Formula IIIa where $R^{41}$ is Hydrogen

Compound of Formula IIIa where $R^{41}$ is hydrogen may be prepared by dissolving compound of Formula IIIc where $R^{41}$ is a protecting group P in a suitable solvent (e.g. ethanol, tetrahydrofuran, dichloromethane) and adding a reagent appropriate for the removal of the protecting group (e.g. potassium hydroxide, tetrabutylammonium fluoride, trifluoroeacetic acid). The reaction is allowed to stir for 30 minutes to several hours with heating. Isolation and purification by conventional means (e.g. extraction, silica gel chromatography) provides compounds of Formula IIIa where $R^{43}$ is hydrogen.

Compounds of Formula II above are similar to compounds of Formula Ib as shown, where $R^{43}$ is defined as M—$R^1$ or a substituent appropriate for further substitution to provide M—$R^1$, and $R^{41}$ is hydrogen or a protecting group P.

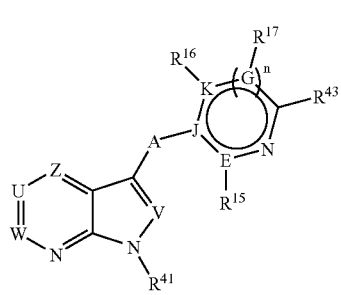

Formula II

Compounds of Formula II where U, V, W, Z, J, E, F, G, K are C and n is 1 form compounds of Formula IIa below.

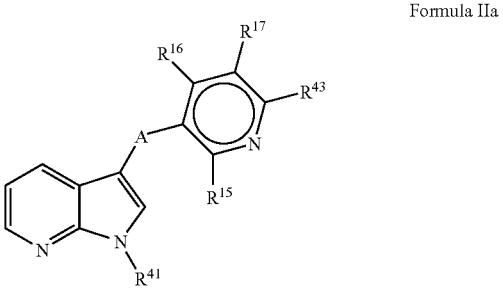

Formula IIa

The examples provided for the synthesis of compounds of Formula Ia are also applicable to many compounds meeting other definitions of Formula Ib and Formula II. For example, 7-azaindole, Compound 1, may be replaced in these syntheses by compounds where U, V, W, and Z are other than C—H.

Example 43

Synthesis of Compounds of Formula IIa, where A is $CH_2$ or C(O)

Compounds of Formula IIa, where A is $CH_2$ or C(O) may be synthesized from compounds of Formula Xb (Formula Xa wherein $R^{42}$ is C(O)H, J, E, F, G and K are C and n is 1) and compound 1 in two Steps according to Scheme 100.

Scheme 100

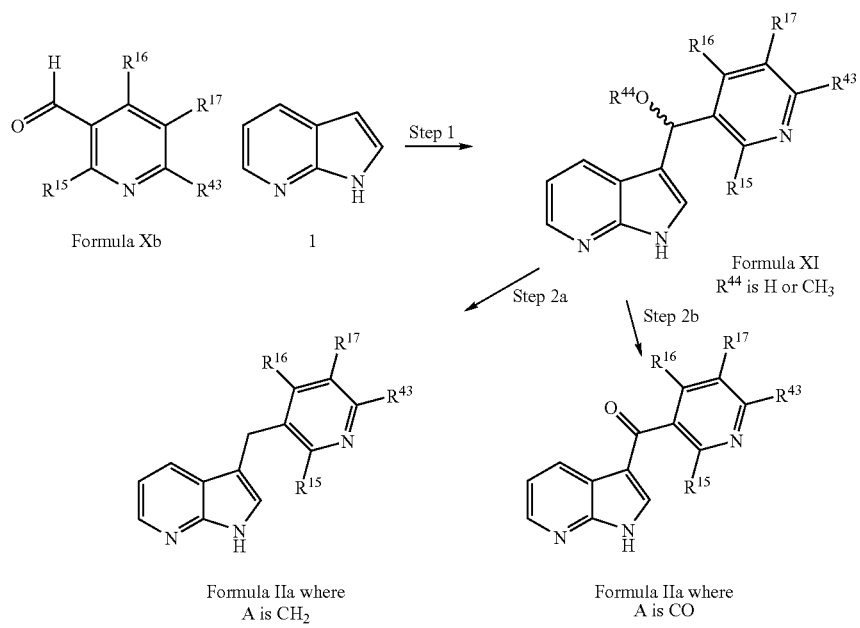

Step 1

Preparation of Formula XI where $R^{44}$ is Hydrogen or Methyl

To 7-azaindole 1 and a compound of Formula Xb is added an appropriate solvent (e.g. polar solvents such as methanol, tetrahydrofuran, and acetonitrile, or apolar solvents such as toluene) followed by an appropriate hydroxide or alkoxide base (e.g. potassium hydroxide, sodium methoxide). The reaction is typically allowed to stir at room temperature overnight. Isolation by conventional means (e.g. extraction and silica gel chromatography) provides compounds of Formula XI where $R^{44}$ is hydrogen or compounds of Formula XI where $R^{44}$ is methyl when methanol is used as a solvent, or a mixture of compounds of Formula XI where $R^{44}$ is hydrogen or methyl when methanol is used as a solvent. A resulting mixture may be separated by chromatography or used as a mixture in Step 2.

Step 2a

Preparation of Formula IIa where A is $CH_2$

To a compound of Formula XI where $R^{44}$ is hydrogen or methyl, in an appropriate polar solvent, (e.g. acetonitrile) is added a reducing agent (e.g. trifluoroacetic acid and triethylsilane). Typically, the reaction is allowed to stir at room temperature overnight. Isolation by conventional means (e.g. extraction and silica gel chromatography) provides compounds of Formula IIa where A is $CH_2$ and $R^{41}$ is H.

Step 2b

Preparation of Formula IIa where A is C(O)

Compound of Formula IIa where A is C(O) is prepared by oxidizing a compound of Formula XI where $R^{44}$ is hydrogen with an appropriate oxidizing agent (e.g. Dess-Martin reagent, TEMPO) in a non-reactive solvent (e.g. tetrahydrofuran). Isolation by conventional means (e.g. extraction and silica gel chromatography) provides compound of Formula IIa where A is C(O) and $R^{41}$ is H.

The reaction of Scheme 100 may be applied generally to compounds of Formula Xa, and also by replacing 7-azaindole 1, with 7-azaindoles substituted at the 4, 5, or 6 positions, preferable the 4 or 5 positions, to provide compounds of Formula I wherein $X_1$ is CH and $X_2$, $Y_1$ and $Y_2$ are $CR^6$, $CR^4$ and $CR^5$, respectively, or Formula Ib wherein V and W are CH and U and Z are independently $CR^{18}$. The compound of Formula Xa may be commercially available, or may be synthesized following the protocols of Examples herein. As such, a compound of Formula IIa where A is $CH_2$ (or analogous Formula I, Formula Ib) is prepared by reacting a 7-azaindole compound, optionally substituted at the 4, 5 or 6 position, with a suitable heteroaryl aldehyde (Formula Xa wherein $R^{42}$ is C(O)H) in an appropriate solvent (e.g. methanol, tetrahydrofuran, acetonitrile, toluene) with a hydroxide or alkoxide base (e.g. potassium hydroxide, sodium methoxide). The resulting compound is reacted in a polar solvent (e.g. acetonitrile) under reducing conditions to provide the desired compound. A compound of Formula IIa where A is C(O) (or analogous Formula I, Formula Ib) is prepared by reacting a 7-azaindole compound, optionally substituted at the 4, 5 or 6 position, with a suitable heteroaryl aldehyde (Formula Xa wherein $R^{42}$ is C(O)H) in an appropriate solvent (e.g. methanol, tetrahydrofuran, acetonitrile, toluene) with a hydroxide or alkoxide base (e.g. potassium hydroxide, sodium methoxide). From the resulting compound, the alcohol intermediate (e.g. Formula XI where $R^{44}$ is OH) is isolated and reacted in a non-reactive solvent (e.g. tetrahydrofuran) under oxidizing conditions to provide the desired compound.

Example 44

Synthesis of Compounds of Formula IIa, where A is $CH_2$ or C(O)

Compounds of Formula IIa, where A is $CH_2$ or C(O) may also be synthesized from compounds of Formula Xc (Formula Xa wherein J, E, F, G and K are C, n is 1, and $R^{42}$ is an organometallic substituent T) and compound IIId (Formula III wherein U, V, W and Z are CH, $R^{40}$ is C(O)H and $R^{41}$ is P) in four Steps according to Scheme 101.

Scheme 101

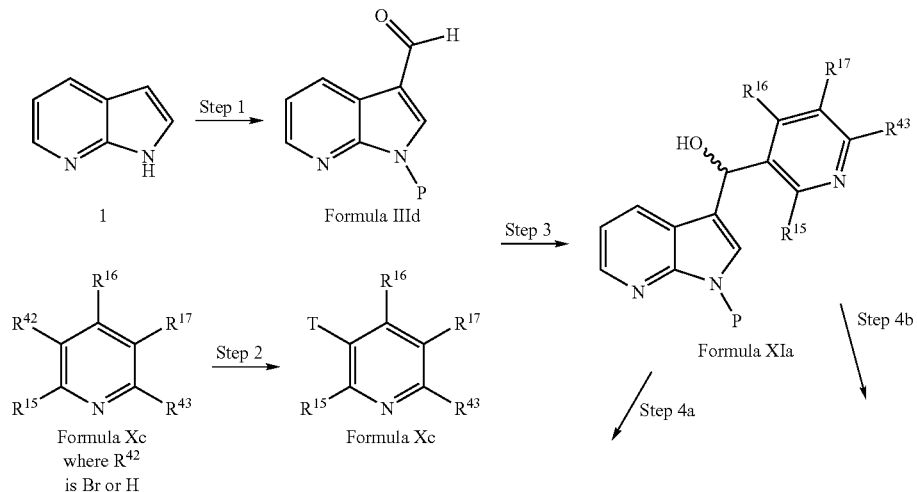

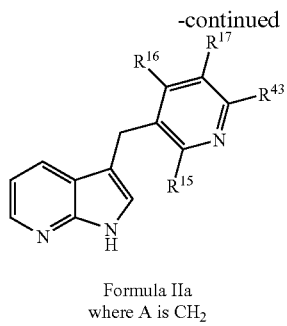

Formula IIa
where A is $CH_2$

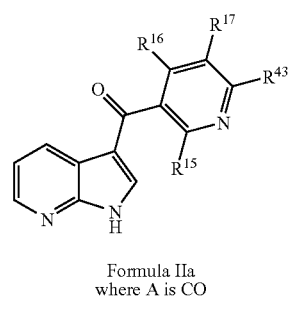

Formula IIa
where A is CO

Step 1

Preparation of Formula IIId 7-azaindole 1 is treated with hexamethyltetramine and acetic acid in water with heating to reflux for a few hours to introduce an aldehyde at the 3-position. This intermediate is isolated by concentration and extraction. A protecting group P is added to the N–1 position of the intermediate as described in Scheme 43, Step 1 to provide compound of Formula IIId.

Step 2

Preparation of Formula Xc where $R^{42}$ is T

Compound of Formula Xc where $R^{42}$ is an organometallic substituent T (e.g. lithium, MgBr) is obtained by treating compound of Formula Xc, where $R^{42}$ is bromine, with an organolithium reagent (e.g. butyllithium) or magnesium, or via ortholithiation with an organolithium reagent (e.g. butyllithium) when $R^{42}$ is hydrogen, in a non-reactive solvent (e.g. tetrahydrofuran), typically at reduced temperature (e.g. –78° C.) and used in Step 3 without isolation.

Step 3

Preparation of Formula XIa

Compound of Formula Xc where $R^{42}$ is T is added to compound of Formula IIIc in a non-reactive solvent (e.g. tetrahydrofuran) at reduced temperature (e.g. –78° C.) and stirred for several hours. After warming to room temperature, isolation by conventional means (e.g. extraction and silica gel chromatography) provides compound of Formula XIa.

Step 4a

Preparation of Formula IIa where A is $CH_2$

To a compound of Formula XIa, in an appropriate polar solvent, (e.g. acetonitrile) is added a reducing agent (e.g. trifluoroacetic acid and triethylsilane). Typically, the reaction is allowed to stir at room temperature overnight. Isolation by conventional means (e.g. extraction and silica gel chromatography), followed by deprotection of the N—P according to Scheme 43, Step 2 provides compounds of Formula IIa where A is $CH_2$ and $R^{41}$ is H.

Step 4b

Preparation of Formula IIa where A is C(O)

Compound of Formula IIa where A is C(O) is prepared from compound of Formula XIa following the protocol of Example 43, Step 2b, followed by deprotection according to Scheme 43, Step 2 to provide compound where $R^{41}$ is H.

Example 45

Synthesis of Compounds of Formula IIa, where A is C(O) or $CH_2$

Compounds of Formula IIa, where A is C(O) or $CH_2$, may be synthesized from compounds of Formula Xd (Formula Xa wherein J, E, F, G and K are C, n is 1, and $R^{42}$ is C(O)Cl) and compound 1 in one and two Steps, respectively, according to Scheme 102.

Scheme 102

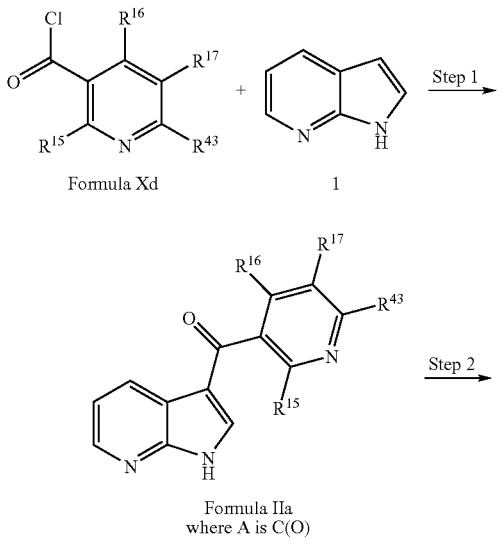

Formula Xd     1

Formula IIa
where A is C(O)

-continued

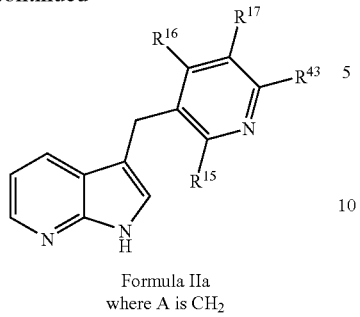

Formula IIa
where A is CH$_2$

Step 1

Preparation of Formula IIa where A is C=O

Compound of Formula IIa where A is a carbonyl is prepared by reacting compound 1 with an acid chloride of Formula Xd in the presence of a Lewis acid (e.g. aluminum trichloride) in a non-reactive solvent (e.g. dichloromethane) with stirring at room temperature for several hours. The reaction may be quenched with methanol and isolation by conventional means (e.g. extraction and silica gel chromatography) provides compound of Formula IIa where A is C=O and R$^{41}$ is H.

Step 2

Preparation of Formula IIa where A is CH$_2$

Compound of Formula IIa where A is CH$_2$ may be prepared by reacting compound IIa where A is C(O) with a reducing agent (e.g. lithium aluminum hydride) in a non-reactive solvent (e.g. tetrahydrofuran) for several hours. Isolation by conventional means (e.g. extraction and silica gel chromatography) provides compound of Formula IIa where A is CH$_2$ and R$^{41}$ is H.

Example 46

Synthesis of Compounds of Formula IIa, where A is CH$_2$

Compounds of Formula IIa, where A is CH$_2$ may be synthesized from compound 1 in two Steps according to Scheme 103.

Scheme 103

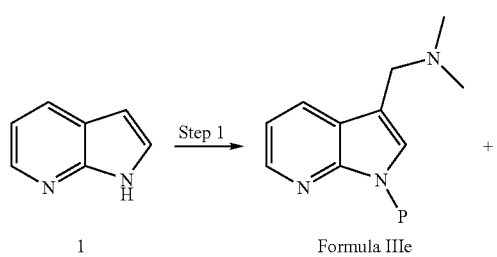

-continued

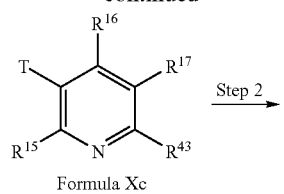

Formula Xc

Step 2

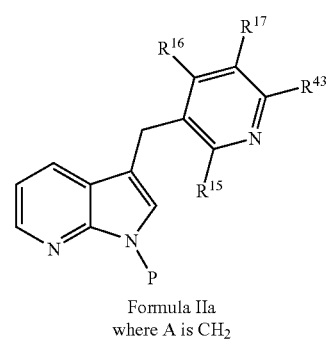

Formula IIa
where A is CH$_2$

Step 1

Preparation of Formula IIIe

Compound of Formula IIIe (Formula III where U, V, W and Z are CH, R$^{41}$ is P and R$^{40}$ is CH$_2$N(CH$_3$)$_2$) is synthesized from compound 1 following the literature procedure (Robinson, J. Am. Chem. Soc., 1955, 77, p. 457), followed by protection of the N—H according to Scheme 43, Step 1.

Step 2

Preparation of Formula IIa where A is CH$_2$

Compounds of Formula IIa where A is CH$_2$ is synthesized through the reaction of compounds of Formula IIIe with isopropyl chloroformate (or ethyl chloroformate) at room temperature in toluene to give a 3-chloromethyl intermediate. This intermediate, cooled to −78° C., is reacted with an organocopper reagent of Formula Xc where R$^{42}$ is the metal (prepared as described in Example 44, step 2) and a solution of copper cyanide and lithium chloride. The reaction may be stirred at −78° C. for one hour then allowed to warm to room temperature and quenched with a solution of 4:1 ammonium chloride:ammonium hydroxide. Isolation by conventional means (e.g. extraction and silica gel chromatography) provides compound of Formula IIa where A is CH$_2$ and R$^{41}$ is P, which can be removed according to Scheme 43 Step 2 to provide the compound where R$^{41}$ is H.

Example 47

Synthesis of Compounds of Formula IIa, where A is O

Compounds of Formula IIa, where A is O may be synthesized from compound 1 in two Steps according to Scheme 104.

Scheme 104

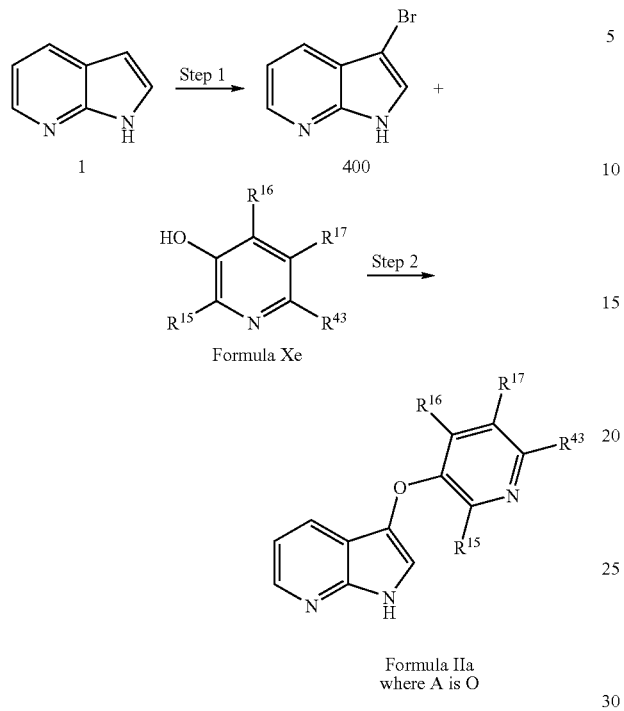

Formula IIa
where A is O

Step 1

Preparation of Compound 400

3-bromo-7-azaindole 400 may be prepared by dissolving 7-azaindole 1 in chloroform and slowly adding $Br_2$ in carbon tetrachloride at 0° C. After stirring for 1-2 hours, the reaction may be quenched in aqueous hydrochloric acid. Isolation by conventional means (e.g. extraction and silica gel chromatography) provides compound 400.

Step 2

Preparation of Formula IIa where A is O

Compound of Formula IIa where A is O is prepared by reacting 3-bromo-7-azaindole 400, protected at N—H according to Scheme 43, Step 1, with compound of Formula Xe (Formula Xa wherein J, E, F, G and K are C, n is 1, and $R^{42}$ is OH) in the presence of a base (e.g. sodium hydride) and a copper catalyst (e.g. copper bromide) in a non-reactive solvent (e.g. dimethylformamide) with heating (e.g. 120° C.) for several hours. Isolation by conventional means (e.g. extraction and silica gel chromatography), followed by removal of the protecting group according to Scheme 43, Step 2 provides compounds of Formula IIa where A is O and $R^{41}$ is H.

Example 48

Synthesis of Intermediate 1-(3-Hydroxy-pyrrolo[2,3-b]pyridin-1-yl)-ethanone (503)

1-(3-Hydroxy-pyrrolo[2,3-b]pyridin-1-yl)-ethanone 503 may be synthesized in three Steps from 2-Amino-nicotinic acid 500 as described in Scheme 105. The compound is an exemplary compound of Formula III wherein U, V, W and Z are CH, $R^{40}$ is OH and $R^{41}$ is P (e.g. acetyl).

Scheme 105

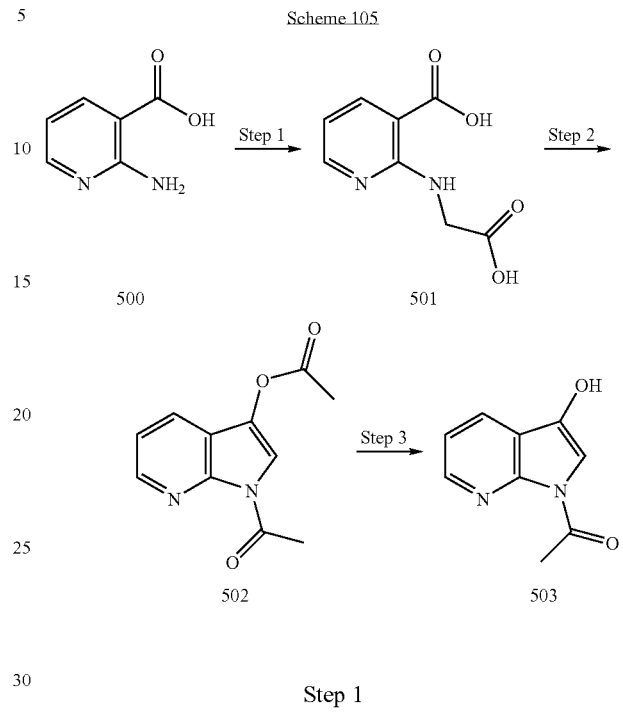

Step 1

Preparation of 2-(Carboxymethyl-amino)-nicotinic acid (501)

2-(Carboxymethyl-amino)-nicotinic acid 501 is prepared by reacting commercially available 2-Amino-nicotinic acid 500 with 2-chloroacetic acid in the presence of base (e.g. sodium carbonate) typically at room temperature for 1-4 hours followed by purification and isolation by conventional means (e.g. acid base extraction and recrystallization).

Step 2

Preparation of Acetic Acid 1-acetyl-1H-pyrrolo[2,3-b]pyridin-3-yl ester (502)

Acetic acid 1-acetyl-1H-pyrrolo[2,3-b]pyridin-3-yl ester 502 is prepared by reacting 2-(Carboxymethyl-amino)-nicotinic acid 501 with sodium acetate in refluxing acetic anhydride for several hours, followed by purification and isolation by conventional means (e.g. recrystallization) (Su & Tsou; *J. Am. Chem. Soc.,* 82, 1960, 1187).

Step 3

Preparation of 1-(3-Hydroxy-pyrrolo[2,3-b]pyridin-1-yl)-ethanone (503)

1-(3-Hydroxy-pyrrolo[2,3-b]pyridin-1-yl)-ethanone 503 is prepared from acetic acid 1-acetyl-1H-pyrrolo[2,3-b]pyridin-3-yl ester 502 by selective removal of the acetate at the 3-position by reaction with sodium in methanol at room tem-

Example 49

Synthesis of Compounds of Formula IIa, where A is O

Compounds of Formula IIa, where A is O may be synthesized from compound of Formula IIIf (Formula III where U, V, W and Z are CH, $R^{41}$ is P and $R^{40}$ is OH) and compound of Formula Xf (Formula Xa wherein J, E, F, G and K are C, n is 1, and $R^{42}$ is leaving group L) in one Step according to Scheme 106.

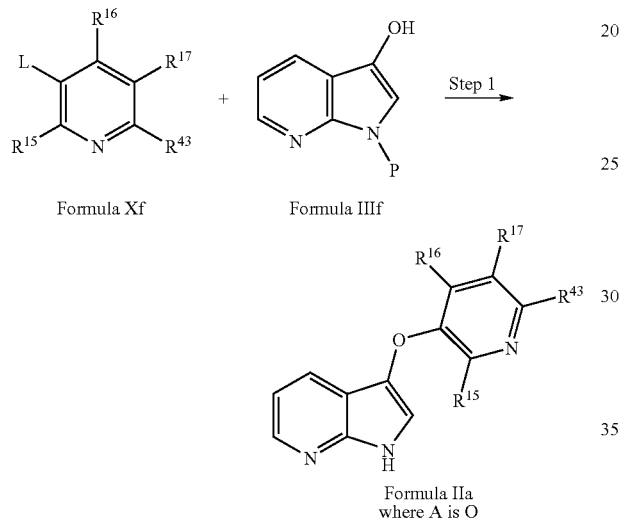

Step 1

Preparation of Formula IIa where A is O

Formula IIa where A is O is prepared by dissolving compound of Formula Xf, where L is a leaving group (e.g. halogen or triflate), in a non-reactive solvent (e.g. dimethylformamide) in the presence of a base (e.g. sodium hydride). Compound of Formula IIIf is added in the presence of a copper catalyst (e.g. copper bromide) with heating for several hours. Removal of the protecting group according to Scheme 43, Step 2 followed by isolation by conventional means (e.g. extraction and silica gel chromatography) provides compounds of Formula IIa where A is O and $R^{41}$ is H.

Example 50

Synthesis of Compounds of Formula IIa, when A is NH or N—$R^{45}$

Compounds of Formula IIa, where A is NH or $NR^{45}$ ($R^{45}$ consistent with definition of A for compounds of Formula Ib or $L^1$ for compounds of Formula I) may be synthesized from 3-bromo-7-azaindole 400 and a compound of Formula Xg (Formula Xa wherein J, E, F, G and K are C, n is 1, and $R^{42}$ is $NH_2$) in two Steps according to Scheme 107.

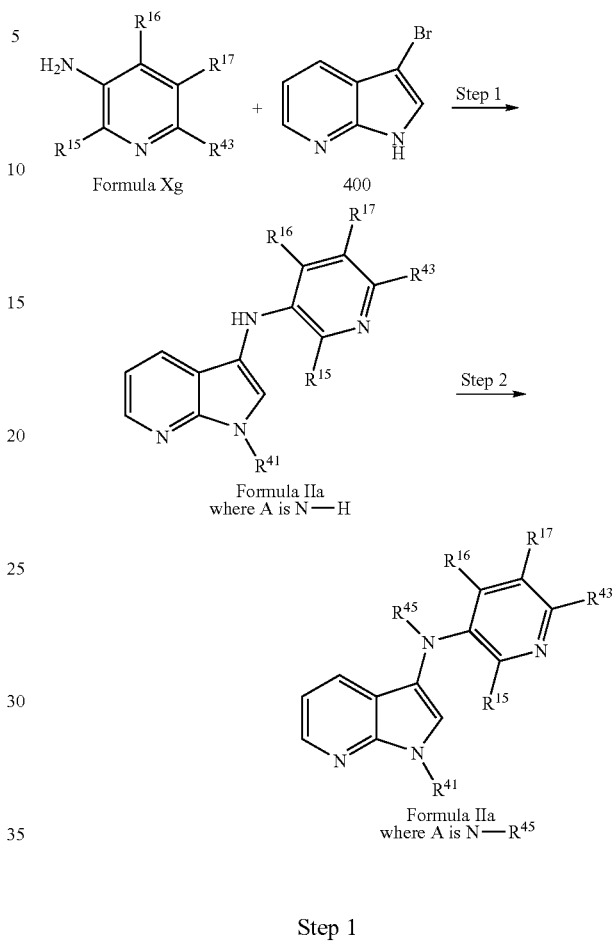

Step 1

Preparation of Formula IIa where A is NH

Compound of Formula IIa where A is NH is prepared by reacting 3-bromo-7-azaindole 400 with neat compound of Formula Xg with heating for several hours (e.g. 150° C.). Alternatively, 400 may be reacted with compound of Formula Xg using palladium catalyzed Buchwald-Hartwig conditions (i.e. a palladium catalyst (e.g. Tris(dibenzylideneacetone)dipalladium(0)), a ligand (e.g. tri-t-butylphosphine), and a base (e.g. sodium t-butoxide) in a non-reactive solvent (e.g. toluene) with heating (e.g. 80° C.) for several hours). Isolation by conventional means (e.g. extraction and silica gel chromatography) provides compound of Formula IIa where A is NH and $R^{41}$ is P. Removal of the protecting group according to Scheme 43, Step 2 provides compounds of Formula IIa where A is NH and $R^{41}$ is H.

Step 2

Preparation of Formula IIa where A is N—$R^{45}$

Compound of Formula IIa where A is N—$R^{45}$ is prepared by reacting compound of Formula IIa, where $R^{41}$ is P and A is NH, with an appropriate reagent with a leaving group (e.g. methyl iodide, acetyl chloride) in the presence of a base (e.g. potassium carbonate, diisopropylethylamine) in a non-reactive solvent (e.g. dimethylformamide) for several hours at room temperature. Removal of the protecting group according to Scheme 43, Step 2 and isolation by conventional means (e.g. extraction and silica gel chromatography) provides compound of Formula IIa where A is N—$R^{45}$ and $R^{41}$ is H.

Example 51

Synthesis of Intermediate of Formula IIIh where $R^{40}$ is $NH_2$

Compounds of Formula IIIh (Formula III where U, V, W and Z are CH, $R^{41}$ is H and $R^{40}$ is $NH_2$) may be synthesized from 7-azaindole 1 in three Steps according to Scheme 108.

Scheme 108

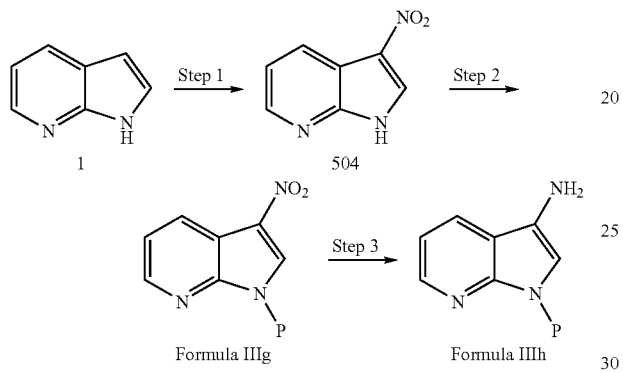

Formula IIIg    Formula IIIh

Step 1

Preparation of 3-nitro-7-azaindole (504)

3-nitro-7-azaindole 504 is prepared by adding 7-azaindole 1 to fuming nitric acid while cooling (e.g. 0° C.). After stirring for one to several hours, water is carefully added and the mixture neutralized with saturated sodium bicarbonate. The solids are collected by filtration and dried to provide 3-nitro-7-azaindole 504.

Step 2

Preparation of Formula IIIg

Compound of IIIg (Formula III where U, V, W and Z are CH, $R^{41}$ is H and $R^{40}$ is $NH_2$) is prepared from 3-nitro-7-azaindole 504 according to Scheme 43, Step 1.

Step 3

Preparation of Formula IIIh

Compound of Formula IIIh is prepared from compound of Formula IIIg by reduction of the nitro group (e.g. hydrogen gas and palladium on carbon in methanol). The mixture is filtered and concentrated to provide compound of Formula IIIh.

Example 52

Synthesis of Compounds of Formula IIa where A is NH or $NR^{45}$

Compounds of Formula IIa where A is NH or $NR^{45}$ ($R^{45}$ consistent with definition of A for compounds of Formula Ib or $L^1$ for compounds of Formula I) may be synthesized from a compound of Formula IIIh and a compound of Formula Xh (Formula Xa wherein J, E, F, G and K are C, n is 1, and $R^{42}$ is Br) in two Steps as described in Scheme 109.

Scheme 109

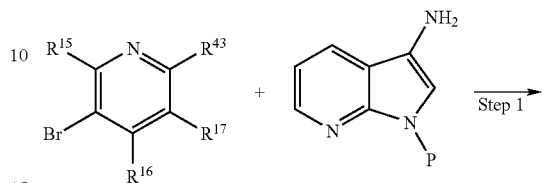

Formula Xh    Formula IIIh

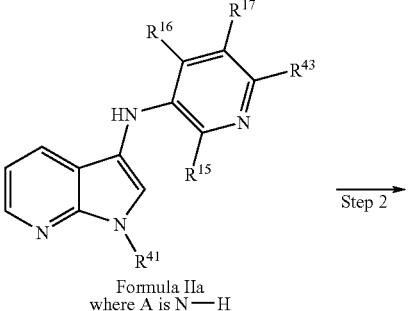

Formula IIa
where A is N—H

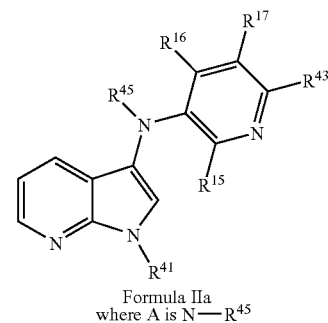

Formula IIa
where A is N—$R^{45}$

Step 1

Preparation of Formula IIa where A is NH

Compound of Formula IIa where A is NH is prepared by reacting compound of Formula Xh with compound of Formula IIIh (prepared as described in Example 51) with heating for several hours (e.g. 100° C.). Alternatively, compound of Formula IIIh is reacted with compound of Formula Xh using palladium catalyzed Buchwald-Hartwig conditions (i.e. a palladium catalyst (e.g. Tris(dibenzylideneacetone)dipalladium(0)), a ligand (e.g. tri-t-butylphosphine), and a base (e.g. sodium t-butoxide) in a non-reactive solvent (e.g. toluene) with heating (e.g. 80° C.) for several hours). Isolation by conventional means (e.g. extraction and silica gel chromatography) provides compound of Formula IIa where A is NH and $R^{41}$ is P. Removal of the protecting group according to Scheme 43, Step 2 provides compounds of Formula IIa where A is NH and $R^{41}$ is H.

Step 2

Preparation of Formula IIa where A is N—R⁴⁵

Compound of Formula IIa where A is N—R⁴⁵ is prepared as described in Example 50, Step 2.

Example 53

Synthesis of Compounds of Formula IIa where A is S

Compounds of Formula IIa where A is S may be synthesized from 7-azaindole 1 and a compound of Formula Xi (Formula Xa wherein J, E, F, G and K are C, n is 1, and $R^{42}$ is an aryl disulfide) in one Step as described in Scheme 110.

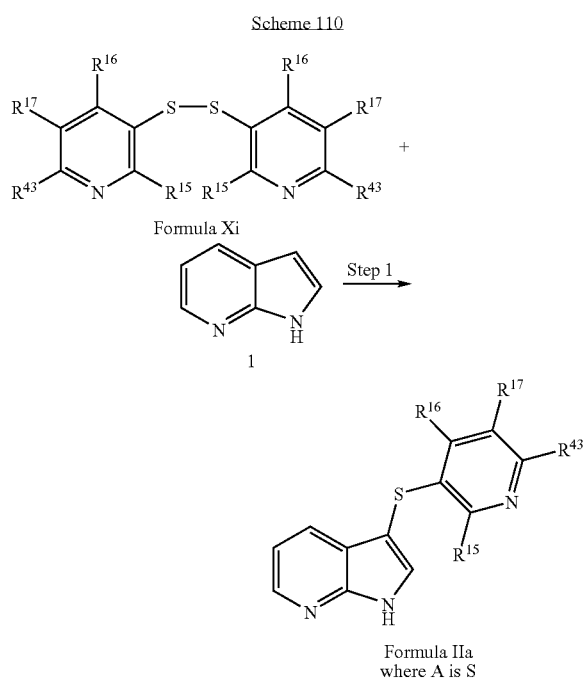

Step 1

Preparation of Formula IIa where A is S

Compound of Formula IIa where A is S is prepared by dissolving 7-azaindole 1 in an appropriate solvent (e.g. dimethylformamide) with a base (e.g. sodium hydride), followed by the addition of a symmetrical aryl disulfide of Formula Xi. After stirring at room temperature for several hours, the reaction is quenched with water, followed by isolation by conventional means (e.g. extraction and silica gel chromatography) to provide compounds of Formula IIa where A is S and $R^{41}$ is H.

Example 54

Synthesis of Compounds of Formula IIa where A is S

Compounds of Formula IIa where A is S may be synthesized from 3-bromo-7-azaindole 400 and a compound of Formula Xj (Formula Xa wherein J, E, F, G and K are C, n is 1, and $R^{42}$ is an SH) in one Step as described in Scheme 111.

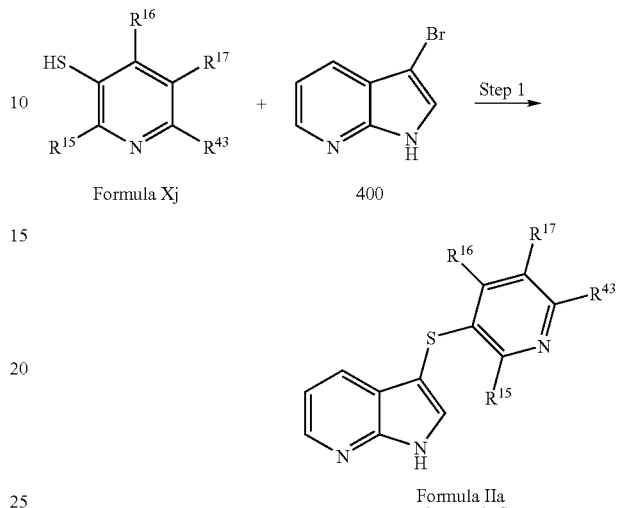

Step 1

Preparation of Formula IIa where A is S

Compound of Formula IIa where A is S is prepared by reacting 3-bromo-7-azaindole 400 with compound of Formula Xj in the presence of a base (e.g. sodium hydride) in an appropriate solvent (e.g. dimethylformamide) with heating for several hours (e.g. 100° C.). Isolation by conventional means (e.g. extraction and silica gel chromatography) provides compound of Formula IIa where A is S and $R^{41}$ is H.

Example 55

Synthesis of Compounds of Formula IIa, where A is $S(O)_2$

Compounds of Formula IIa where A is $S(O)_2$ may be synthesized from a compound of Formula IIa where A is S and $R^{41}$ is H in one Step as described in Scheme 112.

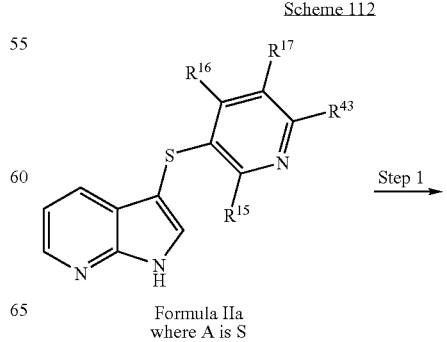

-continued

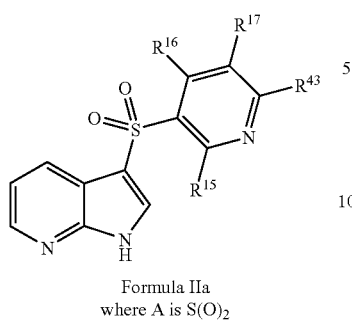

Formula IIa
where A is S(O)₂

Step 1

Preparation of Formula IIa where A is S(O)₂

Compound of Formula IIa where A is S(O)₂ is prepared by reacting a compound of Formula IIa where A is S (prepared as described in Example 53 or 54) with an oxidizing agent (e.g. meta-chloro-peroxybenzoic acid, hydrogen peroxide) in an appropriate aprotic solvent (e.g. dichloromethane). Isolation by conventional means (e.g. extraction and silica gel chromatography) provides compound of Formula IIa where A is S(O)₂ and $R^{41}$ is H.

Example 56

Synthesis of Compounds of Formula IIa where A is S(O)₂

Compounds of Formula IIa where A is S(O)₂ may be synthesized from 7-azaindole 1 and a compound of Formula Xk (Formula Xa wherein J, E, F, G and K are C, n is 1, and $R^{42}$ is an S(O)₂Cl) in one Step as described in Scheme 113.

Scheme 113

Formula Xk + 1 →[Step 1]

Formula IIa
where A is S(O)₂

Step 1

Preparation of Formula IIa where A is S(O)₂

Compound of Formula IIa where A is S(O)₂ is prepared by reacting 7-azaindole 1 with a sulfonyl chloride of Formula Xk dissolved in trifluoroacetic acid, in the presence of a catalyst (e.g. indium trichloride) and trifluorosulfonic acid with heating (e.g. 70° C.) for a few hours. Neutralization with sodium hydroxide and isolation by conventional means (e.g. extraction and silica gel chromatography) provides compound of Formula IIa where A is S(O)₂ and $R^{41}$ is H (Garzya et al., Tetrahedron Lett. 2004, 45:1499-1501).

Example 57

Synthesis of Compounds of Formula IIa where A is CF₂

Compounds of Formula IIa where A is CF₂ may be synthesized from a compound of Formula IIa where A is C(O) and $R^{41}$ is P in one Step as described in Scheme 114.

Scheme 114

Formula IIa
where A is C(O) →[Step 1]

Formula IIa
where A is CF₂

Step 1

Preparation of Formula IIa where A is CF₂

Compound of Formula IIa where A is CF₂ is prepared by reacting a compound of Formula IIa where A is C(O) and $R^{41}$ is P (prepared as described in Example 44) with a fluorinating agent (e.g. (diethylamino)sulfur trifluoride) with heating for several hours. Isolation by conventional means (e.g. extraction and silica gel chromatography) provides compound of Formula IIa where A is $CF_2$ and $R^{41}$ is H.

Example 58

Synthesis of Compounds of Formula IIa where A is C(S)

Compounds of Formula IIa where A is C(S) may be synthesized from a compound of Formula IIa where A is C(O) and $R^{41}$ is H in one Step as described in Scheme 115.

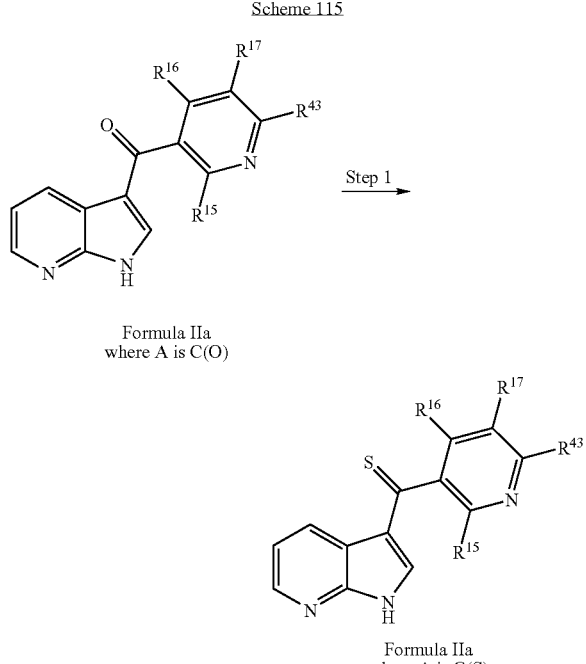

Step 1

Preparation of Formula IIa where A is C(S)

Compound of Formula IIa where A is C(S) is prepared by reacting a compound of Formula IIa where A is C(O) and $R^{41}$ is H (prepared as described in Example 43, 44 or 45) with Lawesson's reagent, (1,3,2,4-dithiadiphosphetane-2,3-disulfide), in an appropriate solvent (e.g. tetrahydrofuran) with heating for several hours. Isolation by conventional means (e.g. extraction and silica gel chromatography) provides compound of Formula IIa where A is C(S) and $R^{41}$ is H.

Example 59

Synthesis of Compounds of Formula IIa where A is S(O)

Compounds of Formula IIa where A is S(O) may be synthesized from a compound of Formula IIa where A is S and $R^{41}$ is H in one Step as described in Scheme 116.

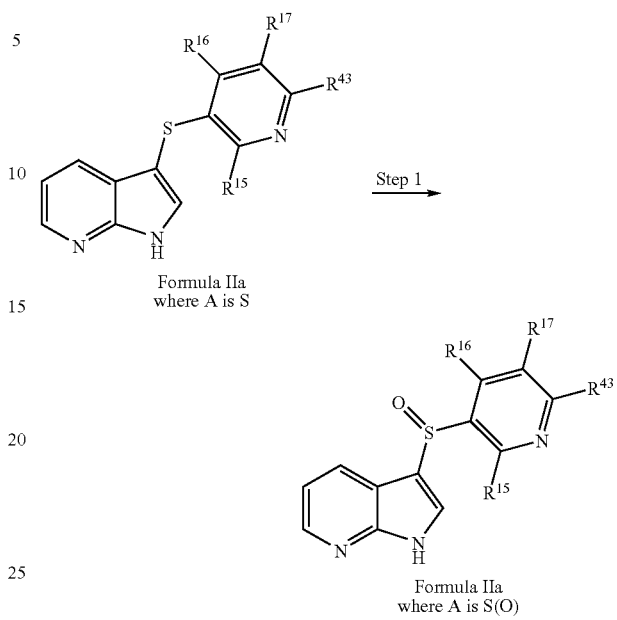

Step 1

Preparation of Formula IIa where A is S(O)

Compound of Formula IIa where A is S(O) is prepared by reacting compound of Formula IIa where A is S and $R^{41}$ is H (prepared as described in Example 53 or 54) with one equivalent of an oxidizing agent (e.g. meta-chloro-peroxybenzoic acid, hydrogen peroxide, oxone) in an appropriate aprotic solvent (e.g. dichloromethane). Isolation by conventional means (e.g. extraction and silica gel chromatography) provides compound of Formula IIa where A is S(O) and $R^{41}$ is H.

Compounds of Formula III may be used in the preparation of compounds of Formula Ib or IIa as described in Examples 43-59 by substituting the 7-azaindole or analog shown in the example with a compound of Formula III. $R^{40}$ is the substituent at the 3-position used in the example appropriate for coupling to compounds of Formula X (e.g. hydrogen, C(O)H, $CH_2N(CH_3)_2$, C(O)Cl, bromo, amino, hydroxy, thio) and $R^{41}$ is hydrogen or protecting group P.

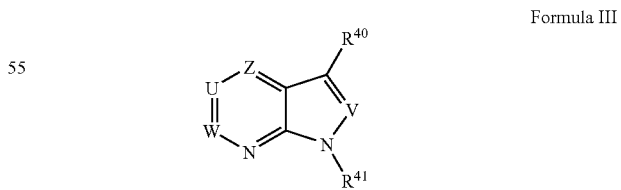

Formula III

Compounds of Formula IIIi, i.e. Formula III where V and W are CH, at least one of U and Z are $CR^{46}$, preferably one of U and Z is $CR^{46}$ and the other of U and Z is CH, where $R^{46}$ is as defined for $R^{18}$, excluding hydrogen, in Formula Ib of [0026], may be used in the synthesis of compounds of Formula Ib and IIa as described for compounds for Formula III.

Formula IIIi

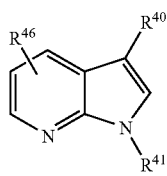

The examples provided for the synthesis of compounds of Formula IIIi are also applicable to many compounds meeting other definitions of Formula III or compounds of Formula IIIi can be further substituted, particularly at the 3-position, to provide compounds of Formula III, or related compounds that may be used to synthesize compounds of Formula I.

Additionally, the techniques used for preparation of compounds of Formula III and IIIi may be applied to compounds of Formula Ib where $R^5$ is bromo, chloro, or amino, to provide other compounds of Formula Ib.

Example 60

Synthesis of Intermediate of Formula IVa

Compounds of Formula IVa may be synthesized from 3-methyl-5-nitro-pyridin-2-ylamine 505 in three Steps as described in Scheme 117.

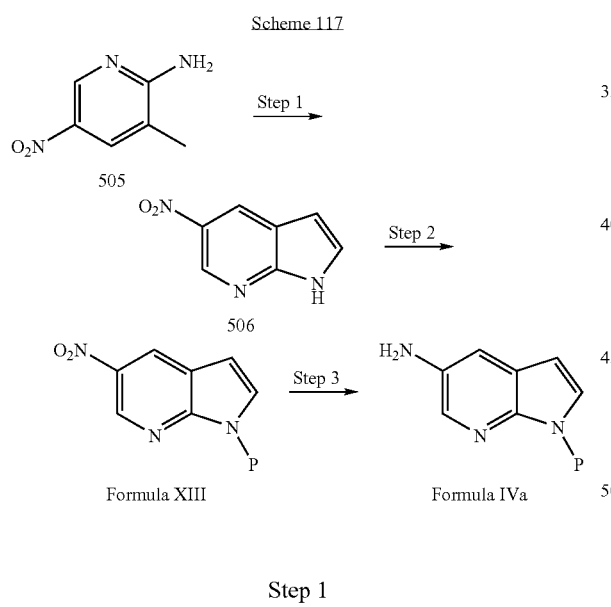

Step 1

Preparation of 5-Nitro-1H-pyrrolo[2,3-b]pyridine (506)

5-Nitro-1H-pyrrolo[2,3-b]pyridine 506 of is prepared by reacting 3-methyl-5-nitro-pyridin-2-ylamine 505 with t-butyloxycarbonyl anhydride in an appropriate solvent (e.g. ethyl acetate and hexanes). Concentration and extraction provides a Boc-protected intermediate that is then reacted with 2 equivalents of butyllithium in an appropriate polar solvent (e.g. tetrahydrofuran) with cooling (e.g. 0° C.), followed by the addition of dimethylformamide and stirring for 30 minutes to one hour, followed by addition of 5.5 M HCl. Isolation by conventional means (e.g. extraction and silica gel chromatography) provides 506. (Hands et. al., Synthesis 1996, 877-882.)

Step 2

Preparation of Formula XIII

Compound of Formula XIII is prepared by reacting 5-Nitro-1H-pyrrolo[2,3-b]pyridine 506 as described in Scheme 43, Step 1.

Step 3

Preparation of Formula IVa

Compound of Formula IVa is prepared from compound of Formula XIII by reduction of the nitro group (e.g. hydrogen gas and palladium on carbon in methanol). The mixture is filtered and concentrated to provide compound of Formula IVa.

Example 61

Synthesis of Intermediate of Formula IVb

Compounds of Formula IVa may be synthesized from 7-azaindole 1 in four Steps as described in Scheme 118.

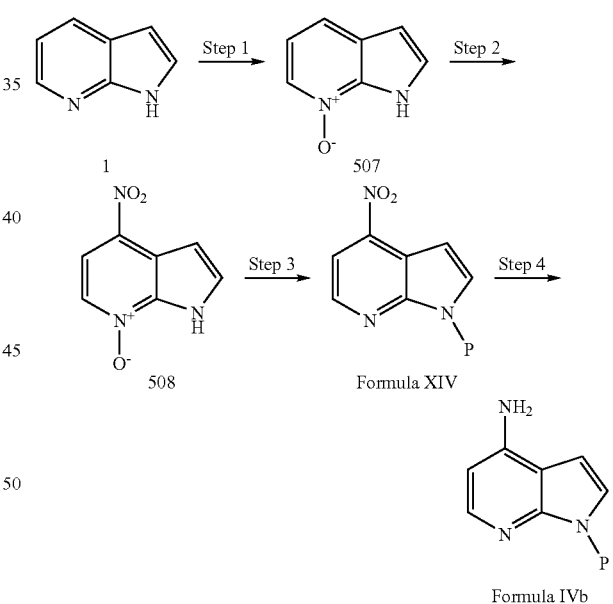

Step 1

Preparation of 1H-Pyrrolo[2,3-b]pyridine 7-oxide (507)

1H-Pyrrolo[2,3-b]pyridine 7-oxide 507 is prepared by reacting 7-azaindole 1 with an oxidizing agent (e.g. m-chloro-peroxybenzoic acid) in an appropriate solvent (e.g. dichloromethane). After stirring at room temperature for 30 minutes to one hour, compound 507 is collected by filtration.

Step 2

Preparation of 4-Nitro-1H-pyrrolo[2,3-b]pyridine 7-oxide (508)

4-Nitro-1H-pyrrolo[2,3-b]pyridine 7-oxide 508 is prepared by dissolving 1H-Pyrrolo[2,3-b]pyridine 7-oxide 507 in nitric acid, followed by the addition of sulfuric acid. Heating (e.g. 70° C.) for one hour, followed by pouring into water provides compound 508, which is isolated by filtration. (Schneller et. al., J. Org. Chem. 1980, 45:4045)

Step 3

Preparation of Compound of Formula XIV

Compound of Formula XIV is prepared from 4-Nitro-1H-pyrrolo[2,3-b]pyridine 7-oxide 508 by addition of phosphorous trichloride in an appropriate solvent (e.g. ethyl acetate) and heating (e.g. 80° C.) for several minutes. Neutralization with base (e.g. potassium carbonate) followed by extraction affords the intermediate that can then be protected at the N–1 hydrogen according to Scheme 43, Step 1, to provide compound of Formula XIV.

Step 4

Preparation of Formula IVb

Compound of IVb is prepared from compound of Formula XIV by reduction of the nitro group (e.g. hydrogen gas and palladium on carbon in methanol). The mixture can be filtered and concentrated to provide compound of Formula IVb.

Example 62

Synthesis of Compounds of Formula IIIi where $R^{46}$ is $NHR^{47}$ and $R^{40}$ is H Compounds of Formula IIIi where $R^{46}$ is $NHR^{47}$ and $R^{40}$ is H may be synthesized from a compound of Formula IVa or IVb in one Step as described in Scheme 119.

Scheme 119

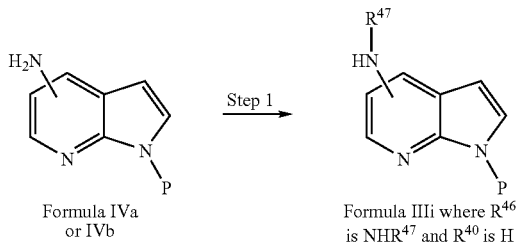

Formula IVa or IVb → Formula IIIi where $R^{46}$ is $NHR^{47}$ and $R^{40}$ is H

Step 1

Preparation of Compound of Formula IIIi where $R^{46}$ is $NHR^{47}$ and $R^{40}$ is H Compound of Formula IIIi where $R^{46}$ is $NHR^{47}$ and $R^{40}$ is H ($R^{47}$ is optionally substituted lower alkyl, optionally substituted lower alkenyl, optionally substituted lower alkynyl, optionally substituted cycloalkyl, optionally substituted heterocycloalkyl, optionally substituted aryl or optionally substituted heteroaryl) is prepared from intermediate Formula IVa (Example 60) or IVb (Example 61) by reaction with $R^{47}$—X, where X is a leaving group, (e.g. alkylating agent such as methyliodide) in the presence of a base (e.g. potassium carbonate) in an appropriate solvent (e.g. dimethylformamide) for several hours at room temperature. Isolation by conventional means (e.g. extraction and silica gel chromatography) provides compounds of Formula IIIi where $R^{46}$ is $NHR^{47}$, $R^{40}$ is H and $R^{41}$ is P.

Example 63

Synthesis of Compounds of Formula IIIi where $R^{46}$ is $NHCH_2R^{48}$ and $R^{40}$ is H Compounds of Formula IIIi where $R^{46}$ is $NHCH_2R^{48}$ and $R^{40}$ is H may be synthesized from a compound of Formula IVa or IVb in one Step as described in Scheme 120.

Scheme 120

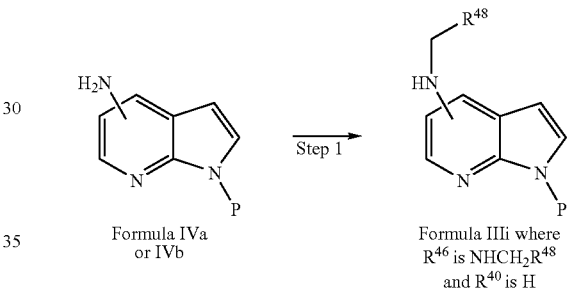

Formula IVa or IVb → Formula IIIi where $R^{46}$ is $NHCH_2R^{48}$ and $R^{40}$ is H

Step 1

Preparation of Compound of Formula IIIc where $R^{46}$ is $NHCH_2R^{48}$ and $R^{40}$ is H Compound of Formula IIIi where $R^{46}$ is $NHCH_2R^{48}$ and $R^{40}$ is H ($R^{48}$ is consistent with optionally substituted lower alkyl) is prepared from intermediate Formula IVa (Example 60) or IVb (Example 61) by reductive amination using an aldehyde of the formula $R^{48}$—C(O)H in the presence of a catalytic amount of acid (e.g. acetic acid) and a reducing agent (e.g. sodium triacetoxyborohydride) in a non-reactive solvent (e.g. dichloroethane). After stirring for several hours, isolation by conventional means (e.g. extraction and silica gel chromatography) provides compounds of Formula IIIi where $R^{46}$ is $NHCH_2R^{48}$, $R^{40}$ is H and $R^{41}$ is P.

Example 64

Synthesis of Compounds of Formula IIIi where $R^{46}$ is $NHC(O)R^{49}$ and $R^{40}$ is H Compounds of Formula IIIi where $R^{46}$ is $NHC(O)R^{49}$ and $R^{40}$ is H may be synthesized from a compound of Formula IVa or IVb in one Step as described in Scheme 121.

Scheme 121

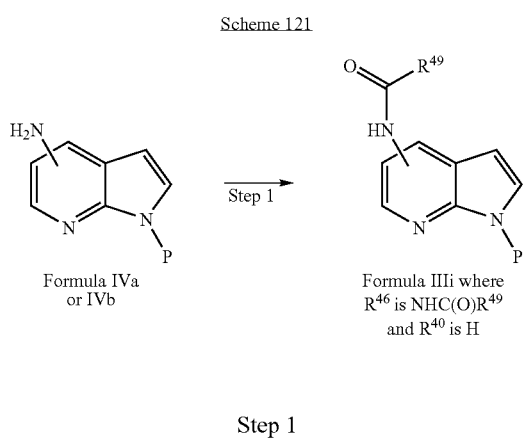

Formula IVa or IVb → Formula IIIi where $R^{46}$ is NHC(O)$R^{49}$ and $R^{40}$ is H

Step 1

Preparation of Compound of Formula IIIi where $R^{46}$ is NHC(O)$R^{49}$ and $R^{40}$ is H Compound of Formula IIIi where $R^{46}$ is NHC(O)$R^{49}$ and $R^{40}$ is H($R^{49}$ is optionally substituted lower alkyl, optionally substituted lower alkenyl, optionally substituted lower alkynyl, optionally substituted cycloalkyl, optionally substituted heterocycloalkyl, optionally substituted aryl or optionally substituted heteroaryl) is prepared from intermediate Formula IVa (Example 60) or IVb (Example 61) by reaction with an activated carboxylic acid of the formula $R^{49}$—C(O)X where X is a leaving group such as chloro (e.g. benzoyl chloride) in the presence of a base (e.g. N,N-diisopropylethylamine (DIEA)) in a non-reactive solvent (e.g. dichloromethane). After stirring for several hours, isolation by conventional means (e.g. extraction and silica gel chromatography) provides compounds of Formula IIIi where $R^{46}$ is NHC(O)$R^{49}$, $R^{40}$ is H and $R^{41}$ is P.

Example 65

Synthesis of Compounds of Formula IIIi where $R^{46}$ is NHC(O)NH$R^{50}$ and $R^{40}$ is H Compounds of Formula IIIi where $R^{46}$ is NHC(O)NH$R^{50}$ and $R^{40}$ is H may be synthesized from a compound of Formula IVa or IVb in one Step as described in Scheme 122.

Scheme 122

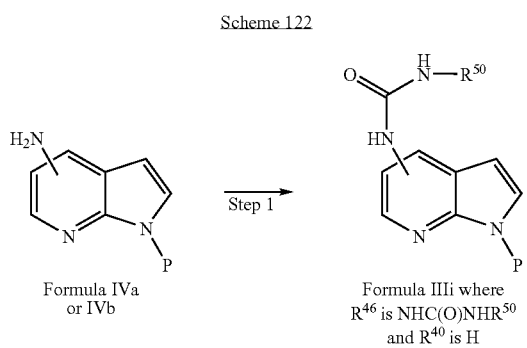

Formula IVa or IVb → Formula IIIi where $R^{46}$ is NHC(O)NH$R^{50}$ and $R^{40}$ is H

Step 1

Preparation of Compound of Formula IIIi where $R^{46}$ is NHC(O)NH$R^{50}$ and $R^{40}$ is H Compound of Formula IIIi where $R^{46}$ is NHC(O)NH$R^{50}$ and $R^{40}$ is H($R^{50}$ is optionally substituted lower alkyl, optionally substituted lower alkenyl, optionally substituted lower alkynyl, optionally substituted cycloalkyl, optionally substituted heterocycloalkyl, optionally substituted aryl or optionally substituted heteroaryl) is prepared from intermediate Formula IVa (Example 60) or IVb (Example 61) by reaction with an isocyanate of the formula $R^{50}$—NCO (e.g. propylisocyanate) in the presence of a base (e.g. DIEA) in a non-reactive solvent (e.g. dichloromethane). After stirring for several hours, isolation by conventional means (e.g. extraction and silica gel chromatography) provides compounds of Formula IIIi where $R^{46}$ is NHC(O)NH$R^{50}$, $R^{40}$ is H and $R^{41}$ is P.

Example 66

Synthesis of Compounds of Formula IIIi where $R^{46}$ is NHC(S)NH$R^{51}$ and $R^{40}$ is H Compounds of Formula IIIi where $R^{46}$ is NHC(S)NH$R^{51}$ and $R^{40}$ is H may be synthesized from a compound of Formula IVa or IVb in one Step as described in Scheme 123.

Scheme 123

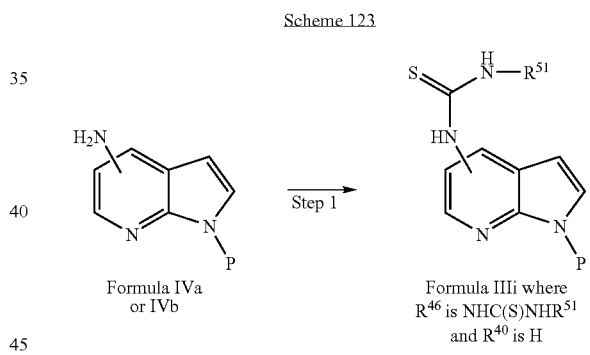

Formula IVa or IVb → Formula IIIi where $R^{46}$ is NHC(S)NH$R^{51}$ and $R^{40}$ is H

Step 1

Preparation of Compound of Formula IIIi where $R^{46}$ is NHC(S)NH$R^{51}$ and $R^{40}$ is H Compound of IIIi where $R^{46}$ is NHC(S)NH$R^{51}$ and $R^{40}$ is H($R^{51}$ is optionally substituted lower alkyl, optionally substituted lower alkenyl, optionally substituted lower alkynyl, optionally substituted cycloalkyl, optionally substituted heterocycloalkyl, optionally substituted aryl or optionally substituted heteroaryl) is prepared from intermediate Formula IVa (Example 60) or IVb (Example 61) by reaction with an isothiocyanate of the formula $R^{51}$—NCS (e.g. propylisothiocyanate) in the presence of a base (e.g. DIEA) in a non-reactive solvent (e.g. dichloromethane). After stirring for several hours, isolation by conventional means (e.g. extraction and silica gel chromatography) provides compounds of Formula IIIi where $R^{46}$ is NHC(S)NH$R^{51}$, $R^{40}$ is H and $R^{41}$ is P.

Example 67

Synthesis of Compounds of Formula IIIi where $R^{46}$ is $NHS(O)_2R^{52}$ and $R^{40}$ is H Compounds of Formula IIIi where $R^{46}$ is $NHS(O)_2R^{52}$ and $R^{40}$ is H may be synthesized from a compound of Formula IVa or IVb in one Step as described in Scheme 124.

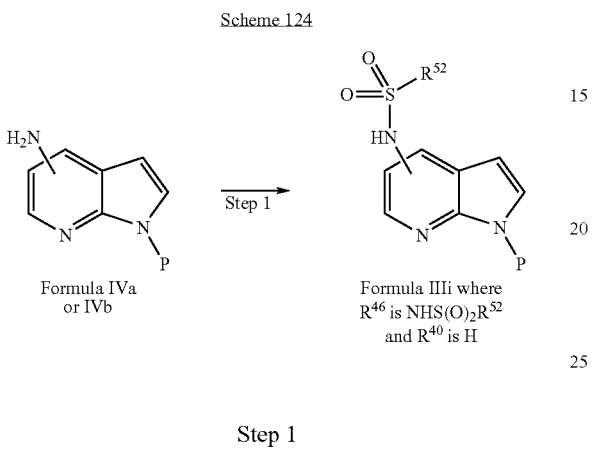

Step 1

Preparation of Compound of Formula IIIi where $R^{46}$ is $NHS(O)_2R^{52}$ and $R^{40}$ is H Compound Formula IIIi where $R^{46}$ is $NHS(O)_2R^{52}$ and $R^{40}$ is H ($R^{52}$ is optionally substituted lower alkyl, optionally substituted lower alkenyl, optionally substituted lower alkynyl, optionally substituted cycloalkyl, optionally substituted heterocycloalkyl, optionally substituted aryl or optionally substituted heteroaryl) is prepared from intermediate Formula IVa (Example 60) or IVb (Example 61) by reaction with a sulfonyl chloride of the formula $R^{52}$—$S(O)_2Cl$ (e.g. propylsulfonyl chloride) in the presence of a base (e.g. DIEA, pyridine) in a non-reactive solvent (e.g. dichloromethane). After stirring for several hours, isolation by conventional means (e.g. extraction and silica gel chromatography) provides compounds of Formula IIIi where $R^{46}$ is $NHS(O)_2R^{52}$, $R^{40}$ is H and $R^{41}$ is P.

Example 68

Synthesis of Intermediate of Formula Va

Compounds of Formula Va may be synthesized from 7-azaindole 1 in two Steps as described in Scheme 125.

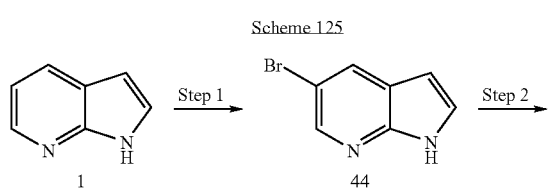

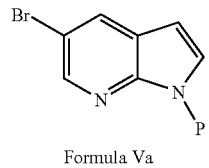

Step 1

Preparation of 5-bromo-7-azaindole (44)

5-bromo-7-azaindol 44 is prepared from 7-azaindole 1 as described in Mazeas et. al., Heterocycles 1999, 50:1065-1080.

Step 2

Preparation of Intermediate of Formula Va

Intermediate of Formula Va is prepared by protecting 5-bromo-7-azaindol 44 as described in Scheme 43, Step 1.

Example 69

Synthesis of Intermediate of Formula Vb

Compounds of Formula Vb may be synthesized from 1H-Pyrrolo[2,3-b]pyridine 7-oxide 507 in two Steps as described in Scheme 126.

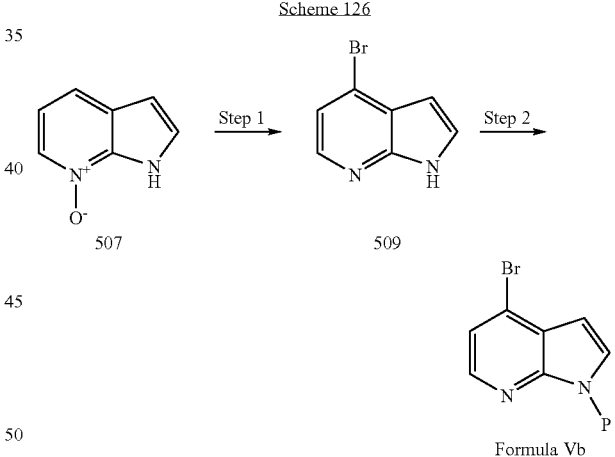

Step 1

Preparation of 4-bromo-7-azaindole (509)

4-bromo-7-azaindole 509 is prepared from 1H-Pyrrolo[2,3-b]pyridine 7-oxide 507 (prepared as described in Example 61) as described in Thibault et. al., Org. Lett. 2003, 5:5023-5025.

Step 2

Preparation of Intermediate of Formula Vb

Intermediate of Formula Vb is prepared by protecting 4-bromo-7-azaindole 509 as described in Scheme 43, Step 1.

Example 70

Synthesis of Compounds of Formula IIIi where $R^{46}$ is a Halogen and $R^{40}$ is H Compounds of Formula IIIi where $R^{46}$ is a halogen and $R^{40}$ is H may be synthesized from a compound of Formula Va or Vb in one Step as described in Scheme 127.

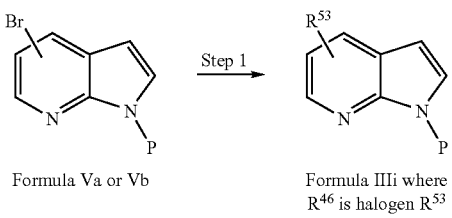

Scheme 127

Formula Va or Vb → Formula IIIi where $R^{46}$ is halogen $R^{53}$

Step 1

Preparation of Compound of Formula IIIi where $R^{46}$ is F or Cl and $R^{40}$ is H Compound of Formula IIIi where $R^{46}$ is halogen $R^{53}$ (preferably fluoro or chloro) and $R^{40}$ is hydrogen is prepared by dissolving the corresponding bromo intermediates of Formula Va (Example 68) or Vb (Example 69) in an appropriate solvent (e.g. tetrahydrofuran) with cooling (e.g. −78° C.) and reacting with an organolithium reagent to effect the lithium-halogen exchange of the bromo (e.g. t-butyllithium), followed by addition of a source of flourine (e.g. N-fluorobenzenesulfimide) or chlorine (e.g. hexachloroethane), similar to that described by Thibault et. al., Org. Lett. 2003, 5:5023-5025. Isolation by conventional means (e.g. extraction and silica gel chromatography) provides compounds of Formula IIIi where $R^{46}$ is F or Cl, $R^{40}$ is H and $R^{41}$ is P.

Example 71

Synthesis of Compounds of Formula IIIi where $R^{46}$ is $NHR^{47}$ and $R^{40}$ is H Compounds of Formula IIIi where $R^{46}$ is $NHR^{47}$ and $R^{40}$ is H may be synthesized from a compound of Formula Va or Vb in one Step as described in Scheme 128.

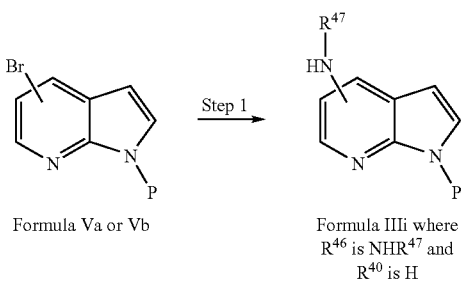

Scheme 128

Formula Va or Vb → Formula IIIi where $R^{46}$ is $NHR^{47}$ and $R^{40}$ is H

Step 1

Preparation of Compound of Formula IIIi where $R^{46}$ is $NHR^{47}$ and $R^{40}$ is H Compound of Formula IIIi where $R^{46}$ is $NHR^{47}$ and $R^{40}$ is H ($R^{47}$ as defined in Example 62) is prepared by reacting intermediate Formula Va (Example 68) or Vb (Example 69) with an amine of Formula $R^{47}$—$NH_2$ using palladium catalyzed Buchwald-Hartwig conditions (i.e. a palladium catalyst (e.g. palladium(II) acetate), a ligand (e.g. dicyclohexyl(o-biphenyl)phosphine), and a base (e.g. sodium t-butoxide) in a non-reactive solvent (e.g. 1,4-dioxane) with heating (e.g. 100° C.) for several hours). Isolation by conventional means (e.g. extraction and silica gel chromatography) provides compound of Formula IIIi where $R^{46}$ is $NHR^{47}$, $R^{40}$ is H and $R^{41}$ is P.

Example 72

Synthesis of Compounds of Formula IIIi where $R^{46}$ is $OR^{54}$ and $R^{40}$ is H Compounds of Formula IIIi where $R^{46}$ is $OR^{54}$ and $R^{40}$ is H may be synthesized from a compound of Formula Va or Vb in one Step as described in Scheme 129.

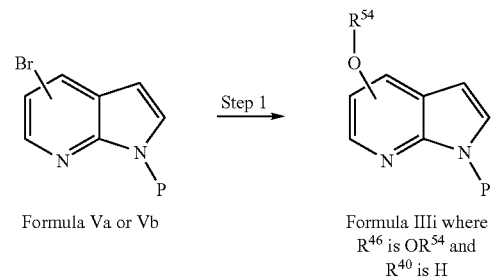

Scheme 129

Formula Va or Vb → Formula IIIi where $R^{46}$ is $OR^{54}$ and $R^{40}$ is H

Step 1

Preparation of Compound of Formula IIIi where $R^{46}$ is $OR^{54}$ and $R^{40}$ is H Compound of Formula IIIi where $R^{46}$ is $OR^{54}$ and $R^{40}$ is H ($R^{54}$ is optionally substituted lower alkyl, optionally substituted lower alkenyl, optionally substituted lower alkynyl, optionally substituted cycloalkyl, optionally substituted heterocycloalkyl, optionally substituted aryl or optionally substituted heteroaryl) is prepared by reacting intermediate Formula Va (Example 68) or Vb (Example 69) with an alcohol of Formula $R^{54}$—OH in the presence of a base (e.g. sodium hydride) and a copper catalyst (e.g. copper bromide) in a non-reactive solvent (e.g. dimethylformamide) with heating (e.g. 120° C.) for several hours. Isolation by conventional means (e.g. extraction and silica gel chromatography), provides compounds of Formula IIIi where $R^{46}$ is $OR^{54}$, $R^{40}$ is H and $R^{41}$ is P.

Example 73

Synthesis of Compounds of Formula IIIi where $R^{46}$ is Optionally Substituted Lower Alkyl and $R^{40}$ is H Compounds of Formula IIIi where $R^{46}$ is optionally substituted lower alkyl and $R^{40}$ is H may be synthesized from a compound of Formula Va or Vb in one Step as described in Scheme 130.

Scheme 130

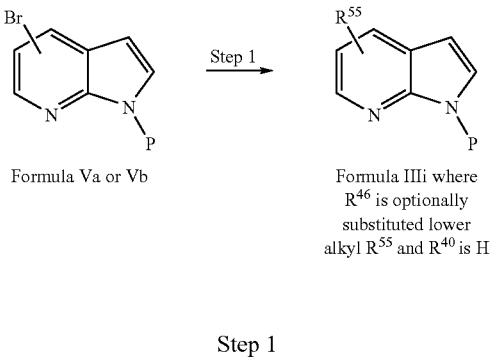

Formula Va or Vb

Formula IIIi where $R^{46}$ is optionally substituted lower alkyl $R^{55}$ and $R^{40}$ is H Step 1

Preparation of Compound of Formula IIIi where $R^{46}$ is Optionally Substituted Lower Alkyl and $R^{40}$ is H Compound of Formula IIIi where $R^{46}$ is optionally substituted lower alkyl $R^{55}$ and $R^{40}$ is H is prepared by dissolving intermediate Formula Va (Example 68) or Vb (Example 69) in an appropriate solvent (e.g. toluene) followed by the addition of a palladium catalyst (e.g. [1,1'-Bis(diphenylphosphino)ferrocene] dichloropalladium(II), complex with dichloromethane (1:1)). After several minutes, a Grignard reagent of the Formula $R^{55}$—MgBr may be added and the reaction heated (e.g. 90° C.) for one to several hours. After filtration through Celite, isolation by conventional means (e.g. extraction and silica gel chromatography), provides compounds of Formula IIIc where $R^{46}$ is optionally substituted lower alkyl, $R^{40}$ is H and $R^{41}$ is P.

Example 74

Synthesis of Compounds of Formula IIIi where $R^{46}$ is Optionally Substituted Aryl or Optionally Substituted Heteroaryl and $R^{40}$ is H Compound of Formula IIIi where $R^{46}$ is optionally substituted aryl or optionally substituted heteroaryl and $R^{40}$ is H may be synthesized from a compound of Formula Va or Vb in one Step as described in Scheme 131.

Scheme 131

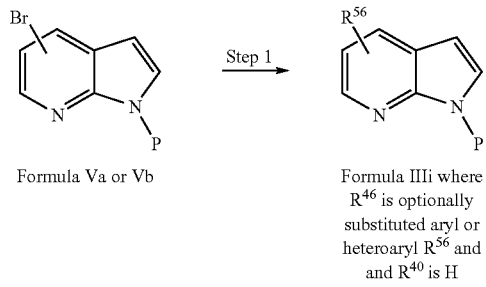

Formula Va or Vb

Formula IIIi where $R^{46}$ is optionally substituted aryl or heteroaryl $R^{56}$ and and $R^{40}$ is H Step 1

Preparation of Compound of Formula IIIi where $R^{46}$ is Optionally Substituted Aryl or Optionally Substituted Heteroaryl and $R^{40}$ is H Compound of Formula IIIi where $R^{46}$ is optionally substituted aryl or optionally substituted heteroaryl $R^{56}$ and $R^{40}$ is H is prepared by reacting intermediate Formula Va (Example 68) or Vb (Example 69) with a boronic acid of the Formula $R^{56}$—B(OH)$_2$ or boronic ester of the Formula $R^{56}$—B(OR)$_2$ under Suzuki coupling conditions (Muyaura and Suzuki, Chem. Rev. 1995, 95:2457), such as in the presence of a palladium catalyst (e.g. Tetrakis(triphenylphosphine)palladium(0)) and a base (e.g. aqueous potassium carbonate) in an appropriate solvent (e.g. tetrahydrofuran, acetonitrile) with heating thermally (e.g. 80° C.) for one to several hours or heating with a microwave instrument (e.g. 120° C. for 10 minutes). Isolation by conventional means (e.g. extraction and silica gel chromatography) provides compounds of Formula IIIi where $R^{46}$ is optionally substituted aryl or optionally substituted heteroaryl, $R^{40}$ is H and $R^{41}$ is P.

Compounds of Formula Ib where V, W, U, and Z are CH, J, E, F, G, and K are C, n is 1, and $R^{15}$, $R^{16}$, and $R^{17}$ are hydrogen form compounds of Formula VI.

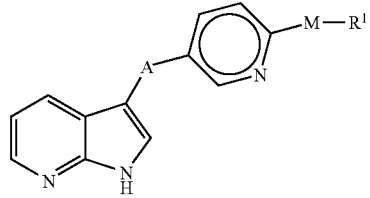

Formula VI

The examples provided for the synthesis of compounds of Formula VI are also applicable to many compounds meeting other definitions of Formula I or Formula Ib.

Example 75

Synthesis of Compounds of Formula VI where M is $NR^{57}$ or O and $R^1$ is Optionally Substituted Aryl or Optionally Substituted Heteroaryl Compound of Formula VIa (Formula VI where M is $NR^{57}$ or O ($R^{57}$ consistent with definition of M for compounds of Formula Ib or $L^2$ for compounds of Formula I) and $R^1$ is optionally substituted aryl or optionally substituted heteroaryl) may be synthesized from a compound of Formula IIb in two Steps as described in Scheme 132.

Scheme 132

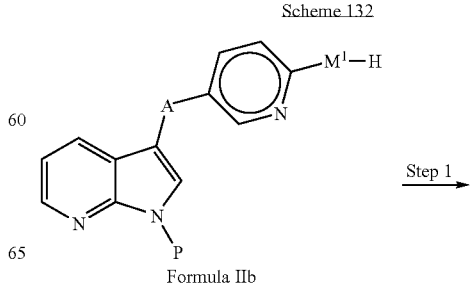

Formula IIb

Step 1

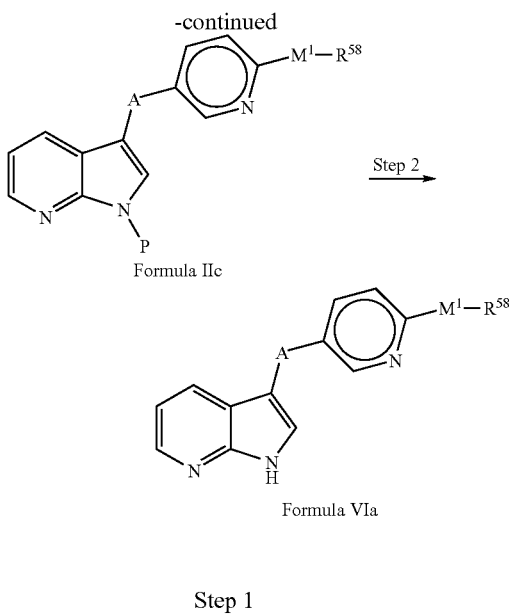

Formula IIc

Formula VIa

Step 1

Preparation of Compound of Formula IIc

Compound of Formula IIc (Formula IIa where $R^{15}$, $R^{16}$ and $R^{17}$ are H, $R^{41}$ is P, $R^{43}$ is $M^1R^{58}$, where $M^1$ is O or $NR^{57}$ and $R^{58}$ is optionally substituted aryl or optionally substituted heteroaryl) is prepared by reacting compound of Formula IIb (Formula IIa where $R^{15}$, $R^{16}$ and $R^{17}$ are H, $R^{41}$ is P, $R^{43}$ is $M^1H$, where $M^1$ is O or $NR^{57}$) with a compound of Formula $R^{58}$—X, where X is an appropriate leaving group such as a halogen or triflate, in the presence of a base (e.g. sodium hydride) in an appropriate solvent (e.g. dimethylformamide) with heating (e.g. 80° C.) for several hours. Alternatively, the reaction may be catalyzed by a metal (e.g. palladium acetate and tri-t-butylphosphine when $M^1$ is $NR^{57}$, copper bromide when $M^1$ is O). Isolation by conventional means (e.g. extraction and silica gel chromatography) provides compounds of Formula IIc.

Step 2

Preparation of Compound of Formula VI where M is $NR^{57}$ or O and $R^1$ is Optionally Substituted Aryl or Optionally Substituted Heteroaryl Compound of Formula VIa (Formula VI where M is $NR^{57}$ or O ($M^1$), $R^1$ is optionally substituted aryl or optionally substituted heteroaryl ($R^{58}$)) is prepared from compound of Formula IIc by removal of the N-1 protecting group according to Scheme 43, Step 2.

Example 76

Synthesis of Compounds of Formula VI where M is $NR^{57}$ or O and $R^1$ is Optionally Substituted Aryl or Optionally Substituted Heteroaryl Compound of Formula VIa (Formula VI where M is $NR^{57}$ or O ($R^{57}$ consistent with definition of M for compounds of Formula Ib or $L^2$ for compounds of Formula I) and $R^1$ is optionally substituted aryl or optionally substituted heteroaryl) may be synthesized from a compound of Formula IId in two Steps as described in Scheme 133.

Scheme 133

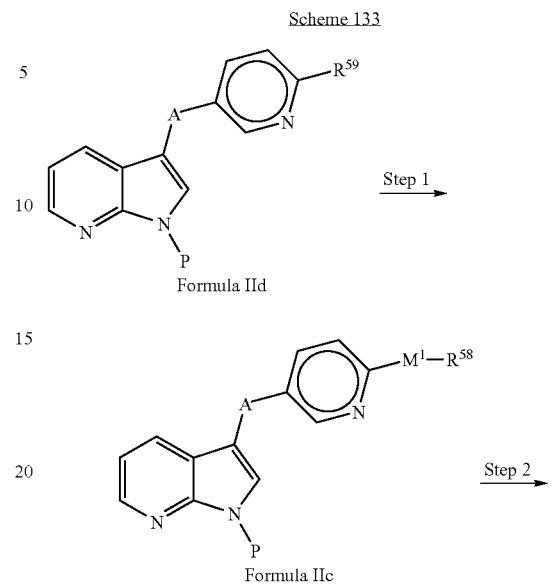

Formula IId

Formula IIc

Formula VIa

Step 1

Preparation of Compound of Formula IIc

Compound of Formula IIc (Formula IIa where $R^{15}$, $R^{16}$ and $R^{17}$ are H, $R^{41}$ is P, $R^{43}$ is $M^1R^{58}$, where $M^1$ is O or $NR^{57}$ and $R^{58}$ is optionally substituted aryl or optionally substituted heteroaryl) is prepared by reacting compound of Formula IId (Formula IIa where $R^{15}$, $R^{16}$ and $R^{17}$ are H, $R^{41}$ is P, and $R^{43}$ is a halogen, $R^{59}$, e.g. chloro) with a compound of Formula $R^{58}$—OH or of Formula $R^{58}$—$NR^{57}$ in the presence of a base (e.g. sodium hydride) in an appropriate solvent (e.g. dimethylformamide) with heating (e.g. 80° C.) for several hours. Alternatively, the reaction may be catalyzed by a metal (e.g. palladium acetate and tri-t-butylphosphine when $M^1$ is $NR^{57}$, copper bromide when $M^1$ is O). Isolation by conventional means (e.g. extraction and silica gel chromatography) provides compounds of Formula IIc.

Step 2

Preparation of Compound of Formula VI where M is $NR^{57}$ or O and $R^1$ is Optionally Substituted Aryl or Optionally Substituted Heteroaryl Compound of Formula VIa (Formula VI where M is $NR^{57}$ or O ($M^1$), $R^1$ is optionally substituted aryl or optionally substituted heteroaryl ($R^{58}$)) is prepared from compound of Formula IIc by removal of the N-1 protecting group according to Scheme 43, Step 2.

Example 77

Synthesis of Compounds of Formula VI where M is —O-alk- or —$NR^{57}$-alk-

Compound of Formula VIb (Formula VI where M is —O-alk- or —$NR^{57}$-alk- ($R^{57}$ consistent with definition of M for compounds of Formula Ib or $L^2$ for compounds of Formula I)) may be synthesized from a compound of Formula IIb in two Steps as described in Scheme 134.

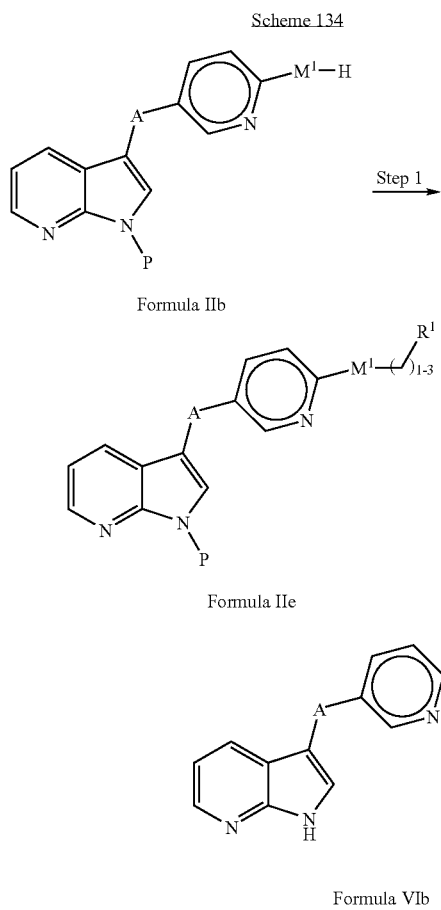

Step 1

Preparation of Compound of Formula IIe

Compound of Formula IIe (Formula IIa where $R^{15}$, $R^{16}$ and $R^{17}$ are H, $R^{41}$ is P, $R^{43}$ is $M^1(CH_2)_{1-3}R^1$ where $M^1$ is O or $NR^{57}$) is prepared by reacting compound of Formula IIb (Formula IIa where $R^{15}$, $R^{16}$ and $R^{17}$ are H, $R^{41}$ is P, $R^{43}$ is $M^1H$, where $M^1$ is O or $NR^{57}$) with a compound of Formula $R^1$—$(CH_2)_{1-3}$—X where X is a leaving group (e.g. halogen, mesylate) in the presence of a base (e.g. sodium hydride, potassium carbonate) in an appropriate solvent (e.g. dimethylformamide, acetonitrile) with heating (e.g. 80° C.) for one to several hours. Isolation by conventional means (e.g. extraction and silica gel chromatography), provides compounds of Formula IIe.

Step 2

Preparation of Compound of Formula VI where M is $M^1(CH_2)_{1-3}$ and $M^1$ is O or $NR^{57}$ Compound of Formula VIb (Formula VI where M is $O(CH_2)_{1-3}$ or $NR^{57}(CH_2)_{1-3}$) is prepared from compound of Formula IIe by removal of the N-1 protecting group according to Scheme 43, Step 2.

Example 78

Synthesis of Compounds of Formula VI where M is —O-alk- or —$NR^{57}$-alk-

Compound of Formula VIb (Formula VI where M is —O-alk- or —$NR^{57}$-alk- ($R^{57}$ consistent with definition of M for compounds of Formula Ib or $L^2$ for compounds of Formula I)) may be synthesized from a compound of Formula IId in two Steps as described in Scheme 135.

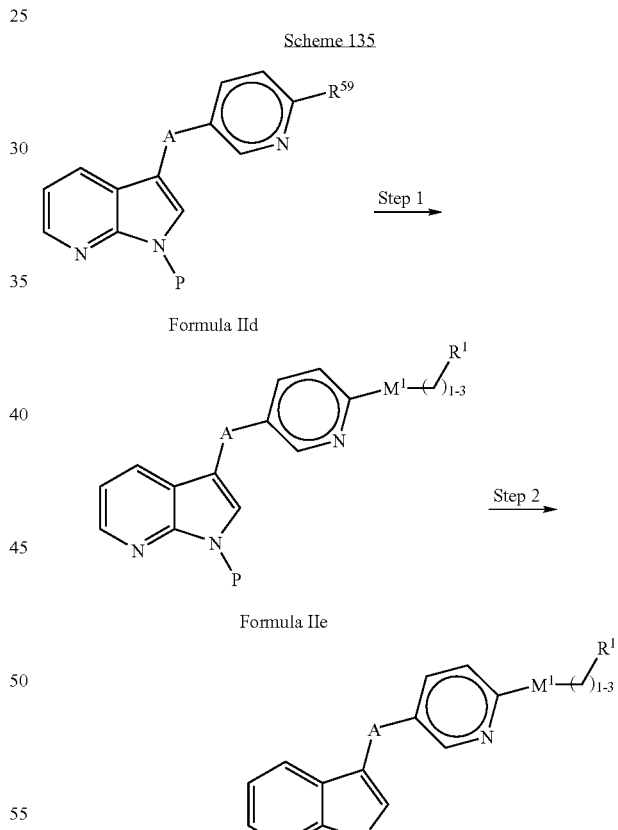

Step 1

Preparation of Compound of Formula IIe

Compound of Formula IIe (Formula IIa where $R^{15}$, $R^{16}$ and $R^{17}$ are H, $R^{41}$ is P, $R^{43}$ is $M^1(CH_2)_{1-3}R^1$ where $M^1$ is O or $NR^{57}$) is prepared by reacting compound of Formula IId (Formula IIa where $R^{15}$, $R^{16}$ and $R^{17}$ are H, $R^{41}$ is P, and $R^{43}$ is a halogen, $R^{59}$, e.g. chloro) with a compound of Formula $R^1$—$(CH_2)_{1-3}$—OH or $R^1$—$(CH_2)_{1-3}$—$NR^{57}$ in the presence of a base (e.g. sodium hydride, potassium carbonate) in an appropriate solvent (e.g. dimethylformamide, acetonitrile) with heating (e.g. 80° C.) for one to several hours. Isolation by conventional means (e.g. extraction and silica gel chromatography), provides compound of Formula IIe.

Step 2

Preparation of Compound of Formula VI where M is $M^1(CH_2)_{1-3}$ and $M^1$ is O or $NR^{57}$ Compound of Formula VIb (Formula VI where M is $O(CH_2)_{1-3}$ or $NR^{57}(CH_2)_{1-3}$) is prepared from compound of Formula IIe by removal of the N-1 protecting group according to Scheme 43, Step 2.

Example 79

Synthesis of Compounds of Formula VI where M is NH-alk-

Compound of Formula VIc (Formula VI where M is —NH-alk-) may be synthesized from a compound of Formula IIf in two Steps as described in Scheme 136.

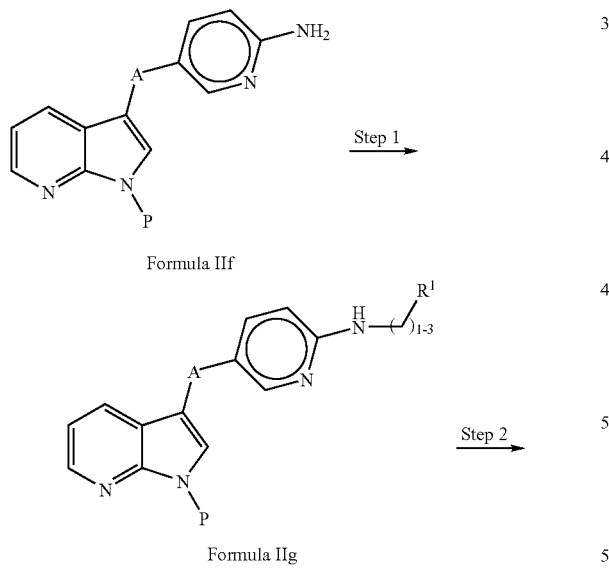

Step 1

Preparation of Compound of Formula IIg

Compound of Formula IIg (Formula IIa where $R^{15}$, $R^{16}$ and $R^{17}$ are H, $R^{41}$ is P, $R^{43}$ is $NH(CH_2)_{1-3}R^1$) is prepared from compound of Formula IIf (Formula IIa where $R^{15}$, $R^{16}$ and $R^{17}$ are H, $R^{41}$ is P, $R^{43}$ is $NH_2$) by reductive amination using an aldehyde of the formula $R^1$—$(CH_2)_{0-2}$—CHO in the presence of a catalytic amount of acid (e.g. acetic acid) and a reducing agent (e.g. sodium triacetoxyborohydride) in a nonreactive solvent (e.g. dichloroethane). After stirring for several hours, isolation by conventional means (e.g. extraction and silica gel chromatography) provides compounds of Formula IIg.

Step 2

Preparation of Compound of Formula VI where M is $NH(CH_2)_{1-3}$

Compound of Formula VIc (Formula VI where M is $NH(CH_2)_{1-3}$) is prepared from compound of Formula IIg by removal of the N-1 protecting group according to Scheme 43, Step 2.

Example 80

Synthesis of Compounds of Formula VI where M is $NR^{57}C(O)$ or $OC(O)$

Compound of Formula VId (Formula VI where M is $NR^{57}C(O)$ or $OC(O)$ where $R^{57}$ is consistent with definition of M for compounds of Formula Ib or $L^2$ for compounds of Formula I) may be synthesized from a compound of Formula IIb in two Steps as described in Scheme 137.

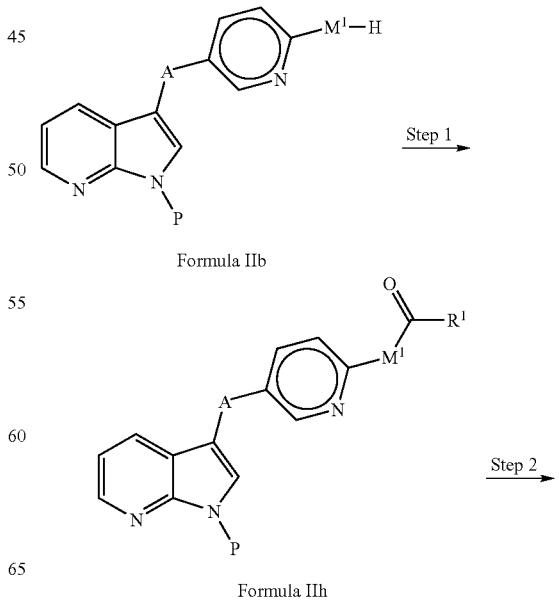

-continued

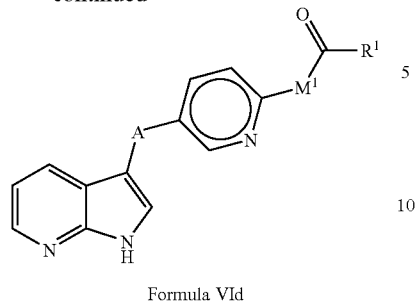

Formula VId

Step 1

Preparation of Compound of Formula IIh

Compound of Formula IIh (Formula IIa where $R^{15}$, $R^{16}$ and $R^{17}$ are H, $R^{41}$ is P, $R^{43}$ is $M^1C(O)R^1$ where $M^1$ is O or $NR^{57}$) is prepared by reacting compound of Formula IIb (Formula IIa where $R^{15}$, $R^{16}$ and $R^{17}$ are H, $R^{41}$ is P, $R^{43}$ is $M^1H$, where $M^1$ is O or $NR^{57}$) with an activated carboxylic acid of Formula $R^1$—COX where X is a leaving group such as chloro (e.g. benzoyl chloride) in the presence of a base (e.g. DIEA) in a non-reactive solvent (e.g. dichloromethane). After stirring for several hours, isolation by conventional means (e.g. extraction and silica gel chromatography) provides compound of Formula IIh.

Step 2

Preparation of Compound of Formula VI where M is OC(O) or $NR^{57}C(O)$

Compounds of Formula VId (Formula VI where M is OC(O) or $NR^{57}C(O)$) is prepared from compound of Formula IIh by removal of the N-1 protecting group according to Scheme 43, Step 2.

Example 81

Synthesis of Compounds of Formula VI where M is $NR^{57}S(O)_2$

Compound of Formula VIe (Formula VI where M is $NR^{57}S(O)_2$ where $R^{57}$ is consistent with definition of M for compounds of Formula Ib or $L^2$ for compounds of Formula I) may be synthesized from a compound of Formula IIh in two Steps as described in Scheme 138.

Scheme 138

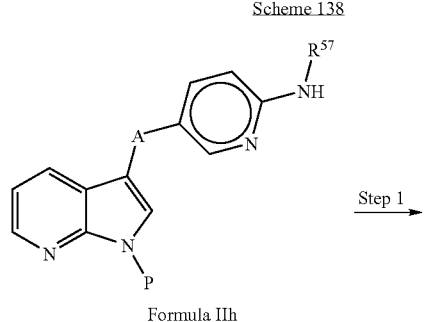

Formula IIh

-continued

Formula IIi

Formula VIe

Step 1

Preparation of Compound of Formula IIi

Compound of Formula IIi (Formula IIa where $R^{15}$, $R^{16}$ and $R^{17}$ are H, $R^{41}$ is P, $R^{43}$ is $NR^{57}S(O)_2R^1$) is prepared by reacting compound of Formula IIh (Formula IIa where $R^{15}$, $R^{16}$ and $R^{17}$ are H, $R^{41}$ is P, and $R^{43}$ is $NR^{57}H$) by reaction with a sulfonyl chloride of the formula $R^1$—$SO_2Cl$ (e.g. phenylsulfonyl chloride) in the presence of a base (e.g. DIEA, pyridine) in a non-reactive solvent (e.g. dichloromethane). After stirring for several hours, isolation by conventional means (e.g. extraction and silica gel chromatography) provides compounds of Formula IIi.

Step 2

Preparation of Compound of Formula VI where M is $NR^{57}S(O)_2$

Compound of Formula VIe (Formula VI where M is $NR^{57}S(O)_2$) is prepared from compound of Formula IIi by removal of the N-1 protecting group according to Scheme 43, Step 2.

Example 82

Synthesis of Compounds of Formula VI where M is $NR^{57}C(O)NH(CH_2)_{1-3}$ or $NR^{57}C(S)NH(CH_2)_{1-3}$ Compound of Formula VIf (Formula VI where M is $NR^{57}C(O)NH(CH_2)_{1-3}$ or $NR^{57}C(S)NH(CH_2)_{1-3}$, where $R^{57}$ is consistent with definition of M for compounds of Formula Ib or $L^2$ for compounds of Formula I) may be synthesized from a compound of Formula IIh in two Steps as described in Scheme 139.

Scheme 139

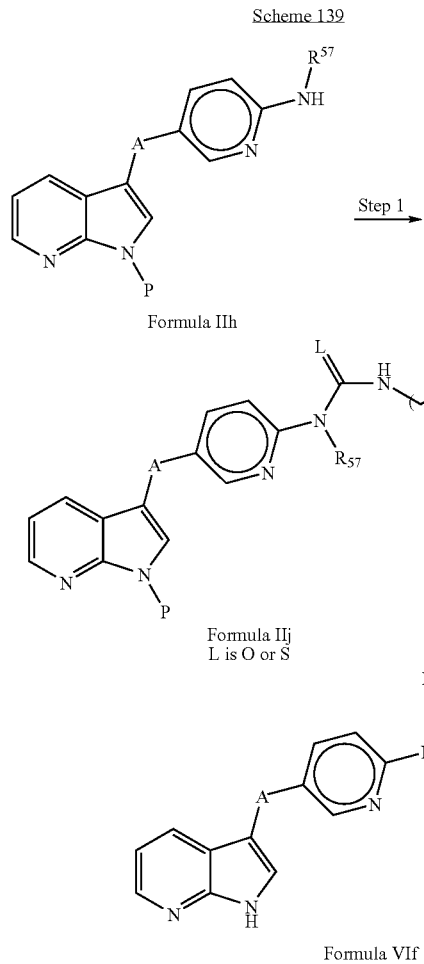

Step 1

Preparation of Compound of Formula IIj

Compound of Formula IIj (Formula IIa where $R^{15}$, $R^{16}$ and $R^{17}$ are H, $R^{41}$ is P, $R^{43}$ is $NR^{57}C(L)NH(CH_2)_{1-3}R^1$, where L is O or S) is prepared by reacting compound of Formula IIh (Formula IIa where $R^{15}$, $R^{16}$ and $R^{17}$ are H, $R^{41}$ is P, and $R^{43}$ is $NR^{57}H$) with a compound of the formula $R^1$—$(CH_2)_{1-3}NCL$ where L is either O to form an isocyanate (e.g. phenyl isocyanate) or L is S to form a thioisocyanate (e.g. phenyl isothiocyanate) in the presence of a base (e.g. DIEA) in a non-reactive solvent (e.g. dichloromethane). After stirring for several hours, isolation by conventional means (e.g. extraction and silica gel chromatography) provides compounds of Formula IIj.

Step 2

Preparation of Compound of Formula VI where B is NR and D is $C(\!=\!L)NH(CH_2)_q$ Compound of Formula VIf (Formula VI where M is $NR^{57}C(O)NH(CH_2)_{1-3}$ or $NR^{57}C(S)NH(CH_2)_{1-3}$) is prepared from compound of Formula IIj by removal of the N-1 protecting group according to Scheme 43, Step 2.

Example 83

Synthesis of Compounds of Formula VI where M is $NR^{57}S(O)_2NH(CH_2)_{1-3}$

Compound of Formula VIg (Formula VI where M is $NR^{57}S(O)_2NH(CH_2)_{1-3}$, where $R^{57}$ is consistent with definition of M for compounds of Formula Ib or $L^2$ for compounds of Formula I) may be synthesized from a compound of Formula IIh in three Steps as described in Scheme 140.

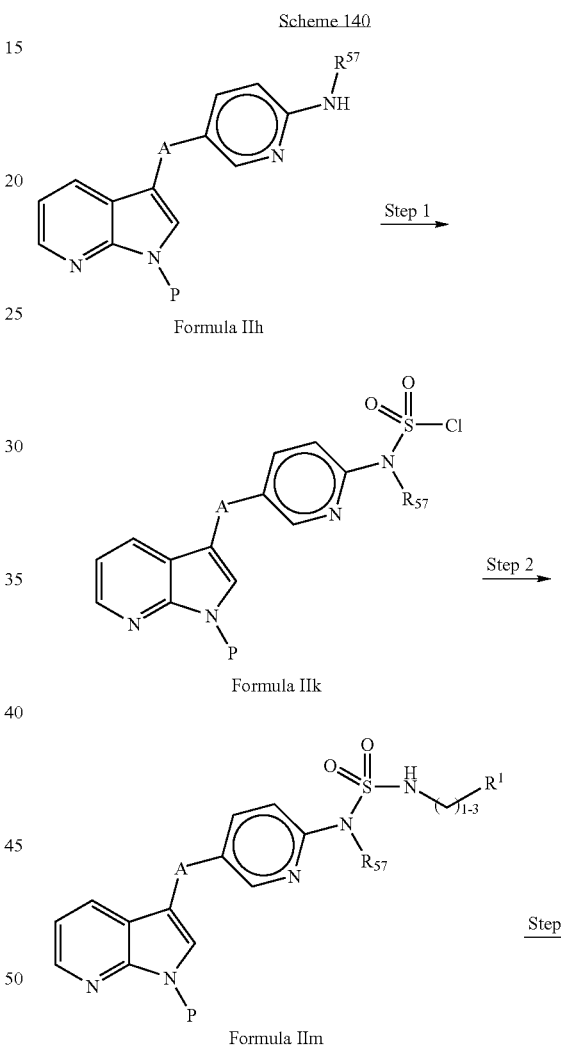

Step 1

Preparation of Compound of Formula IIk

Compound of Formula IIk (Formula IIa where $R^{15}$, $R^{16}$ and $R^{17}$ are H, $R^{41}$ is P, $R^{43}$ is $NR^{57}S(O)_2Cl$) is prepared by reacting compound of Formula IIh (Formula IIa where $R^{15}$, $R^{16}$ and $R^{17}$ are H, $R^{41}$ is P, and $R^{43}$ is $NR^{57}H$) with sulfuryl chloride in a non-reactive solvent (e.g. dichloromethane) possibly with heating (eg. 60° C.). After stirring for several hours, the reaction can be concentrated to provide compound of Formula IIk that is used without further purification.

Step 2

Preparation of Compound of Formula IIm

Compound of Formula IIm (Formula IIa where $R^{15}$, $R^{16}$ and $R^{17}$ are H, $R^{41}$ is P, $R^{43}$ is $NR^{57}S(O)_2NH(CH_2)_{1-3}R^1$) is prepared from compound of Formula IIk by reaction with an amine of the formula $NH_2(CH_2)_{1-3}R^1$ in the presence of a base (e.g. DIEA) in a non-reactive solvent (e.g. dichloromethane). After stirring for several hours, isolation by conventional means (e.g. extraction and silica gel chromatography) provides compounds of Formula IIm.

Step 3

Preparation of Compound of Formula VI where M is $NR^{57}S(O)_2NH(CH_2)_{1-3}$

Compound of Formula VIg (Formula VI where M is $NR^{57}S(O)_2NH(CH_2)_{1-3}$) is prepared from compound of Formula IIm by removal of the N-1 protecting group according to Scheme 43, Step 2.

Example 84

Synthesis of Compounds of Formula VI where M is $S(O)_2(CH_2)_{0-3}$ or $S(CH_2)_{0-3}$ Compound of Formula VIh (Formula VI where M is $S(O)_2(CH_2)_{0-3}$ or $S(CH_2)_{0-3}$) may be synthesized from a compound of Formula IId in two Steps as described in Scheme 141.

Scheme 141

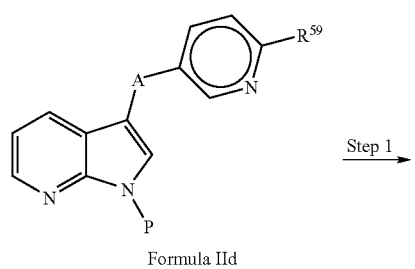

Formula IId

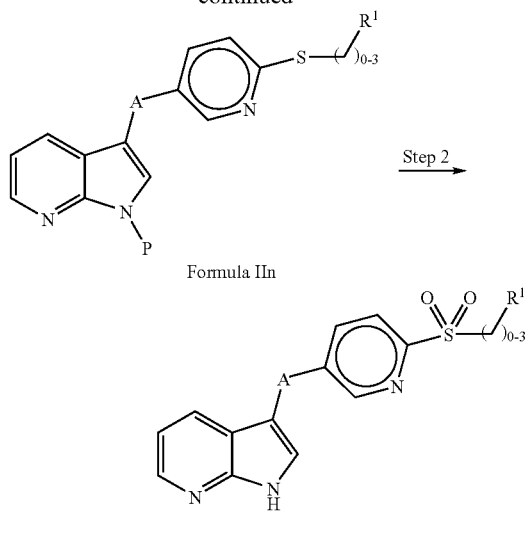

Formula IIn

Formula VIh

Step 1

Preparation of Compound of Formula IIn

Compound of Formula IIn (Formula IIa where $R^{15}$, $R^{16}$ and $R^{17}$ are H, $R^{41}$ is P, $R^{43}$ is $S(CH_2)_{0-3}R^1$) is prepared by reacting compound of Formula IId (Formula IIa where $R^{15}$, $R^{16}$ and $R^{17}$ are H, $R^{41}$ is P, and $R^{43}$ is a halogen, $R^{59}$, e.g. chloro) with a compound of Formula $R^1$—$(CH_2)_{0-3}$—SH in the presence of a base (e.g. sodium hydride, potassium carbonate) in an appropriate solvent (e.g. dimethylformamide, acetonitrile) with heating (e.g. 80° C.) for one to several hours. Isolation by conventional means (e.g. extraction and silica gel chromatography) provides compound of Formula IIn. This can be taken to the next step, or the N-1 protecting group P can be removed according to Scheme 43, Step 2 to provide compound of Formula VI where M is $S(CH_2)_{0-3}$.

Step 2

Preparation of Compound of Formula VI where M is $SO_2(CH_2)_{0-3}$

Compounds of Formula VIh (Formula VI where M is $S(O)_2(CH_2)_{0-3}$) is prepared from compound of Formula IIn by reacting with an oxidizing agent (e.g. meta-chloro-peroxybenzoic acid, hydrogen peroxide) in an appropriate aprotic solvent (e.g. dichloromethane). Isolation by conventional means (e.g. extraction and silica gel chromatography) followed by removal of the N-1 protecting group according to Scheme 43, Step 2 provides compound of Formula VIh.

Example 85

Synthesis of Compounds of Formula VI where M is $C(O)(CH_2)_{0-3}$

Compound of Formula VIi (Formula VI where M is $C(O)(CH_2)_{0-3}$) may be synthesized from a compound of Formula IId in three Steps as described in Scheme 142.

Scheme 142

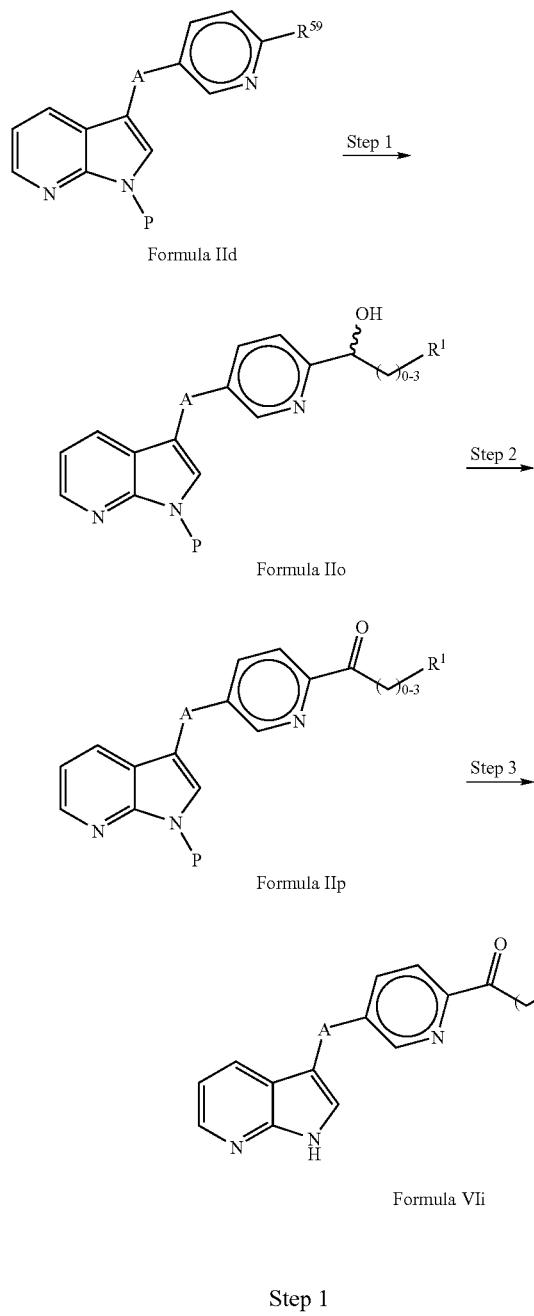

Formula IId

Formula IIo

Formula IIp

Formula VIi

Step 1

Preparation of Compound of Formula IIo

Compound of Formula IIo (Formula IIa where $R^{15}$, $R^{16}$ and $R^{17}$ are H, $R^{41}$ is P, $R^{43}$ is $C(OH)(CH_2)_{0-3}R^1$) is prepared by reacting compound of Formula IId (Formula IIa where $R^{15}$, $R^{16}$ and $R^{17}$ are H, $R^{41}$ is P, and $R^{43}$ is a halogen, $R^{59}$, e.g. chloro) with an organolithium reagent (e.g. butyllithium) to effect the lithium-halogen exchange at reduced temperature (e.g. $-78°$ C.) in an appropriate solvent (e.g. tetrahydrofuran) followed by addition of an aldehyde of Formula $R^1$—$(CH_2)_{0-3}$—C(O)H. After stirring for several hours and warming to room temperature, isolation by conventional means (e.g. extraction and silica gel chromatography) provides compound of Formula IIo.

Step 2

Preparation of Compound of Formula IIp

Compound of Formula IIp (Formula IIa where $R^{15}$, $R^{16}$ and $R^{17}$ are H, $R^{41}$ is P, $R^{43}$ is $C(O)(CH_2)_{0-3}R^1$) is prepared by reacting compound of Formula IIo with an oxidizing agent (e.g. Dess-Martin periodinane), in an appropriate solvent (e.g. tetrahydrofuran). After stirring for one to several hours, isolation by conventional means (e.g. extraction and silica gel chromatography) provides compound of Formula IIp.

Step 3

Preparation of Compound of Formula VI where B is C=O and D is $(CH_2)_w$

Compound of Formula VIi (Formula VI where M is $C(O)(CH_2)_{0-3}$) is prepared from compound of Formula IIp by removal of the N–1 protecting group according to Scheme 43, Step 2.

Example 86

Synthesis of Compounds of Formula IIr

Compound of Formula IIr ((Formula IIa where $R^{15}$, $R^{16}$ and $R^{17}$ are H, $R^{41}$ is P, and $R^{43}$ is $S(O)_2Cl$) may be synthesized from a compound of Formula IIf in two Steps as described in Scheme 143.

Scheme 143

Formula IIf

Formula IIq

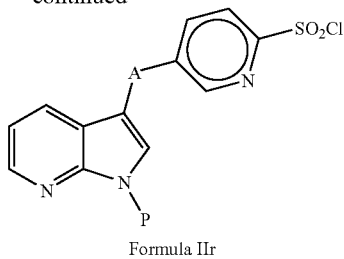

Formula IIr

Step 1

Preparation of Compound of Formula IIq

Compound of Formula IIq ((Formula IIa where $R^{15}$, $R^{16}$ and $R^{17}$ are H, $R^{41}$ is P, and $R^{43}$ is $N_2^+$) is prepared by reacting compound of Formula IIf (Formula IIa where $R^{15}$, $R^{16}$ and $R^{17}$ are H, $R^{41}$ is P, and $R^{43}$ is $NH_2$) with aqueous hydrochloric acid and aqueous sodium nitrite. Addition of water and salt results in precipitation of the compound and filtration affords the chloride salt of the diazonium of Formula IIq.

Step 2

Preparation of Compound of Formula IIr

Compound of Formula IIr (Formula IIa where $R^{15}$, $R^{16}$ and $R^{17}$ are H, $R^{41}$ is P, and $R^{43}$ is $S(O)_2Cl$) is prepared by reacting compound of Formula IIq (Formula IIa where $R^{15}$, $R^{16}$ and $R^{17}$ are H, $R^{41}$ is P, and $R^{43}$ is $N_2^+$) with a mixture of cuprous chloride in acetic acid saturated with sulfur dioxide, while cooling (e.g. 10° C.). After stirring for 30 minutes to one hour, the mixture is poured into water and the compound is isolated by extraction and concentration of the dried organic portions to provide compound of Formula IIr. (Organic Syntheses, Coll. Vol. 7, p. 508; Vol. 60, p. 121).

Example 87

Synthesis of Compounds of Formula IIt

Compound of Formula IIt ((Formula IIa where $R^{15}$, $R^{16}$ and $R^{17}$ are H, $R^{41}$ is P, and $R^{43}$ is COOH) may be synthesized from a compound of Formula IIs in one Step as described in Scheme 144.

Scheme 144

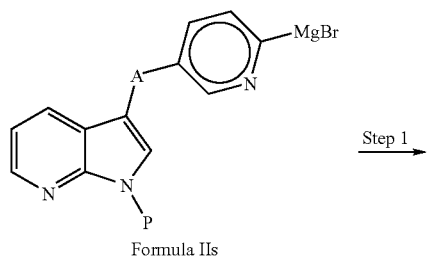

Formula IIs

Step 1

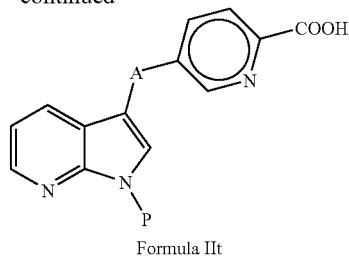

Formula IIt

Step 1

Preparation of Compound of Formula IIt

Compound of Formula IIt (Formula IIa where $R^{15}$, $R^{16}$ and $R^{17}$ are H, $R^{41}$ is P, and $R^{43}$ is COOH) is prepared by reacting compound of Formula IIs (Formula IIa where $R^{15}$, $R^{16}$ and $R^{17}$ are H, $R^{41}$ is P, and $R^{43}$ is MgBr) dissolved in an appropriate solvent (e.g. tetrahydrofuran) with dry ice. Addition of water and acid-base extraction of the compound provides compound of Formula IIt.

Example 88

Synthesis of Compounds of Formula VI where M is $C(O)NR^{57}(CH_2)_{0-3}$ or $S(O)_2NR^{57}(CH_2)_{0-3}$ Compound of Formula VIj (Formula VI where M is $C(O)NR^{57}(CH_2)_{0-3}$ or $S(O)_2NR^{57}(CH_2)_{0-3}$), where $R^{57}$ is consistent with definition of M for compounds of Formula Ib or $L^2$ for compounds of Formula I) may be synthesized from a compound of Formula IIu in three Steps as described in Scheme 145.

Scheme 145

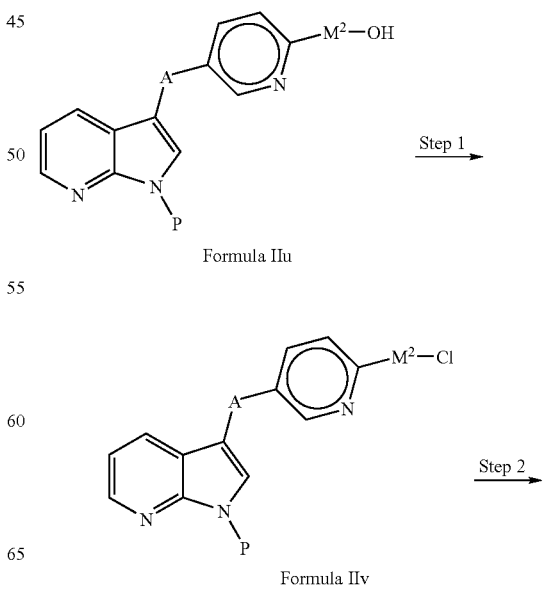

Formula IIu

Step 1

Formula IIv

Step 2

-continued

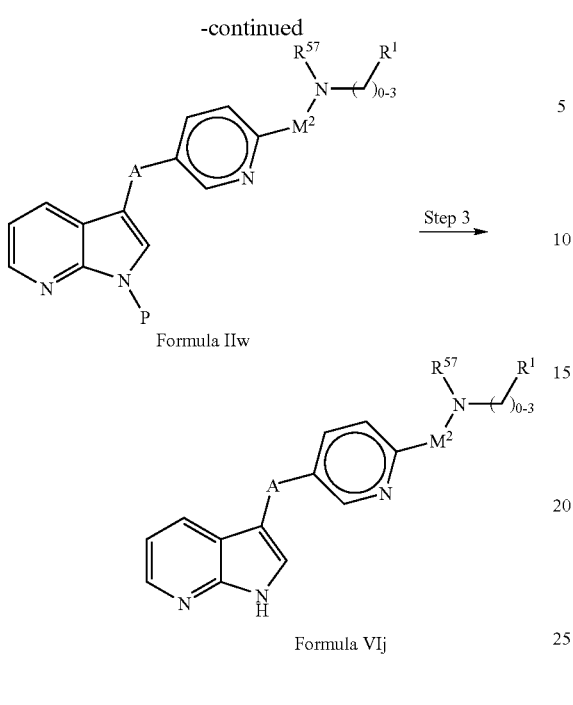

Formula IIw

Formula VIj

Step 1

Preparation of Compound of Formula IIv

Compound of Formula IIv (Formula IIa where $R^{15}$, $R^{16}$ and $R^{17}$ are H, $R^{41}$ is P, and $R^{43}$ is $M^2Cl$, where $M^2$ is C(O) or $S(O)_2$) is prepared by reacting compound of Formula IIu (Formula IIa where $R^{15}$, $R^{16}$ and $R^{17}$ are H, $R^{41}$ is P, and $R^{43}$ is $M^2OH$, where $M^2$ is C(O) or $S(O)_2$) with an appropriate reagent to effect the formation of the acid chloride or sulfonyl chloride (e.g. thionyl chloride) with heating (e.g. 80° C.) for several hours, possibly in a solvent (e.g. toluene). Concentration of the reaction mixture provides compound of Formula IIv that is used without further purification.

Step 2

Preparation of Compound of Formula IIw

Compound of Formula IIw (Formula IIa where $R^{15}$, $R^{16}$ and $R^{17}$ are H, $R^{41}$ is P, and $R^{43}$ is $M^2NR^{57}(CH_2)_{0-3}R^1$, where $M^2$ is C(O) or $S(O)_2$) is prepared by reacting compound of Formula IIv with an amine of the formula $NR^{57}H(CH_2)_{0-3}R^1$ in the presence of a base (e.g. DIEA) in an appropriate aprotic solvent (e.g. dimethylformamide, dichloromethane). After stirring for one to several hours, isolation by conventional means (e.g. extraction and silica gel chromatography) provides compounds of Formula IIw.

Step 3

Preparation of Compound of Formula VI where M is $C(O)NR^{57}(CH_2)_{0-3}$ or $S(O)_2NR^{57}(CH_2)_{0-3}$ Compounds of Formula VIj (Formula VI where M is $C(O)NR^{57}(CH_2)_{0-3}$ or $S(O)_2NR^{57}(CH_2)_{0-3}$) is prepared from compound of Formula IIw by removal of the N–1 protecting group according to Scheme 43, Step 2.

Compounds of Formula X or Xa, where $R^{43}$ is a substituent appropriate for further substitution to provide $M-R^1$ (e.g. chloro, $NH_2$, $NHR^{57}$, OH, MgBr, C(O)OH, $S(O)_2OH$; as described in Examples 78-88), and $R^{42}$ is a functionality appropriate for coupling to the 7-azaindole ring or its analog to form A or $L^1$, are useful in the synthesis of compounds of Formula I or Ib or compounds of Formula II as described in Examples 43-59.

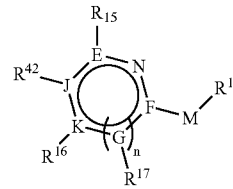

Formula X

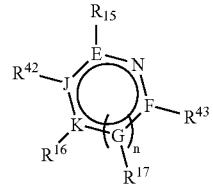

Formula Xa

Many compounds of Formula X or Xa are commercially available; for example, many 5- and 6-membered nitrogen-containing heterocycles where $R^{43}$ is chloro or amino and $R^{42}$ is a carboxylic acid or aldehyde are commercially available or may be prepared using known methods.

Compounds of Formula Xa where E, F, G, K, L are C and n is 1 form compounds of Formula $X_{10}$. Examples for the synthesis of compounds of Formula $X_{10}$ and their use in the synthesis of compounds of Formula I, Ib, and II may also be applied to other compounds fitting the definition of Formula X.

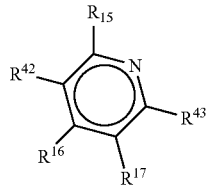

Formula $X_{10}$

Compounds of Formula Xa, where $R^{42}$ is a hydrogen or halogen ($R^{60}$), and $R^{15}$, $R^{16}$ and $R^{17}$ are either as defined for Formula Xa or are appropriate substituents for further modification to provide compounds of Formula $X_{10}$, form compounds of Formula $X_{20}$, which are useful in the synthesis of compounds of Formula Xa.

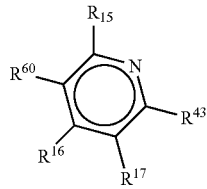

Formula $X_{20}$

Use of compounds of Formula $X_{10}$ or $X_{20}$ are exemplified in the following examples as representative examples of reactions that may also be useful in the analogous reactions using compounds of Formula X or Xa.

Example 89

Synthesis of Compounds of Formula $X_{10}$ where $R^{42}$ is C(O)H

Compound of Formula $X_{10}$a (Formula $X_{10}$ where $R^{42}$ is C(O)H) may be synthesized from a compound of Formula $X_{20}$a in one Step as described in Scheme 146.

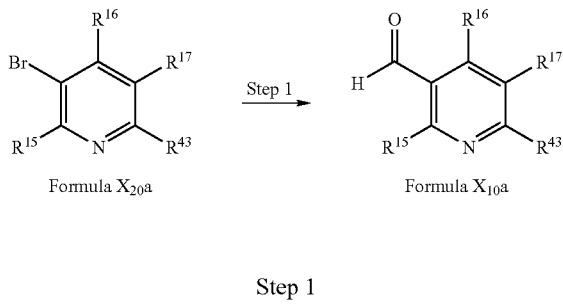

Scheme 146

Formula $X_{20}$a → Formula $X_{10}$a

Step 1

Preparation of Compound of Formula $X_{20}$b

Compound of Formula $X_{10}$a (Formula $X_{10}$ where $R^{42}$ is C(O)H) is prepared by reacting compound of Formula $X_{20}$a (Formula $X_{20}$ where $R^{60}$ is Br) with an organolithium reagent (e.g. butyllithium) to effect the lithium-halogen exchange at reduced temperature (e.g. −78° C.) in an appropriate solvent (e.g. tetrahydrofuran) followed by addition of a formylating reagent (e.g. dimethylformamide). After stirring for several hours and warming to room temperature, isolation by conventional means (e.g. extraction and silica gel chromatography), provides compounds of Formula $X_{10}$a. Preferred compounds of $X_{20}$a for this reaction have $R^{15}$ as optionally substituted lower alkyl, trifluoromethyl, $CH_2CF_3$, OR, or SR, wherein R is optionally substituted lower alkyl.

Example 90

Synthesis of Compounds of Formula $X_{10}$ where $R^{42}$ is C(O)OH

Compound of Formula $X_{10}$b (Formula $X_{10}$ where $R^{42}$ is C(O)OH) may be synthesized from a compound of Formula $X_{20}$a in one Step as described in Scheme 147.

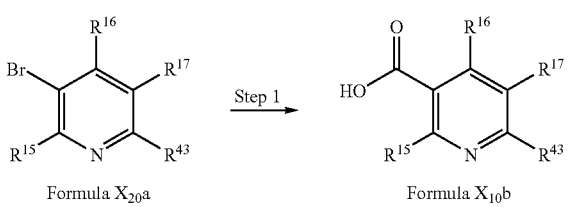

Scheme 147

Formula $X_{20}$a → Formula $X_{10}$b

Step 1

Preparation of Compound of Formula $X_{10}$b

Compound of Formula $X_{10}$b (Formula $X_{10}$ where $R^{42}$ is C(O)OH) is prepared by reacting compound of Formula $X_{20}$a (Formula $X_{20}$ where $R^{60}$ is Br) with solid magnesium in an appropriate solvent (e.g. tetrahydrofuran) possibly with a catalyst (e.g. iodine) and with heating (e.g. 80° C.) to afford the corresponding Grignard reagent. Dry ice is then added to the reaction to quench the Grignard and form the carboxylic acid at $R^{42}$. Isolation by evaporation and acid-base extraction provides compound of Formula $X_{10}$b.

Example 91

Synthesis of Compounds of Formula $X_{10}$ where $R^{15}$ is Optionally Substituted Lower Alkyl and $R^{42}$ is C(O)H Compound of Formula $X_{10}$c (Formula $X_{10}$ where $R^{42}$ is C(O)H and $R^{15}$ is optionally substituted lower alkyl) may be synthesized from a compound of Formula $X_{20}$b in two Steps as described in Scheme 148.

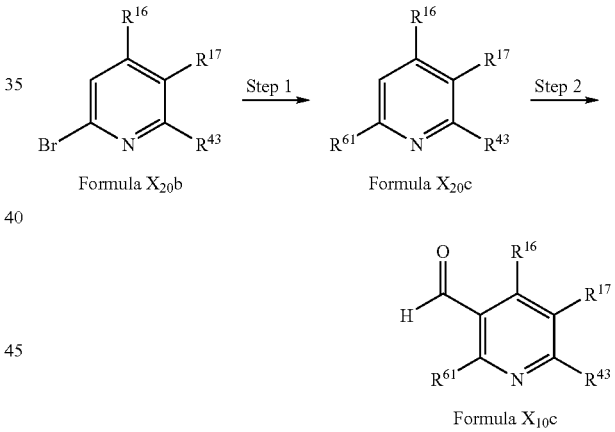

Scheme 148

Formula $X_{20}$b → Formula $X_{20}$c → Formula $X_{10}$c

Step 1

Preparation of Compound of Formula $X_{20}$c

Compound of Formula $X_{20}$c (Formula $X_{20}$ where $R^{60}$ is H and $R^{15}$ is optionally substituted lower alkyl $R^{61}$) is prepared by dissolving compound of Formula $X_{20}$b (Formula $X_{20}$ where $R^{60}$ is H and $R^{15}$ is Br) in an appropriate solvent (e.g. toluene), followed by the addition of a palladium catalyst (e.g. [1,1'-Bis(diphenylphosphino)-ferrocene]dichloropalladium(II), complex with dichloromethane (1:1)). After several minutes, a Grignard reagent of the formula $R^{61}$—MgBr (where $R^{61}$ is optionally substituted lower alkyl) may be added and the reaction heated (e.g. 90° C.) for one to several hours. After filtration through Celite, isolation by conventional means (e.g. extraction and silica gel chromatography) provides compound of Formula $X_{20}c$.

Step 2

Preparation of Compound of Formula $X_{10}c$

Compound of Formula $X_{10}c$ (Formula $X_{10}$ where $R^{42}$ is C(O)H and $R^{15}$ is optionally substituted lower alkyl) is prepared by reacting compound of Formula $X_{20}c$ with an organolithium reagent (e.g. lithium diisopropylamine) to effect the lithiation at the $R^{42}$ position at reduced temperature (e.g. −78° C.) in an appropriate solvent (e.g. tetrahydrofuran) followed by addition of a formylating reagent (e.g. dimethylformamide). After stirring for several hours and warming to room temperature, isolation by conventional means (e.g. extraction and silica gel chromatography) provides compound of Formula $X_{10}c$.

Example 92

Synthesis of Compounds of Formula $X_{10}$ where $R^{15}$ is $OR^{62}$ or $SR^{62}$ and $R^{42}$ is C(O)H Compound of Formula $X_{10}d$ (Formula $X_{10}$ where $R^{42}$ is C(O)H and $R^{15}$ is $OR^{62}$ or $SR^{62}$, where $R^{62}$ is optionally substituted lower alkyl) may be synthesized from a compound of Formula $X_{20}d$ in two Steps as described in Scheme 149.

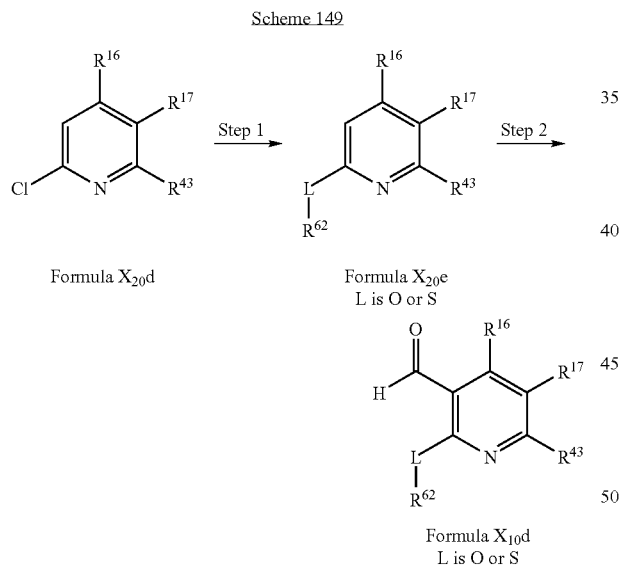

Step 1

Preparation of Compound of Formula $X_{20}e$

Compound of Formula $X_{20}e$ (Formula $X_{20}$ where $R^{60}$ is H and $R^{15}$ is $LR^{62}$, where L is O or S and $R^{62}$ is optionally substituted lower alkyl) is prepared by reacting compound of Formula $X_{20}d$ (Formula $X_{20}$ where $R^{60}$ is H and $R^{15}$ is Cl) with a compound of Formula $R^{62}$—OH or $R^{62}$—SH in the presence of a base (e.g. sodium hydride) in an appropriate solvent (e.g. dimethylformamide, tetrahydrofuran) with heating (e.g. 80° C.). After stirring for several hours, isolation by conventional means (e.g. extraction and silica gel chromatography) provides compound of Formula $X_{20}e$.

Step 2

Preparation of Compound of Formula $X_{10}d$

Compound of Formula $X_{10}d$ (Formula $X_{10}$ where $R^{42}$ is C(O)H and $R^{15}$ is $LR^{62}$, where L is O or S and $R^{62}$ is optionally substituted lower alkyl) is prepared by reacting compound of Formula $X_{20}e$ with an organolithium reagent (e.g. lithium diisopropylamine) to effect the ortholithiation at the $R^{42}$ position at reduced temperature (e.g. −78° C.) in an appropriate solvent (e.g. tetrahydrofuran) followed by addition of a formylating reagent (e.g. dimethylformamide). After stirring for several hours and warming to room temperature, isolation by conventional means (e.g. extraction and silica gel chromatography) provides compound of Formula $X_{10}d$.

Example 93

Synthesis of Compounds of Formula $X_{10}$ where $R^{15}$ is Halogen and $R^{42}$ is C(O)H Compound of Formula $X_{10}e$ (Formula $X_{10}$ where $R^{42}$ is C(O)H and $R^{15}$ is halogen) may be synthesized from a compound of Formula $X_{20}f$ in two Steps as described in Scheme 150.

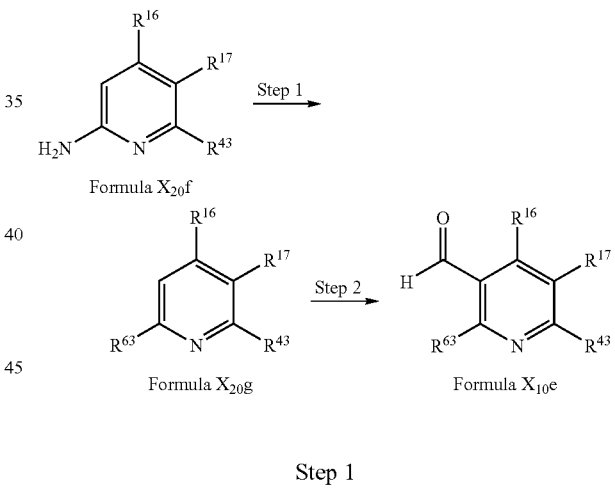

Step 1

Preparation of Compound of Formula $X_{20}g$

Compound of Formula $X_{20}g$ (Formula $X_{20}$ where $R^{60}$ is H and $R^{15}$ is chloro or bromo (halogen $R^{63}$)) is prepared by reacting compound of Formula $X_{20}f$ (Formula $X_{20}$ where $R^{60}$ is H and $R^{15}$ is $NH_2$) in glacial acetic acid with sodium nitrite in acid (e.g. hydrochloric acid, sulfuric acid) to afford the diazonium intermediate. To form the compounds where $R^{63}$ is chloro or bromo, the diazonium salt is added to cuprous chloride or cuprous bromide, respectively, in hydrochloric acid with heating (e.g. 80° C.) for 30 minutes to one hour. Upon addition of the reaction to water, followed by isolation by conventional means (e.g. extraction and silica gel chromatography), compound of Formula $X_{20}g$ where $R^{63}$ is chloro or bromo are obtained.

Compound of Formula $X_{20}g$ (Formula $X_{20}$ where $R^{60}$ is H and $R^{15}$ is fluoro (halogen $R^{63}$)) is prepared by reacting compound of Formula $X_{20}f$ in an appropriate aprotic solvent (e.g. tetrahydrofuran or dichloromethane) with boron trifluoride etherate. Subsequently, tert-butyl nitrite is added while the reaction is cooled (e.g. −15° C.) to afford the diazonium tetrafluoroborate intermediate as a precipitate that can be collected by filtration. To form the compound where $R^{63}$ is fluoro, the diazonium salt is heated dry with a burner to initiate the evolution borontrifluoride which subsequently proceeds spontaneously. After isolation by conventional means (e.g. extraction and silica gel chromatography) compound of Formula $X_{20}g$ where $R^{63}$ is fluoro are obtained. (Doyle and Bryker, J. Org. Chem. 1979, 44:1572; Schiemann and Winkelmüller, Org. Syn. Coll. Vol. 2:299).

Step 2

Preparation of Compound of Formula $X_{10}e$

Compound of Formula $X_{10}e$ (Formula $X_{10}$ where $R^{42}$ is C(O)H and $R^{15}$ is halogen $R^{63}$) is prepared by reacting compound of Formula $X_{20}g$ with an organolithium reagent (e.g. lithium diisopropylamine) to effect the ortholithiation at the $R^{42}$ position at reduced temperature (e.g. −78° C.) in an appropriate solvent (e.g. tetrahydrofuran) followed by addition of a formylating reagent (e.g. dimethylformamide). After stirring for several hours and warming to room temperature, isolation by conventional means (e.g. extraction and silica gel chromatography) provides compound of Formula $X_{10}e$.

Example 94

Synthesis of Compounds of Formula $X_{10}$ where $R^{16}$ is Optionally Substituted Lower Alkyl and $R^{42}$ is C(O)H Compound of Formula $X_{10}f$ (Formula $X_{10}$ where $R^{42}$ is C(O)H and $R^{16}$ is optionally substituted lower alkyl) may be synthesized from a compound of Formula $X_{20}h$ in two Steps as described in Scheme 151.

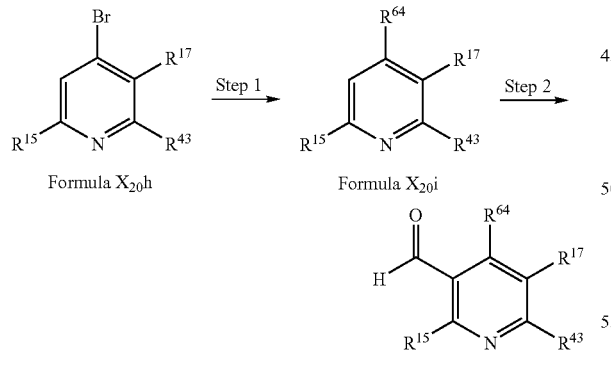

Step 1

Preparation of Compound of Formula $X_{20}i$

Compound of Formula $X_{20}i$ (Formula $X_{20}$ where $R^{60}$ is H and $R^{16}$ is optionally substituted lower alkyl $R^{64}$) is prepared by dissolving compound of Formula $X_{20}h$ (Formula $X_{20}$ where $R^{60}$ is H and $R^{16}$ is Br) in an appropriate solvent (e.g. toluene), followed by the addition of a palladium catalyst (e.g. [1,1′-Bis(diphenylphosphino)-ferrocene]dichloropalladium(II) complex with dichloromethane (1:1)). After several minutes, a Grignard reagent of the Formula $R^{64}$—MgBr ($R^{64}$ is optionally substituted lower alkyl) is added and the reaction heated (e.g. 90° C.) for one to several hours. After filtration through Celite, isolation by conventional means (e.g. extraction and silica gel chromatography) provides compound of Formula $X_{20}i$.

Step 2

Preparation of Compound of Formula $X_{10}f$

Compound of Formula $X_{10}f$ (Formula $X_{10}$ where $R^{42}$ is C(O)H and $R^{16}$ is optionally substituted lower alkyl $R^{64}$) is prepared by reacting compound of Formula $X_{20}i$ with an organolithium reagent (e.g. lithium diisopropylamine) to effect the lithiation at the $R^{42}$ position at reduced temperature (e.g. −78° C.) in an appropriate solvent (e.g. tetrahydrofuran) followed by addition of a formylating reagent (e.g. dimethylformamide). After stirring for several hours and warming to room temperature, isolation by conventional means (e.g. extraction and silica gel chromatography) provides compound of Formula $X_{10}f$.

Example 95

Synthesis of Compounds of Formula $X_{10}$ where $R^{16}$ is Halogen and $R^{42}$ is C(O)H Compound of Formula $X_{10}g$ (Formula $X_{10}$ where $R^{42}$ is C(O)H and $R^{16}$ is halogen) may be synthesized from a compound of Formula $X_{20}j$ in two Steps as described in Scheme 152.

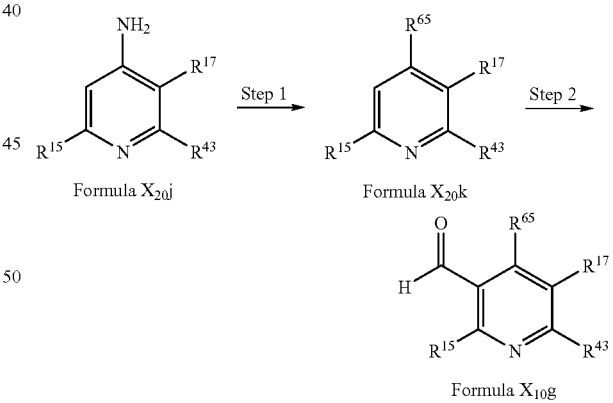

Step 1

Preparation of Compound of Formula $X_{20}k$

Compound of Formula $X_{20}k$ (Formula $X_{20}$ where $R^{60}$ is H and $R^{16}$ is chloro or bromo (halogen $R^{65}$)) is prepared by reacting compound of Formula $X_{20}j$ (Formula $X_{20}$ where $R^{60}$ is H and $R^{16}$ is $NH_2$) in glacial acetic acid with sodium nitrite in acid (e.g. hydrochloric acid, sulfuric acid) to afford the diazonium intermediate. To form the compound where $R^{65}$ is chloro or bromo, the diazonium salt is added to cuprous chloride or cuprous bromide, respectively, in hydrochloric acid with heating (e.g. 80° C.) for 30 minutes to one hour. Upon addition of the reaction to water, followed by isolation by conventional means (e.g. extraction and silica gel chromatography) compound of Formula $X_{20}k$ where $R^{65}$ is bromo or chloro are obtained.

Compound of Formula $X_{20}k$ (Formula $X_{20}$ where $R^{60}$ is H and $R^{16}$ is fluoro (halogen $R^{65}$)) is prepared by reacting compound of Formula $X_{20}j$ in an appropriate aprotic solvent (e.g. tetrahydrofuran or dichloromethane) with boron trifuloride etherate. Subsequently, tert-butyl nitrite may be added while the reaction is cooled (e.g. −15° C.) to afford the diazonium tetrafluoroborate intermediate as a precipitate that may be collected by filtration. To form the compounds where $R^{65}$ is fluoro, the diazonium salt is heated dry with a burner to initiate the evolution borontrifluoride which subsequently proceeds spontaneously. After isolation by conventional means (e.g. extraction and silica gel chromatography), compound of Formula $X_{20}k$ where R15 is H and $R^{65}$ is fluoro are obtained. (Doyle and Bryker, J. Org. Chem. 1979, 44:157; Schiemann and Winkelmüller, Org. Syn. Coll. Vol. 2:299.)

Step 2

Preparation of Compound of Formula $X_{10}g$

Compound of Formula $X_{10}g$ (Formula $X_{10}$ where $R^{42}$ is C(O)H and $R^{16}$ is halogen $R^{65}$) is prepared by reacting compound of Formula $X_{20}k$ Formula Xa with an organolithium reagent (e.g. lithium diisopropylamine) to effect the lithiation at the $R^{42}$ position at reduced temperature (e.g. −78° C.) in an appropriate solvent (e.g. tetrahydrofuran) followed by addition of a formylating reagent (e.g. dimethylformamide). After stirring for several hours and warming to room temperature, isolation by conventional means (e.g. extraction and silica gel chromatography) provides compounds of Formula $X_{10}g$.

Example 96

Synthesis of Compounds of Formula $X_{10}$ where $R^{16}$ is $OR^{66}$ and $R^{42}$ is C(O)H Compound of Formula $X_{10}h$ (Formula $X_{10}$ where $R^{42}$ is C(O)H and $R^{16}$ is $OR^{66}$, where $R^{66}$ is optionally substituted lower alkyl) may be synthesized from a compound of Formula $X_{20}h$ in two Steps as described in Scheme 153.

-continued

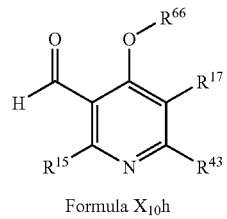

Formula $X_{10}h$

Step 1

Preparation of Compound of Formula $X_{20}m$

Compound of Formula $X_{20}m$ (Formula $X_{20}$ where $R^{60}$ is H and $R^{16}$ is $OR^{66}$, where $R^{66}$ is optionally substituted lower alkyl) is prepared by reacting compound of Formula $X_{20}h$ (Formula $X_{20}$ where $R^{60}$ is H and $R^{16}$ is Br) with compound of the Formula $R^{66}$—OH ($R^{66}$ is optionally substituted lower alkyl) in the presence of a base (e.g. sodium hydride) and a copper catalyst (e.g. copper bromide) in a non-reactive solvent (e.g. dimethylformamide) with heating (e.g. 120° C.) for several hours. Isolation by conventional means (e.g. extraction and silica gel chromatography) provides compound of Formula $X_{20}m$.

Step 2

Preparation of Compound of Formula $X_{10}h$

Compound of Formula $X_{10}h$ (Formula $X_{10}$ where $R^{42}$ is C(O)H and $R^{16}$ is $OR^{66}$, where $R^{66}$ is optionally substituted lower alkyl) is prepared by reacting compound of Formula $X_{20}m$ with an organolithium reagent (e.g. lithium diisopropylamine) to effect the ortholithiation at the $R^{42}$ position at reduced temperature (e.g. −78° C.) in an appropriate solvent (e.g. tetrahydrofuran) followed by addition of a formylating reagent (e.g. dimethylformamide). After stirring for several hours and warming to room temperature, isolation by conventional means (e.g. extraction and silica gel chromatography) provides compound of Formula $X_{10}h$.

Example 97

Synthesis of Compounds of Formula $X_{10}$ where $R^{17}$ is Halogen and $R^{42}$ is C(O)H Compound of Formula $X_{10}i$ (Formula $X_{10}$ where $R^{42}$ is C(O)H and $R^{17}$ is halogen) may be synthesized from a compound of Formula $X_{20}n$ in two Steps as described in Scheme 154.

Scheme 153

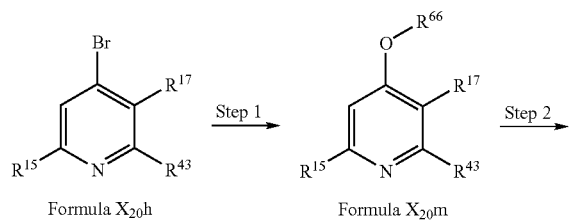

Scheme 154

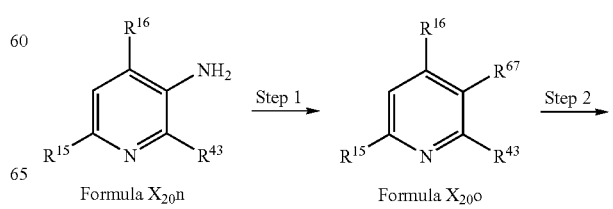

-continued

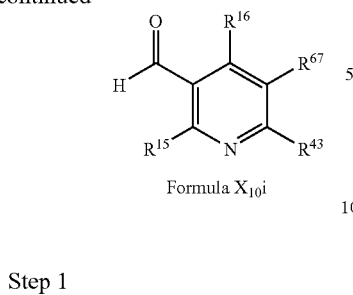

Formula $X_{10}i$

Step 1

Preparation of Compound of Formula $X_{20}o$

Compound of Formula $X_{20}o$ (Formula $X_{20}$ where $R^{60}$ is H and $R^{17}$ is chloro or bromo (halogen $R^{67}$)) is prepared by reacting compound of Formula $X_{20}n$ (Formula $X_{20}$ where $R^{60}$ is H and $R^{17}$ is $NH_2$) in glacial acetic acid with sodium nitrite in acid (e.g. hydrochloric acid, sulfuric acid) to afford the diazonium intermediate. To form the compounds where $R^{67}$ is chloro or bromo, the diazonium salt is added to cuprous chloride or cuprous bromide, respectively, in hydrochloric acid with heating (e.g. 80° C.) for 30 minutes to one hour. Upon addition of the reaction to water, followed by isolation by conventional means (e.g. extraction and silica gel chromatography) compound of Formula $X_{20}o$ where $R^{67}$ is bromo or chloro are obtained.

Compound of Formula $X_{20}o$ (Formula $X_{20}$ where $R^{60}$ is H and $R^{17}$ is fluoro (halogen $R^{67}$)) is prepared by reacting compound of Formula $X_{20}n$ in an appropriate aprotic solvent (e.g. tetrahydrofuran or dichloromethane) with boron trifuloride etherate. Subsequently, tert-butyl nitrite may be added while the reaction is cooled (e.g. −15° C.) to afford the diazonium tetrafluoroborate intermediate as a precipitate that can be collected by filtration. To form the compounds where $R^{67}$ is fluoro, the diazonium salt is heated dry with a burner to initiate the evolution borontrifluoride which subsequently proceeds spontaneously. After isolation by conventional means (e.g. extraction and silica gel chromatography) compounds of Formula $X_{20}o$ where $R^{67}$ is fluoro are obtained. (Doyle and Bryker, J. Org. Chem. 1979, 44:1572. Schiemann and Winkelmüller, Org. Syn. Coll. Vol. 2:299).

Step 2

Preparation of Compound of Formula $X_{10}i$

Compound of Formula $X_{10}i$ (Formula $X_{10}$ where $R^{42}$ is C(O)H and $R^{17}$ is halogen $R^{67}$) is prepared by reacting compound of Formula $X_{20}o$ with an organolithium reagent (e.g. lithium diisopropylamine) to effect the lithiation at the $R^{42}$ position at reduced temperature (e.g. −78° C.) in an appropriate solvent (e.g. tetrahydrofuran) followed by addition of a formylating reagent (e.g. dimethylformamide). After stirring for several hours and warming to room temperature, isolation by conventional means (e.g. extraction and silica gel chromatography) provides compounds of Formula $X_{10}i$.

Example 98

Synthesis of Compounds of Formula $X_{10}$ where $R^{17}$ is $OR^{68}$ and $R^{42}$ is C(O)H Compound of Formula $X_{10}j$ (Formula $X_{10}$ where $R^{42}$ is C(O)H and $R^{17}$ is $OR^{68}$, where $R^{68}$ is optionally substituted lower alkyl) may be synthesized from a compound of Formula $X_{20}p$ in two Steps as described in Scheme 155.

Scheme 155

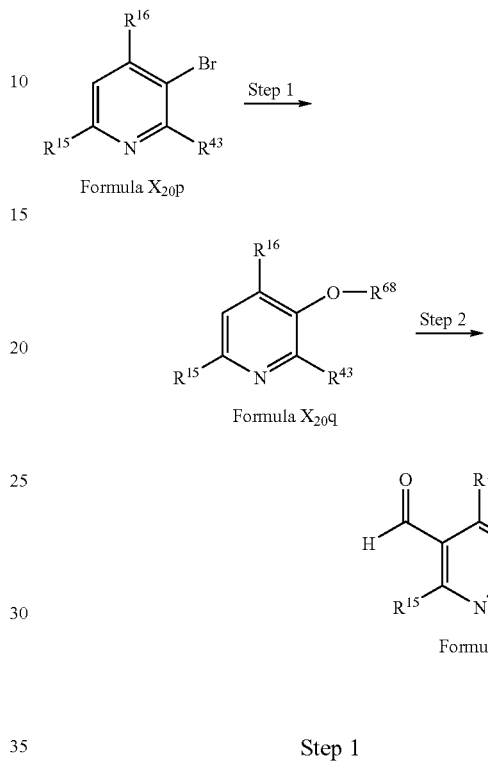

Step 1

Preparation of Compound of Formula $X_{20}q$

Compound of Formula $X_{20}q$ (Formula $X_{20}$ where $R^{60}$ is H and $R^{17}$ is $OR^{68}$, where $R^{68}$ is optionally substituted lower alkyl) is prepared by reacting compound of Formula $X_{20}p$ (Formula $X_{20}$ where $R^{60}$ is H and $R^{17}$ is Br) with compound of the Formula $R^{68}$—OH ($R^{68}$ is optionally substituted lower alkyl) in the presence of a base (e.g. sodium hydride) and a copper catalyst (e.g. copper bromide) in a non-reactive solvent (e.g. dimethylformamide) with heating (e.g. 120° C.) for several hours. Isolation by conventional means (e.g. extraction and silica gel chromatography) provides compound of Formula $X_{20}q$.

Step 2

Preparation of Compound of Formula $X_{10}j$

Compound of Formula $X_{10}j$ (Formula $X_{10}$ where $R^{42}$ is C(O)H and $R^{17}$ is $OR^{68}$, where $R^{68}$ is optionally substituted lower alkyl) is prepared by reacting compound of Formula $X_{20}q$ with an organolithium reagent (e.g. lithium diisopropylamine) to effect the lithiation at the $R^{42}$ position at reduced temperature (e.g. −78° C.) in an appropriate solvent (e.g. tetrahydrofuran) followed by addition of a formylating reagent (e.g. dimethylformamide). After stirring for several hours and warming to room temperature, isolation by con-

Example 99

Synthesis of Compounds of Formula X where n=1; G is N; K, J, F and E are C; R15 and R16 are Optionally Substituted Lower Alkyl; M is NH-D- and $R^{42}$ is C(O)H Compounds of Formula X where n=1 and G is N are pyrimidine derivatives that may be prepared through many routes known in the literature and used in reactions analogous to those described for compounds of Formula Xa, such as in Examples 89-98. M is NH-D, where D is consistent with the definition of M. The synthesis of one such compound is exemplified in Scheme 156 as follows.

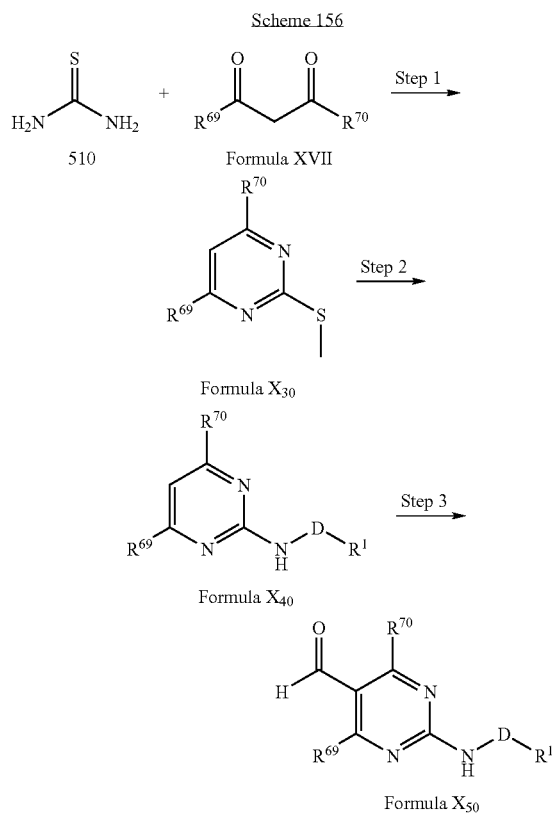

Step 1

Preparation of Compound of Formula $X_{30}$

Compound of Formula $X_{30}$ (Formula Xa where n=1, G is N, K, J, F and E are C, $R^{15}$ and $R^{16}$ are optionally substituted lower alkyl ($R^{69}$ and $R^{70}$, respectively), $R^{43}$ is S-Me and $R^{42}$ is H) is prepared by reacting thiourea 510 with compound of Formula XVII ($R^{69}$ and $R^{70}$ are independently optionally substituted lower alkyl) in the presence of a base (e.g. sodium hydroxide) in a non-reactive solvent (e.g. ethanol) for several hours. Subsequently, the addition of methyl iodide with heating (e.g. 60° C.) for several hours, followed by isolation by conventional means (e.g. extraction and silica gel chromatography) provides compound of Formula $X_{30}$.

Step 2

Preparation of Compound of Formula $X_{40}$

Compounds of Formula $X_{40}$ (Formula X where n=1, G is N, K, J, F and E are C, $R^{15}$ and $R^{16}$ are optionally substituted lower alkyl ($R^{69}$ and $R^{70}$, respectively), M is NH-D- (D is consistent with definition of M of Formula Ib or $L^2$ or Formula I) and $R^{42}$ is H) is prepared by reacting compound of Formula $X_{30}$ with compound of Formula $NH_2$-D-$R^1$ (e.g. benzyl amine or other suitable nucleophile) in the presence of a base (e.g. sodium hydride) in a non-reactive solvent (e.g. dimethylformamide) for several hours. Isolation by conventional means (e.g. extraction and silica gel chromatography) provides compounds of Formula $X_{40}$.

Step 3

Preparation of Compound of Formula $X_{50}$

Compounds of Formula $X_{50}$ (Formula X where n=1, G is N, K, J, F and E are C, $R^{15}$ and $R^{16}$ are optionally substituted lower alkyl ($R^{69}$ and $R^{70}$, respectively), M is NH-D- (D is consistent with definition of M of Formula Ib or $L^2$ or Formula I) and $R^{42}$ is C(O)H is prepared by reacting compound of Formula $X_{40}$ with an organolithium reagent (e.g. lithium diisopropylamine) to effect the lithiation at the $R^{42}$ position at reduced temperature (e.g. −78° C.) in an appropriate solvent (e.g. tetrahydrofuran) followed by addition of a formylating reagent (e.g. dimethylformamide). After stirring for several hours and warming to room temperature, isolation by conventional means (e.g. extraction and silica gel chromatography) provides compounds of Formula $X_{50}$, which may be used in the synthesis of compound of Formula II, which may be used in the synthesis of compound of Formula Ib.

Example 100

Synthesis of Compounds of Formula Xa where n=0; K is S; J, E, and F are C; $R^{43}$ is NHP; $R^{15}$ is Optionally Substituted Lower Alkyl or Optionally Substituted Lower Alkoxy and $R^{42}$ is COOH Compounds of Formula X where n=0 are 5-membered heterocycles that may be prepared through many routes known in the literature and used in reactions analogous to those described for compounds of Formula Xa, such as in Examples 89-98. The synthesis of one such compound is exemplified in Scheme 157 as follows.

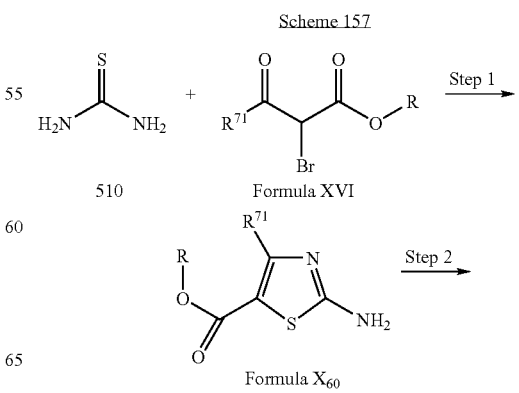

235

-continued

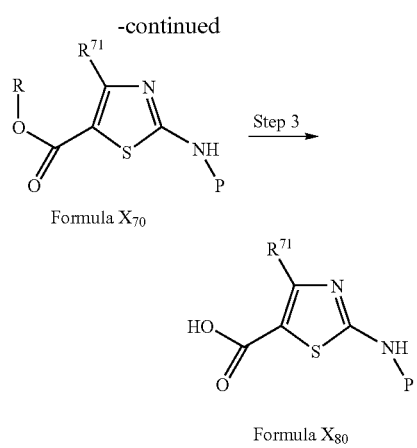

Formula X<sub>70</sub>

Formula X<sub>80</sub>

Step 1

Preparation of Compound of Formula $X_{60}$

Compound of Formula $X_{60}$ (Formula Xa where n=0, K is S, J, E, and F are C, $R^{43}$ is $NH_2$, $R^{15}$ is $R^{71}$ ($R^{71}$ is optionally substituted lower alkyl or $O—R^{72}$, where $R^{72}$ is optionally substituted lower alkyl) and $R^{42}$ is $CO_2R$, where R is lower alkyl) is prepared by reacting thiourea 510 with compound of Formula XVI where $R^{71}$ is optionally substituted lower alkyl or $O—R^{72}$ ($R^{72}$ is optionally substituted lower alkyl) and R is lower alkyl in a non-reactive solvent (e.g. dimethylformamide, ethanol) with heating (e.g. 60° C.) for several hours. Isolation by conventional means (e.g. extraction and silica gel chromatography) provides compound of Formula $X_{60}$.

Step 2

Preparation of Compound of Formula $X_{70}$

Compound of Formula $X_{70}$ (Formula Xa where n=0, K is S, J, E, and F are C, $R^{43}$ is NHP, where P is a protecting group [e.g. triisopropylsilyl, t-butyloxycarbonyl]), $R^{15}$ is $R^{71}$ and $R^{42}$ is $CO_2R$, where R is lower alkyl) is prepared by reacting compound of Formula $X_{60}$ with a reagent appropriate to introduce the protecting group (e.g. triisopropylsilyl chloride, Boc anhydride) in the presence of a base (e.g. sodium hydride, diisopropylethylamine) in a non-reactive solvent (e.g. dimethylformamide) for several hours. Isolation by conventional means (e.g. extraction and silica gel chromatography) provides compound of Formula $X_{70}$.

Step 3

Preparation of Compound of Formula $X_{80}$

Compound of Formula $X_{80}$ (Formula Xa where n=0, K is S, J, E, and F are C, $R^{43}$ is NHP, $R^{15}$ is $R^{71}$ and $R^{42}$ is $CO_2H$) is prepared by reacting compound of Formula $X_{70}$ with a base (e.g. lithium hydroxide) in an appropriate solvent (e.g. tetrahydrofuran and water) for several hours. Isolation by conventional means (e.g. acid-base extraction) provides compound of $X_{80}$, which may be used in the synthesis of compound of Formula II where $R^{43}$ is NHP, which may be used to make compound of Formula Ib.

Example 101

Synthesis of 3,5-Dimethyl-4-(1H-pyrrolo[2,3-b]pyridin-3-ylmethyl)-pyrazole-1-carboxylic acid benzylamide P-0084

3,5-Dimethyl-4-(1H-pyrrolo[2,3-b]pyridin-3-ylmethyl)-pyrazole-1-carboxylic acid benzylamide P-0084 was synthesized in 6 steps from dimethyl-(1H-pyrrolo[2,3-b]pyridin-3-ylmethyl)-amine 2 as shown in scheme 158.

Scheme 158

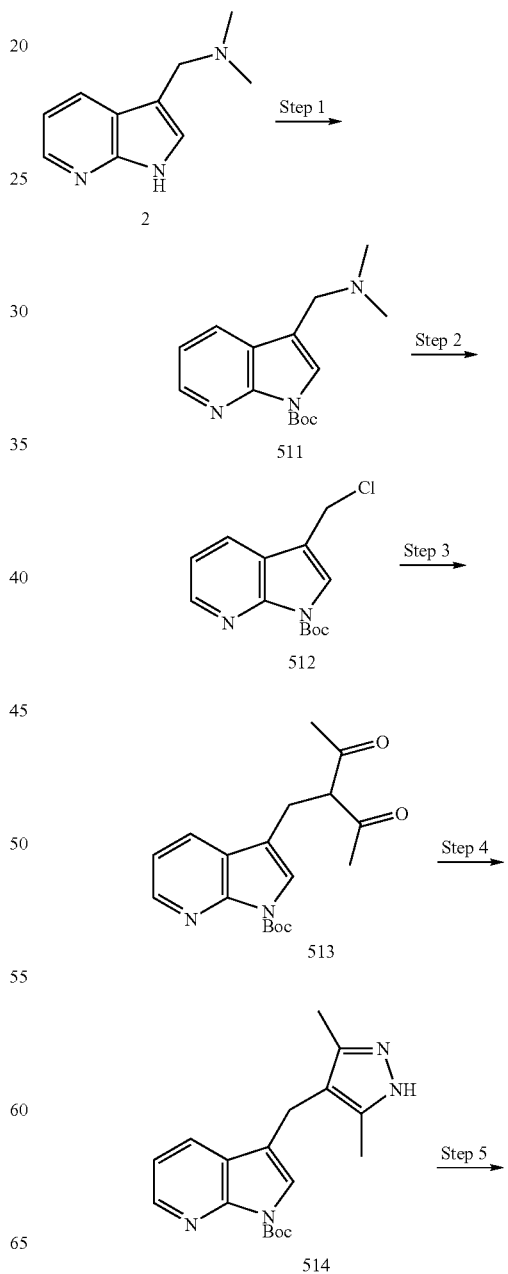

-continued

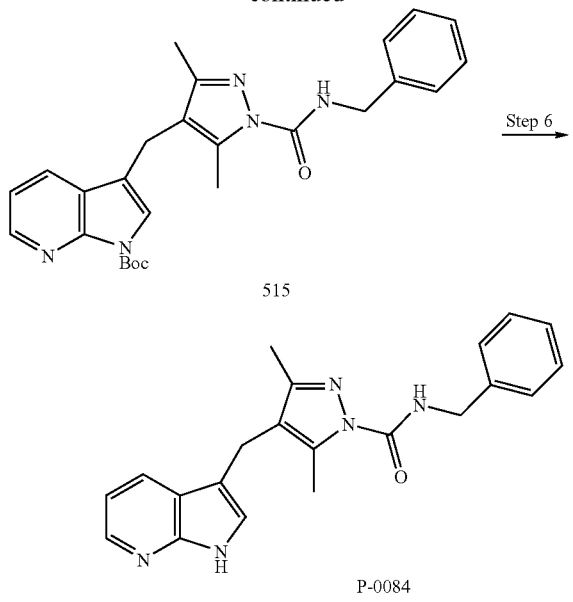

515

P-0084

Step 1

Preparation of 3-Dimethylaminomethyl-pyrrolo[2,3-b]pyridine-1-carboxylic acid tert-butyl ester (511)

To dimethyl-(1H-pyrrolo[2,3-b]pyridin-3-ylmethyl)-amine (2, 2.50 g, 14.3 mmol, prepared as described in Example 2, Scheme 4, Step 1) in tetrahydrofuran (200.0 mL) was added sodium hydride (0.685 g, 60% in mineral oil, 17.1 mmol). After 10 minutes, di-tert-butyldicarbonate (3.74 g, 17.1 mmol) was added to the reaction. The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 30% ethyl acetate in hexane to give as a white solid (511, 3.80 g, 96.7%).

Step 2

Preparation of 3-Chloromethyl-pyrrolo[2,3-b]pyridine-1-carboxylic acid tert-butyl ester (512)

To 3-dimethylaminomethyl-pyrrolo[2,3-b]pyridine-1-carboxylic acid tert-butyl ester (511, 2.60 g, 9.44 mmol) in toluene (50.00 mL) was added isopropyl chloroformate (11.3 mL, 1.0 M in toluene) under an atmosphere of nitrogen. The reaction was stirred at room temperature for 3 hours. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give a white solid (512, 2.0 g, 79.4%).

Step 3

Preparation of 3-(2-Acetyl-3-oxo-butyl)-pyrrolo[2,3-b]pyridine-1-carboxylic acid tert-butyl ester (513)

To acetylacetone (0.563 g, 5.62 mmol) in dimethyl sulfoxide (29.0 mL) was added sodium hydride (0.225 g, 60% in mineral oil, 5.62 mmol). After 20 minutes, 3-chloromethyl-pyrrolo[2,3-b]pyridine-1-carboxylic acid tert-butyl ester (512, 1.00 g, 3.75 mmol) was added to the reaction. The reaction was stirred at room temperature for 2 hours. The reaction was poured into water and extracted with ethyl acetate. The organic layer was dried over anhydrous sodium sulfate and filtered. The filtrate was concentrated and purified by silica gel column chromatography eluting with 40% ethyl acetate in hexane to give a colorless oil (513, 0.59 g, 48.0%). MS (ESI) [M+H$^+$]$^+$=331.4.

Step 4

Preparation of 3-(3,5-Dimethyl-1H-pyrazol-4-ylmethyl)-pyrrolo[2,3-b]pyridine-1-carboxylic acid tert-butyl ester (514)

To 3-(2-acetyl-3-oxo-butyl)-pyrrolo[2,3-b]pyridine-1-carboxylic acid tert-butyl ester (513, 1.20 g, 3.63 mmol) in methanol (15.0 mL), cooled to −20° C. under an atmosphere of nitrogen, was added hydrazine (0.128 g, 4.00 mmol) in dichloromethane (6.0 mL). The reaction was stirred for 2 hours. The reaction was concentrated to remove the solvents, and the residue was poured into water and extracted with ethyl acetate. The organic layer was dried over anhydrous sodium sulfate and filtered. The filtrate was concentrated and purified by silica gel column chromatography eluting with 60% ethyl acetate in hexane to give a white solid (514, 1.0 g, 84.4%). MS (ESI) [M+H$^+$]$^+$=327.4.

Step 5

Preparation of 3-(1-Benzylcarbamoyl-3,5-dimethyl-1H-pyrazol-4-ylmethyl)-pyrrolo[2,3-b]pyridine-1-carboxylic acid tert-butyl ester (515)

To 3-(3,5-dimethyl-1H-pyrazol-4-ylmethyl)-pyrrolo[2,3-b]pyridine-1-carboxylic acid tert-butyl ester (514, 60.0 mg, 0.18 mmol) in dichloromethane (6.0 mL) were added 1,8-diazabicyclo[5.4.0]undec-7-ene (0.033 mL, 0.220 mmol) and benzyl isocyanate (29.4 mg, 0.220 mmol) under an atmosphere of nitrogen. The reaction was stirred at room temperature for 2 hours. The reaction was concentrated and purified by silica gel column chromatography eluting with 30% ethyl acetate in hexane to give crude compound (515, approx. 50 mg) that was used in the next step directly. MS (ESI) [M+H$^+$]$^+$=460.5.

Step 6

3,5-Dimethyl-4-(1H-pyrrolo[2,3-b]pyridin-3-ylmethyl)-pyrazole-1-carboxylic acid benzylamide (P-0084)

To 3-(1-benzylcarbamoyl-3,5-dimethyl-1H-pyrazol-4-ylmethyl)-pyrrolo[2,3-b]pyridine-1-carboxylic acid tert-butyl ester (515, 50.0 mg, 0.11 mmol) in dichloromethane (6.0 mL) was added trifluoroacetic acid (0.20 mL, 2.6 mmol) under an atmosphere of nitrogen. The reaction was stirred at room temperature for 20 minutes. The reaction was poured into aqueous potassium carbonate and extracted with ethyl acetate. The organic layer was dried over anhydrous sodium sulfate and filtered. The filtrate was concentrated and purified by silica gel column chromatography eluting with 30% ethyl acetate in hexane to give a white solid (P-0084, 11.0 mg, 28.1%). MS (ESI) [M+H$^+$]$^+$=360.5.

Additional compounds were prepared following the protocol of Scheme 158, replacing benzyl isocyanate with an appropriate electrophile in Step 5. The following compounds were made following this procedure:

3,5-Dimethyl-4-(1H-pyrrolo[2,3-b]pyridin-3-ylmethyl)-pyrazole-1-carboxylic acid phenylamide (P-0085)[3,5-Dimethyl-4-(1H-pyrrolo[2,3-b]pyridin-3-ylmethyl)-pyrazol-1-yl]-phenyl-methanone (P-0086), 1-[3,5-Dimethyl-4-(1H-pyrrolo[2,3-b]pyridin-3-ylmethyl)-pyrazol-1-yl]-3-phenyl-propan-1-one (P-0087),
3-(3,5-Dimethyl-1-phenylmethanesulfonyl-1H-pyrazol-4-ylmethyl)-1H-pyrrolo[2,3-b]pyridine (P-0088),
3-[1-(Butane-1-sulfonyl)-3,5-dimethyl-1H-pyrazol-4-ylmethyl]-1H-pyrrolo[2,3-b]pyridine (P-0089),
3,5-Dimethyl-4-(1H-pyrrolo[2,3-b]pyridin-3-ylmethyl)-pyrazole-1-carboxylic acid butylamide (P-0090), and
3,5-Dimethyl-4-(1H-pyrrolo[2,3-b]pyridin-3-ylmethyl)-pyrazole-1-carboxylic acid phenethyl-amide (P-0091).

The electrophile used in place of benzyl isocyanate in Step 5 is indicated in Column 2 of the following table, with the compound structure given in Column 3. Column 1 provides the compound number and Column 4 the experimental mass spectrometry result.

| | Electrophile | Compound | MS (ESI) [M + H$^+$]$^+$ observed |
|---|---|---|---|
| P-0085 | | | 346.4 |
| P-0086 | | | 331.2 |
| P-0087 | | | 359.2 |
| P-0088 | | | 381.2 |
| P-0089 | | | 347.2 |

-continued

| Electrophile | Compound | MS (ESI) [M + H⁺]⁺ observed |
|---|---|---|
| P-0090 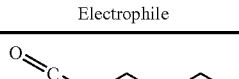 | 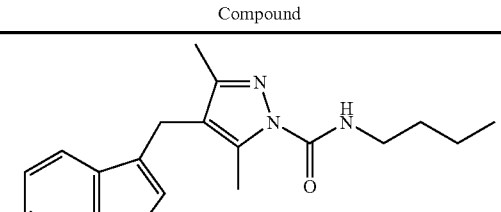 | 326.2 |
| P-0091  |  | |

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to provide additional compounds of Formula I and/or various methods of administration can be used. Thus, such additional embodiments are within the scope of the present invention and the following claims.

The invention illustratively described herein suitably may be practiced in the absence of any element or elements, limitation or limitations which is not specifically disclosed herein.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A compound having the chemical structure

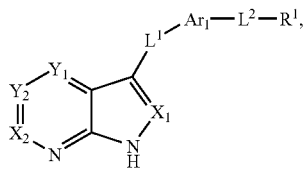

all salts, tautomers, and stereoisomers thereof,
wherein:
$X_1$ is $CR^2$, $X_2$ is $CR^6$, $Y_1$ is $CR^4$, and $Y_2$ is $CR^5$;
$L^1$ is —$CH_2$—;
$L^2$ is selected from the group consisting of —O—$CH_2$—, —NH—$CH_2$, —NH—$CH(CH_3)$—, and —NH—C(O);
$R^1$ is cycloalkyl or phenyl, wherein phenyl is substituted with a substituent selected from the group consisting of fluoro, chloro, methyl, methoxy and trifluoromethyl;
$R^2$ and $R^6$ are hydrogen;
one of $R^4$ and $R^5$ is selected from the group consisting of fluoro, chloro, bromo, lower alkyl optionally substituted with one or more fluoro, lower alkenyl, lower alkynyl, cycloalkyl, —CN, and lower alkoxy optionally substituted with one or more fluoro, lower alkoxy, di-alkylamino or cycloalkylamino, and the other of $R^4$ and $R^5$ is selected from the group consisting of hydrogen, fluoro, chloro, bromo, lower alkyl optionally substituted with one or more fluoro, lower alkenyl, lower alkynyl, cycloalkyl, —CN, and lower alkoxy optionally substituted with one or more fluoro, lower alkoxy, dialkylamino, or cycloalkylamino;
$Ar_1$ is a 6 membered optionally substituted heteroarylene having the structure

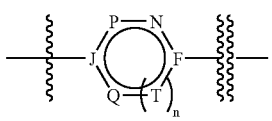

wherein

indicates the point of attachment of $L^1$ and

indicates the point of attachment of $L^2$, and wherein the indicated N is either =N— or —N=;
n is 1;
F and J are both C;
P is CR and Q is CH, wherein R is hydrogen, methyl or methoxy;
T is CH.

2. The compound according to claim 1, wherein $Y_1$ is CH and $Y_2$ is $CR^5$.

3. The compound according to claim 2, wherein $R^5$ is fluoro, chloro, lower alkyl or lower alkoxy.

4. The compound according to claim 2, wherein $R^5$ is chloro or methoxy.

5. The compound according to claim 1, wherein $Y_2$ is CH and $Y_1$ is $CR^4$.

6. The compound according to claim 5, wherein $R^4$ is fluoro, chloro, lower alkyl or lower alkoxy.

7. The compound according to claim 5, wherein $R^4$ is chloro or methoxy.

8. A composition comprising:
a pharmaceutically acceptable carrier; and
a compound according to claim 1.

9. A kit comprising a composition according to claim 8.

* * * * *